(12) United States Patent
Tabart et al.

(10) Patent No.: US 7,119,115 B2
(45) Date of Patent: Oct. 10, 2006

(54) INDAZOLE OR INDOLE DERIVATIVES, AND USE THEREOF IN HUMAN MEDICINE AND MORE PARTICULARLY IN ONCOLOGY

(75) Inventors: Michel Tabart, La Norville (FR); Eric Bacqué, Gif sur Yvette (FR); Sylvie Wentzler, Fresnes (FR); Cécile Combeau, Fontenay Aux Roses (FR); Conception Nemecek, Thiais (FR); Patrick Mailliet, Fontenay Sous Bois (FR); Fabienne Thompson, Paris (FR)

(73) Assignee: Aventis Pharma S.A., Antony (FR)

(*) Notice: Subject to any disclaimer, the term of this patent is extended or adjusted under 35 U.S.C. 154(b) by 0 days.

(21) Appl. No.: 10/761,982

(22) Filed: Jan. 21, 2004

(65) Prior Publication Data

US 2004/0162276 A1    Aug. 19, 2004

Related U.S. Application Data

(63) Continuation of application No. PCT/FR02/02638, filed on Jul. 24, 2002.

(30) Foreign Application Priority Data

Jul. 27, 2001  (FR) .................................. 01 10118

(51) Int. Cl.
  *A61K 31/416* (2006.01)
  *C07D 231/56* (2006.01)
(52) U.S. Cl. .............. 514/405; 514/338; 514/364; 514/63; 546/275.7; 548/131; 548/110; 548/360.1
(58) Field of Classification Search ............... 548/131, 548/110, 360.1; 546/275.7; 514/405, 338, 514/364, 63
See application file for complete search history.

(56) References Cited

FOREIGN PATENT DOCUMENTS

WO      WO 01/53268 A2      7/2001

OTHER PUBLICATIONS

Golub et al., Science, vol. 286, Oct. 15, 1999, pp. 531-537.*
Padwa Albert et al., Reaction of Carbonyl Compounds with Ethyl Lithiodiazoacetate. Studies Dealing with the Rhodium (II)-Catalyzed Behavior of the Resulting Adducts, Journal of Organic Chemistry; vol. 55; 1990; pp. 4144-4153.

* cited by examiner

*Primary Examiner*—Laura L. Stockton
(74) *Attorney, Agent, or Firm*—Balaram Gupta

(57) ABSTRACT

The present invention relates to novel compounds derived from indazoles or indoles of formula (1) or formula (2), to methods for treating tumors or cancerous cells with compounds of formula (1) or formula (2) and to pharmacaetutical compositions comprising a pharmaceutically acceptable carrier and a compound of formula (1) or formula (2)

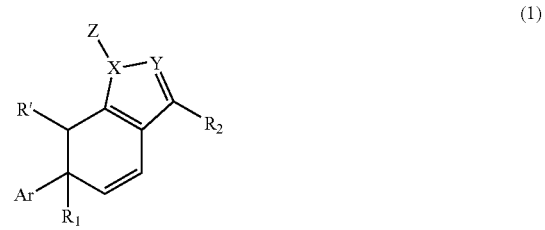

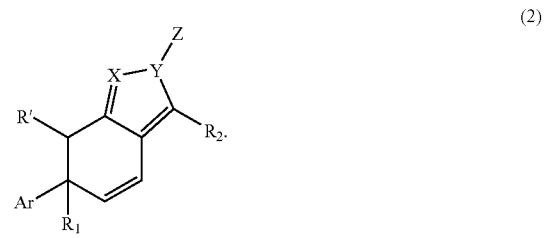

22 Claims, No Drawings

INDAZOLE OR INDOLE DERIVATIVES, AND USE THEREOF IN HUMAN MEDICINE AND MORE PARTICULARLY IN ONCOLOGY

This application is a continuation of International Application No. PCT/FR02/02638 filed Jul. 24, 2002, which claims the benefit of priority of French Application No. 01 10118, filed Jul. 27, 2001.

BACKGROUND OF THE INVENTION

1. Field of the Invention

The present invention relates to novel chemical compounds derived from indazoles or indoles, and to their use in human medicine and more particularly in oncology.

2. Description of the Art

The compounds of the present invention act more particularly as agents that bind to tubulin and possibly inhibit the vascularization of tumours. The microtubules of eukaryotic cells constitute a dynamic assembly and disassembly system in which tubulin dimers polymerize to form microtubules. In cancerous cells, the agents that inhibit the polymerization of the microtubules similarly inhibit mitosis and consequently the proliferation of cells and thus allow the death of the cell.

Numerous agents that inhibit microtubule polymerization are currently marketed. Mention may be made of vinca alkaloids, colchicine and its derivatives, and combretastatins.

Novel antitubulin agents are constantly being sought, making it possible to act on cells that are resistant to the treatments currently available on the market or treatments that show lower toxicity or higher selectivity for any given type of cancer. A product for inhibiting tumour vascularization is also being sought.

BRIEF SUMMARY OF THE INVENTION

One subject of the present invention is novel compounds corresponding to one of the formulae (1) and (2) below:

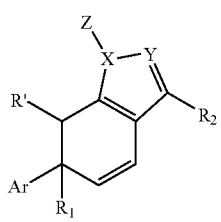

(1)

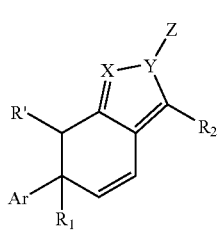

(2)

in which the heterocycle containing X—Y forms an aromatic 5-membered ring and

Ar is chosen from phenyl groups optionally substituted with one or more halogen atoms or with alkyl, alkoxy, thioalkyl, alkylamino or dialkylamino radicals in which the alkyl portions may optionally form a 3- to 6-membered ring which may contain a second hetero atom chosen from O, S and N; and from aromatic heterocycles (optionally substituted like the above phenyl group), containing from 5 to 6 members and one or two hetero atoms chosen from O, N and S;

X and Y are chosen from N and CH with at least one of them representing a nitrogen atom N;

Z represents H or a sulphonyl, acyl or 4-aminophenyl group;

$R_1$=H, alkyl, cycloalkyl (of from 3 to 6 carbon atoms), or Ar (having the same definition as above); it is understood that when $R_1$ represents an Ar group, the two Ar groups may be identical or different;

R' represents H or alkyl when Z=H, $R_2$ represents a substituent such as:

a cyano group, a radical C(O)—$ORa_1$ in which $Ra_1$ represents a methyl, ethyl or isopropyl radical, a radical C(O)—$NHRa_2$ in which, $Ra_2$ represents a cyclopropyl radical or a radical C(O)—$N(Ra_2')$ in which $N(Ra_2')$ represents an aziridinyl or azetidinyl radical, optionally substituted with an alkyl group or an Ar group (having the same definition as above), a radical C(O)—$N(Ra_3)$—$ORa_3$ in which the groups $Ra_3$, which may be identical or different, represent a methyl, ethyl or cycloalkyl radical, a radical C(O)$Ra_4$, in which $Ra_4$ represents an Ar group (as defined above) or a cycloalkyl radical, optionally substituted with an alkyl group or an Ar group (having the same definition as above), a radical C($Ra_4$)=N—Rb, in which $Ra_4$ is either H or is as defined above and Rb represents a hydroxyl, alkoxy or alkylideneoxy radical, optionally containing a halogen atom or a group chosen from carboxyl, alkoxy, amino ($NH_2$, NHalkyl, $Nalk_2$ in which the alkyl groups may form together a ring optionally containing another hetero atom chosen from O, S and N) and $(CH_2)_n$Ar (n=0 or 1; Ar as defined above), alkyl containing from 1 to 2 carbon atoms or cycloalkyl, a radical $NHRa_4$ in which $Ra_4$ is as defined above an Ar radical as defined above. In the case where Ar is an aromatic heterocycle, the latter may contain 5 to 6 members and one to three hetero atoms chosen from O, N and S, when Z represents a sulphonyl group $SO_2R_3$ or an acyl group $COR_3$, $R_2$ represents a carboxyl group or an amino, alkylamino, dialkylamino or cycloalkylamino group. $R_3$ represents a C3–C6 alkyl or cycloalkyl radical or an aryl ring as defined above or a C2–C6 alkenyl or C2–C6 alkynyl chain.

It is understood that the alkyl portions mentioned are in the form of a straight or branched chain and contain from 1 to 4 carbon atoms, unless otherwise stated. Similarly, the cycloalkyl radicals mentioned contain from 3 to 5 carbon atoms, unless otherwise stated.

DETAILED DESCRIPTION OF THE INVENTION
The indazoles of general formula (1a):
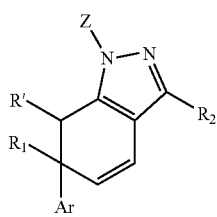
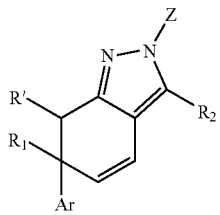
in which Ar, Z, $R_1$ and $R_2$ are as defined above, may be prepared according to Schemes 1 to 3 below:
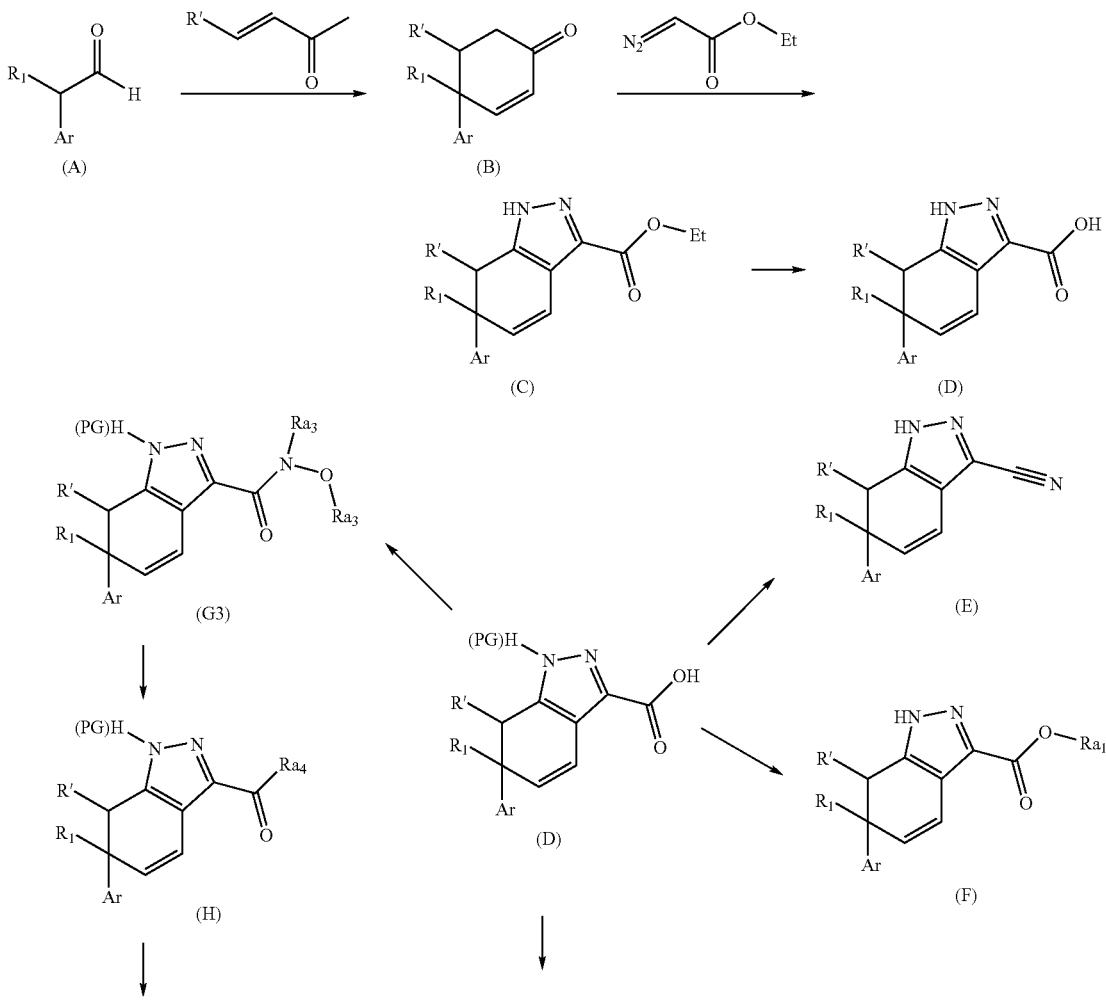
Scheme 1:
Synthesis of the Indazoles of general formula 1a

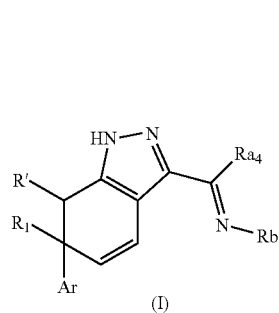
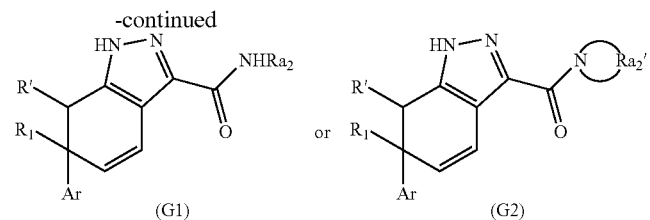
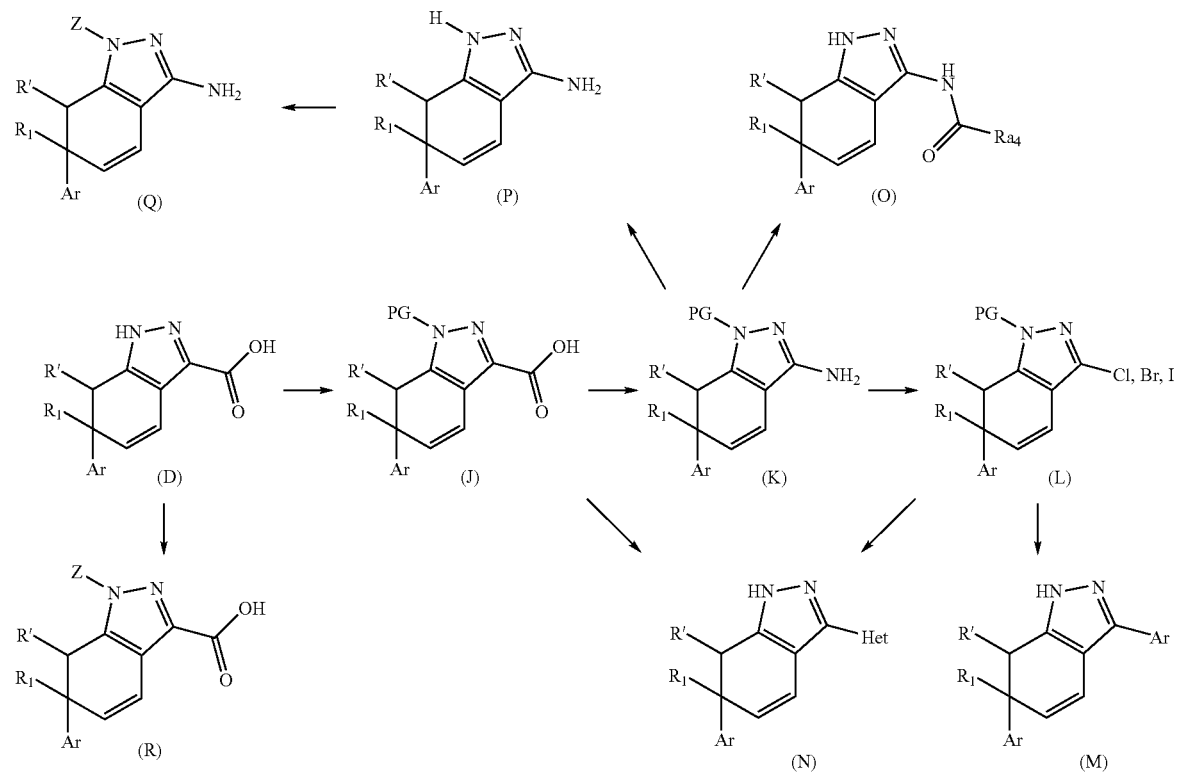
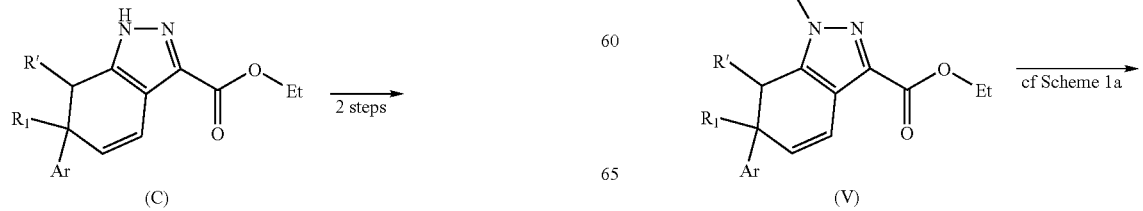

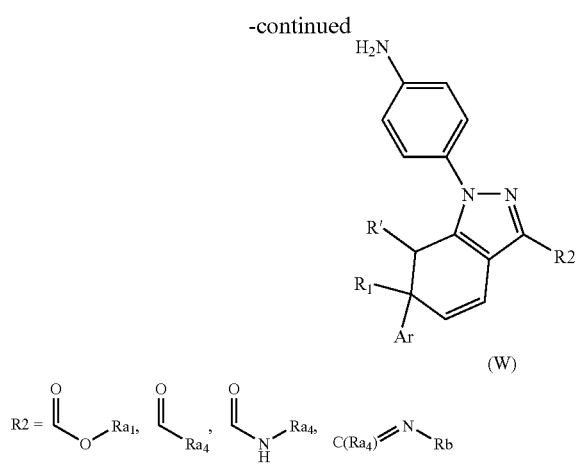

Padwa (J. Org. Chem. 1990, 55, 4144–4153), gives the ethyl 6-aryl-6,7-dihydro-1H-indazole-3-carboxylates of general formula (C). The heating of the reaction medium is generally performed either at the reflux temperature of toluene, in the presence of an acid such as para-toluenesulphonic acid or acetic acid, or in the presence of a chlorinating agent such as phosphorus oxychloride or thionyl chloride in the presence of an organic base such as 1,8-diazabicyclo[5.4.0]undec-7-ene or pyridine. The reaction may be either performed in a single step "one pot", or in two or three steps by isolating one or other or both intermediates formed according to Scheme 4 below:

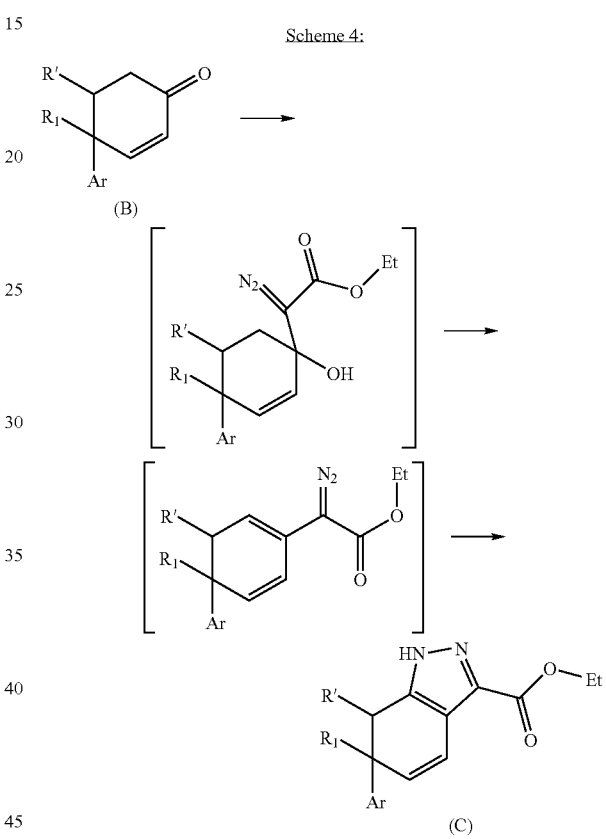

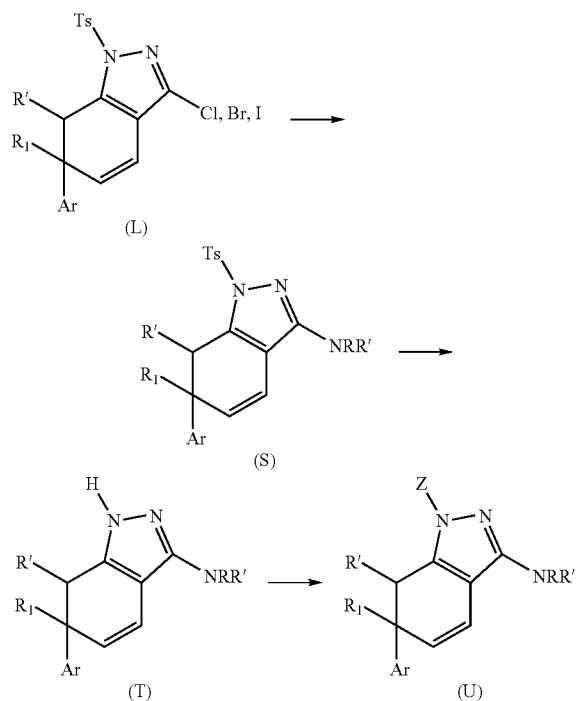

More particularly, treatment of the arylacetaldehydes of general formula (A) with methyl vinyl ketone, or more generally with an alkyl vinyl ketone, at elevated temperature in an alkaline medium, generally in the presence of sodium hydroxide or potassium hydroxide at the reflux temperature of an alcohol such as ethanol, for instance under the conditions described by J. C. Amedio (Synth. Comm. 1998, 28, 3895–3906), gives the 4-arylcyclhex-2-enones of general formula (B).

More particularly, treatment of the 4-arylcyclohexen-2-ones of general formula (B) with ethyl diazoacetate in the presence of a strong base, such as lithium diisopropylamide, in a solvent such as tetrahydrofuran at a temperature of between –78° C. and 0° C., followed by heating of the reaction medium, under the conditions described by A.

More particularly, treatment of the 6-aryl-6,7-dihydro-1H-indazole-3-carboxylates of general formula (C), in alkaline medium, gives the 6-aryl-6,7-dihydro-1H-indazole-3-carboxylic acids of general formula (D). Generally, the procedure is performed by the action of lithium or sodium hydroxide, in a solvent such as ethanol, at a temperature of between 20° C. and the reflux temperature of the reaction medium.

More particularly, the 6-aryl-6,7-dihydro-1H-indazole-3-carbonitriles of general formula (E) may be prepared according to the conditions described by H. Ebel et al. (Tetrahedron Lett. 1998, 39 (50), 9165–9166) by prior coupling of the corresponding acids of general formula (D) with $NH_3$ (aqueous 28% solution), under the action of a coupling agent such as 1-(3-dimethylaminopropyl)-3-ethylcarbodiimide hydrochloride (EDCI) in the presence of 1-hydroxybenzotriazole hydrate (HOBT), at room temperature. The 6-aryl-6,7-dihydro-1H-indazole-3-carboxamides obtained then undergo dehydration, for example under the conditions described by C. Janiak et al. (Synth. Commun. 1999, 29 (19), 3341–3352), by the action of trifluoroacetic anhydride in dioxane, in the presence of pyridine, at a temperature of between 0° C. and 20° C.

More particularly, the esters of the 6-aryl-6,7-dihydro-1H-indazole-3-carboxylic acids of general formula (F) may be obtained by treating the corresponding acids of general formula (D) with an alcohol, generally used as reaction solvent, in the presence of a catalytic amount of sulphuric acid or para-toluenesulphonic acid.

More particularly, the 6-aryl-6,7-dihydro-1H-indazole-3-carboxamides of general formula (G1) or (G2) or (G3) are obtained by coupling the corresponding acids of general formula (D) with the corresponding amines. Generally, the coupling is performed in an organic solvent, such as dichloromethane, in the presence of a coupling agent, such as 1-(3-dimethylaminopropyl)-3-ethylcarbodiimide hydrochloride (EDCI), in the presence of 1-hydroxybenzotriazole hydrate (HOBT), at a temperature in the region of room temperature. It is also possible to perform the coupling on a solid phase by attaching beforehand the 6-aryl-6,7-dihydro-1H-indazole-3-carboxylic acids of general formula (D) to an iodine resin, for example via a linker arm of 4-(2-aminoacetyl)-2,3,5,6-tetrafluorophenyloxy type, followed by reacting the corresponding amines.

More particularly, the ketones of general formula (H) may be obtained by condensation of an organometallic reagent such as an organolithium or organomagnesium reagent with the amide of general formula (G3) in which Ra3 represents a methyl group, according to the conditions described by M. Kratzel et al. (J. Chem. Soc., Perkin Trans. 1, 1997, 1009–1012). Generally, tetrahydrofuran is used as solvent and the reaction is performed at a temperature of between 0° C. and 25° C.

More particularly, the aldehydes of general formula (H) in which PG represents a 4-methylphenylsulphonyl group may be obtained by reducing the compounds of general formula (G3) in an organic solvent such as tetrahydrofuran with a hydride such as diisobutylaluminium hydride at a temperature in the region of 0° C.

More particularly, the compounds of general formula (I) may be obtained by treating the corresponding ketones or aldehydes (Ra$_4$=H and PG=4-methylphenylsulphonyl) of general formula (H), by the action of RbNH$_2$, optionally in the hydrochloride form, in an alcoholic medium (for example ethanol) or in a chlorinated solvent (such as dichloromethane), between room temperature and the reflux temperature of the solvent. When a hydrochloride is used, the reaction is performed in the presence of a base such as sodium acetate, triethylamine or pyridine. In the case of aldehydes, the 4-methylphenylsulphonyl protecting group may be cleaved by the action of a base such as sodium hydroxide (in aqueous solution) in an organic solvent such as dioxane at a temperature of between 20° C. and the reflux temperature of the reaction medium.

More particularly, the 6-aryl-6,7-dihydro-(4-methylphenyl)sulphonylindazole-3-carboxylic acids of general formula (J) may be obtained by protecting the NH group present in the acids of general formula (D), by the action of 4-methylphenylsulphonyl chloride, in an organic solvent, such as ethyl ether, in the presence of a base such as aqueous sodium hydroxide, at a temperature in the region of room temperature.

More particularly, the 6-aryl-6,7-dihydro-(2-trimethylsilanylethoxymethyl)indazole-3-carboxylic acids of general formula (J) may be obtained by protecting the NH group present in the acids of general formula (D), by the action of (2-chloromethoxyethyl)trimethylsilane, in an organic solvent, such as dimethylformamide, in the presence of a base such as sodium hydride, at a temperature in the region of room temperature.

More particularly, the 3-amino-6-aryl-6,7-dihydro-(4-methylphenyl)-sulphonylindazoles or 3-amino-6-aryl-6,7-dihydro-(2-trimethylsilanylethoxymethyl)indazoles of general formula (K) may be obtained from the 6-aryl-6,7-dihydro-(4-methylphenyl)sulphonylindazole-3-carboxylic acids or 6-aryl-6,7-dihydro-(2-trimethylsilanylethoxymethyl)indazole-3-carboxylic acids of general formula (J), via a Curtius rearrangement, in the presence of an alcohol, according to the conditions described by M. Sibi et al. (J. Organic. Chem. 1997, 62, 5864–5872), followed by cleavage of the carbamate obtained. Generally, for the Curtius reaction, a mixture of toluene and tert-butanol is used as solvent and triethylamine is added to the reaction medium. This medium is then heated to the reflux temperature before addition of diphenylphosphoryl oxide. After rearrangement at this temperature, the resulting carbamate is isolated and then treated with trifluoroacetic acid, in dichloromethane, at a temperature of between 0° C. and 20° C., to give the amines of general formula (K).

More particularly, the 3-halo-6-aryl-6,7-dihydro-(4-methylphenyl)sulphonylindazoles or 3-halo-6-aryl-6,7-dihydro-(2-trimethylsilanylethoxymethyl)indazoles of general formula (L) may be obtained by diazotization of the corresponding 3-amino-6-aryl-6,7-dihydro-(4-methylphenyl)sulphonylindazoles or 3-amino-6-aryl-6,7-dihydro-(2-trimethylsilanylethoxymethyl)indazoles of general formula (K), followed by a Sandmeyer reaction. In the case of the iodinated derivative, the procedure may be performed under the conditions described by L. B. Townsend et al. (J. Med. Chem., 1995, 38 (20), 4098–4105), by the action of isoamyl nitrite in diiodomethane, at a temperature of between 80° C. and 120° C. In the case of the chloro and bromo derivatives, the procedure is performed by the action of an alkyl nitrite, for example isoamyl nitrite, in acetonitrile, at a temperature of between 0° C. and 60° C., in the presence of a copper(II) halide (chloride or bromide) or of dibromine. Alternatively, sodium nitrite may be reacted, in an aqueous acidic medium, in order to obtain the intermediate diazonium salt. This diazonium salt is treated with a copper(II) halide (chloride or bromide) or with a mixture of copper(II) sulphate and a halide salt (for example NaBr).

More particularly, the 3,6-diaryl-6,7-dihydro-1H-indazoles of general formula (M), and also the 3-heteroaryl-6-aryl-6,7-dihydro-1H-indazoles of general formula (N), may be obtained by Suzuki coupling of the 3-halo-6-aryl-6,7-dihydro-(4-methylphenyl)sulphonylindazoles or 3-halo-6-aryl-6,7-dihydro-(2-trimethylsilanylethoxymethyl)indazoles of general formula (L) (preferably the iodo derivative), with the corresponding aryl/heteroarylboronic acids or esters followed by cleavage of the tosyl group. For the Suzuki coupling, the procedure is performed according to the conditions described by N. Miyaura, A. Suzuki et al. (Synth. Comm. 1981, 11, 513–519), in the presence of catalysts such as tetrakis(triphenylphosphine)palladium, of a base such as sodium hydroxide, sodium carbonate, sodium ethoxide, sodium acetate or potassium phosphate. The deprotection step may be performed under the action either of a base such as aqueous 1N sodium hydroxide, in an ethereal solvent such as THF or dioxane, at a temperature of between 20° C. and the reflux temperature of the solvent, or in an acidic medium, for instance in the presence of aqueous hydrochloric acid, in an ethereal solvent such as THF or dioxane, at a temperature of between 20° C. and the reflux temperature of the solvent. Alternatively, the products of general formula (M) and (N) may be obtained by coupling haloaromatic or heteroaromatic derivatives (preferably iodo or bromo derivatives), with 6-aryl-6,7-dihydro-(4-methylphenyl)sulphonylindazole-3-boronic or 6-aryl-6,7-dihydro-(2-trimethylsilanylethoxymethyl)-indazole-3-boronic acids or esters, which are themselves obtained by coupling bispinacolatoborane and 3-halo-6-aryl-6,7-dihydro-(4-methylphenyl)sulphonylindazoles or 3-halo-6-aryl-6,7-dihydro-(2-trimethylsilanylethoxymethyl)indazoles (preferably iodo or bromo derivatives), according to the method described by N. Miyaura et al. (J. Org. Chem., 1995, 60, 7508–7510), in a solvent such as dimethyl sulphoxide, dimethylformamide or dioxane, in the presence of a catalyst such as [1,1'-bis(diphenylphosphino)ferrocene]palladium dichloride [PdCl$_2$(dppf)] and a base such as potassium acetate, sodium carbonate, sodium ethoxide or potassium phosphate. This coupling reaction is followed by cleavage of the tosyl or 2-trimethylsilanylethoxymethyl group as described above.

In the particular case of the heterocycles of general formula (N) in which Het represents a 3-(3-methyl[1,2,4]oxadiazol-5-yl) radical, it is possible to perform the procedure according to the conditions described by K. E. Andersen et al. (Eur. Med. Chem. 1994, 29, 393–399), by reacting the 6-aryl-6,7-dihydro-(4-methylphenylsulphonyl)-1H-indazole-3-carboxylic acid chlorides of general formula (J) with N-hydroxyacetamidine, at the reflux temperature of pyridine, followed by cleavage of the tosyl group as described above. The 6-aryl-6,7-dihydro-(4-methyl-phenylsulphonyl)-1H-indazole-3-carboxylic acid chlorides may be obtained by the action of oxalyl chloride in dichloromethane at between 20° C. and 40° C. or alternatively by the action of thionyl chloride, at the reflux temperature of toluene, on the corresponding 6-aryl-6,7-dihydro-(4-methylphenylsulphonyl)-1H-indazole-3-carboxylic acids of general formula (J). N-Hydroxyacetamidine is prepared as described by C. D. Clifford (J. Med. Chem. 1986, 29, 11, 2174–2183), from acetonitrile, by the action of hydroxylamine in the presence of sodium hydroxide, in refluxing aqueous ethanol.

More particularly, the carboxamides of general formula (O) are obtained by prior condensation of the corresponding carboxylic acids or acyl chlorides with the 6-aryl-6,7-dihydro-(4-methylphenyl)sulphonylindazole-3-yl amines of general formula (K). Generally, in the case of the acids, the coupling is performed in an organic solvent, such as dichloromethane, in the presence of a coupling agent, such as 1-(3-dimethylaminopropyl)-3-ethylcarbodiimide hydrochloride (EDCI), in the presence of 1-hydroxybenzotriazole hydrate (HOBT), at a temperature in the region of room temperature. After cleavage of the tosyl group as described above, the amides of general formula (O) are obtained.

More particularly, the amines of general formula (P) are obtained by cleavage of the tosyl group from the amines of general formula (K), as described above. The amines of general formula (O) are obtained by reacting the amines of general formula (P) with the corresponding sulphonyl or acyl chlorides, in the presence of a base such as triethylamine or pyridine, in a chlorinated solvent (such as dichloromethane) or an ethereal solvent (such as tetrahydrofuran), at a temperature of between 0° C. and the reflux temperature of the solvent.

More particularly, the compounds of formula (V) may be obtained by aromatic nucleophilic substitution of the fluorine of 1-fluoro-4-nitrobenzene with the esters of general formula (C) in the presence of a base, for instance sodium hydride, in an organic solvent such as dimethylformamide, at a temperature of between 20° C. and 80° C., followed by chemical reduction of the nitro group with a metal such as zinc in an acidic medium such as acetic acid at a temperature in the region of 20° C.

More particularly, the compounds of general formula (W) may be obtained from the compounds (V) according to the methods described for the synthesis of the compounds (H), (F), (G1) and (G2) and (I) from the compounds (D) (see Scheme 1a).

The amines of general formula (S) are obtained by reacting the halo derivatives (preferably chloro derivative) of general formula (L) with the corresponding amines, at atmospheric pressure or alternatively under pressure (in an autoclave), in a solvent such as an alcohol, pyridine, dimethylformamide or dimethyl sulphoxide, at a temperature of between room temperature and the reflux temperature of the solvent, optionally in the presence of a base such as triethylamine. The amines of general formula (T) are obtained either from the amines of general formula (S) by cleavage of the tosyl group according to the conditions described above, or directly by concomitant detosylation from the halo derivatives (L) under the conditions described above in order to gain access to the amines (S). The amines of general formula (U) are obtained by reacting the amines of general formula (T) with the corresponding sulphonyl or acyl chlorides, in the presence of a base such as triethylamine or pyridine, in a chlorinated solvent (such as dichloromethane) or an ethereal solvent (such as tetrahydrofuran), at a temperature of between 0° C. and the reflux temperature of the solvent.

The isoindoles of general formula (1b),

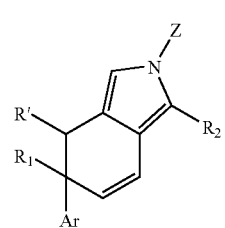

(1b)

in which Ar, Z, R$_1$ and R$_2$ are as defined above, may be prepared according to Scheme 5 below:

Scheme 5:
Synthesis of the isoindoles of general formula (1b)

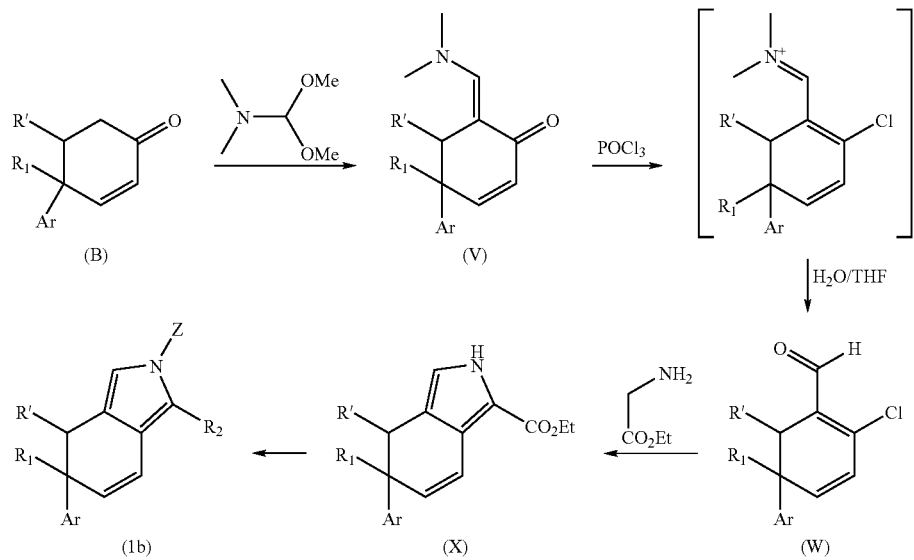

More particularly, the ethyl 5-aryl-4,5-dihydro-2H-isoindole-1-carboxylates of general formula (X) may be obtained by analogy with J. T. Gupton et al. (Tetrahedron 1998, 54, 5075–5088): the 4-arylcyclohexen-2-ones of general formula (B) are treated with N,N-dimethylformamide dimethyl acetal, at the reflux temperature of N,N-dimethylformamide, to give the 4-aryl-6-dimethylaminomethylenecyclohexen-2-ones of general formula (V) which, via the action of phosphorus oxychloride in an organic solvent such as dichloromethane, at a temperature of about 40° C. and after hydrolysis in refluxing aqueous THF, give the 2-chloro-5-arylcyclohexa-1,3-dienecarbaldehydes of general formula (W). These aldehydes lead to the ethyl 5-aryl-4,5-dihydro-2H-isoindole-1-carboxylates (X) by the action of ethyl glycinate hydrochloride, at the reflux temperature of N,N-dimethylformamide.

From the ethyl 5-aryl-4,5-dihydro-2H-isoindole-1-carboxylates of general formula (X), it is possible to obtain, in the same manner as in Schemes 1 to 3 and by analogy with the methods described above, the compounds of general formula (1b), in which Ar, Z, $R_1$ and $R_2$ show the same variations.

The indoles of general formula (1c),

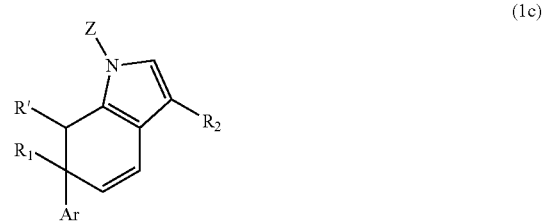

in which Ar, Z, $R_1$ and $R_2$ are as defined above, may be prepared according to Scheme 6 below:

Scheme 6:
Synthesis of the indoles of general formula (1c)

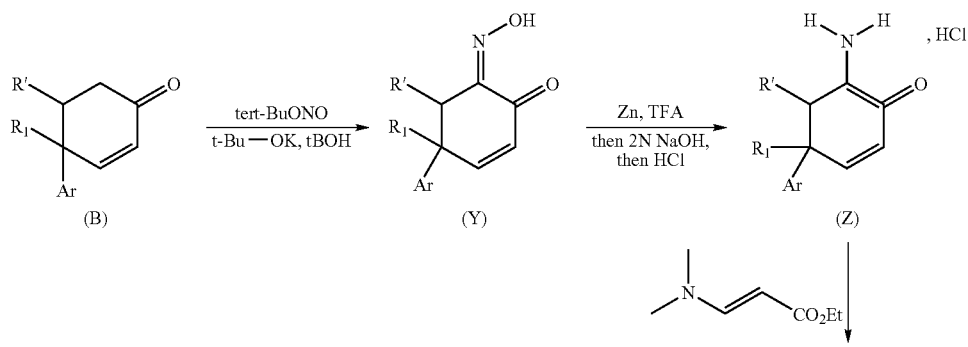

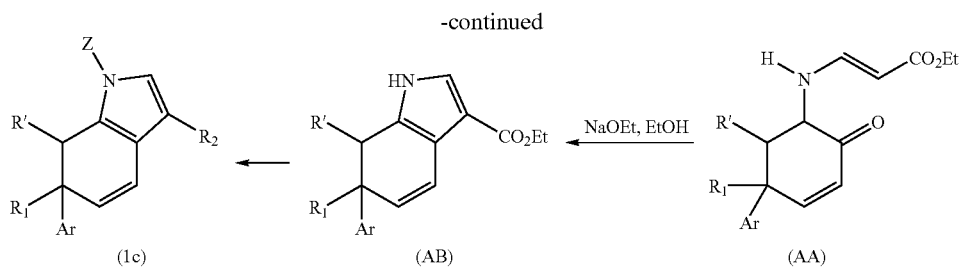

More particularly, the treatment of the 4-arylcyclohexen-2-ones of general formula (B) with tert-butyl nitrite and potassium tert-butoxide in tert-butanol, at a temperature in the region of 20° C., as described by M. P. Cava (J. Org. Chem. 1962, 27, 1908–1909), gives the 5-arylcyclohex-3-ene-1,2-dione-1-oximes of general formula (Y). These oximes, when treated with zinc in trifluoroacetic acid, at a temperature in the region of 20° C., by analogy with the conditions described by S. Negi (Synthesis, 1996, 991–996) become reduced to give the 6-amino-4-arylcyclohex-2-enones of general formula (Z). These enones, via transamination with ethyl 3-dimethylacrylate in an organic solvent such as methanol, at a temperature in the region of 20° C., give the ethyl 3-(2-oxo-5-arylcyclohex-3-enylamino)acrylates of general formula (AA) which, in turn, via the action of sodium ethoxide in ethanol, at a temperature in the region of 20° C., as described by A. Alberola, (J. Chem. Soc. Perkin Trans 1, 1990, 10, 2681–2685), give the ethyl 6-aryl-6,7-dihydro-1H-indole-3-carboxylates of general formula (AB).

From the ethyl 6-aryl-6,7-dihydro-1H-indole-3-carboxylates of general formula (AB), it is possible to obtain, in the same manner as in Schemes 1 to 3 and by analogy with the methods described above, the compounds of general formula (1c), in which Ar, $R_1$ and $R_2$ show the same variations.

The present invention also relates to therapeutic compositions containing a compound according to the invention, in combination with a pharmaceutically acceptable excipient depending on the chosen mode of administration. The pharmaceutical composition may be in solid or liquid form or in the form of liposomes.

Among the solid compositions that may be mentioned are powders, gelatin capsules and tablets. Among the oral forms, solid forms protected against the acidic medium of the stomach may also be included. The supports used for the solid forms consist in particular of mineral supports such as phosphates or carbonates, or organic supports such as lactose, celluloses, starch or polymers. The liquid forms consist of solutions, suspensions or dispersions. They contain, as dispersive support, either water or an organic solvent (ethanol, NMP or the like) or mixtures of surfactants and solvents or of complexing agents and solvents.

The administered dose of the compounds of the invention will be adapted by the practitioner depending on the route of administration to the patient and the condition of the said patient.

The compounds of the present invention may be administered alone or as a mixture with other anticancer agents. Among the possible combinations, that may be mentioned are:

alkylating agents and especially cyclophosphamide, melphalan, ifosfamide, chlorambucil, busulfan, thiotepa, prednimustine, carmustine, lomustine, semustine, steptozotocin, decarbazine, temozolomide, procarbazine and hexamethylmelamine;

platinum derivatives especially such as cisplatin, carboplatin or oxaliplatin;

antibiotic agents especially such as bleomycin, mitomycin or dactinomycin;

antimicrotubule agents especially such as vinblastine, vincristine, vindesine, vinorelbine or taxoids (paclitaxel and docetaxel);

anthracyclines especially such as doxorubicin, daunorubicin, idarubicin, epirubicin, mitoxantrone or losoxantrone;

group I and II topoisomerases such as etoposide, teniposide, amsacrine, irinotecan, topotecan and tomudex;

fluoropyrimidines such as 5-fluorouracil, UFT or floxuridine;

cytidine analogues such as 5-azacytidine, cytarabine, gemcitabine, 6-mercaptomurine or 6-thioguanine;

adenosine analogues such as pentostatin, cytarabine or fludarabine phosphate;

methotrexate and folinic acid;

various enzymes and compounds such as L-asparaginase, hydroxyurea, trans-retinoic acid, suramin, dexrazoxane, amifostine, herceptin and oestrogen and androgen hormones;

antivascular agents such as combretastatin or colchicine derivatives and prodrugs thereof.

It is also possible to combine the compounds of the present invention with a radiation treatment. These treatments may be administered simultaneously, separately or sequentially. The treatment will be adapted to the patient to be treated by the practitioner.

More particularly, the products of the present invention will be used in their first therapeutic application to inhibit the growth of cancerous cells and at the same time the growth of new blood vessels. The inhibition of the growth of new blood vessels is determined by a cell detachment test as described below.

EXAMPLES

Evaluation of the Inhibition of Tubulin Polymerization

Tubulin is purified from pig brain according to published methods (Shelanski et al., Proc. Natl. Acad. Sci. USA, 70, 765–768. Weingarten et al., 1975, Proc. Natl. Acad. Sci. USA, 72, 1858–1862). Briefly, the brains are ground and centrifuged in an extraction buffer. The tubulin contained in the supernatant of the extract undergoes two successive cycles of polymerization at 37° C. and depolymerization at 4° C., before being separated from the MAPs (Microtubule Associated Proteins) by chromatography on a phosphocellulose P11 column (Whatman). The tubulin thus isolated is more than 95% pure. It is stored in a buffer known as RB/2 30% glycerol, the composition of which is 50 mM MES-NaOH [2-(N-morpholino)ethanesulphonic acid], pH 6.8; 0.25 mM $MgCl_2$; 0.5 mM EGTA; 30% glycerol (v/v), 0.2 mM GTP (guanosine-5'-triphosphate).

The polymerization of tubulin to microtubules is monitored by turbidimetry as follows: the tubulin is adjusted to a concentration of 10 µM (1 mg/ml) in RB/2 30% glycerol buffer to which 1 mM GTP and 6 mM $MgCl_2$ are added. The polymerization is triggered by an increase in temperature from 6° C. to 37° C. in a cuvette with an optical path length of 1 cm, placed in a UVIKON 931 spectrophotometer (Kontron) equipped with a thermostatically maintained cuvette holder. The increase in the turbidity of the solution is monitored at 350 nm.

The products are dissolved at 10 mM in DMSO and added at variable concentrations (0.5 to 10 µM) to the tubulin solution before polymerization. The $IC_{50}$ value is defined as the concentration of product that inhibits the rate of polymerization by 50%. A product whose $IC_{50}$ value is less than or equal to 3 µM is considered as being very active.

Test for Determining the Inhibition of Vascularization

A test for determining the detachment of the endothelial cells was developed in order to select the products with regard to their "in vitro" activity. This test for determining the detachment of endothelial cells is characterized in that the endothelial cells, inoculated into plates whose bottom is covered with a binder preferably chosen from gelatin, fibronectin and vitronectin, after culturing, are supplemented with a medium containing the test compound, and the cells are then labelled with a fluorescent substance, the cells which have become detached are removed by washing and the fluorescence of the remaining cells is counted in a fluorimeter.

This test consists in measuring the detachment of endothelial cells cultured on substrata based on a binder preferably chosen from fibronectin, vitronectin and gelatin. Preferably, a day after the inoculation of the cells in plates containing, for example, 96 wells, the culture medium is replaced with a medium containing the test compound in the absence of serum. The same preparation is prepared six times at three different concentrations (0.1, 0.3 and 0.6 µM) and the control six times without addition of antivascular product. After two hours of treatment with the test substance, the cells are labelled with calcein-AM (1.6 µg/ml) in culture medium supplemented with 0.1% BSA. The cells that have become detached are removed by washing with the culture medium containing 0.1% bovine serum albumin; 100 µl of medium are added to each well. The fluorescence of the remaining cells is counted in a fluorimeter. The data obtained are expressed relative to the control (untreated cells).

The evaluation of the detachment of the endothelial cells in vitro is determined in the following manner. HDMEC cells (Human Dermal Microvascular Endothelial Cells, Promocell, c-122102) are cultured in an ECGM-MV medium that contains 5% foetal calf serum, growth factors (EGF 10 ng/ml, hydrocortisone 1 µg/ml, 0.4% growth supplement with heparin) and antibiotics (amphotericin 50 ng/ml, gentamycin 50 µg/ml). For the detachment test, the HDMECs are inoculated at a rate of 5 000 cells in clear-bottomed 96-well plates (Costar) precoated with fibronectin (10 µg/ml), vitronectin (1 µg/ml) or gelatin. Twenty-four hours later, the culture medium is replaced with ECGM-MV 0.1% BSA medium containing the products indicated. The concentrations tested are 0.1–0.3 and 1 µM for each product.

After two hours of treatment, the cells are labelled for one hour with calcein (1.6 µg/ml, Molecular Probes) in ECGM-MV 0.1% BSA medium. The detached cells are then removed by washing with ECGM-MV 0.1% BSA medium; 100 µl of medium is added to each well. The fluorescence of the cells that remain attached to the substratum of the well is counted using a fluorimeter, Spectrafluor Plus (Tecan excitation 485 nm, and emission 535 nm). The data are the mean of six different samples and are expressed as the percentage of the control (untreated cells).

A cell detachment effect of greater than or equal to 15% is considered as significant.

The present invention will be more fully described with the aid of the examples that follow, which should not be considered as limiting the invention.

Example 1

Ethyl 6,6-diphenyl-6,7-dihydro-2H-indazole-3-carboxylate may be prepared in the following manner:

20 $cm^3$ of ethyl diazoacetate, followed by slow addition of 210 $cm^3$ of a solution of lithium diisopropylamide prepared beforehand from 140.7 $cm^3$ of 1.6M n-butyllithium and 35.55 $cm^3$ of diisopropylamine in solution in 35 $cm^3$ of tetrahydrofuran are added dropwise to a solution, maintained at −78° C., of 35 g of 4,4-diphenylcyclohex-2-enone in 315 $cm^3$ of tetrahydrofuran. After addition, the reaction mixture is stirred at a temperature in the region of −78° C. for 2 hours. 28.2 $cm^3$ of glacial acetic acid are then added and the temperature is allowed to rise to the region of 20° C. 350 $cm^3$ of toluene are then added and the resulting solution is successively washed with 200 $cm^3$ of saturated aqueous sodium bicarbonate solution and 200 $cm^3$ of water. The organic phase obtained is concentrated under reduced pressure in order to remove the tetrahydrofuran. The resulting toluene phase is refluxed for 4 hours in a round-bottomed flask surmounted with a Dean-Stark trap and then concentrated to dryness under reduced pressure. The residue obtained is purified by flash chromatography on silica gel (35–70 µm), eluting with a cyclohexane/ethyl acetate (80/20) mixture; 43.1 g of ethyl 6,6-diphenyl-6,7-dihydro-2H-indazole-3-carboxylate are obtained in the form of a white powder, the characteristics of which are as follows:

melting point: 150° C. (Köfler block)

$^1$H NMR spectrum: (300 MHz, $(CD_3)_2SO$ d6, δ in ppm): 1.31 (t, J=7 Hz: 3H); 3.41 (unresolved complex: 2H); 4.29 (q, J=7 Hz: 2H); 6.53 (unresolved complex: 1H); 6.86 (d, J=10 Hz: 1H); 7.21 (mt: 6H); 7.30 (broad t, J=7.5 Hz: 4H); 13.42 (unresolved complex: 1H).

Example 2-1

Isopropyl 6,6-diphenyl-6,7-dihydro-2H-indazole-3-carboxylate may be prepared in the following manner:

1 $cm^3$ of 36% hydrochloric acid solution is added to a solution of 0.1 g of 6,6-diphenyl-6,7-dihydro-1H-indazole-3-carboxylic acid in 10 $cm^3$ of isopropanol. The resulting mixture is heated at a temperature in the region of 82° C. for 5 hours. The solution is then neutralized by addition of saturated aqueous sodium hydrogen carbonate solution. The organic phase is extracted with three times 3 $cm^3$ of ethyl acetate, dried over magnesium sulphate and then evaporated to dryness under reduced pressure. The residue obtained is stirred in 5 $cm^3$ of dichloromethane to give, after filtration and drying, 50 mg of isopropyl 6,6-diphenyl-6,7-dihydro-1H-indazole-3-carboxylate, in the form of a white foam, the characteristics of which are as follows:

mass spectrum (DCI): M/Z=359 (MH$^+$)

$^1$H NMR spectrum: (300 MHz, (CD$_3$)$_2$SO d6, δ in ppm): 1.29 (d, J=6.5 Hz: 6H); 3.37 (broad s: 2H); 5.10 (mt: 1H); 6.34 and 6.54 (2 broad d, J=10 Hz: 1H in total); 6.83 (d, J=10 Hz: 1H); from 7.15 to 7.35 (mt: 10H).

6,6-Diphenyl-6,7-dihydro-1H-indazole-3-carboxylic acid may be obtained in the following manner:

A solution of 2 g of ethyl 6,6-diphenyl-6,7-dihydro-1H-indazole-3-carboxylate in 20 cm$^3$ of ethanol and 8.7 cm$^3$ of 1N sodium hydroxide solution are heated for 3 hours at a temperature in the region of 70° C. The ethanol is then removed under reduced pressure to give a solution, which is acidified to a pH in the region of 3 by addition of 1N hydrochloric acid. The resulting mixture is filtered to give 1.48 g of 6,6-diphenyl-6,7-dihydro-1H-indazole-3-carboxylic acid in the form of a white solid, the characteristics of which are as follows:

melting point: >260° C.

$^1$H NMR spectrum: (300 MHz, (CD$_3$)$_2$SO d6, δ in ppm): 3.40 (broad s: 2H); 6.44 (broad d, J=10 Hz: 1H); 6.87 (d, J=10 Hz: 1H); from 7.15 to 7.35 (mt: 10H); 13.20 (unresolved complex: 2H).

Example 2-2

Methyl 6,6-diphenyl-6,7-dihydro-2H-indazole-3-carboxylate may be prepared in the following manner:

56 mg of 6,6-diphenyl-6,7-dihydro-1H-indazole-3-carboxylic acid and 10 cm$^3$ of methanol are treated as in Example 2-1 to give 39 mg of methyl 6,6-diphenyl-6,7-dihydro-2H-indazole-3-carboxylate, in the form of a white foam, the characteristics of which are as follows:

Rf TLC silica [eluent: cyclohexane/ethyl acetate (70/30)] =0.22

$^1$H NMR spectrum: (300 MHz, (CD$_3$)$_2$SO d6, δ in ppm): 3.41 (broad s: 2H); 3.82 (s: 3H); 6.48 (very broad d, J=10 Hz: 1H), 6.86 (d, J=10 Hz: 1H); from 7.15 to 7.35 (mt: 10H); 13.47 (unresolved complex: 1H).

Example 3-1

N-(cyclopropyl)-6,6-diphenyl-6,7-dihydro-1H-indazole-3-carboxamide may be prepared in the following manner:

Starting with a mixture of 1.23 g of 6,6-diphenyl-6,7-dihydro-1H-indazole-3-carboxylic acid, 0.26 cm$^3$ of cyclopropylamine, 0.86 g of 1-ethyl-3-(3-dimethylaminopropyl) carbodiimide hydrochloride and 60 mg of hydroxybenzotriazole in solution in 30 cm$^3$ of dichloromethane, and after stirring for 18 hours at a temperature in the region of 20° C., washing with twice 30 cm$^3$ of distilled water and purifying the crude product obtained by flash chromatography on silica gel (30–70 μm), eluting with a cyclohexane/ethyl acetate (60/40) mixture, 0.58 g of (N-cyclopropyl)-6,6-diphenyl-6,7-dihydro-1H-indazole-3-carboxamide is obtained in the form of a yellow solid, the characteristics of which are as follows:

melting point: 240° C. (Köfler block)

$^1$H NMR spectrum: (300 MHz, (CD$_3$)$_2$SO d6, δ in ppm): 0.57 (mt: 2H); 0.66 (mt: 2H); 2.77 (mt: 1H); from 3.30 to 3.60 (unresolved complex: 2H); 6.29 (broad d, J=10 Hz: 1H); 6.93 (d, J=10 Hz: 1H); from 7.15 to 7.35 (mt: 10H); 8.01 (broad d, J=4.5 Hz: 1H).

Example 3-2

Azetidin-1-yl(6,6-diphenyl-6,7-dihydro-1H-indazol-3-yl)methanone may be prepared in the following manner:

0.256 g of 1-hydroxybenzotriazole hydrate and 0.364 g of 1-(3-dimethylaminopropyl)-3-ethylcarbodiimide hydrochloride are added to 0.5 g of 6,6-diphenyl-6,7-dihydro-1H-indazole-3-carboxylic acid in suspension in 100 cm$^3$ of dichloromethane. After stirring for 30 minutes at a temperature in the region of 20° C., a solution of 0.114 g of azetidine and 0.303 g of triethylamine in 10 cm$^3$ of dichloromethane is added to the reaction mixture. After stirring at a temperature in the region of 20° C. for about 20 hours, the reaction mixture is diluted with 300 cm$^3$ of dichloromethane and then washed with 3 times 100 cm$^3$ of water. The resulting organic phase is dried over magnesium sulphate, filtered and then concentrated to dryness under reduced pressure (13 kPa). The residue is purified by flash chromatography on a column of silica [eluent: dichloromethane/methanol (95/5 by volume)] to give 0.37 g of azetidin-1-yl(6,6-diphenyl-6,7-dihydro-1H-indazol-3-yl)methanone, in the form of a white powder, the characteristics of which are as follows:

melting point: melting at 285° C. (Köfler block)

$^1$H NMR spectrum: (400 MHz, (CD$_3$)$_2$SO d6, δ in ppm): 2.25 (mt: 2H); 3.43 (s: 2H); 3.99 (broad t, J=7.5 Hz: 2H); 4.42 (mt: 2H); 6.23 (broad d, J=10 Hz: 1H); 6.93 (broad d, J=10 Hz: 1H); from 7.15 to 7.25 (mt: 6H); 7.29 (broad t, J=7.5 Hz: 4H); 13.05 (unresolved complex: 1H).

Example 3-3

(N-Methoxy-N-methyl)-6,6-diphenyl-6,7-dihydro-1H-indazole-3-carboxamide may be prepared as described in Example 3-2:

But starting with 0.4 g of 6,6-diphenyl-6,7-dihydro-1H-indazole-3-carboxylic acid, 0.19 g of 1-hydroxybenzotriazole hydrate, 0.26 g of 1-(3-dimethylaminopropyl)-3-ethylcarbodiimide hydrochloride, 0.13 g of N,O-dimethylhydroxylamine hydrochloride and 0.2 cm$^3$ of triethylamine in 10 cm$^3$ of dichloromethane. After purification by flash chromatography on a column of silica [eluent: dichloromethane], 0.2 g of (N-methoxy-N-methyl)-6,6-diphenyl-6,7-dihydro-1H-indazole-3-carboxamide is thus obtained in the form of a solid, the characteristics of which are as follows:

melting point: 173° C. (Köfler block)

$^1$H NMR spectrum: (300 MHz, (CD$_3$)$_2$SO d6, δ in ppm): 3.30 (broad s: 3H); 3.41 (broad s, 2H); 3.62 (s: 3H); 6.34 (broad d, J=10 Hz: 1H); 6.86 (d, J=10 Hz: 1H); from 7.15 to 7.35 (mt: 10H).

Example 3-4

Aziridin-1-yl(6,6-diphenyl-6,7-dihydro-1H-indazol-3-yl) methanone may be prepared in the following manner:

6 cm$^3$ of a commercial 1 M solution of tetrabutylammonium fluoride in tetrahydrofuran are added to a solution of 0.235 g of aziridin-1-yl(6,6-diphenyl-1-(2-trimethylsilanylethoxymethyl)-6,7-dihydro-1H-indazol-3-yl)methanone in 2.5 cm$^3$ of tetrahydrofuran cooled to a temperature in the region of 0° C. After stirring for about 48 hours at a temperature in the region of 20° C., the mixture is poured into 30 cm$^3$ of an ice plus water mixture and extracted with three times 50 cm$^3$ of diethyl ether. The combined organic phases are washed with three times 25 cm$^3$ of water and 25 cm$^3$ of saturated aqueous sodium chloride solution, dried over magnesium sulphate, filtered and concentrated to dryness under reduced pressure (13 kPa). After flash chromatography on a column of silica [eluent: dichloromethane/ methanol (90/10 by volume)], 0.80 g of aziridin-1-yl(6,6- diphenyl-6,7-dihydro-1H-indazol-3-yl)methanone is thus obtained in the form of a solid, the characteristics of which are as follows:

melting point: melting at 214° C. (Köfler block)

$^1$H NMR spectrum: (300 MHz, $(CD_3)_2SO$ d6, δ in ppm): 3.40 (s: 2H); 3.93 (t, J=10 Hz: 2H); 4.35 (broad t, J=10 Hz: 2H); 6.38 (very broad d, J=10 Hz: 1H); 6.87 (d, J=10 Hz: 1H); from 7.15 to 7.35 (mt: 10H); from 13.10 to 13.30 (unresolved complex: 1H).

Aziridin-1-yl(6,6-diphenyl-1-(2-trimethylsilanylethoxymethyl)-6,7-dihydro-1H-indazol-3-yl)methanone may be prepared in the following manner:

A solution of 0.2 g of 6,6-diphenyl-1 (2-trimethylsilanylethoxymethyl)-6,7-dihydro-1H-indazole-3-carboxylic acid (2-chloroethyl)amide in 7 cm$^3$ of dimethylformamide is added dropwise to a suspension of 0.023 g of sodium hydride (at 60% in oil) in 3 cm$^3$ of dimethylformamide cooled to a temperature in the region of 5° C. The reaction mixture is stirred for two hours at a temperature in the region of 20° C. The solution obtained is poured into a mixture of 30 cm$^3$ of water and 0.3 cm$^3$ of aqueous 1N hydrochloric acid solution while maintaining the temperature in the region of 5° C., and the mixture is extracted with three times 30 cm$^3$ of ethyl acetate. The combined organic phases are washed with three times 30 cm$^3$ of water and 30 cm$^3$ of saturated aqueous sodium chloride solution, dried over magnesium sulphate, filtered and concentrated to dryness under reduced pressure (13 kPa). After flash chromatography on a column of silica [eluent: cyclohexane/ethyl acetate (70/30 by volume)], 0.078 g of aziridin-1-yl(6,6-diphenyl-1-(2-trimethylsilanylethoxymethyl)-6,7-dihydro-1H-indazol-3-yl)methanone is thus obtained in the form of a resin, the characteristics of which are as follows:

Rf TLC silica [eluent: cyclohexane/ethyl acetate (70/30 by volume)]=0.57 mass spectrum
EI m/z=471 M$^+$ base peak
m/z=398 [M-Si(CH$_3$)$_3$]$^+$
m/z=340 [M-CH$_2$OCH$_2$CH$_2$Si(CH$_3$)$_3$]$^+$
m/z=73 [Si(CH$_3$)$_3$]$^+$ 6,6-Diphenyl-1-(2-trimethylsilanylethoxymethyl)-6,7-dihydro-1H-indazole-3-carboxylic acid (2-chloroethyl)amide may be prepared in the following manner:

0.677 g of 1-hydroxybenzotriazole hydrate, 0.958 g of 1-(3-dimethylaminopropyl)-3-ethylcarbodiimide hydrochloride, 1.16 g of 2-chloroethylamine hydrochloride and 1.4 cm$^3$ of triethylamine are successively added to a solution of 1.8 g of 6,6-diphenyl-1-(2-trimethylsilanylethoxymethyl)-6,7-dihydro-1H-indazole-3-carboxylic acid in 300 cm$^3$ of dichloromethane. After stirring the reaction mixture for about 4 hours at a temperature in the region of 20° C., it is washed with three times 60 cm$^3$ of water, dried over magnesium sulphate, filtered and concentrated to dryness under reduced pressure (13 kPa). After flash chromatography on a column of silica [eluent: cyclohexane/ethyl acetate (85/15 by volume)], 1.2 g of 6,6-diphenyl-1-(2-trimethylsilanylethoxymethyl)-6,7-dihydro-1H-indazole-3-carboxylic acid (2-chloroethyl)amide are thus obtained in the form of a resin, the characteristics of which are as follows:

Rf TLC silica [eluent: dichloromethane/methanol (90/10 by volume)]=0.73 mass spectrum
EI m/z=507 M$^+$
m/z=434 [M-Si(CH$_3$)$_3$]$^+$
m/z=376 [M-CH$_2$OCH$_2$CH$_2$Si(CH$_3$)$_3$]$^+$ base peak
m/z=73 [Si(CH$_3$)$_3$]$^+$ 6,6-Diphenyl-1-(2-trimethylsilanylethoxymethyl)-6,7-dihydro-1H-indazole-3-carboxylic acid may be prepared in the following manner:

A solution of 5 g of 6,6-diphenyl-6,7-dihydro-1H-indazole-3-carboxylic acid in 100 cm$^3$ of dimethylformamide is added dropwise to a suspension of 1.45 g of sodium hydride (at 60% in oil) in 25 cm$^3$ of dimethylformamide cooled to a temperature in the region of 0° C. After stirring for 2 hours at a temperature in the region of 20° C., the reaction mixture is cooled to a temperature in the region of 0° C. and 4.18 cm$^3$ of (2-chloromethoxyethyl)trimethylsilane are added dropwise. The mixture is stirred for about 20 hours at a temperature in the region of 20° C. After cooling this mixture to a temperature in the region of 0° C., 100 cm$^3$ of water and 16 cm$^3$ of aqueous 1N hydrochloric acid solution are added. The mixture is extracted three times with 100 cm$^3$ of ethyl acetate. The combined organic phases are washed with three times 100 cm$^3$ of water, dried over magnesium sulphate, filtered and concentrated to dryness under reduced pressure (13 kPa). After flash chromatography on a column of silica [eluent: dichloromethane/methanol (98/2 by volume)], 1.8 g of 6,6-diphenyl-1-(2-trimethylsilanylethoxymethyl)-6,7-dihydro-1H-indazole-3-carboxylic acid are thus obtained in the form of a resin, the characteristics of which are as follows:

Rf TLC silica [eluent: dichloromethane/methanol (90/10 by volume)]=0.35 mass spectrum
EI m/z=446 M$^+$
m/z=401 [M-CO$_2$H]$^+$
m/z=373 [M-Si(CH$_3$)$_3$]$^+$
m/z=330 [M-OCH$_2$CH$_2$Si(CH$_3$)$_3$]$^+$
m/z=73 [Si(CH$_3$)$_3$]$^+$ base peak Example 4

6,6-Diphenyl-6,7-dihydro-1H-indazole-3-carbonitrile may be prepared in the following manner:

0.845 cm$^3$ of pyridine and 0.74 cm$^3$ of trifluoroacetic anhydride are successively added dropwise to a solution, cooled to a temperature in the region of 5° C., of 1.1 g of 6,6-diphenyl-6,7-dihydro-1H-indazole-3-carboxamide in 100 cm$^3$ of dioxane. After warming to a temperature in the region of 20° C., the reaction mixture is stirred for about 20 hours at this temperature. 2 cm$^3$ of pyridine and 2 cm$^3$ of trifluoroacetic anhydride are added to the solution and the reaction mixture is refluxed for about 4 hours. After cooling to a temperature in the region of 20° C., the mixture is concentrated to dryness under reduced pressure (13 kPa). The residue is taken up in 50 cm$^3$ of water and 150 cm$^3$ of ethyl acetate; the pH of the mixture is brought to the region of 8 by addition of sodium bicarbonate. After separation of the phases by settling, the aqueous phase is extracted with three times 50 cm$^3$ of ethyl acetate, and the combined organic phases are washed with three times 50 cm$^3$ of water and then dried over magnesium sulphate, filtered and concentrated to dryness under reduced pressure (13 kPa). The residue is purified by flash chromatography on a column of silica [eluent: dichloromethane/ethyl acetate (90/10 by volume)]. 0.8 g of 6,6-diphenyl-6,7-dihydro-1H-indazole-3-carbonitrile is thus obtained in the form of a white powder, the characteristics of which are as follows:

melting point: melting at 156° C. (Köfler block)

$^1$H NMR spectrum: (400 MHz, $(CD_3)_2SO$ d6, δ in ppm): 3.50 (s: 2H); 6.44 (d, J=10 Hz: 1H); 6.68 (d, J=10 Hz: 1H); from 7.15 to 7.25 (mt: 6H); 7.30 (broad t, J=7.5 Hz: 4H); from 13.50 to 14.20 (broad unresolved complex: 1H).

6,6-Diphenyl-6,7-dihydro-1H-indazole-3-carboxamide may be prepared in the following manner:

0.718 g of 1-hydroxybenzotriazole hydrate and 1.27 g of 1-(3-dimethylaminopropyl)-3-ethylcarbodiimide hydrochloride are added to 1.4 g of 6,6-diphenyl-6,7-dihydro-1H-indazole-3-carboxylic acid in suspension in 200 cm$^3$ of chloroform. After stirring for 30 minutes at a temperature in the region of 20° C., 1.5 cm$^3$ of aqueous 28% ammonium hydroxide solution are added dropwise to the reaction mixture. After stirring at a temperature in the region of 20° C. for about 20 hours, the reaction mixture is diluted with 300 cm$^3$ of chloroform and washed with three times 100 cm$^3$ of water. The organic phases are dried over magnesium sulphate, filtered and concentrated to dryness under reduced pressure (13 kPa). The solid is taken up in 10 cm$^3$ of dichloromethane, cooled to a temperature in the region of 5° C., drained by suction, washed with three times 5 cm$^3$ of diisopropyl ether and dried over potassium hydroxide under reduced pressure (13 kPa), at a temperature in the region of 20° C. 1.2 g of 6,6-diphenyl-6,7-dihydro-1H-indazole-3-carboxamide are thus obtained in the form of a cream-coloured powder, the characteristics of which are as follows:

melting point: melting at 244° C. (Köfler block)

$^1$H NMR spectrum: (300 MHz, (CD$_3$)$_2$SO d6, δ in ppm): 3.40 (broad s: 2H); from 6.15 to 6.45 (broad unresolved complex: 1H); 6.96 (d, J=10 Hz: 1H); from 7.05 to 7.40 (mt: 12H).

Example 5-1

Cyclopropyl(6,6-diphenyl-6,7-dihydro-1H-indazol-3-yl) methanone may be prepared in the following manner:

2 cm$^3$ of a solution of 5.46 cm$^3$ of bromocyclopropane diluted in 10 cm$^3$ of tetrahydrofuran are added to 1.66 g of magnesium turnings in suspension in 5 cm$^3$ of tetrahydrofuran. The reaction mixture is heated to a temperature of about 40° C. and the temperature then rises spontaneously to the reflux temperature of the solvent. The remainder of the bromocyclopropane solution is poured in dropwise at the reflux temperature of the tetrahydrofuran. After refluxing the reaction mixture for one hour and then cooling to a temperature of about 20° C., a solution of 4.9 g of (N-methoxy-N-methyl)-6,6-diphenyl-6,7-dihydro-1H-indazole-3-carboxamide dissolved in 60 cm$^3$ of tetrahydrofuran is added dropwise to the above mixture. After stirring this mixture for about 16 hours at a temperature in the region of 20° C., 100 cm$^3$ of aqueous 2N hydrochloric acid solution are added dropwise at a temperature in the region of 20° C. After stirring for about ten minutes at this same temperature, 350 cm$^3$ of saturated aqueous sodium chloride solution are added, and the mixture is extracted with four times 200 cm$^3$ of ethyl acetate. The combined organic phases are washed with three times 40 cm$^3$ of saturated aqueous sodium chloride solution and then dried over magnesium sulphate, treated with activated charcoal, filtered and concentrated to dryness under reduced pressure (13 kPa). The residue is purified by flash chromatography on a column of silica [eluent: cyclohexane/ethyl acetate (50/50 by volume)], collecting 60 cm$^3$ fractions. After concentrating to dryness under reduced pressure (13 kPa), the residue is taken up in 35 cm$^3$ of pentane, drained by suction, washed with three times 10 cm$^3$ of pentane and then dried under reduced pressure (13 kPa), at a temperature in the region of 30° C. 4 g of cyclopropyl(6,6-diphenyl-6,7-dihydro-1H-indazol-3-yl)methanone are thus obtained in the form of a solid, the characteristics of which are as follows:

melting point: melting at 178° C. (Köfler block)

$^1$H NMR spectrum: (300 MHz, (CD$_3$)$_2$SO d6, δ in ppm): 1.10 (d, J=7 Hz: 4H); 2.85 (unresolved complex: 1H); 3.46 (s: 2H); 6.39 (broad d, J=10 Hz: 1H); 6.95 (d, J=10 Hz: 1H); from 7.15 to 7.25 (mt: 6H); 7.29 (broad t, J=7.5 Hz: 4H).

Example 5-2

Cyclobutyl(6,6-diphenyl-6,7-dihydro-1H-indazol-3-yl) methanone may be prepared as described in Example 5-1:

But starting with 1.08 g of magnesium, 6.09 g of bromocyclobutane and 4 g of (N-methoxy-N-methyl)-6,6-diphenyl-6,7-dihydro-1H-indazole-3-carboxamide in 80 cm$^3$ of tetrahydrofuran. After purification by flash chromatography on a column of silica [eluent: dichloromethane/methanol (98/2 by volume)], 2.6 g of cyclobutyl(6,6-diphenyl-6,7-dihydro-1H-indazol-3-yl)methanone are thus obtained in the form of a white solid, the characteristics of which are as follows:

melting point: melting at 196° C. (Köfler block)

$^1$H NMR spectrum: (300 MHz, (CD$_3$)$_2$SO d6, δ in ppm): 1.80 (mt: 1H); 2.01 (mt: 1H); 2.19 (mt: 4H); 3.43 (broad s: 2H); 3.99 (mt: 1H); 6.42 (very broad d, J=10 Hz: 1H); 6.95 (d, J=10 Hz: 1H); from 7.15 to 7.25 (mt: 6H); 7.29 (broad t, J=7.5 Hz: 4H).

Example 5-3

(6,6-Diphenyl-6,7-dihydro-1H-indazol-3-yl)phenylmethanone may be prepared as in Example 5-1:

But starting with 0.28 g of (N-methoxy-N-methyl)-6,6-diphenyl-6,7-dihydro-1H-indazole-3-carboxamide in 3 cm$^3$ of tetrahydrofuran and 1.5 cm$^3$ of a commercial 1.8M solution of phenyllithium in a mixture of cyclohexane and diethyl ether (70/30 by volume). The addition of the phenyllithium takes place at a temperature in the region of 0° C., and, after two hours at a temperature in the region of 20° C., the reaction mixture is treated in the same manner as in Example 5-1. After purification by flash chromatography on a column of silica [eluent: dichloromethane], 0.12 g of (6,6-diphenyl-6,7-dihydro-1H-indazol-3-yl)phenylmethanone is thus obtained in the form of a yellow solid, the characteristics of which are as follows:

melting point: melting at 90° C. (Köfler block)

$^1$H NMR spectrum: (300 MHz, (CD$_3$)$_2$SO d6, δ in ppm): 3.51 (broad s: 2H); 6.40 (broad d, J=10 Hz: 1H); from 6.70 to 7.15 (very broad unresolved complex: 1H); from 7.15 to 7.40 (mt: 10H); 7.55 (broad t, J=7.5 Hz: 2H); 7.67 (broad t, J=7.5 Hz: 1H); from 7.90 to 8.25 (unresolved complex: 2H); from 13.30 to 13.70 (broad unresolved complex: 1H).

Example 5-4

(6,6-Diphenyl-6,7-dihydro-1H-indazol-3-yl)-(1H-pyrrol-3-yl)methanone may be prepared in the following manner:

0.83 cm$^3$ of a commercial 1 M solution of tetrabutylammonium fluoride in tetrahydrofuran is added to a solution of 0.29 g of (6,6-diphenyl-6,7-dihydro-1H-indazol-3-yl)-(1-triisopropylsilanyl-1H-pyrrol-3-yl)methanone in 50 cm$^3$ of tetrahydrofuran. The solution is stirred for about 4 hours in the region of 20° C. and then concentrated to dryness under reduced pressure (13 kPa). The residue is taken up in 50 cm$^3$ of ethyl acetate; the solution is washed with three times 30 cm$^3$ of water, dried over magnesium sulphate, filtered and concentrated to dryness under reduced pressure. After flash chromatography on a column of silica [eluent: dichloromethane/methanol (98/2 by volume)], 0.1 g of (6,6-diphenyl-6,7-dihydro-11H-indazol-3-yl)-(1H-pyrrol-3-yl)methanone is thus obtained in the form of a solid, the characteristics of which are as follows:

melting point: melting at 185° C. (Köfler block)

$^1$H NMR spectrum: (300 MHz, (CD$_3$)$_2$SO d6 with addition of a few drops of CD$_3$COOD d4, δ in ppm): 3.46 (s: 2H); 6.31 (d, J=10 Hz: 1H); 6.65 (mt: 1H): 6.85 (t, J=2 Hz: 1H); 6.95 (d, J=10 Hz: 1H); from 7.10 to 7.35 (mt: 10H); 7.78 (broad s, 1H).

(6,6-Diphenyl-6,7-dihydro-1H-indazol-3-yl)-(1-triisopropylsilanyl-1H-pyrrol-3-yl)methanone may be prepared in the following manner:

2.5 cm$^3$ of a commercial 1.6 M solution of n-butyllithium in hexane are added dropwise to a solution of 1.21 g of 3-bromo-1-triisopropylsilanyl-1H-pyrrole in 10 cm$^3$ of tetrahydrofuran cooled to the region of −70° C., while maintaining the temperature at about −70° C. The mixture is stirred for 5 hours at this same temperature. A solution of 0.359 g of (N-methoxy-N-methyl)-6,6-diphenyl-6,7-dihydro-1H-indazole-3-carboxamide in 30 cm$^3$ of tetrahydrofuran is poured in dropwise in the region of −70° C. The mixture is stirred for about 20 hours, allowing the temperature to slowly return to the region of 20° C. The reaction mixture is poured into 100 cm$^3$ of aqueous 2N hydrochloric acid solution, and the aqueous phase is saturated with sodium chloride and extracted with three times 150 cm$^3$ of ethyl acetate. The combined organic phases are dried over magnesium sulphate, filtered and concentrated to dryness under reduced pressure (13 kPa). After flash chromatography on a column of silica [eluent: dichloromethane/methanol (99/1 by volume)], 0.29 g of (6,6-diphenyl-6,7-dihydro-1H-indazol-3-yl)-(1-triisopropylsilanyl-1H-pyrrol-3-yl)methanone is thus obtained in the form of a resin, the characteristics of which are as follows:

Rf TLC silica [eluent: dichloromethane/ethyl acetate (80/20 by volume)]=0.35 mass spectrum

DCI m/z=522 MH$^+$

Example 6-1

The Z and E isomers of cyclopropyl(6,6-diphenyl-6,7-dihydro-1H-indazol-3-yl)methanone oxime may be prepared in the following manner:

A mixture of 0.34 g of cyclopropyl(6,6-diphenyl-6,7-dihydro-1H-indazol-3-yl)methanone, 0.278 g of hydroxylamine hydrochloride, 0.328 g of sodium acetate and 2 cm$^3$ of water in 32 cm$^3$ of ethanol is refluxed for about 18 hours. The reaction mixture is poured in 100 cm$^3$ of water and cooled for about one hour at a temperature in the region of 0° C. The solid is drained by suction and washed with three times 5 cm$^3$ of ice-cold water. The two Z and E isomers are separated on a column of silica [eluent: dichloromethane/methanol (98/2 by volume)], collecting 50 cm$^3$ fractions.

Fractions 34 to 46 are combined and concentrated to dryness under reduced pressure (13 kPa). The residue is taken up in 5 cm$^3$ of diisopropyl ether, washed with twice 1 cm$^3$ of diisopropyl ether and then dried under reduced pressure at a temperature of about 25° C. 0.113 g of the A isomer of cyclopropyl(6,6-diphenyl-6,7-dihydro-1H-indazol-3-yl)methanone oxime is obtained in the form of a white powder, the characteristics of which are as follows:

melting point: melting at 183° C. (Köfler block)

$^1$H NMR spectrum: (300 MHz, (CD$_3$)$_2$SO d6, δ in ppm): from 0.70 to 0.90 (mt: 4H); 1.79 (mt: 1H); 3.39 (s: 2H); 6.30 (broad d, J=10 Hz: 1H); 6.95 (broad d, J=10 Hz: 1H); from 7.15 to 7.35 (mt: 10H); from 11.25 to 11.55 (broad unresolved complex: 1H); from 12.50 to 12.80 (broad unresolved complex: 1H).

Fractions 48 to 68 are combined and concentrated to dryness under reduced pressure (13 kPa). The residue is taken up in 5 cm$^3$ of pentane, drained by suction, washed with twice 2 cm$^3$ of pentane and then dried under reduced pressure (13 kPa) at a temperature of about 25° C. 0.09 g of the B isomer of cyclopropyl(6,6-diphenyl-6,7-dihydro-1H-indazol-3-yl)methanone oxime is obtained in the form of a white powder, the characteristics of which are as follows:

melting point: melting at 100° C. (Köfler block)

$^1$H NMR spectrum: (300 MHz, (CD$_3$)$_2$SO d6, with addition of a few drops of CD$_3$COOD d4, δ in ppm): 0.80 (mt: 2H); 0.91 (mt: 2H); 2.25 (mt: 1H); 3.37 (s: 2H); 6.16 (d, J=10 Hz: 1H); 6.72 (d, J=10 Hz: 1H); from 7.10 to 7.35 (mt: 10H).

Example 6-2

The Z and E isomers of cyclobutyl(6,6-diphenyl-6,7-dihydro-1H-indazol-3-yl)methanone oxime may be prepared as in Example 6-1:

But starting with 0.345 g of cyclobutyl(6,6-diphenyl-6,7-dihydro-1H-indazol-3-yl)methanone, 0.278 g of hydroxylamine hydrochloride and 0.328 g of sodium acetate. The mixture of Z and E isomers is separated by flash chromatography on a column of silica [eluent: dichloromethane/methanol (98/2 by volume)], collecting 60 cm$^3$ fractions.

Fractions 35 to 60 are combined and concentrated to dryness under reduced pressure (13 kPa). The residue is taken up in 10 cm$^3$ of diisopropyl ether, washed with twice 5 cm$^3$ of diisopropyl ether and then dried under reduced pressure at a temperature of about 50° C. 0.21 g of the A isomer of cyclobutyl(6,6-diphenyl-6,7-dihydro-1H-indazol-3-yl)methanone oxime is thus obtained in the form of a solid, the characteristics of which are as follows:

melting point: melting at 185° C. (Köfler block)

$^1$H NMR spectrum: (300 MHz, (CD$_3$)$_2$SO d6, δ in ppm): from 1.65 to 2.20 (mt: 6H); 3.38 (s: 2H); 3.54 (mt: 1H); 6.28 (very broad d, J=10 Hz: 1H); 6.80 (d, J=10 Hz: 1H); from 7.15 to 7.35 (mt: 10H); 11.50 (unresolved complex: 1H); 12.53 (unresolved complex: 1H).

Fractions 62 to 110 are combined and concentrated to dryness under reduced pressure (13 kPa). The residue is taken up in 5 cm$^3$ of diisopropyl ether, washed with three times 1 cm$^3$ of diisopropyl ether and then dried under reduced pressure (13 kPa), at a temperature in the region of 50° C. 0.08 g of the B isomer of cyclobutyl(6,6-diphenyl-6,7-dihydro-1H-indazol-3-yl)methanone oxime is thus obtained in the form of a solid, the characteristics of which are as follows:

melting point: melting at 170° C. (Köfler block)

$^1$H NMR spectrum: (300 MHz, (CD$_3$)$_2$SO d6, δ in ppm): from 1.60 to 2.30 (mt: 6H); from 3.35 to 3.50 (unresolved complex: 2H); 3.79 (unresolved complex: 1H); 6.15 (broad d, J=10 Hz: 1H); 6.68 (unresolved complex: 1H); from 7.15 to 7.35 (mt: 10H); 11.10 (unresolved complex: 1H); from 12.30 to 12.85 (very broad unresolved complex: 1H).

Example 6-3

The Z and E isomers of cyclopropyl(6,6-diphenyl-6,7-dihydro-2H-indazol-3-yl)methanone O-methyloxime may be prepared as in Example 6-1:

But starting with 0.34 g of cyclopropyl(6,6-diphenyl-6,7-dihydro-1H-indazol-3-yl)methanone, 0.334 g of methoxylamine hydrochloride and 0.328 g of sodium acetate. The mixture of the Z and E isomers is separated by flash chromatography on a column of silica [eluent: dichloromethane], collecting 50 cm³ fractions.

Fractions 66 to 90 are combined and concentrated to dryness under reduced pressure (13 kPa). The residue is taken up in 4 cm³ of pentane, drained by suction, washed with twice 1 cm³ of pentane and then dried under reduced pressure (13 kPa), at a temperature in the region of 35° C. The A isomer of cyclopropyl(6,6-diphenyl-6,7-dihydro-2H-indazol-3-yl)methanone is thus obtained in the form of a solid, the characteristics of which are as follows:

melting point: melting at 134° C. (Köfler block)

$^1$H NMR spectrum: (300 MHz, (CD$_3$)$_2$SO d6, δ in ppm): 0.77 and 0.84 (2 mts: 4H in total); 1.79 (mt: 1H); 3.39 (broad s: 2H); 3.80 (broad s: 3H); 6.34 (broad d, J=10 Hz: 1H); 6.92 (broad d, J=10 Hz: 1H); from 7.15 to 7.35 (mt: 10H); 12.66 (unresolved complex: 1H).

Fractions 120 to 156 are combined and concentrated to dryness under reduced pressure (13 kPa). The residue is taken up in 3 cm³ of pentane, drained by suction, washed with twice 1 cm³ of pentane and then dried under reduced pressure (13 kPa), at a temperature in the region of 35° C. The B isomer of cyclopropyl(6,6-diphenyl-6,7-dihydro-2H-indazol-3-yl)methanone O-methyloxime is thus obtained in the form of a solid, the characteristics of which are as follows:

melting point: melting at 162° C. (Köfler block)

$^1$H NMR spectrum: (400 MHz, (CD$_3$)$_2$SO d6 with addition of a few drops of CD$_3$COOD d4, δ in ppm): 0.82 (mt: 2H); 1.02 (mt: 2H); 2.03 (mt: 1H); 3.35 (s: 2H); 3.85 (s: 3H); 6.19 (d, J=10 Hz; 1H); 6.74 (d, J=10 Hz: 1H); from 7.10 to 7.25 (mt: 6H); 7.27 (broad t, J=7.5 Hz: 4H).

Example 6-4

The Z and E isomers of 6,6-diphenyl-6,6-dihydro-1H-indazole-3-carbaldehyde O-methyloxime may be prepared in the following manner:

2.4 cm³ of aqueous 1N sodium hydroxide solution are added to a solution of 0.385 g of a Z and E mixture of 6,6-diphenyl-1-(4-toluenesulphonyl)-6,7-dihydro-1H-indazole-3-carbaldehyde O-methyloxime in 24 cm³ of dioxane. The solution is refluxed for about 30 minutes. After concentrating under reduced pressure (13 kPa), the residue is taken up in 50 cm³ of dichloromethane. The solution is washed with three times 50 cm³ of water and then 30 cm³ of saturated aqueous sodium chloride solution, dried over magnesium sulphate, filtered and then concentrated under reduced pressure (13 kPa). 0.218 g of a Z and E mixture of 6,6-diphenyl-6,7-dihydro-1H-indazole-3-carbaldehyde O-methyloxime is thus obtained in the form of a white powder, the characteristics of which are as follows:

melting point: melting at 80° C. (Köfler block)

$^1$H NMR spectrum: (300 MHz, (CD$_3$)$_2$SO d6 with addition of a few drops of CD$_3$COOD d4, δ in ppm): 3.37 (s: 2H); 3.87 (s: 3H); 6.30 (d, J=10 Hz; 1H); 6.81 (d, J=10 Hz: 1H); from 7.10 to 7.35 (mt: 10H); 8.13 (s: 1H).

75/25 mixture of Z and E isomer. Description of the predominant isomer.

The Z and E mixture of 6,6-diphenyl-1-(4-toluenesulphonyl)-6,7-dihydro-1H-indazole-3-carbaldehyde O-methyloxime may be prepared in the following manner:

0.185 g of O-methylhydroxylamine hydrochloride is added to a solution of 0.4 g of 6,6-diphenyl-1-(4-toluenesulphonyl)-6,7-dihydro-1H-indazole-3-carbaldehyde and 0.292 g of sodium acetate in 11 cm³ of ethanol and 3.3 cm³ of water, and the mixture is stirred at a temperature in the region of 20° C. for about 20 hours. The precipitate is drained by suction and washed with 3 cm³ of water and 7 cm³ of ethanol. 0.397 g of a Z and E mixture of 6,6-diphenyl-1-(4-toluenesulphonyl)-6,7-dihydro-1H-indazole-3-carbaldehyde O-methyloxime is thus obtained in the form of a solid, the characteristics of which are as follows:

Rf TLC silica [eluent: cyclohexane/ethyl acetate (80/20 by volume)]=0.39 and 0.49 mass spectrum

EI m/z=483 M$^+$ m/z=451 [M-OCH$_3$]$^+$ m/z=328 [M-CH$_3$C$_6$H$_4$SO$_2$]$^+$ base peak m/z=297 [328-OCH$_2$]$^+$ m/z=91 [CH$_2$C$_6$H$_5$]$^+$ 6,6-Diphenyl-1-(4-toluenesulphonyl)-6,7-dihydro-1H-indazole-3-carbaldehyde may be prepared in the following manner:

A commercial solution of 6.4 cm³ of 20% diisobutylaluminium hydride in toluene is added dropwise to a solution, cooled to a temperature in the region of 0° C., of 2.12 g of (N-methoxy-N-methyl)-6,6-diphenyl-1-(4-toluenesulphonyl)-6,7-dihydro-1H-indazole-3-carboxamide in 90 cm³ of anhydrous tetrahydrofuran, while keeping the temperature in the region of 0° C. After stirring the reaction mixture for about 6 hours at this same temperature, 100 cm³ of ice-cold water and 50 cm³ of diethyl ether are added. The aqueous phase is extracted with three times 100 cm³ of diethyl ether. The organic phases are combined, washed with 200 cm³ of water and then 200 cm³ of saturated aqueous sodium chloride solution, dried over magnesium sulphate, filtered and concentrated to dryness under reduced pressure (13 kPa). After purification by flash chromatography on a column of silica [eluent: cyclohexane/ethyl acetate (70/30 by volume)], 1.2 g of 6,6-diphenyl-1-(4-toluenesulphonyl)-6,7-dihydro-1H-indazole-3-carbaldehyde are obtained in the form of a solid, the characteristics of which are as follows:

melting point: melting at 228° C. (Köfler block)

mass spectrum

EI m/z=454 M$^+$ m/z=299 [M-CH$_3$C$_6$H$_4$SO$_2$]$^+$ base peak m/z=271 [299-CO]$^+$ m/z=91 [CH$_2$C$_6$H$_5$]$^+$ (N-Methoxy-N-methyl)-6,6-diphenyl-1-(4-toluenesulphonyl)-6,7-dihydro-1H-indazole-3-carboxamide may be prepared as described in Example 3-2:

But starting with 3.1 g of 6,6-diphenyl-1-(4-toluenesulphonyl)-6,7-dihydro-1H-indazole-3-carboxylic acid, 1.02 g of 1-hydroxybenzotriazole hydrate, 1.45 g of 1-(3-dimethylaminopropyl)-3-ethylcarbodiimide hydrochloride, 0.7 g of N,O-dimethylhydroxylamine hydrochloride and 0.99 cm³ of triethylamine in 62 cm³ of dichloromethane. After flash chromatography on a column of silica [eluent: cyclohexane/ethyl acetate (70/30 by volume)], 2.12 g of (N-methoxy-N-methyl)-6,6-diphenyl-1-(4-toluenesulphonyl)-6,7-dihydro-1H-indazole-3-carboxamide are thus obtained in the form of a solid, the characteristics of which are as follows:

melting point: melting at 184° C. (Köfler block)

mass spectrum

EI m/z=453 M$^+$ m/z=451 [M-C$_2$H$_6$NO]$^+$ m/z=358 [M-CH$_3$C$_6$H$_4$SO$_2$]$^+$ base peak m/z=327 [328-OCH$_2$]$^+$ m/z=298 [358-C$_2$H$_6$NO]$^+$ m/z=91 [CH$_2$C$_6$H$_5$]$^+$

Example 6-5

Cyclobutyl(6,6-diphenyl-6,7-dihydro-1H-indazol-3-yl) methanone O-allyloxime A isomer may be prepared as in Example 6-1:

But starting with 0.354 g of cyclobutyl(6,6-diphenyl-6,7-dihydro-1H-indazol-3-yl)methanone, 0.438 g of O-allylhydroxylamine hydrochloride and 0.328 g of sodium acetate. The mixture of the Z and E isomers is separated by flash chromatography on a column of silica [eluent: dichloromethane/methanol (98/2 by volume)], collecting 65 cm$^3$ fractions.

Fractions 20 to 36 are combined and concentrated to dryness under reduced pressure (13 kPa). The residue is taken up in 7 cm$^3$ of diisopropyl ether, drained by suction, washed with twice 2 cm$^3$ of diisopropyl ether and then dried under reduced pressure over potassium hydroxide at a temperature in the region of 20° C. 0.15 g of cyclobutyl(6,6-diphenyl-6,7-dihydro-1H-indazol-3-yl)methanone O-allyloxime A isomer in the form of a solid, the characteristics of which are as follows:

melting point: melting at 228° C. (Köfler block)

$^1$H NMR spectrum: (300 MHz, (CD$_3$)$_2$SO d6, δ in ppm): from 1.65 to 2.20 (mt: 6H); 3.39 (s: 2H); 3.56 (mt: 1H); 4.60 (broad d, J=5.5 Hz: 2H); 5.17 (broad d, J=10 Hz: 1H); 5.24 (broad d, J=18 Hz: 1H); 6.00 (mt: 1H); 6.22 (unresolved complex: 1H); 6.63 (d, J=10 Hz: 1H); from 7.10 to 7.35 (mt: 10H); from 12.40 to 12.70 (unresolved complex: 1H).

Example 6-6

The Z and E isomers of cyclopropyl(6,6-diphenyl-6,7-dihydro-1H-indazol-3-yl)methanone O-allyloxime may be prepared as in Example 6-1:

But starting with 0.68 g of cyclopropyl(6,6-diphenyl-6,7-dihydro-1H-indazol-3-yl)methanone, 0.88 g of O-allylhydroxylamine hydrochloride and 0.66 g of sodium acetate. The mixture of the Z and E isomers is separated by flash chromatography on a column of silica [eluent: dichloromethane/methanol (98/2 by volume)], collecting 70 cm$^3$ fractions.

Fractions 40 to 54 are combined and concentrated to dryness under reduced pressure (13 kPa). The residue is taken up in 2.5 cm$^3$ of diisopropyl ether and 30 cm$^3$ of pentane, drained by suction, washed with three times 2 cm$^3$ of pentane and dried under reduced pressure over phosphorus pentoxide at a temperature in the region of 20° C. 0.23 g of the Z isomer of cyclopropyl(6,6-diphenyl-6,7-dihydro-1H-indazol-3-yl)methanone O-allyloxime, corresponding to Example 6-6A, is thus obtained in the form of a solid, the characteristics of which are as follows:

melting point: melting at 128° C. (Köfler block)

$^1$H NMR spectrum: (400 MHz, (CD$_3$)$_2$SO d6 with a temperature of 393 K, δ in ppm): 0.80 (mt: 4H); 1.85 (mt: 1H); 3.46 (s: 2H); 4.55 (broad d, J=4 Hz: 2H); 5.17 (broad d, J=10 Hz: 1H); 5.23 (dd, J=18 Hz and 1.5 Hz: 1H); 5.98 (mt: 1H); 6.24 (unresolved complex: 1H); 6.82 (unresolved complex: 1H); from 7.10 to 7.35 (mt: 10H); from 12.10 to 12.45 (broad unresolved complex: 1H).

Fractions 61 to 72 are combined and concentrated to dryness under reduced pressure (13 kPa). 0.39 g of the E isomer of cyclopropyl(6,6-diphenyl-6,7-dihydro-1H-indazol-3-yl)methanone O-allyloxime, corresponding to Example 6-6B, is thus obtained in the form of an oil, the characteristics of which are as follows:

Rf TLC silica [eluent: dichloromethane/methanol (98/2 by volume)]=0.37

$^1$H NMR spectrum: (400 MHz, (CD$_3$)$_2$SO d6 at a temperature of 383 K, δ in ppm): from 0.60 to 1.35 (mt: 4H); from 2.10 to 2.45 (broad unresolved complex: 1H); 3.41 (s: 2H); 4.61 (d, J=6 Hz: 2H); 5.23 (broad d, J=11 Hz: 1H); 5.33 (broad d, J=17 Hz: 1H); 6.04 (mt: 1H); 6.16 (unresolved complex: 1H); 6.66 (broad d, J=9.5 Hz: 1H); from 7.10 to 7.35 (mt: 10H); from 12.20 to 12.55 (broad unresolved complex: 1H).

Example 6-7

The Z isomer of cyclopropyl(6,6-diphenyl-6,7-dihydro-1H-indazol-3-yl)methanone O-(2-methoxyethyl)oxime may be prepared in the following manner:

A suspension of 0.74 g of cyclopropyl(6,6-diphenyl-6,7-dihydro-1H-indazol-3-yl)methanone and 0.70 g of O-(2-methoxyethyl)hydroxylamine hydrochloride in 50 cm$^3$ of pyridine is refluxed for about 7 hours. The solution obtained is concentrated to dryness under reduced pressure (13 kPa). The residue is taken up in 150 cm$^3$ of dichloromethane. The solution is washed with three times 80 cm$^3$ of water, dried over magnesium sulphate, filtered and concentrated to dryness under reduced pressure (13 kPa). The mixture of the Z and E isomers is separated by flash chromatography on a column of silica [eluent: dichloromethane/methanol (98/2 by volume)], collecting 60 cm$^3$ fractions.

Fractions 111 to 135 are combined and concentrated to dryness under reduced pressure (13 kPa). 0.37 g of the Z isomer of cyclopropyl(6,6-diphenyl-6,7-dihydro-1H-indazol-3-yl)methanone O-(2-methoxyethyl)oxime, corresponding to Example 6-7A, is thus obtained in the form of a resin, the characteristics of which are as follows:

$^1$H NMR spectrum: (300 MHz, (CD$_3$)$_2$SO d6 with addition of a few drops of CD$_3$COOD d4, δ in ppm): from 0.70 to 0.90 (mt: 4H); 1.81 (mt: 1H); 3.22 (s: 3H); 3.40 (s: 2H); 3.56 (t, J=5.5 Hz: 2H); 4.13 (t, J=5.5 Hz: 2H); 6.25 (d, J=10 Hz: 1H); 6.89 (d, J=10 Hz: 1H); from 7.10 to 7.30 (mt: 10H).

IR spectrum (solvent CCl$_4$) 3459; 3316; 2932; 2882; 1597; 1492; 1446; 1386; 1291; 1145; 1126; 1069; 1027; 1007; 952; 894; 700; 683 and 541 cm$^{-1}$ O-(2-Methoxyethyl)hydroxylamine hydrochloride may be prepared as described by Dae-Kee Kim et al., J. Med. Chem., 40, 15, 1997, 2363–2373.

The E isomer of cyclopropyl(6,6-diphenyl-6,7-dihydro-1H-indazol-3-yl)methanone O-(2-methoxyethyl)oxime may be prepared in the following manner:

1.47 cm$^3$ of a commercial 1 M solution of tetrabutylammonium fluoride in tetrahydrofuran are added to a solution of 0.32 g of the E isomer of cyclopropyl(6,6-diphenyl-1-(2-trimethylsilanylethoxymethyl)-6,7-dihydro-1H-indazol-3-yl)methanone O-(2-methoxyethyl)oxime in 50 cm$^3$ of tetrahydrofuran, and the mixture is stirred in the region of 20° C. for 4 days. The solution is concentrated to dryness under reduced pressure and the residue is taken up in 50 cm$^3$ of ethyl acetate; the solution is washed with three times 30 cm$^3$ of water, dried over magnesium sulphate, filtered and concentrated to dryness under reduced pressure (13 kPa). After flash chromatography on a column of silica [eluent: dichloromethane/ethyl acetate (90/10 by volume)], 0.073 g of the E isomer of cyclopropyl(6,6-diphenyl-6,7-dihydro-1H-indazol-3-yl)methanone O-(2-methoxyethyl)oxime, corresponding to Example 6-7B, is thus obtained in the form of a resin, the characteristics of which are as follows:

Rf TLC silica [eluent: dichloromethane/methanol (95/5 by volume)]=0.57

$^1$H NMR spectrum: (300 MHz, (CD$_3$)$_2$SO d6, δ in ppm): 0.85 (mt: 2H); from 1.10 to 1.40 (mt: 2H); from 1.85 to 2.50

(very broad unresolved complex: 1H); 3.30 (s: 3H); 3.37 (s: 2H); 3.60 (t, J=5 Hz; 2H); 4.19 (t, J=5 Hz: 2H); 6.20 (very broad d, J=10 Hz: 1H); 6.77 (very broad d, J=10 Hz: 1H); from 7.16 to 7.35 (mt: 10H); from 12.60 to 13.00 (broad unresolved complex: 1H).

The E isomer of cyclopropyl(6,6-diphenyl-1-(2-trimethylsilanylethoxymethyl)-6,7-dihydro-1H-indazol-3-yl)methanone O-(2-methoxyethyl)oxime may be prepared in the following manner:

A solution of 0.35 g of the E isomer of cyclopropyl(6,6-diphenyl-1-(2-trimethylsilanylethoxymethyl)-6,7-dihydro-1H-indazol-3-yl)methanone oxime in 10 cm³ of tetrahydrofuran is added dropwise to a suspension of 0.036 g of sodium hydride (at 60% in oil) in 7 cm³ of tetrahydrofuran. After stirring the reaction mixture for about 2 hours in the region of 20° C., a solution of 0.16 g of 1-bromo-2-methoxyethane in 5 cm³ of tetrahydrofuran is poured into the solution obtained. After stirring in the region of 20° C. for about two and a half hours, 5 cm³ of water are added and the solution is concentrated to dryness under reduced pressure (13 kPa). The residue is taken up in 20 cm³ of water and extracted with three times 40 cm³ of dichloromethane. The organic phases are combined, dried over magnesium sulphate, filtered and concentrated. After flash chromatography on a column of silica [eluent: dichloromethane/ethyl acetate (99/1 by volume)], 0.32 g of the E isomer of cyclopropyl(6,6-diphenyl-1-(2-trimethylsilanylethoxymethyl)-6,7-dihydro-1H-indazol-3-yl)methanone O-(2-methoxyethyl)oxime is thus obtained in the form of a resin, the characteristics of which are as follows:

$^1$H NMR spectrum: (300 MHz, $(CD_3)_2SO$ d6, δ in ppm): −0.02 (s: 9H); 0.84 (mt: 2H); 0.88 (broad t, J=8 Hz: 2H); 1.28 (mt: 2H); 2.39 (mt: 1H); 3.30 (s: 3H); 3.46 (s: 2H); 3.48 (d, J=8 Hz: 2H); 3.60 (broad t, J=5 Hz: 2H); 4.19 (broad t, J=5 Hz: 2H); 5.49 (s: 2H); 6.26 (d, J=10 Hz: 1H); 6.76 (d, J=10 Hz: 1H); from 7.15 to 7.35 (mt: 10H).

mass spectrum
EI m/z=543 M$^+$
m/z=468 [M-OCH$_2$CH$_2$O CH$_3$]$^+$
m/z=426 [M-OCH$_2$CH$_2$Si(CH$_3$)$_3$]$^+$
m/z=350 [468-OCH$_2$CH$_2$Si(CH$_3$)$_3$]$^+$ base peak
m/z=336 [350-OCH$_2$]$^+$
m/z=73 [Si(CH$_3$)$_3$]$^+$ The E isomer of cyclopropyl(6,6-diphenyl-1-(2-trimethylsilanylethoxymethyl)-6,7-dihydro-1H-indazol-3-yl) methanone oxime may be prepared in the following manner:

A mixture of 2.35 g of cyclopropyl(6,6-diphenyl-1-(2-trimethylsilanylethoxymethyl)-6,7-dihydro-1H-indazol-3-yl)methanone, 1.39 g of hydroxylamine hydrochloride, 1.64 g of sodium acetate in a mixture of 15 cm³ of water and 230 cm³ of ethanol is refluxed for 48 hours. The mixture is concentrated to dryness under reduced pressure (13 kPa). The residue is taken up in 50 cm³ of water and extracted with three times 80 cm³ of dichloromethane. The organic phases are combined, dried over magnesium sulphate, filtered and concentrated to dryness under reduced pressure (13 kPa). The mixture of the Z and E isomers is separated by flash chromatography on a column of silica [eluent: dichloromethane/ethyl acetate (95/5 by volume)], collecting 70 cm³ fractions.

Fractions 128 to 162 are combined and concentrated to dryness under reduced pressure (13 kPa). 1.74 g of cyclopropyl(6,6-diphenyl-1-(2-trimethylsilanylethoxymethyl)-6,7-dihydro-1H-indazol-3-yl)methanone oxime E isomer are thus obtained in the form of a solid, the characteristics of which are as follows:

melting point: melting at 128° C. (Köfler block)

$^1$H NMR spectrum: (300 MHz, $(CD_3)_2SO$ d6, δ in ppm): −0.03 (s: 9H); 0.77 (mt: 2H); 0.85 (broad t, J=8 Hz: 2H); 1.23 (mt: 2H); 2.43 (mt: 1H); 3.46 (s: 2H); 3.47 (d, J=8 Hz: 2H); 5.47 (s: 2H); 6.21 (d, J=10 Hz: 1H); 6.74 (d, J=10 Hz: 1H); from 7.15 to 7.35 (mt: 10H); 11.05 (s: 1H).

IR spectrum (solvent CCl$_4$) 3598; 3290; 2954; 1492; 1445; 1349; 1251; 1184; 1080; 1034; 970; 940; 861; 837 and 700 cm$^{-1}$ Cyclopropyl(6,6-diphenyl-1-(2-trimethylsilanylethoxymethyl)-6,7-dihydro-1H-indazol-3-yl)methanone may be prepared in the following manner:

A solution of 2.55 g of cyclopropyl(6,6-diphenyl-6,7-dihydro-1H-indazol-3-yl)methanone in 40 cm³ of dimethylformamide is added dropwise at a temperature in the region of 5° C. to a suspension, cooled to this same temperature, of 0.39 g of sodium hydride (at 60% in oil) in 20 cm³ of dimethylformamide. After stirring the mixture at this same temperature for about one and a half hours, a solution of 1.87 g of (2-chloromethoxyethyl)trimethylsilane in 20 cm³ of dimethylformamide is added dropwise without exceeding a temperature of 10° C. After warming to a temperature in the region of 20° C., the mixture is stirred for 2 hours at this same temperature. 20 cm³ of water are then added and the mixture is concentrated under reduced pressure (13 kPa). The residue is taken up in 80 cm³ of water and extracted three times with 60 cm³ of dichloromethane. The combined organic phases are dried over magnesium sulphate, filtered and concentrated to dryness under reduced pressure. After flash chromatography on a column of silica [eluent: dichloromethane/methanol (99/1 by volume)], 2.5 g of cyclopropyl (6,6-diphenyl-1-(2-trimethylsilanylethoxymethyl)-6,7-dihydro-1H-indazol-3-yl)methanone are thus obtained in the form of a solid, the characteristics of which are as follows:

melting point: melting at 121° C. (Köfler block)

$^1$H NMR spectrum: (300 MHz, $(CD_3)_2SO$ d6, δ in ppm): −0.02 (s: 9H); 0.88 (broad t, J=8 Hz: 2H); 0.99 (d, J=6.5 Hz: 4H); 2.96 (mt: 1H); 3.56 (s: 2H); 3.57 (t, J=8 Hz: 2H); 5.65 (s: 2H); 6.42 (d, J=10 Hz: 1H); 6.91 (d, J=10 Hz: 1H); from 7.15 to 7.35 (mt: 10H).

Example 6-8

The Z and E isomers of cyclopropyl(6,6-diphenyl-6,7-dihydro-1H-indazol-3-yl)methanone O-benzyloxime may be prepared as in Example 6-1:

But starting with 0.34 g of cyclopropyl(6,6-diphenyl-6,7-dihydro-1H-indazol-3-yl)methanone, 0.64 g of O-benzylhydroxylamine hydrochloride and 0.33 g of sodium acetate. The mixture of the Z and E isomers is separated by flash chromatography on a column of silica [eluent: dichloromethane/methanol (99/1 by volume)], collecting 60 cm³ fractions.

Fractions 16 to 36 are combined and concentrated to dryness under reduced pressure (13 kPa). The residue is taken up in 5 cm³ of pentane, dried, washed with twice 2 cm³ of pentane and dried under reduced pressure over phosphorus pentoxide at a temperature in the region of 20° C. 0.15 g of the Z isomer of cyclopropyl(6,6-diphenyl-6,7-dihydro-1H-indazol-3-yl)methanone O-benzyloxime corresponding to Example 6-8A is thus obtained in the form of a solid, the characteristics of which are as follows:

melting point: melting at 123° C. (Köfler block)

$^1$H NMR spectrum: (400 MHz, $(CD_3)_2SO$ d6, δ in ppm): from 0.65 to 0.85 (mt: 4H); 1.83 (mt: 1H); 3.38 (s: 2H); 5.05

(s: 2H); 6.17 (unresolved complex: 1H); 6.78 (unresolved complex: 1H); from 7.10 to 7.40 (mt: 15H); 12.69 (unresolved complex: 1H).

Fractions 60 to 73 are combined and concentrated to dryness under reduced pressure (13 kPa). The residue is taken up in 50 cm$^3$ of diethyl ether and washed three times with 40 cm$^3$ of aqueous 1N hydrochloric acid solution. The organic phase is dried over magnesium sulphate, filtered and concentrated under reduced pressure. The residue is taken up in 2 cm$^3$ of diethyl ether and the insoluble material is filtered off and washed with twice 1 cm$^3$ of pentane. The filtrate is diluted with 50 cm$^3$ of diethyl ether, washed with three times 30 cm$^3$ of saturated aqueous sodium hydrogen carbonate solution, dried over magnesium sulphate, filtered and concentrated under reduced pressure (13 kPa). 0.135 g of the E isomer of cyclopropyl(6,6-diphenyl-6,7-dihydro-1H-indazol-3-yl)methanone O-benzyloxime, corresponding to Example 6-8B, is thus obtained in the form of a foam, the characteristics of which are as follows:

$^1$H NMR spectrum: (300 MHz, (CD$_3$)$_2$SO d6 with addition of a few drops of CD$_3$COOD d4, δ in ppm): 0.85 (mt: 2H); 1.09 (mt: 2H); 2.30 (mt: 1H); 3.36 (s: 2H); 5.14 (s: 2H); 6.14 (d, J=10 Hz: 1H); 6.65 (d, J=10 Hz: 1H); from 7.10 to 7.45 (mt: 15H).

mass spectrum
EI m/z=445 M$^+$
m/z=338 [M-OCH$_2$C$_6$H$_5$]$^+$ base peak
m/z=91 [CH$_2$C$_6$H$_5$]$^+$ Example 6-9

The Z and E isomers of cyclopropyl(6,6-diphenyl-6,7-dihydro-1H-indazol-3-yl)methanone O-(4-nitrobenzyl)oxime may be prepared as in Example 6-1:

But starting with 0.56 g of cyclopropyl(6,6-diphenyl-6,7-dihydro-1H-indazol-3-yl)methanone, 1.31 g of O-(4-nitrobenzyl)hydroxylamine hydrochloride and 0.52 g of sodium acetate. The mixture of the Z and E isomers is separated by flash chromatography on a column of silica [eluent: dichloromethane], collecting 60 cm$^3$ fractions.

Fractions 83 to 94 are combined and concentrated to dryness under reduced pressure (13 kPa). 0.12 g of the Z isomer of cyclopropyl(6,6-diphenyl-6,7-dihydro-1H-indazol-3-yl)methanone O-(4-nitrobenzyl)oxime, corresponding to Example 6-9A, is thus obtained in the form of a resin, the characteristics of which are as follows:

Rf TLC silica [eluent: dichloromethane/methanol (98/2 by volume)]=0.75

$^1$H NMR spectrum: (300 MHz, (CD$_3$)$_2$SO d6, δ in ppm): 0.72 (mt: 2H); 0.82 (mt: 2H); 1.83 (mt: 1H); 3.42 (s: 2H); 5.21 (s: 2H); 6.30 (unresolved complex: 1H); 6.87 (unresolved complex: 1H); from 7.10 to 7.35 (mt: 10H); 7.56 (broad d, J=8 Hz: 2H); 8.18 (d, J=8 Hz: 2H); 12.83 (unresolved complex: 1H).

Fractions 107 to 127 are combined and concentrated to dryness under reduced pressure (13 kPa). 0.085 g of the E isomer of cyclopropyl(6,6-diphenyl-6,7-dihydro-1H-indazol-3-yl)methanone O-(4-nitrobenzyl)oxime, corresponding to Example 6-9B is thus obtained in the form of a foam, the characteristics of which are as follows:

Rf TLC silica [eluent: dichloromethane/methanol (98/2 by volume)]=0.45

$^1$H NMR spectrum: (300 MHz, (CD$_3$)$_2$SO d6, δ in ppm): 0.89 (mt: 2H); from 1.05 to 1.35 (broad unresolved complex: 2H); from 2.25 to 2.50 (broad unresolved complex: 1H); 3.36 (s: 2H); 5.31 (s: 2H); 6.13 (unresolved complex: 1H); 6.59 (d, J=10 Hz: 1H); from 7.10 to 7.35 (mt: 10H); 7.67 (d, J=8.5 Hz: 2H); 8.27 (d, J=8.5 Hz: 2H); 12.80 (unresolved complex: 1H).

Example 6-10

The Z and E isomers of cyclopropyl(6,6-diphenyl-6,7-dihydro-1H-indazol-3-yl)methanone O-(2-dimethylaminoethyl)oxime may be prepared as in Example 6-7:

But starting with 0.51 g of cyclopropyl(6,6-diphenyl-6,7-dihydro-1H-indazol-3-yl)methanone, 0.31 g of O-(2-dimethylaminoethyl)hydroxylamine hydrochloride in 40 cm$^3$ of pyridine and 2 cm$^3$ of ethanol. The mixture of the Z and E isomers is separated by flash chromatography on a column of silica [eluent: dichloromethane/methanol (90/10 by volume)], collecting 70 cm$^3$ fractions.

Fractions 105 to 132 are combined and concentrated to dryness under reduced pressure (13 kPa). 0.12 g of the Z isomer of cyclopropyl(6,6-diphenyl-6,7-dihydro-1H-indazol-3-yl)methanone O-(2-dimethylaminoethyl)oxime, corresponding to Example 6-10A, is thus obtained in the form of a resin, the characteristics of which are as follows:

$^1$H NMR spectrum: (300 MHz, (CD$_3$)$_2$SO d6 at a temperature of 353 K, δ in ppm): from 0.75 to 0.95 (mt: 4H); 1.83 (mt: 1H); 2.23 (s: 6H); 2.58 (mt: 2H); 3.44 (s: 2H): 4.13 (mt: 2H); 6.28 (unresolved complex: 1H); 6.90 (unresolved complex: 1H); from 7.10 to 7.35 (mt: 10H); 12.56 (unresolved complex: 1H).

mass spectrum
EI m/z=426 M$^+$
m/z=338 [M-OCH$_2$CH$_2$N(CH$_3$)$_2$]$^+$
m/z=58 [CH$_2$N(CH$_3$)$_2$]$^+$ base peak Fractions 154 to 182 are combined and concentrated to dryness under reduced pressure (13 kPa). 0.33 g of the E isomer of cyclopropyl(6,6-diphenyl-6,7-dihydro-1H-indazol-3-yl)methanone O-(2-dimethylaminoethyl)oxime, corresponding to Example 6-10B, is thus obtained in the form of a resin, the characteristics of which are as follows:

$^1$H NMR spectrum: (300 MHz, (CD$_3$)$_2$SO d6 with addition of a few drops of CD$_3$COOD d4, δ in ppm): 0.86 (mt: 2H); 1.08 (mt: 2H); 2.30 (mt: 1H); 2.69 (s: 6H); 3.23 (t, J=5.5 Hz: 2H); 3.37 (s: 2H); 4.35 (t, J=5.5 Hz: 2H); 6.20 (d, J=10 Hz: 1H); 6.77 (d, J=10 Hz: 1H); from 7.10 to 7.35 (mt: 10H).

mass spectrum
DCI m/z=427 [M+H]$^+$ base peak
m/z=340 [M-OCH$_2$CH$_2$N(CH$_3$)$_2$]$^+$ O-(2-dimethylaminoethyl)hydroxylamine hydrochloride may be prepared as described by F. Winternitz and R. Lachazette, Bull. Soc. Chim. Fr. 1958, 664–667.

Example 6-11

The Z and E isomers of cyclopropyl(6,6-diphenyl-6,7-dihydro-1H-indazol-3-yl)methanone O-(2-fluoroethyl)oxime may be prepared as in Example 6-7.

But starting with 0.68 g of cyclopropyl(6,6-diphenyl-6,7-dihydro-1H-indazol-3-yl)methanone, 0.58 g of O-(2-fluoroethyl)hydroxylamine hydrochloride in 50 cm$^3$ of pyridine. The mixture of the Z and E isomers is separated by flash chromatography on a column of silica ([eluent: dichloromethane/methanol (99.5/0.5 by volume)], collecting 65 cm$^3$ fractions.

Fractions 8 to 125 are combined and concentrated to dryness under reduced pressure (13 kPa). The residue is taken up in 5 cm$^3$ of diethyl ether, drained by suction and washed with three times 1 cm$^3$ of diethyl ether, dried under reduced pressure over phosphorus pentoxide at a temperature in the region of 20° C. 0.2 g of the Z isomer of cyclopropyl(6,6-diphenyl-6,7-dihydro-1H-indazol-3-yl) methanone O-(2-fluoroethyl)oxime, corresponding to Example 6-11A is thus obtained in the form of a solid, the characteristics of which are as follows:

melting point: melting at 147° C. (Köfler block)

$^1$H NMR spectrum: (300 MHz, $(CD_3)_2SO$ d6 with addition of a few drops of $CD_3COOD$ d4, δ in ppm): 0.80 (mt: 4H); 1.83 (mt: 1H); 3.41 (s: 2H); 4.26 (dt, J=30 and 4 Hz: 2H), 4.64 (dt, J=48 and 4 Hz: 2H); 6.26 (d, J=10 Hz: 1H); 6.87 (d, J=10 Hz: 1H); from 7.10 to 7.35 (mt: 10H).

Fractions 131 to 155 are combined and concentrated to dryness under reduced pressure (13 kPa). 0.36 g of the E isomer of cyclopropyl(6,6-diphenyl-6,7-dihydro-1H-indazol-3-yl)methanone O-(2-fluoroethyl)oxime, corresponding to Example 6-11B, is thus obtained in the form of a foam, the characteristics of which are as follows:

$^1$H NMR spectrum: (300 MHz, $(CD_3)_2SO$ d6 with addition of a few drops of $CD_3COOD$ d4, δ in ppm): 0.86 (mt: 2H); 1.10 (mt: 2H); 2.29 (mt: 1H); 3.36 (s: 2H); 4.30 (dt, J=30 and 4 Hz: 2H), 4.66 (dt, J=48 and 4 Hz: 2H); 6.19 (d, J=10 Hz: 1H); 6.75 (d, J=10 Hz: 1H); from 7.10 to 7.35 (mt: 10H).

mass spectrum

EI m/z=401 M$^+$ m/z=338 [M-OCH$_2$CH$_2$F]$^+$ base peak m/z=77 [C$_6$H$_5$]$^+$ O-(2-Fluoroethyl)hydroxylamine hydrochloride may be prepared as described by Akio Miyake et al., J. Antibiot., 53, 10, 2000, 1071–1085

Example 7-1

6,6-Diphenyl-1-(4-toluenesulphonyl)-6,7-dihydro-1H-indazol-3-ylamine may be prepared in the following manner:

0.5 cm$^3$ of trifluoroacetic acid is added to a solution of 0.2 g of tert-butyl [6,6-diphenyl-1-(4-toluenesulphonyl)-6,7-dihydro-1H-indazol-3-yl]carbamate in 2 cm$^3$ of dichloromethane, cooled to a temperature in the region of 0° C. After one hour at a temperature in the region of 0° C., the reaction mixture is stirred for one hour at a temperature in the region of 20° C. and then concentrated to dryness under reduced pressure (13 kPa). The residue is taken up in 25 cm$^3$ of dichloromethane and 10 cm$^3$ of water. The pH is brought to about 10 by addition of a normal aqueous sodium hydroxide solution. After separation of the phases by settling, the aqueous phase is extracted with twice 10 cm$^3$ of dichloromethane. The combined organic phases are successively washed with once 20 cm$^3$ of 0.1N aqueous sodium hydroxide solution, twice 30 cm$^3$ of water and once 30 cm$^3$ of saturated aqueous sodium chloride solution and then dried over magnesium sulphate, filtered and concentrated to dryness under reduced pressure (13 kPa). The residue is taken up in 3 cm$^3$ of diethyl ether, washed with twice 1 cm$^3$ of diethyl ether and then dried under reduced pressure (13 kPa) at a temperature in the region of 50° C. 0.08 g of 6,6-diphenyl-1-(4-toluenesulphonyl)-6,7-dihydro-1H-indazol-3-ylamine is thus obtained in the form of a white solid, the characteristics of which are as follows:

melting point: melting at 257° C. (Köfler block)

$^1$H NMR spectrum: (300 MHz, $(CD_3)_2SO$ d6, δ in ppm): 2.39 (s: 3H); 3.67 (broad s, 2H); 5.77 (s, 2H); 6.23 (d, J=10 Hz: 1H); 6.53 (d, J=10 Hz: 1H); from 7.15 to 7.35 (mt: 10H); 7.35 (d, J=8 Hz: 2H); 7.55 (d, J=8 Hz: 2H).

tert-Butyl [6,6-diphenyl-1-(4-toluenesulphonyl)-6,7-dihydro-1H-indazol-3-yl]carbamate may be prepared in the following manner:

0.09 cm$^3$ of triethylamine is added to a suspension of 0.25 g of 6,6-diphenyl-1-(4-toluenesulphonyl)-6,7-dihydro-1H-indazol-3-carboxylic acid in 1.5 cm$^3$ of toluene and 1.5 cm$^3$ of tert-butanol. The solution obtained is heated to the reflux temperature and 0.12 cm$^3$ of diphenylphosphonyl azide is added dropwise. Refluxing of the reaction mixture is continued for eight hours. After forty-eight hours at a temperature in the region of 20° C., the reaction mixture is concentrated to dryness under reduced pressure (13 kPa) and the residue is purified by flash chromatography on a column of silica [eluent: dichloromethane]. 0.06 g of tert-butyl [6,6-diphenyl-1-(4-toluenesulphonyl)-6,7-dihydro-1H-indazol-3-yl]carbamate is thus obtained in the form of a white foam, which is used directly, the characteristics of which are as follows:

Rf TLC silica [eluent: cyclohexane/ethyl acetate (70/30 by volume)]=0.55

$^1$H NMR spectrum: (300 MHz, $(CD_3)_2SO$ d6, δ in ppm): 1.40 (s: 9H); 2.42 (broad s, 3H); 3.79 (broad s: 2H); 6.31 (d, J=10 Hz: 1H); 6.60 (d, J=10 Hz: 1H); 7.18 (broad d, J=7.5 Hz; 4H); from 7.20 to 7.35 (mt: 6H); 7.44 (broad d, J=8 Hz: 2H); 7.73 (broad d, J=8 Hz: 2H); 9.73 (broad s: 1H).

6,6-Diphenyl-1-(4-toluenesulphonyl)-6,7-dihydro-1H-indazol-3-carboxylic acid may be prepared in the following manner:

A solution of 1 g of p-toluenesulphonyl chloride in 10 cm$^3$ of diethyl ether is added, at a temperature in the region of 20° C., to a solution of 1 g of 6,6-diphenyl-6,7-dihydro-1H-indazol-3-carboxylic acid in 10 cm$^3$ of water and 10 cm$^3$ of a normal aqueous sodium hydroxide solution. The reaction mixture, which sets to a solid after about ten minutes of vigorous stirring, is diluted with 10 cm$^3$ of water. After stirring for about eighteen hours at a temperature in the region of 20° C., the reaction mixture is filtered. The solid is washed with three times 20 cm$^3$ of water and then suspended in 20 cm$^3$ of water. 10 cm$^3$ of a normal aqueous hydrochloric acid solution are added. The mixture is extracted with three times 50 cm$^3$ of ethyl acetate. The combined organic phases are successively washed with three times 70 cm$^3$ of water and once 70 cm$^3$ of saturated aqueous sodium chloride solution and then dried over magnesium sulphate, filtered and concentrated under reduced pressure (13 kPa). The residue is purified by flash chromatography on a column of silica [eluent: dichloromethane/methanol (95/5 by volume)]. 0.94 g of 6,6-diphenyl-1-(4-toluenesulphonyl)-6,7-dihydro-1H-indazol-3-carboxylic acid is thus obtained in the form of a solid, the characteristics of which are as follows:

melting point: melting at 246° C. (Köfler block)

$^1$H NMR spectrum: (300 MHz, $(CD_3)_2SO$ d6, δ in ppm): 2.44 (s: 3H); 3.84 (s: 2H); 6.43 (broad d, J=10 Hz: 1H); 6.87 (d, J=10 Hz: 1H); 7.17 (d mt, J=8 Hz: 4H); from 7.20 to 7.35 (mt: 6H); 7.49 (d, J=8 Hz: 2H); 7.83 (d, J=8 Hz: 2H); from 13.00 to 14.00 (very broad unresolved complex: 1H).

Example 7-2

1-(3-Amino-6,6-diphenyl-6,7-dihydroindazol-1-yl)propenone may be prepared in the following manner:

A suspension of 0.260 g of 6,6-diphenyl-6,7-dihydro-1H-indazol-3-ylamine and of 0.15 cm$^3$ [lacuna] in 10 cm$^3$ of dichloromethane is cooled to a temperature in the region of 0° C. 0.09 cm$^3$ of acryloyl chloride is added at this same temperature. After stirring for 2 hours at a temperature in the region of 0° C. and then for 18 hours at a temperature in the region of 20° C., 10 cm³ of dichloromethane and 10 cm³ of water are added. After separation of the phases by settling, the organic phase is washed with 10 cm³ of water and then with 10 cm³ of saturated aqueous sodium chloride solution, and then dried over magnesium sulphate, filtered and concentrated under reduced pressure (13 kPa). After purification by flash chromatography on a column of silica [eluent: cyclohexane/ethyl acetate (85/15 by volume)], 0.02 g of 1-(3-amino-6,6-diphenyl-6,7-dihydroindazol-1-yl)propenone is obtained in the form of a foam, the characteristics of which are as follows:

Rf TLC silica [eluent: cyclohexane/ethyl acetate (70/30 by volume)]=0.57

$^1$H-NMR spectrum: (300 MHz, $(CD_3)_2$SO d6, δ in ppm): 3.23 (s: 2H); 6.06 (dd, J=10.5 and 2 Hz: 1H); 6.12 (d, J=9.5 Hz: 1H); 6.50 (dd, J=17 and 2 Hz: 1H); 6.68 (d, J=9.5 Hz: 1H); 6.95 (broad s: 2H); from 7.15 to 7.30 (mt: 6H); 7.30 (broad t, J=7.5 Hz: 4H); 7.41 (dd, J=17 and 10.5 Hz: 1H).

6,6-Diphenyl-6,7-dihydro-1H-indazol-3-ylamine may be prepared in the following manner:

A suspension of 0.22 g of 6,6-diphenyl-1-(4-toluenesulphonyl)-6,7-dihydro-1H-indazol-3-ylamine and 1.5 cm³ of aqueous 1N sodium hydroxide solution in 5 cm³ of tetrahydrofuran is heated at a temperature in the region of 50° C. for about 24 hours. 5 cm³ of dioxane are added to the preceding mixture and the resulting mixture is heated at a temperature in the region of 100° C. for 2 hours. After concentrating the reaction mixture to dryness under reduced pressure (13 kPa), the residue is taken up in 30 cm³ of ethyl acetate and 30 cm³ of water. The aqueous phase is extracted with twice 30 cm³ of ethyl acetate and the combined organic phases are washed with 30 cm³ of saturated aqueous sodium bicarbonate solution, 30 cm³ of water and 30 cm³ of saturated aqueous sodium chloride solution and then dried over magnesium sulphate, filtered and concentrated under reduced pressure (13 kPa). After purification by flash chromatography on a column of silica [eluent: dichloromethane/methanol (95/5 by volume)], the residue is taken up in 5 cm³ of diisopropyl ether, drained by suction, washed with 2 cm³ of diisopropyl ether and dried under reduced pressure (13 kPa) at a temperature in the region of 30° C. 0.06 g of 6,6-diphenyl-6,7-dihydro-1H-indazol-3-ylamine is thus obtained in the form of a solid, the characteristics of which are as follows:

melting point: melting at 178° C. (Köfler block)

$^1$H NMR spectrum: (300 MHz, $(CD_3)_2$SO d6, δ in ppm): 3.13 (unresolved complex: 2H); from 5.00 to 5.30 (broad unresolved complex: 2H); 5.86 (d, J=9.5 Hz: 1H); 6.54 (d, J=9.5 Hz: 1H); from 7.10 to 7.35 (mt: 10H); from 10.90 to 11.10 (broad unresolved complex: 1H).

Example 7-3

N-(6,6-Diphenyl-6,7-dihydro-1H-indazol-3-yl)cyclopropylamide may be prepared in the following manner:

2.2 cm³ of a normal aqueous sodium hydroxide solution are added to a suspension of N-[6,6-diphenyl-1-(4-toluenesulphonyl)-6,7-dihydro-1H-indazol-3-yl]cyclopropylamide in 10 cm³ of tetrahydrofuran. The mixture is stirred for twenty-two hours at a temperature in the region of 40° C. The reaction mixture is then concentrated to dryness under reduced pressure (13 kPa), the residue is taken up in 10 cm³ of water. The precipitate is drained by suction, washed with four times 5 cm³ of water and then dried under reduced pressure (13 kPa), at a temperature in the region of 50° C. After recrystallization from 17 cm³ of ethanol, the solid is drained by suction, washed with twice 5 cm³ of diethyl ether and then dried under reduced pressure (13 kPa) at a temperature in the region of 70° C. 0.128 g of N-(6,6-diphenyl-6,7-dihydro-1H-indazol-3-yl)cyclopropylamide is thus obtained in the form of a solid, the characteristics of which are as follows:

melting point: melting at 264° C. (Köfler block)

$^1$H NMR spectrum: (300 MHz, $(CD_3)_2$SO d6, δ in ppm): 0.80 (broad d, J=4.5 Hz: 4H); 1.81 (mt: 1H); 3.29 (unresolved complex: 2H); 6.08 (unresolved complex: 1H); 6.73 (d, J=10 Hz: 1H); from 7.15 to 7.35 (mt: 10H); from 10.35 to 11.15 (broad unresolved complex: 1H); 12.22 (unresolved complex: 1H).

N-[6,6-Diphenyl-1-(4-toluenesulphonyl)-6,7-dihydro-1H-indazol-3-yl]cyclopropylamide may be obtained in the following manner:

0.1 cm³ of cyclopropanecarbonyl chloride is added dropwise, in the region of 20° C., to a suspension of 0.44 g of 6,6-diphenyl-1-(4-toluenesulphonyl)-6,7-dihydro-1H-indazol-3-ylamine and 0.15 cm³ of triethylamine in 7 cm³ of dichloromethane. The solution obtained is stirred for about 18 hours at this same temperature, and then washed with 10 cm³ of saturated aqueous sodium hydrogen carbonate solution, 10 cm³ of water and 10 cm³ of saturated aqueous sodium chloride solution, dried over magnesium sulphate, filtered and concentrated under reduced pressure. After flash chromatography on a column of silica [eluent: cyclohexane/ethyl acetate (80/20 by volume)], 0.42 g of N-[6,6-diphenyl-1-(4-toluenesulphonyl)-6,7-dihydro-1H-indazol-3-yl]cyclopropylamide is thus obtained in the form of a solid, the characteristics of which are as follows:

Rf TLC silica [eluent: cyclohexane/ethyl acetate (70/30 by volume)]=0.32 elemental analysis: C, 71.09%; H, 5.67%; N, 7.83%; S, 5.53%.

Calculated for $C_{30}H_{27}N_3O_3S$: C, 70.70%; H, 5.34%; N, 8.25%; S, 6.29%.

Example 7-4

N-[6,6-Diphenyl-6,7-dihydro-1H-indazol-3-yl]benzamide may be prepared as described in Example 7-3:

But starting with 0.14 g of N-[6,6-diphenyl-1-(4-toluenesulphonyl)-6,7-dihydro-1H-indazol-3-yl)benzamide and 0.78 cm³ of aqueous 1N sodium hydroxide solution in 10 cm³ of tetrahydrofuran. 0.27 g of N-(6,6-diphenyl-6,7-dihydro-1H-indazol-3-yl)benzamide is thus obtained in the form of a solid, the characteristics of which are as follows:

melting point: melting at 134° C. (Köfler block)

$^1$H NMR spectrum: (400 MHz, $(CD_3)_2$SO d6 at a temperature of 373 K, δ in ppm): 3.42 (broad s, 2H); 6.12 (broad d, J=9 Hz: 1H); 6.81 (broad d, J=9 Hz: 1H); from 7.15 to 7.35 (mt: 10H); 7.52 (t, J=7.5 Hz: 2H); 7.60 (t, J=7.5 Hz: 1H); 8.00 (d, J=7.5 Hz: 2H).

N-(6,6-Diphenyl-6,7-dihydro-1H-indazol-3-yl)benzamide may be prepared as in Example 7-3:

But starting with 0.3 g of 6,6-diphenyl-1-(4-toluenesulphonyl)-6,7-dihydro-1H-indazole-3ylamine, 0.095 cm³ of triethylamine and 0.088 cm³ of benzoyl chloride in cm³ of dichloromethane. After flash chromatography on a column of silica [eluent: dichloromethane], 0.14 g of N-(6,6-diphenyl-6,7-dihydro-1H-indazol-3-yl)benzamide is thus obtained in the form of a foam, the characteristics of which are as follows:

Rf TLC silica [eluent: dichloromethane]=0.54 mass spectrum

EI m/z=390 $[M-CH_3C_6H_4SO_2]^+$ m/z=105 [C$_6$H$_5$CO]$^+$ base peak
m/z=91 [CH$_2$C$_6$H$_5$]$^+$
DCI m/z=546 MH$^+$ base peak
m/z=392 [MH—CH$_2$C$_6$H$_4$SO$_2$]$^+$ Example 8-1

3-(3-Methyl[1,2,4]oxadiazol-5-yl)-6,6-diphenyl-6,7-dihydro-1H-indazole may be prepared in the following manner:

0.315 cm$^3$ of oxalyl chloride is added to 0.5 g of 6,6-diphenyl-1-(4-toluenesulphonyl)-6,7-dihydro-1H-indazole-3-carboxylic acid suspended in 30 cm$^3$ of dichloromethane. The solution is refluxed for one hour. The mixture is concentrated to dryness under reduced pressure (13 kPa). The residue is taken up in 15 cm$^3$ of pyridine, 0.148 g of N-hydroxyacetamidine is added and the mixture is refluxed for two and a half hours. After returning to a temperature in the region of 20° C., and maintaining at this temperature for about 20 hours, the mixture is concentrated to dryness under reduced pressure (13 kPa). The residue is taken up in 20 cm$^3$ of water. The pH is brought to about 3 by addition of aqueous 2N hydrochloric acid solution and the aqueous phase is extracted with three times 50 cm$^3$ of ethyl acetate. The combined organic phases are dried over magnesium sulphate, filtered and concentrated to dryness under reduced pressure (13 kPa). The residue is purified by flash chromatography on a column of silica [eluent: cyclohexane/ethyl acetate (50/50 by volume)]. 0.184 g of impure 3-(3-methyl[1,2,4]oxadiazol-5-yl)-6,6-diphenyl-6,7-dihydro-1H-indazole is obtained. After a second purification by flash chromatography on a column of silica [eluent: dichloromethane and then dichloromethane/methanol (98/2 by volume)], 0.09 g of 3-(3-methyl[1,2,4]oxadiazol-5-yl)-6,6-diphenyl-6,7-dihydro-1H-indazole is obtained in the form of a white powder, the characteristics of which are as follows:

melting point: melting at 154° C. (Köfler block)
$^1$H NMR spectrum: (300 MHz, (CD$_3$)$_2$SO d6, δ in ppm): 2.41 (s: 3H); 3.51 (s: 2H); 6.47 (broad d, J=10 Hz: 1H); 6.98 (d, J=10 Hz: 1H); from 7.15 to 7.35 (mt: 10H).

N-Hydroxyacetamidine may be prepared under the conditions described by C. D. Clifford (J. Med. Chem. 1986, 29, 11, 2174–2183) starting with acetonitrile and hydroxylamine in the presence of sodium hydroxide in refluxing aqueous ethanol.

Example 8-2

3,6,6-Triphenyl-6,7-dihydro-1H-indazole may be prepared in the following manner:

A mixture of 0.16 g of 3,6,6-triphenyl-1-(2-trimethylsilanylethoxymethyl)-6,7-dihydro-1H-indazole and 3,6,6-triphenyl-2-(2-trimethylsilanylethoxymethyl)-6,7-dihydro-1H-indazole is dissolved in 3.4 cm$^3$ of ethanol and 1 cm$^3$ of water, and 3.4 cm$^3$ of an approximately 2N ethanolic solution of hydrogen chloride are then added. The solution is stirred for about 4 hours at a temperature in the region of 65° C. The reaction mixture is concentrated to dryness under reduced pressure (13 kPa). The residue is taken up in 50 cm$^3$ of water, and the pH is brought to about 10 by addition of aqueous 0.1N sodium hydroxide solution. After extraction with three times 50 cm$^3$ of ethyl acetate, the combined organic phases are washed with 50 cm$^3$ of aqueous 0.1N sodium hydroxide solution, 50 cm$^3$ of water and 50 cm$^3$ of saturated aqueous sodium chloride solution, dried over magnesium sulphate, filtered and concentrated to dryness under reduced pressure (13 kPa). After flash chromatography on a column of silica [eluent: dichloromethane], 0.06 g of 3,6,6-triphenyl-6,7-dihydro-1H-indazole is thus obtained in the form of a solid, the characteristics of which are as follows:

melting point: melting at 104–110° C. (Köfler block)
Rf TLC silica [eluent: dichloromethane]=0.12
$^1$H NMR spectrum: (300 MHz, (CD$_3$)$_2$SO d6, δ in ppm): 3.40 (broad s: 2H); 6.34 (broad d, J=10 Hz: 1H); 6.92 (d, J=10 Hz: 1H); from 7.10 to 7.35 (mt: 10H); 7.36 (broad t, J=7 Hz: 1H); 7.48 (broad t, J=7 Hz: 2H); 7.64 (broad d, J=7 Hz: 2H); 12.80 (broad s: 1H).

The mixture of 3,6,6-triphenyl-1-(2-trimethylsilanylethoxymethyl)-6,7-dihydro-1H-indazole and 3,6,6-triphenyl-2-(2-trimethylsilanylethoxymethyl)-6,7-dihydro-1H-indazole may be obtained in the following manner:

A solution of 0.4 g of a mixture of 3-iodo-6,6-diphenyl-1-(2-trimethylsilanylethoxymethyl)-6,7-dihydro-1H-indazole and 3-iodo-6,6-diphenyl-2-(2-trimethylsilanylethoxymethyl)-6,7-dihydro-1H-indazole in 9.6 cm$^3$ of toluene and 0.4 cm$^3$ of ethanol is degassed by bubbling argon through for about 1 hour. 0.055 g of tetrakis(triphenylphosphine)palladium, 0.19 g of phenylboronic acid and 0.19 g of sodium hydrogen carbonate dissolved in 3.2 cm$^3$ of water are added to the above mixture. The mixture is refluxed for about 4 hours. After the temperature has returned to the region of 20° C., 15 cm$^3$ of water and 25 cm$^3$ of ethyl acetate are added to the mixture. The aqueous phase is re-extracted with twice 25 cm$^3$ of ethyl acetate. The combined organic phases are washed with twice 50 cm$^3$ of water, dried over magnesium sulphate, filtered and concentrated to dryness under reduced pressure (13 kPa). After flash chromatography on a column of silica [eluent: dichloromethane], 0.162 g of a mixture of 3,6,6-triphenyl-1-(2-trimethylsilanylethoxymethyl)-6,7-dihydro-1H-indazole and 3,6,6-triphenyl-2-(2-trimethylsilanylethoxymethyl)-6,7-dihydro-1H-indazole is thus obtained, the characteristics of which are as follows:

Rf TLC silica [eluent: dichloromethane]=0.39 and 0.50
A mixture of 3-iodo-6,6-diphenyl-1-(2-trimethylsilanylethoxymethyl)-6,7-dihydro-1H-indazole and 3-iodo-6,6-diphenyl-2-(2-trimethylsilanylethoxymethyl)-6,7-dihydro-1H-indazole may be prepared in the following manner:

A solution of 0.85 g of 3-iodo-6,6-diphenyl-6,7-dihydro-1H-indazole in 7 cm$^3$ of dimethylformamide is added dropwise to a suspension of 0.112 g of sodium hydride (at 60% in oil) in 3 cm$^3$ of dimethylformamide cooled to a temperature in the region of 0° C. After stirring the mixture for about 1 hour 30 minutes and then cooling to a temperature in the region of 0° C., 0.565 cm$^3$ of (2-chloromethoxyethyl)trimethylsilane is added dropwise. The mixture obtained is stirred for about 20 hours in the region of 20° C., poured into 20 cm$^3$ of an ice plus water mixture and extracted with three times 50 cm$^3$ of ethyl acetate. The combined organic phases are washed three times with 50 cm$^3$ of water, dried over magnesium sulphate, filtered and concentrated to dryness under reduced pressure (13 kPa). 1.12 g of a mixture of 3-iodo-6,6-diphenyl-1-(2-trimethylsilanylethoxymethyl)-6,7-dihydro-1H-indazole and 3-iodo-6,6-diphenyl-2-(2-trimethylsilanylethoxymethyl)-6,7-dihydro-1H-indazole are thus obtained in the form of a resin, the characteristics of which are as follows:

Rf TLC silica [eluent: dichloromethane]=0.65 and 0.74
mass spectrum
EI m/z=528 M$^+$ base peak
m/z=441 [M-OCH$_2$CH$_2$Si(CH$_3$)$_3$]$^+$
m/z=285 [412-I]$^+$
m/z=73 [Si(CH$_3$)$_3$]$^+$ 3-Iodo-6,6-diphenyl-6,7-dihydro-1H-indazole may be prepared in the following manner:

3 cm³ of aqueous 1N sodium hydroxide solution are added to a solution of 0.55 g of 3-iodo-6,6-diphenyl-1-(4-toluenesulphonyl)-6,7-dihydro-1H-indazole in 10 cm³ of tetrahydrofuran. After stirring for about 36 hours at a temperature in the region of 20° C., 30 cm³ of ethyl acetate are added. After separation of the phases by settling, the organic phase is washed with three times 15 cm³ of water, 20 cm³ of saturated aqueous sodium chloride solution, dried over magnesium sulphate, filtered and concentrated to dryness under reduced pressure (13 kPa). 0.436 g of 3-iodo-6,6-diphenyl-6,7-dihydro-1H-indazole is obtained in the form of a solid, the characteristics 30' of which are as follows:

Rf TLC silica [eluent: cyclohexane/ethyl acetate (70/30 by volume)]=0.27 mass spectrum
EI m/z=398 M⁺ base peak
m/z=271 [M-I]⁺
m/z=194 [271-C₆H₅]⁺
m/z=77 [C₃H₅]⁺

3-Iodo-6,6-diphenyl-1-(4-toluenesulphonyl)-6,7-dihydro-1H-indazole may be prepared in the following manner:

1.21 cm³ of isoamyl nitrite are added to a solution of 1 g of 6,6-diphenyl-1-(4-toluenesulphonyl)-6,7-dihydro-1H-indazol-3-ylamine in 10 cm³ of diiodomethane, and the solution obtained is heated in the region of 80° C. for one hour. The mixture is purified directly by flash chromatography on a column of silica [eluent: cyclohexane/ethyl acetate (95/5 by volume)], and 0.6 g of 3-iodo-6,6-diphenyl-1-(4-toluenesulphonyl)-6,7-dihydro-1H-indazole is obtained in the form of a solid, the characteristics of which are as follows:

melting point: melting at 190° C. (Köfler block)
mass spectrum
EI m/z=552 M⁺ base peak
m/z=398 [M-CH₂C₆H₄SO₂]⁺
m/z=320 [398-C₆H₆]⁺
m/z=269 [398-I]⁺
m/z=91 [CH₂C₆H₅]⁺

Example 8-3

6,6-Diphenyl-3-pyrid-3-yl-6,7-dihydro-1H-indazole may be prepared in the following manner:

Aqueous 1N sodium hydroxide solution is added to a solution of 0.08 g of 6,6-diphenyl-3-pyrid-3-yl-1-(4-toluenesulphonyl)-6,7-dihydro-1H-indazole in 2 cm³ of tetrahydrofuran. After stirring in the region of 40° C. for about 20 hours, the mixture is concentrated to dryness under reduced pressure (13 kPa). The residue is taken up in 20 cm³ of ethyl acetate. The solution obtained is washed with twice 10 cm³ of water and with 10 cm³ of saturated aqueous sodium chloride solution, dried over magnesium sulphate, filtered and concentrated under reduced pressure (13 kPa). The residue is taken up in 2 cm³ of diisopropyl ether and drained by suction. 0.035 g of 6,6-diphenyl-3-pyrid-3-yl-6,7-dihydro-1H-indazole is thus obtained in the form of a solid, the characteristics of which are as follows:

melting point: melting at 222° C. (Köfler block)
¹H NMR spectrum: (300 MHz, (CD₃)₂SO d6, δ in ppm): 3.44 (s: 2H); 6.34 (broad d, J=10 Hz: 1H); 6.95 (d, J=10 Hz: 1H); from 7.10 to 7.35 (mt: 11H); 7.49 (mt: 1H); 8.03 (broad d, J=8 Hz: 1H); 8.55 (broad d, J=4.5 Hz: 1H); 12.96 (unresolved complex: 1H).

6,6-Diphenyl-3-pyrid-3-yl-1-(4-toluenesulphonyl)-6,7-dihydro-1H-indazole may be prepared in the following manner:

A solution of 0.5 g of 3-iodo-6,6-diphenyl-1-(4-toluenesulphonyl)-6,7-dihydro-1H-indazole in 8 cm³ of tetrahydrofuran is degassed by bubbling argon through for about 1 hour. 0.133 g of 3-pyridylboronic acid, 0.052 g of tetrakis (triphenylphosphine)palladium and 0.206 g of copper 2-thiophenecarboxylate are added to this solution. The mixture obtained is stirred for about 30 hours in the region of 40° C. After the temperature has returned to the region of 20° C., the suspension is filtered and the filtrate is concentrated to dryness under reduced pressure (13 kPa). After flash chromatography on a column of silica [eluent: dichloromethane], 0.82 g of 6,6-diphenyl-3-pyrid-3-yl-1-(4-toluenesulphonyl)-6,7-dihydro-1H-indazole is thus obtained in the form of a foam, the characteristics of which are as follows:

Rf TLC silica [eluent: dichloromethane/methanol (95/5 by volume)]=0.62 mass spectrum
EI m/z=503 M⁺
m/z=348 [M-CH₃C₆H₄SO₂]⁺ base peak
m/z=271 [348-C₆H₅]⁺

Example 8-4

6,6-Diphenyl-3-thiophen-3-yl-6,7-dihydro-1H-indazole may be prepared as in Example 8-2:

But starting with 0.107 g of a mixture of 6,6-diphenyl-3-thiophen-3-yl-1-(2-trimethylsilanylethoxymethyl)-6,7-dihydro-1H-indazole and 6,6-diphenyl-3-thiophen-3-yl-2-(2-trimethylsilanylethoxymethyl)-6,7-dihydro-1H-indazole, 2.2 cm³ of ethanol and 2.2 cm³ of a 2N ethanolic solution of hydrogen chloride. After flash chromatography on a column of silica [eluent: dichloromethane], 0.024 g of 6,6-diphenyl-3-thiophen-3-yl-6,7-dihydro-1H-indazole is thus obtained in the form of a solid, the characteristics of which are as follows:

Rf TLC silica [eluent: dichloromethane/methanol (90/10 by volume)]=0.62

¹H NMR spectrum: (300 MHz, (CD₃)₂SO d6, δ in ppm): 3.37 (s: 2H); 6.30 (d, J=10 Hz: 1H); 6.95 (d, J=10 Hz: 1H); from 7.10 to 7.35 (mt: 10H); 7.49 (dd, J=4.5 and 1.5 Hz: 1H); 7.67 (dd, J=5 and 3 Hz: 1H); 7.82 (broad d, J=3 Hz: 1H); 12.68 (unresolved complex: 1H).

A mixture of 6,6-diphenyl-3-thiophen-3-yl-1-(2-trimethylsilanylethoxymethyl)-6,7-dihydro-1H-indazole and 6,6-diphenyl-3-thiophen-3-yl-2-(2-trimethylsilanylethoxymethyl)-6,7-dihydro-1H-indazole may be prepared as in Example 8-2:

But starting with 0.2 g of a mixture of 3-iodo-6,6-diphenyl-1-(2-trimethylsilanylethoxymethyl)-6,7-dihydro-1H-indazole and 3-iodo-6,6-diphenyl-2-(2-trimethylsilanylethoxymethyl)-6,7-dihydro-1H-indazole, 0.027 g of tetrakis-(triphenylphosphine)palladium, 0.066 g of 3-thiopheneboronic acid and 0.095 g of sodium hydrogen carbonate dissolved in 1.6 cm³ of water in 4.8 cm³ of toluene and 1.6 cm³ of water. After flash chromatography on a column of silica [eluent: cyclohexane/ethyl acetate (90/10 by volume)], 0.107 g of a mixture of 6,6-diphenyl-3-thiophen-3-yl-1-(2-trimethylsilanylethoxymethyl)-6,7-dihydro-1H-indazole and 6,6-diphenyl-3-thiophen-3-yl-2-(2-trimethylsilanylethoxymethyl)-6,7-dihydro-1H-indazole is thus obtained in the form of a resin, the characteristics of which are as follows:

Rf TLC silica [eluent: dichloromethane]=0.42
mass spectrum
EI m/z=484 M+
m/z=367 [M-OCH$_2$CH$_2$Si(CH$_3$)$_3$]+ base peak
m/z=73 [Si(CH$_3$)$_3$]+

Example 9-1

Ethyl 6-(R,S)-6-methyl-6-phenyl-6,7-dihydro-1H-indazole-3-carboxylate may be prepared in the following manner:

0.43 cm$^3$ of phosphorus oxychloride is added dropwise to a solution, cooled to −10° C., of 350 mg of ethyl 4-(R,S)-diazo(1-hydroxy-4-methyl-4-phenylcyclohex-2-enyl)acetate in 3.5 cm$^3$ of pyridine. The reaction mixture is stirred at −10° C. for 2 hours and then poured onto about 50 g of crushed ice. The resulting mixture is extracted with [lacuna] times 20 cm$^3$ of dichloromethane. The organic phase thus obtained is washed with twice 20 cm$^3$ of distilled water, dried over magnesium sulphate and then concentrated to dryness under reduced pressure. The residue is purified by flash chromatography on silica gel (35–70 μm), eluting with a cyclohexane/ethyl acetate (80/20) mixture to give 60 mg of ethyl 6-(R,S)-6-methyl-6-phenyl-6,7-dihydro-1H-indazole-3-carboxylate in the form of a colourless lacquer, the characteristics of which are as follows:

Rf TLC silica [eluent: cyclohexane/ethyl acetate (80/20)]=0.27
$^1$H NMR spectrum: (300 MHz, (CD$_3$)$_2$SO d6, δ in ppm): 1.32 (t, J=7 Hz: 3H); 1.46 (s: 3H); 2.90 (broad d, J=16 Hz: 1H); 3.04 (d, J=16 Hz: 1H); 4.31 (q, J=7 Hz: 2H); 5.98 (unresolved complex: 1H); 6.78 (d, J=10 Hz: 1H); 7.21 (tt, J=7.5 and 1.5 Hz: 1H); 7.30 (broad t, J=7.5 Hz: 2H); 7.42 (d mt, J=7.5 Hz: 2H); 13.35 (unresolved complex: 1H).

4-(R,S)-Diazo-(1-hydroxy-4-methyl-4-phenylcyclohex-2-enyl)acetic acid may be prepared in the following manner:

0.56 cm$^3$ of ethyl diazoacetate is added to a solution, cooled to −78° C., of 1 g of 4-(R,S)-4-methyl-4-phenylcyclohex-2-enone in 45 cm$^3$ of tetrahydrofuran, followed by slow addition of 3.5 cm$^3$ of commercial lithium diisopropylamide as a 2 M solution in hexane. The reaction mixture is then stirred at a temperature in the region of −78° C. for 2 hours, followed by adding 1 cm$^3$ of glacial acetic acid, warming to the region of 20° C. and adding 100 cm$^3$ of distilled water. The mixture obtained is extracted with three times 50 cm$^3$ of ethyl acetate. The organic phases are combined and washed with twice 60 cm$^3$ of distilled water, dried over magnesium sulphate and then concentrated to dryness under reduced pressure. The residue obtained is purified by flash chromatography on basic alumina, eluting with a cyclohexane/ethyl acetate (95/05) mixture; 622 mg of ethyl 4-(R,S)-diazo-(1-hydroxy-4-methyl-4-phenylcyclohex-2-enyl)acetate are thus obtained in the form of a yellow oil, the characteristics of which are as follows:

Rf TLC silica eluent: cyclohexane/ethyl acetate (95/05)−0.45
mass spectrum (EI, DCI, IS): M/Z=301 (MH+)
4-(R,S)-4-Methyl-4-phenylcyclohex-2-enone may be obtained in the following manner:

7 cm$^3$ of methyl vinyl ketone and 1.66 g of potassium hydroxide pellets dissolved in 10 cm$^3$ of ethanol are successively added to a solution, cooled to 0° C., of 10 g of 2-phenylpropionaldehyde in 100 cm$^3$ of ethyl ether. After addition, the temperature of the reaction mixture is maintained at about 0° C. for 3 hours and is then brought to the region of 20° C. and maintained at this value for 24 hours. 50 cm$^3$ of distilled water are then added and the mixture obtained is extracted with twice 25 cm$^3$ of ethyl ether and with once 25 cm$^3$ of ethyl acetate. The organic phases are combined and washed with three times 20 cm$^3$ of distilled water, dried over magnesium sulphate and then concentrated to dryness under reduced pressure. The residue is purified by flash chromatography on a silica gel (20 μm), eluting with a cyclohexane-ethyl acetate (95/05) mixture to give 4 g of 4-(R,S)-4-methyl-4-phenylcyclohex-2-enone in the form of a pale yellow oil, the characteristics of which are as follows:

Rf TLC silica eluent: cyclohexane/ethyl acetate (95/05)=0.1
$^1$H NMR spectrum: (300 MHz, CDCl$_3$, δ in ppm): 1.58 (s: 3H); from 2.05 to 2.50 (mt: 4H); 6.14 (d, J=10.5 Hz: 1H); 7.38 (broad d, J=10.5 Hz: 1H); from 7.20 to 7.45 (mt: 5H).

Example 9-2

The isolation of the dextrorotatory enantiomer of ethyl 6-(R,S)-6-methyl-6-phenyl-6,7-dihydro-1H-indazole-3-carboxylate may be performed in the following manner:

480 mg of the racemic mixture of ethyl 6-(R,S)-6-methyl-6-phenyl-6,7-dihydro-1H-indazole-3-carboxylate, obtained in Example 9-1, are resolved on a Chiracel OJ™ chiral column, in 1 injection and by eluting with a mixture of n-heptane/ethanol/isopropanol/triethylamine (90/5/5/0.1 by volume). By collecting the second eluted fraction (retention time 45 min), and after concentration of the solvent under reduced pressure, 107 mg of the dextrorotatory enantiomer of ethyl 6-methyl-6-phenyl-6,7-dihydro-1H-indazole-3-carboxylate are obtained in the form of a beige-coloured oil, the characteristics of which are as follows:

analytical HPLC: retention time=21 min (stationary phase: Chiracel OJ, length 25 cm; mobile phase: mixture of n-heptane/ethanol/isopropanol/triethylamine 90/5/5/0.1 by volume, flow rate 1 ml/min).

$^1$H NMR spectrum: (300 MHz, (CD$_3$)$_2$SO d6, δ in ppm): 1.32 (t, J=7 Hz: 3H); 1.45 (s: 3H); 2.88 (broad d, J=16.5 Hz: 1H); 3.13 (d, J=16.5 Hz: 1H); 4.30 (broad q, J=7 Hz: 2H); 5.97 (unresolved complex: 1H); 6.77 (d, J=10 Hz: 1H); 7.20 (broad t, J=7.5 Hz: 1H); 7.31 (broad t, J=7.5 Hz: 2H); 7.41 (broad d, J=7.5 Hz: 2H); 13.37 (unresolved complex: 1H).

Example 9-3

The eutomer of ethyl 6-(R,S)-6-phenyl-6,7-dihydro-2H-indazole-3-carboxylate may be obtained in the following manner:

300 mg of the racemic mixture of ethyl 6-(R,S)-6-phenyl-6,7-dihydro-2H-indazole-3-carboxylate obtained in Example 9-3 are resolved on a Chiralpak AD chiral column, in 1 injection and by eluting with a mixture of n-heptane/ethanol (60/40 by volume).

By collecting the second eluted fraction (retention time 60 min), and after concentration of the solvent under reduced pressure, 49.6 mg of the eutomer of ethyl 6-phenyl-6,7-dihydro-2H-indazole-3-carboxylate are obtained in the form of a yellow oil, the characteristics of which are as follows:

analytical HPLC: retention time=161 min (stationary phase: Chiralpak, length 25 cm; mobile phase: 60/40 mixture by volume of n-heptane/ethanol, flow rate 1 ml/min).

$^1$H NMR spectrum: (300 MHz, (CD$_3$)$_2$SO d6, δ in ppm): 1.34 (t, J=7 Hz: 3H); 2.82 (dd, J=16 and 9.5 Hz: 1H); 3.13 (dd, J=16 and 8 Hz: 1H); 3.90 (mt: 1H); 4.32 (q, J=7 Hz: 2H); 5.94 (unresolved complex: 1H); 6.83 (dd, J=10 and 1.5 Hz: 1H); from 7.20 to 7.40 (mt: 5H); 13.40 (unresolved complex: 1H).

Ethyl 6-(R,S)-phenyl-6,7-dihydro-2H-indazole-3-carboxylate may be obtained in the following manner:

1.15 cm³ of ethyl diazoacetate is added dropwise, at −78° C., to a solution of 2 g of 4-phenylcyclohex-2-enone in 2 cm³ of tetrahydrofuran, followed by slow addition of 30 cm³ of lithium diisopropylamide solution prepared beforehand from 8 cm³ of 1.6 M n-butyllithium in hexane and 2 cm³ of diisopropylamine in solution in 20 cm³ of tetrahydrofuran. After stirring the reaction mixture at a temperature in the region of −78° C. for 4 hours, 1.6 cm³ of glacial acetic acid are added and the temperature of the reaction mixture is allowed to rise to the region of 20° C. 20 cm³ of toluene are then added and the resulting mixture is successively washed with 20 cm³ of saturated aqueous sodium bicarbonate solution and 20 cm³ of water. The organic phase obtained is concentrated under reduced pressure to remove the tetrahydrofuran. The resulting toluene solution is refluxed for 4 hours in a round-bottomed flask equipped with a Dean-Stark trap and then concentrated to dryness under reduced pressure. The residue obtained is purified by flash chromatography on silica gel (35–70 μm), eluting with a cyclohexane/ethyl acetate (80/20) mixture to give 320 mg of ethyl 6-(R,S)-6-phenyl-6,7-dihydro-2H-indazole-3-carboxylate in the form of a yellow oil, the characteristics of which are as follows:

Tf TLC silica: [eluent: cyclohexane/ethyl acetate (70/30)] =0.64

$^1$H NMR spectrum: (300 MHz, $(CD_3)_2SO$ d6 with addition of a few drops of $CD_3COOD$ d4, δ in ppm): 1.33 (t, J=7 Hz: 3H); 2.82 (dd, J=16 and 9.5 Hz: 1H); 3.13 (dd, J=16 and 8 Hz: 1H); 3.90 (mt: 1H); 4.12 (q, J=7 Hz: 2H); 5.90 (dd, J=10 and 4 Hz: 1H); 6.84 (dd, J=10 and 1.5 Hz: 1H); from 7.20 to 7.40 (mt: 5H).

4-Phenylcyclohex-2-enone may be prepared in the following manner:

A mixture of 19.5 cm³ of phenylacetaldehyde, 16.7 cm³ of methyl vinyl ketone, 0.17 cm³ of 36% sulphuric acid and 85 cm³ of toluene is heated for 1 hour at a temperature in the region of the reflux temperature. After cooling to a temperature in the region of 20° C., 50 cm³ of ethyl acetate are added to the reaction mixture. The resulting mixture is washed with 100 cm³ of saturated aqueous sodium bicarbonate solution and then dried over magnesium sulphate, filtered and concentrated to dryness under reduced pressure. The residue is purified by flash chromatography on a column of silica [eluent: cyclohexane/ethyl acetate (90/10)] to give 4.7 g of 4-phenylcyclohex-2-enone in the form of a yellow oil, the characteristics of which are as follows:

Rf TLC silica eluent: cyclohexane/ethyl acetate (80/20) =0.38

$^1$H NMR spectrum: (300 MHz, $(CD_3)_2SO$ d6, δ in ppm): 1.97 (mt: 1H); from 2.20 to 2.65 (mt: 3H); 3.86 (mt: 1H); 6.08 (dd, J=10 and 3 Hz: 1H); 7.07 (ddd, J=10–3 and 1.5 Hz; 1H): from 7.20 to 7.35 (mt: 3H); 7.38 (broad t, J=7.5 Hz: 2H).

Example 10-1

Ethyl 6,6-bis(4-methoxyphenyl)-6,7-dihydro-1H-indazole-3-carboxylate may be obtained in the following manner:

0.9 cm³ of ethyl diazoacetate is added, dropwise, to a solution, cooled to −78° C., of 2 g of 4,4-bis(4-methoxyphenyl)cyclohex-2-enone in 50 cm³ of tetrahydrofuran, followed by slow addition of 13 cm³ of a lithium diisopropylamide solution prepared beforehand from 6.5 cm³ of 1.6 M n-butyllithium in hexane and 1.46 cm³ of diisopropylamine in solution in 15 cm³ of tetrahydrofuran. After stirring the reaction mixture at a temperature in the region of −70° C. for 3 hours, 1.2 cm³ of glacial acetic acid are added and the temperature is allowed to rise to the region of 20° C. 250 cm³ of ethyl ether are then added and the resultant mixture is then washed with twice 200 cm³ of distilled water and then dried over sodium sulphate and concentrated to dryness under reduced pressure. The residue is dissolved in 65 cm³ of toluene and then heated at a temperature in the region of 110° C. for 1.5 hours, followed by concentrating to dryness under reduced pressure. The residue obtained is purified by flash chromatography on a silica gel (35–70 μm), eluting with a cyclohexane/ethyl acetate (70/30) mixture to give 0.48 g of ethyl 6,6-bis(4-methoxyphenyl)-6,7-dihydro-1H-indazole-3-carboxylate in the form of a yellow foam, the characteristics of which are as follows:

Rf TLC silica eluent: cyclohexane/ethyl acetate (70/30) =0.15

$^1$H NMR spectrum: (300 MHz, $(CD_3)_2SO$ d6, δ in ppm): 1.31 (t, J=7 Hz: 3H); 3.32 (broad s: 2H); 3.72 (s: 6H); 4.29 (broad q, J=7 Hz: 2H); 6.26 and 6.46 (respectively unresolved complex and broad d, J=10 Hz: 1H in total); 6.80 (d, J=10 Hz: 1H); 6.84 (d, J=8.5 Hz: 4H); 7.11 (broad d, J=8.5 Hz: 4H); 13.37 and 13.41 (2 unresolved complexes: 1H in total).

4,4-bis(4-Methoxyphenyl)cyclohex-2-enone may be obtained according to Chem. Abstr., 64, 2004h. 1966.

Example 10-2

Ethyl 6-(R,S)-6-(3,4-dimethoxyphenyl)-6-phenyl-6,7-dihydro-1H-indazole-3-carboxylate may be obtained in the following manner:

0.44 cm³ of ethyl diazoacetate is added dropwise to a solution, cooled to −70° C., of 1 g of 4-(R,S)-4-(3,4-dimethoxyphenyl)-4-phenylcyclohex-2-enone in 10 cm³ of tetrahydrofuran, followed by slow addition of 2.3 cm³ of commercial lithium diisopropylamide as a 2 M solution in tetrahydrofuran. After stirring the reaction mixture at a temperature in the region of −70° C. for 5 hours, 0.38 cm³ of glacial acetic acid is added and the temperature is allowed to rise to the region of 20° C. 40 cm³ of ethyl acetate are then added and the resulting mixture is washed with twice 30 cm³ of distilled water and then dried over sodium sulphate and concentrated to dryness under reduced pressure. The residue obtained is purified by flash chromatography on silica gel (35–70 μm), eluting with a dichloromethane/ethyl acetate (98/02 to 90/10) gradient mixture to give 80 mg of ethyl 6-(R,S)-6-(3,4-dimethoxyphenyl)-6-phenyl-6,7-dihydro-1H-indazole-3-carboxylate in the form of a white foam, the characteristics of which are as follows:

Rf TLC silica eluent: dichloromethane/ethyl acetate (90/10)=0.12

$^1$H NMR spectrum: (400 MHz, $(CD_3)_2SO$ d6, δ in ppm): 1.30 (t, J=7 Hz: 3H); 3.39 (broad s: 2H); 3.64 (s: 3H); 3.72 (s: 3H); 4.29 (q, J=7 Hz: 2H); 6.47 (broad d, J=10 Hz: 1H); 6.70 (dd, J=8.5 and 2 Hz: 1H); 6.76 (d, J=2 Hz: 1H); 6.83 (d, J=10 Hz: 1H); 6.84 (d, J=8.5 Hz: 1H); from 7.15 to 7.25 (mt: 3H); 7.29 (broad t, J=7.5 Hz: 2H); from 13.40 to 13.60 (broad unresolved complex: 1H).

4-(R,S)-4-(3,4-Dimethoxyphenyl)-4-phenylcyclohex-2-enone may be obtained in the following manner:

5.85 cm³ of methyl vinyl ketone and 1.3 g of potassium hydroxide pellets dissolved in 7 cm³ of ethanol are successively added to a solution, cooled to 0° C., of 15.2 g of (R,S)-(3,4-dimethoxyphenyl)phenylacetaldehyde in 120 cm³ of ethyl ether. The resulting mixture is left at a temperature in the region of 20° C. for 4 hours. The reaction mixture is then concentrated to dryness under reduced pressure. The residue is dissolved in 500 cm³ of dichloromethane and the resulting solution is washed with twice 400 cm³ of distilled water and with once 400 cm³ of saturated aqueous sodium chloride solution. The organic phase thus obtained is dried over magnesium sulphate and then concentrated to dryness under reduced pressure. The residue is purified by flash chromatography on silica gel (30–70 µm), eluting with a cyclohexane/ethyl acetate (85/15) mixture to give 8.3 g of 4-(R,S)-4-(3,4-dimethoxyphenyl)-4-phenylcyclohex-2-enone in the form of a viscous yellow oil, the characteristics of which are as follows:

Rf TLC silica eluent: cyclohexane/ethyl acetate (70/30) =0.23 mass spectrum (EI): M/Z=309 (MH⁺)

¹H NMR spectrum: (300 MHz, (CD₃)₂SO d6, δ in ppm): 2.29 (mt: 2H); 2.66 (mt: 2H); 3.69 (s: 3H); 3.75 (s: 3H); 6.13 (d, J=10.5 Hz; 1H); 6.80 (mt: 2H); 6.94 (mt: 1H); from 7.20 to 7.35 (mt: 3H); 7.36 (broad t, J=7.5 Hz: 2H); 7.57 (broad d, J=10.5 Hz: 1H).

(R,S)-(3,4-Dimethoxyphenyl)phenylacetaldehyde may be obtained in the following manner:

A mixture of 47.85 g of 1-(R,S)-1-(3,4-dimethoxyphenyl)-2-methoxy-1-phenylethanol and 50 cm³ of formic acid is refluxed for 13 hours. The reaction mixture is then poured into 750 cm³ of saturated aqueous sodium carbonate solution and the resulting mixture is extracted with three times 400 cm³ of ethyl acetate. The organic phases are combined, washed with twice 500 cm³ of distilled water and with once 300 cm³ of saturated aqueous sodium chloride solution and then dried over magnesium sulphate and concentrated to dryness under reduced pressure. The residue is purified by flash chromatography on a silica gel (35–70 µm), eluting with a cyclohexane-ethyl acetate (85/15) mixture to give 15.2 g of (R,S)-(3,4-dimethoxyphenyl)phenylacetaldehyde in the form of a colourless viscous oil, the characteristics of which are as follows:

Rf TLC silica eluent: cyclohexane-ethyl acetate (70/30) =0.22 mass spectrum (EI): M/Z=257 (MH⁺)

1-(R,S)-1-(3,4-Dimethoxyphenyl)-2-methoxy-1-phenylethanol may be obtained in the following manner:

7.4 cm³ of 4-bromo-1,2-dimethoxybenzene in solution in 10 cm³ of tetrahydrofuran are added to a mixture of 1.56 g of magnesium, 2 cm³ of 4-bromo-1,2-dimethoxybenzene and 5 cm³ of tetrahydrofuran heated to a temperature in the region of 60° C. The resulting mixture is heated at a temperature in the region of 60° C. for 2 hours. 3 cm³ of 2-methoxyacetophenone in solution in 15 cm³ of tetrahydrofuran are added to the solution thus obtained, cooled to a temperature in the region of 20° C. After stirring for 24 hours at a temperature in the region of 20° C., the reaction mixture is poured into saturated aqueous ammonium chloride solution. The mixture thus obtained is extracted with twice 50 cm³ of ethyl acetate. The organic phases are washed with twice 100 cm³ of distilled water and then dried over magnesium sulphate and concentrated to dryness under reduced pressure. The residue obtained is purified by flash chromatography on a silica gel (35–70 µm), eluting with a cyclohexane/ethyl acetate (80/20) mixture to give 4.3 g of 1-(R,S)-1-(3,4-dimethoxyphenyl)-2-methoxy-1-phenylethanol in the form of a yellow solid, the characteristics of which are as follows:

melting point: 66–68° C. (Köfler block)

mass spectrum (EI): M/Z=289 (MH⁺)

Example 10-3

Ethyl(R,S)-6-(4-fluorophenyl)-6-phenyl-6,7-dihydro-1H-indazole-3-carboxylate may be prepared in the following manner:

0.5 cm³ of ethyl diazoacetate is added dropwise to a solution, cooled to −70° C., of 1 g of 4-(4-fluorophenyl)-4-phenylcyclohex-2-enone in 10 cm³ of tetrahydrofuran, followed by slow addition of 14.64 cm³ of lithium diisopropylamide solution prepared from 3.8 cm³ of 1.6 M n-butyllithium and 0.84 cm³ of diisopropylamine in solution in 10 cm³ of tetrahydrofuran. After stirring the reaction mixture at a temperature in the region of −70° C. for 4 hours, 0.44 cm³ of glacial acetic acid are added and the temperature is allowed to rise to the region of 20° C. 100 cm³ of ethyl ether are added and the organic phases are then washed with four times 50 cm³ of distilled water, dried over sodium sulphate and concentrated to dryness under reduced pressure. The residue is dissolved in 60 Cm³ of toluene, heated at a temperature in the region of 110° C. for 3 hours and then concentrated to dryness under reduced pressure. The residue obtained is purified by flash chromatography on silica gel (35–70 µm), eluting with a cyclohexane/ethyl acetate (80/20) mixture; 0.3 g of ethyl (R,S)-6-(4-fluorophenyl)-6-phenyl-6,7-dihydro-1H-indazole-3-carboxylate, corresponding to Example 10-3A, is thus obtained in the form of a white powder, the characteristics of which are as follows:

melting point=105° C. (Köfler block)

Rf TLC silica eluent: dichloromethane/ethyl acetate (70/30)=0.3

¹H NMR spectrum: (300 MHz, (CD₃)₂SO d6, δ in ppm): 1.31 (t, J=7.5. Hz: 3H); 3.41 (s: 2H); 4.29 (q, J=7.5 Hz: 2H); 6.48 (d, J=10 Hz: 1H); 6.86 (d, J=10 Hz: 1H); 7.12 (broad t, J=9 Hz: 2H); from 7.15 to 7.35 (mt: 7H).

Isolation of the enantiomers of ethyl (R,S)-6-(4-fluorophenyl)-6-phenyl-6,7-dihydro-1H-indazole-3-carboxylate:

200 mg of ethyl (R,S)-6-(4-fluorophenyl)-6-phenyl-6,7-dihydro-1H-indazole-3-carboxylate are resolved on a Chiracel OJ™ chiral column by injection and by eluting with a heptane/ethanol/triethylamine (85/15/0.05 by volume) mixture.

By collecting the first eluted fraction (retention time 17.7 min), and after concentration of the solvent under reduced pressure, 98.1 mg of the laevorotatory enantiomer of ethyl 6-(4-fluorophenyl)-6-phenyl-6,7-dihydro-1H-indazole-3-carboxylate, corresponding to Example 10-3B, are obtained in the form of a pink powder, the characteristics of which are as follows:

¹H NMR spectrum: (300 MHz, (CD₃)₂SO d6, δ in ppm): 1.31 (t, J=7.5 Hz: 3H); 3.41 (s: 2H); 4.29 (q, J=7.5 Hz: 2H); 6.48 (broad d, J=10 Hz: 1H); 6.87 (d, J=10 Hz: 1H); 7.12 (broad t, J=9 Hz: 2H); from 7.15 to 7.35 (mt: 7H); 13.46 (unresolved complex: 1H).

optical rotation: $\alpha_D^{20}$ (c=0.5/DMSO)=−25.7+/−0.9

By collecting the second eluted fraction (retention time 21.4 min), and after concentration of the solvent under reduced pressure, 97 mg of the dextrorotatory enantiomer of ethyl 6,6-(4-fluorophenyl)-6-phenyl-6,7-dihydro-1H-indazole-3-carboxylate, corresponding to Example 10-3C, are obtained in the form of a pink powder, the characteristics of which are as follows:

¹H NMR spectrum: (300 MHz, (CD₃)₂SO d6, δ in ppm): 1.31 (t, J=7.5 Hz: 3H); 3.41 (s: 2H); 4.29 (q, J=7.5 Hz: 2H); 6.48 (broad d, J=10 Hz: 1H); 6.87 (d, J=10 Hz: 1H); 7.12 (broad t, J=9 Hz: 2H); from 7.15 to 7.35 (mt: 7H); 13.46 (unresolved complex: 1H).

optical rotation: $\alpha_D^{20}$ (c=0.5/DMSO)=+20.5+/−0.8

4-(4-Fluorophenyl)-4-phenylcyclohex-2-enone may be prepared in the following manner:

3.5 cm³ of methyl vinyl ketone and 0.67 g of potassium hydroxide pellets dissolved in 8.5 cm³ of ethanol are successively added to a solution, cooled to 0° C., of 7.85 g of (4-fluorophenyl)phenylacetaldehyde in 120 cm³ of ethyl ether. The temperature is left in the region of 20° C. for 3 hours. The mixture is concentrated to dryness under reduced pressure, 300 cm³ of ethyl ether are added and the mixture is washed with twice 200 cm³ of distilled water and once with 100 cm³ of saturated aqueous sodium chloride solution. After drying over magnesium sulphate and concentrating to dryness under reduced pressure, the residue is purified by flash chromatography on silica gel (30–70 μm), eluting with a cyclohexane/ethyl acetate (95/05) mixture, 5.2 g of 4-(4-fluorophenyl)-4-phenylcyclohex-2-enone are thus obtained in the form of a white powder, the characteristics of which are as follows:

melting point=83° C. (Köfler block)

¹H NMR spectrum: (300 MHz (CD₃)₂SO d6, δ in ppm): 2.28 (broad t, J=6.5 Hz: 2H); 2.67 (broad t, J=6.5 Hz: 2H); 6.16 (d, J=10.5 Hz: 1H); 7.19 (broad t, J=9 Hz: 2H); from 7.20 to 7.45 (mt: 7H); 7.57 (d, J=10.5 Hz: 1H).

(4-Fluorophenyl)phenylacetaldehyde may be prepared in the following manner:

1 g of 1-(4-fluorophenyl)-2-methoxy-1-phenylethanol and 1.5 cm³ of formic acid are refluxed for 6 hours. The reaction mixture is poured into 40 cm³ of saturated aqueous sodium carbonate solution, extracted with twice 30 cm³ of ethyl acetate and washed with twice 30 cm³ of distilled water. After drying over magnesium sulphate and concentrating to dryness under reduced pressure, the residue is purified by flash chromatography on silica gel (35–70 μm), eluting with a cyclohexane/ethyl acetate (95/05) mixture, 0.46 g of (4-fluorophenyl)phenylacetaldehyde is thus obtained in the form of a viscous yellow oil, the characteristics of which are as follows:

Rf TLC silica eluent: cyclohexane/ethyl acetate (85/15) =0.43 mass spectrum=(EI, DCI): M/Z=215 (MH⁺)

1-(4-Fluorophenyl)-2-methoxy-1-phenylethanol may be prepared in the following manner:

4.4 g of magnesium, 2 cm³ of 4-bromofluorobenzene and 10 cm³ of tetrahydrofuran are heated to a temperature in the region of 60° C. 18 cm³ of 4-bromofluorobenzene in solution in 50 cm³ of tetrahydrofuran are added and the mixture is heated at a temperature in the region of 60° C. for 2 hours. 8.4 cm³ of 2-methoxyacetophenone in solution in 60 cm³ of tetrahydrofuran are added to the solution prepared above, cooled to a temperature in the region of 5° C. After stirring for 24 hours at a temperature in the region of 20° C., the reaction mixture is poured into 200 cm³ of saturated aqueous ammonium chloride solution and extracted with twice 150 cm³ of ethyl ether, and the organic phases are washed with twice 150 cm³ of distilled water, dried over magnesium sulphate and concentrated to dryness under reduced pressure. The residue obtained is purified by flash chromatography on silica gel (35–70 μm), eluting with a cyclohexane/ethyl acetate (95/05) mixture; 13.2 g of 1-(4-fluorophenyl)-2-methoxy-1-phenylethanol are thus obtained in the form of a white oil, the characteristics of which are as follows:

mass spectrum (EI): M/Z=247 (MH⁺)

¹H NMR spectrum: (300 MHz (CD₃)₂SO d6, δ in ppm): 3.31 (s: 3H); 3.88 (AB, J=10 Hz: 2H); 5.81 (s: 1H); 7.11 (broad t, J=9 Hz: 2H); 7.22 (tt, J=7 and 1.5 Hz: 1H); 7.31 (broad t, J=7.5 Hz: 2H); from 7.35 to 7.50 (mt: 4H).

Example 10-4

(R,S)-Cyclopropyl[6-(4-fluorophenyl)-6-phenyl-6,7-dihydro-1H-indazol-3-yl]methanone may be prepared in the following manner:

The procedure is performed as described in Example 5-1, but starting with 0.36 g of magnesium, 1.2 cm³ of bromocyclopropane and 1.15 g of (R,S)-(N-methoxy-N-methyl)-6-(4-fluorophenyl)-6-phenyl-6,7-dihydro-1H-indazole-3-carboxamide in 25 cm³ of tetrahydrofuran. After purification by flash chromatography on a column of silica [eluent: cyclohexane/ethyl acetate (80/20 by volume)], 0.9 g of (R,S)-cyclopropyl[6-(4-fluorophenyl)-6-phenyl-6,7-dihydro-1H-indazol-3-yl]methanone, corresponding to Example 10-4A, is thus obtained in the form of a white foam, the characteristics of which are as follows:

Rf TLC silica eluent cyclohexane/ethyl acetate (50/50) =0.5

¹H NMR spectrum: (300 MHz (CD₃)₂SO d6, δ in ppm): 0.99 (d, J=6 Hz: 4H); from 2.75 to 2.95 (unresolved complex: 1H); 3.45 (s: 2H); 6.37 (very broad d, J=10 Hz: 1H); 6.96 (d, J=10 Hz: 1H); 7.11 (broad t, J=9 Hz: 2H); from 7.15 to 7.35 (mt: 7H); 13.42 (unresolved complex: 1H).

Isolation of the laevorotatory and dextrorotatory enantiomers of (R,S)-cyclopropyl[6-(4-fluorophenyl)-6-phenyl-6,7-dihydro-1H-indazol-3-yl]methanone 23 g of (R,S)-cyclopropyl[6-(4-fluorophenyl)-6-phenyl-6,7-dihydro-1H-indazol-3-yl]methanone, obtained in Example 10-4, are resolved on a Chiralpak AD chiral column, eluting with an n-heptane/ethanol/methanol (85/10/5 by volume) mixture.

By collecting the first eluted fraction (retention time 13.27 min), and after concentrating the solvent under reduced pressure, 8.67 g of the laevorotatory enantiomer of cyclopropyl[6-(4-fluorophenyl)-6-phenyl-6,7-dihydro-1H-indazol-3-yl]methanone, corresponding to Example 10-4B, are obtained in the form of a white solid, the characteristics of which are as follows:

¹H NMR spectrum: (300 MHz (CD₃)₂SO d6, δ in ppm): 0.99 (d, J=6 Hz: 4H); from 2.75 to 2.95 (mt: 1H); 3.45 (s: 2H); 6.37 (very broad d, J=10 Hz: 1H); 6.96 (d, J=10 Hz: 1H); 7.11 (broad t, J=9 Hz: 2H); from 7.15 to 7.35 (mt: 7H); from 13.20 to 13.70 (unresolved complex: 1H).

optical rotation: $\alpha_D^{20}$ (c=0.5/MeOH)=−18.6+/−0.7

By collecting the second eluted fraction (retention time 17.06 min), and after concentrating the solvent under reduced pressure, 9.76 g of the dextrorotatory enantiomer of cyclopropyl[6-(4-fluorophenyl)-6-phenyl-6,7-dihydro-1H-indazol-3-yl]methanone, corresponding to Example 10-4C, are obtained in the form of a white solid, the characteristics of which are as follows:

¹H NMR spectrum: (300 MHz, (CD₃)₂SO d6, δ in ppm): 0.99 (d, J=6 Hz: 4H); from 2.75 to 2.95 (mt: 1H); 3.45 (s: 2H); 6.37 (very broad d, J=10 Hz: 1H); 6.96 (d, J=10 Hz: 1H); 7.11 (broad t, J=9 Hz: 2H); from 7.15 to 7.35 (mt: 7H); from 13.20 to 13.70 (unresolved complex: 1H).

optical rotation: $\alpha_D^{20}$ (c=0.5/MeOH)=+18.9°+/−0.7

(R,S)-(N-Methoxy-N-methyl)-6-(4-fluorophenyl)-6-phenyl-6,7-dihydro-1H-indazole-3-carboxamide may be prepared in the following manner:

The procedure is performed as described in Example 3-2, but starting with 1.35 g of 6-(4-fluorophenyl)-6-phenyl-6,7-dihydro-1H-indazole-3-carboxylic acid, 0.64 g of 1-hydroxybenzotriazole hydrate, 0.92 g of 1-(3-dimethylaminopropyl)-3-ethylcarbodiimide hydrochloride, 1.56 g of N,O-dimethylhydroxylamine hydrochloride and 2.25 cm³ of triethylamine in 40 cm³ of dichloromethane. After purification by flash chromatography on a column of silica, eluting with a cyclohexane/ethyl acetate (60/40) mixture, 1.16 g of (R,S)-(N-methoxy-N-methyl)-6-(4-fluorophenyl)-6-phenyl-6,7-dihydro-1H-indazole-3-carboxamide are thus obtained in the form of a white foam, the characteristics of which are as follows:

$^1$H NMR spectrum: (400 MHz, $(CD_3)_2SO$ d6 with addition of a few drops of $CD_3COOD$ d4, δ in ppm): 3.28 (broad s: 3H); 3.40 (s: 2H); 3.61 (s: 3H); 6.31 (d, J=10 Hz: 1H); 6.86 (d, J=10 Hz: 1H); 7.08 (broad t, J=9 Hz: 2H); from 7.10 to 7.35 (mt: 7H).

(R,S)-6-(4-Fluorophenyl)-6-phenyl-6,7-dihydro-1H-indazole-3-carboxylic acid may be prepared in the following manner:

A solution of 1.6 g of ethyl (R,S)-6-(4-fluorophenyl)-6-phenyl-6,7-dihydro-1H-indazole-3-carboxylate, obtained in Example 10-3A, in 15 cm$^3$ of ethanol and 6.6 cm$^3$ of 1N sodium hydroxide solution is heated at a temperature in the region of 70° C. for 3 hours. After removing the ethanol under reduced pressure, the solution is acidified with 4N hydrochloric acid to a pH in the region of 2, and, on filtration, 1.38 g of (R,S)-6-(4-fluorophenyl)-6-phenyl-6,7-dihydro-1H-indazole-3-carboxylic acid are obtained in the form of a white solid, the characteristics of which are as follows:

melting point=250° C. (Köfler block)

$^1$H NMR spectrum: (300 MHz, $(CD_3)_2SO$ d6, δ in ppm): 3.38 (s: 2H); 6.41 (broad d, J=10 Hz: 1H); 6.86 (d, J=10 Hz: 1H); 7.10 (broad t, J=9 Hz: 2H); from 7.15 to 7.35 (mt: 7H); 13.28 (unresolved complex: 2H).

Example 10-5

The Z and E isomers of (R,S)-cyclopropyl[6-(4-fluorophenyl)-6-phenyl-6,7-dihydro-1H-indazol-3-yl]methanone oxime may be prepared in the following manner:

The procedure is performed as in Example 6-1, but starting with 0.87 g of (R,S)-cyclopropyl[6-(4-fluorophenyl)-6-phenyl-6,7-dihydro-1H-indazol-3-yl]methanone, obtained in Example 10-4A, 0.63 g of hydroxylamine hydrochloride and 0.79 g of sodium acetate.

The mixture of the Z and E isomers is separated by flash chromatography on a column of silica [eluent: dichloromethane/ethanol (95/05 by volume)], collecting 10 cm$^3$ fractions.

Fractions 14 to 16 are combined and concentrated to dryness under reduced pressure (13 kPa). 0.24 g of the Z isomer of (R,S)-cyclopropyl[6-(4-fluorophenyl)-6-phenyl-6,7-dihydro-1H-indazol-3-yl]methanone oxime, corresponding to Example 10-5A, is thus obtained in the form of a white foam, the characteristics of which are as follows:

Rf TLC silica (eluent dichloromethane/ethanol 97/03) =0.23

$^1$H NMR spectrum: (300 MHz, $(CD_3)_2SO$ d6, δ in ppm): 0.78 (mt: 4H); 1.79 (mt: 1H); 3.38 (s: 2H); 6.28 (broad d, J=10 Hz: 1H); 6.95 (broad d, J=10 Hz: 1H); 7.10 (broad t, J=9 Hz: 2H); from 7.15 to 7.35 (mt: 7H); from 11.20 to 11.60 (broad unresolved complex: 1H); from 12.50 to 12.80 (unresolved complex: 1H).

Fractions 24 to 26 are combined and concentrated to dryness under reduced pressure (13 kPa). 0.11 g of the E isomer of (R,S)-cyclopropyl[6-(4-fluorophenyl)-6-phenyl-6,7-dihydro-1H-indazol-3-yl]methanone oxime, corresponding to Example 10-5B, is thus obtained in the form of a white foam, the characteristics of which are as follows:

Rf TLC silica (eluent dichloromethane/ethanol 97/03) =0.12

$^1$H NMR spectrum: (300 MHz, $(CD_3)_2SO$ d6 with addition of a few drops of $CD_3COOD$ d4, δ in ppm): 0.82 (mt: 2H); 0.92 (mt: 2H); 2.25 (mt: 1H); 3.36 (s: 2H); 6.14 (d, J=10 Hz: 1H); 6.72 (d, J=10 Hz: 1H); 7.08 (broad t, J=9 Hz: 2H); from 7.15 to 7.35 (mt: 7H).

The Z and E isomers of the laevorotatory enantiomer of cyclopropyl[6-(4-fluorophenyl)-6-phenyl-6,7-dihydro-1H-indazol-3-yl]methanone oxime may be prepared by performing the procedure as in Example 6-1 but starting with 6 g of the laevorotatory enantiomer of cyclopropyl[6-(4-fluorophenyl)-6-phenyl-6,7-dihydro-1H-indazol-3-yl]methanone, obtained in Example 10-4B, 38 g of hydroxylamine hydrochloride and 5.4 cm$^3$ of pyridine.

The mixture of the Z and E isomers is separated by flash chromatography on a column of silica [eluent: dichloromethane/ethanol (97/03 by volume)], collecting 50 cm$^3$ fractions.

The first eluted fractions are combined and concentrated to dryness under reduced pressure (13 kPa). After recrystallization from ethanol, 1.27 g of the Z isomer of cyclopropyl[6-(4-fluorophenyl)-6-phenyl-6,7-dihydro-1H-indazol-3-yl]methanone oxime laevorotatory enantiomer, corresponding to Example 10-5C, are obtained in the form of a white powder, the characteristics of which are as follows:

melting point=193° C. (Köfler block)

optical rotation: $\alpha_D^{20}$ (c=0.5/DMF)=−22.3°+/−0.7

$^1$H NMR spectrum: (300 MHz, $(CD_3)_2SO$ d6, δ in ppm): from 0.65 to 0.90 (mt: 4H); 1.79 (mt: 1H); 3.38 (s: 2H); 6.28 (broad d, J=10 Hz: 1H); 6.96 (broad d, J=10 Hz: 1H); 7.09 (broad t, J=9 Hz: 2H); from 7.15 to 7.35 (mt: 7H); from 11.10 to 11.70 (broad unresolved complex: 1H); from 12.40 to 12.90 (broad unresolved complex: 1H).

The last eluted fractions are combined and concentrated to dryness under reduced pressure (13 kPa). After recrystallization from isopropanol, 2.22 g of the E isomer of cyclopropyl[6-(4-fluorophenyl)-6-phenyl-6,7-dihydro-1H-indazol-3-yl]methanone oxime laevorotatory enantiomer, corresponding to Example 10-D, are obtained in the form of a white foam, the characteristics of which are as follows:

optical rotation: $\alpha_D^{20}$ (c=0.5/DMF)=−15.4+/−0.5

$^1$H NMR spectrum: (300 MHz, $(CD_3)_2SO$ d6 with addition of a few drops of $CD_3COOD$ d4, δ in ppm): 0.80 (mt: 2H); 0.91 (mt: 2H); 2.24 (mt: 1H); 3.35 (s: 2H); 6.14 (d, J=10 Hz: 1H); 6.72 (d, J=10 Hz: 1H); 7.07 (broad t, J=9 Hz: 2H); from 7.10 to 7.35 (mt: 7H).

The Z isomer of the dextrorotatory enantiomer of cyclopropyl[6-(4-fluorophenyl)-6-phenyl-6,7-dihydro-1H-indazol-3-yl]methanone oxime may be prepared by performing the procedure as in Example 6-1, but starting with 6 g of the dextrorotatory enantiomer of cyclopropyl[6-(4-fluorophenyl)-6-phenyl-6,7-dihydro-1H-indazol-3-yl]methanone, 4.38 g of hydroxylamine hydrochloride and 4.4 cm$^3$ of pyridine.

The Z isomer is separated out by flash chromatography on a column of silica [eluent: dichloromethane/ethanol (97/03 by volume)], collecting 50 cm$^3$ fractions.

The first eluted fractions are combined and concentrated to dryness under reduced pressure (13 kPa). The white powder obtained is recrystallized from ethanol and 1.92 g of the Z isomer of cyclopropyl[6-(4-fluorophenyl)-6-phenyl-6,7-dihydro-1H-indazol-3-yl]methanone oxime (Z), dextrorotatory enantiomer, corresponding to Example 10-5E, are thus obtained in the form of a white powder, the characteristics of which are as follows:

melting point=193° C. (Köfler block)

optical rotation: $\alpha_D^{20}$ (c=0.5/DMF)=+24.4°+/−0.7

¹H NMR spectrum: (300 MHz, (CD₃)₂SO d6, δ in ppm): from 0.65 to 0.90 (mt: 4H); 1.79 (mt: 1H); 3.38 (s: 2H); 6.28 (broad d, J=10 Hz: 1H); 6.96 (broad d, J=10 Hz: 1H); 7.09 (broad t, J=9 Hz: 2H); from 7.15 to 7.35 (mt: 7H); from 11.10 to 11.70 (broad unresolved complex: 1H); from 12.40 to 12.90 (broad unresolved complex: 1H).

Example 10-6

Ethyl 6,6-bis(4-fluorophenyl)-6,7-dihydro-1H-indazole-3-carboxylate may be prepared in the following manner:

1.4 cm³ of ethyl diazoacetate are added dropwise to a solution, cooled to −70° C., of 3 g of 4,4-bis(4-fluorophenyl)cyclohex-2-enone in 75 cm³ of tetrahydrofuran, followed by slow addition of 37.9 cm³ of lithium diisopropylamide solution prepared from 10.5 cm³ of 1.6 M n-butyllithium and 2.4 cm³ of diisopropylamine in solution in 25 cm³ of tetrahydrofuran. After stirring the reaction mixture at a temperature in the region of −70° C. for 3 hours, 1.9 cm³ of glacial acetic acid are added and the temperature is allowed to rise to the region of 20° C. 250 cm³ of ethyl acetate are added and the organic phases are then washed with twice 150 cm³ of distilled water, dried over sodium sulphate and concentrated to dryness under reduced pressure. The residue is dissolved in 100 cm³ of toluene and heated at a temperature in the region of 110° C. for 3 hours and then concentrated to dryness under reduced pressure. The residue obtained is purified by flash chromatography on silica gel (35–70 μm), eluting with a dichloromethane/diisopropyl ether (50/50) mixture; 1.2 g of ethyl 6,6-bis(4-fluorophenyl)-6,7-dihydro-1H-indazole-3-carboxylate are thus obtained in the form of a beige-coloured foam, the characteristics of which are as follows:

Rf TLC silica eluent: dichloromethane/diisopropyl ether (50/50)=0.48

¹H NMR spectrum: (400 MHz, (CD₃)₂SO d6 with addition of a few drops of CD₃COOD d4, δ in ppm): 1.30 (t, J=7.5 Hz: 3H); 3.39 (s: 2H); 4.28 (q, J=7.5 Hz: 2H); 6.43 (broad d, J=10 Hz: 1H); 6.85 (d, J=10 Hz: 1H); 7.10 (broad t, J=9 Hz: 4H); 7.22 (broad dd, J=7 and 4 Hz: 4H).

4,4-Bis(4-fluorophenyl)cyclohex-2-enone may be prepared in the following manner:

1.7 cm³ of methyl vinyl ketone and 0.39 g of potassium hydroxide pellets dissolved in 3 cm³ of ethanol are successively added to a solution, cooled to 0° C., of 4 g of bis(4-fluorophenyl)acetaldehyde in 35 cm³ of ethyl ether. The temperature is left in the region of 20° C. for 24 hours. The mixture is concentrated to dryness under reduced pressure, 75 cm³ of dichloromethane are added and the mixture is washed with twice 75 cm³ of distilled water. After drying over magnesium sulphate and concentrating to dryness under reduced pressure, the residue is purified by flash chromatography on silica gel (30–70 μm), eluting with pure dichloromethane; 3 g of 4,4-bis(4-fluorophenyl)cyclohex-2-enone are thus obtained in the form of a pale yellow oil, the characteristics of which are as follows:

Rf TLC silica (eluent: dichloromethane)=0.39

¹H NMR spectrum: (300 MHz, (CD₃)₂SO d6, δ in ppm): 2.27 (broad t, J=6.5 Hz: 2H); 2.66 (broad t, J=6.5 Hz: 2H); 6.15 (d, J=10.5 Hz: 1H); 7.20 (broad t, J=9 Hz: 4H); 7.32 (broad dd, J=9 and 5 Hz: 4H); 7.55 (d, J=10.5 Hz: 1H).

Bis(4-fluorophenyl)acetaldehyde may be prepared in the following manner:

5 g of 1,1-bis(4-fluorophenyl)-2-methoxyethanol and 5 cm³ of formic acid are refluxed for 3 hours. The reaction mixture is poured into 100 cm³ of saturated aqueous sodium carbonate solution, extracted with three times 75 cm³ of ethyl acetate and washed with twice 75 cm³ of distilled water. After drying over magnesium sulphate and concentrating to dryness under reduced pressure, 4 g of bis(4-fluorophenyl)acetaldehyde are thus obtained in the form of a pale yellow oil, the characteristics of which are as follows, and which is used without further modification in the next step.

Rf TLC silica (eluent: dichloromethane)=0.69

1,1-Bis(4-fluorophenyl)-2-methoxyethanol may be prepared in the following manner:

4.9 g of magnesium, 5 cm³ of 4-bromofluorobenzene and 25 cm³ of tetrahydrofuran are heated to a temperature in the region of 60° C. 17 cm³ of 4-bromofluorobenzene in solution in 25 cm³ of tetrahydrofuran are added and the mixture is heated at a temperature in the region of 60° C. for 2 hours. 5 cm³ of methyl methoxyacetate in solution in 25 cm³ of tetrahydrofuran are added to the solution prepared above, cooled to a temperature in the region of 0° C. After stirring for 24 hours at a temperature in the region of 20° C., the reaction mixture is poured into 200 cm³ of saturated aqueous ammonium chloride solution and extracted with three times 75 cm³ of ethyl acetate, and the organic phases are washed with twice 100 cm³ of distilled water, dried over magnesium sulphate and concentrated to dryness under reduced pressure. The residue obtained is purified by flash chromatography on silica gel (35–70 μm), eluting with pure dichloromethane; 9.8 g of 1,1-bis(4-fluorophenyl)-2-methoxyethanol are thus obtained in the form of a yellow oil, the characteristics of which are as follows:

¹H NMR spectrum: (300 MHz, (CD₃)₂SO d6, δ in ppm): 3.30 (s: 3H); 3.86 (s: 2H); 5.91 (s: 1H); 7.12 (broad t, J=9 Hz: 4H); 7.43 (broad dd, J=9 and 6 Hz: 4H).

mass spectrum (EI): M/Z=265 (MH⁺)

Example 10-7

Cyclopropyl[6,6-bis(4-fluorophenyl)-6,7-dihydro-1H-indazol-3-yl]methanone may be prepared in the following manner:

The procedure is performed as described in Example 5-1, but starting with 0.3 g of magnesium, 1 cm³ of bromocyclopropane and 1 g of (N-methoxy-N-methyl)-6,6-bis(4-fluorophenyl)-6,7-dihydro-1H-indazole-3-carboxamide in 20 cm³ of tetrahydrofuran. After purification by flash chromatography on a column of silica [eluent: dichloromethane/diisopropyl ether (80/20 by volume)], 0.75 g of cyclopropyl[6,6-bis(4-fluorophenyl)-6,7-dihydro-1H-indazol-3-yl]methanone is thus obtained in the form of a white foam, the characteristics of which are as follows:

Rf TLC silica (eluent: dichloromethane/diisopropyl ether, 50/50 by volume)=0.28

¹H NMR spectrum: (300 MHz, (CD₃)₂SO d6, δ in ppm): 1.00 (d, J=6 Hz: 4H); 2.84 (unresolved complex: 1H); 3.45 (s: 2H); 6.36 (unresolved complex: 1H); 6.96 (d, J=10 Hz: 1H); 7.14 (broad t, J=9 Hz: 4H); 7.24 (broad dd, J=9 and 6 Hz: 4H); from 13.30 to 13.65 (broad unresolved complex: 1H).

(N-Methoxy-N-methyl)-6,6-bis(4-fluorophenyl)-6,7-dihydro-1H-indazole-3-carboxamide may be prepared in the following manner:

The procedure is performed as described in Example 3-2, but starting with 1.4 g of 6,6-bis(4-fluorophenyl)-6,7-dihydro-1H-indazole-3-carboxylic acid, 0.64 g of 1-hydroxybenzotriazole hydrate, 0.92 g of 1-(3-dimethylaminopropyl)-3-ethylcarbodiimide hydrochloride, 1.6 g of N,O-dimethylhydroxylamine hydrochloride and 2.25 cm³ of triethylamine in 40 cm³ of dichloromethane. After purification by flash chromatography on a column of silica, eluting with an isopropanol/isopropyl ether (50/25) mixture, 1 g of (N-methoxy-N-methyl)-6,6-bis(4-fluorophenyl)-6,7-dihydro-1H-indazole-3-carboxamide is thus obtained in the form of a white powder, the characteristics of which are as follows:

melting point=198° C. (Köfler block)

$^1$H NMR spectrum: (300 MHz, $(CD_3)_2SO$ d6 with addition of a few drops of $CD_3COOD$ d4, δ in ppm): 3.29 (broad s: 3H); 3.41 (broad s: 2H); 3.61 (broad s: 3H); 6.30 (broad d, J=10 Hz: 1H); 6.87 (d, J=10 Hz: 1H); 7.11 (broad t, J=9 Hz: 4H); 7.25 (broad dd, J=9 and 6 Hz: 4H).

6,6-Bis(4-fluorophenyl)-6,7-dihydro-1H-indazole-3-carboxylic acid may be prepared in the following manner:

A solution of 2.1 g of ethyl 6,6-bis(4-fluorophenyl)-6,7-dihydro-1H-indazole-3-carboxylate in 20 cm$^3$ of ethanol and 8.2 cm$^3$ of 1N sodium hydroxide solution is heated at a temperature in the region of 70° C. for 2 hours. After removing the ethanol under reduced pressure, the solution is acidified with 4N hydrochloric acid to a pH in the region of 2, and, after filtration, 1.4 g of 6,6-bis(4-fluorophenyl)-6,7-dihydro-1H-indazole-3-carboxylic acid are obtained in the form of a beige-coloured powder, the characteristics of which are as follows:

$^1$H NMR spectrum: (300 MHz, $(CD_3)_2SO$ d6, δ in ppm): 3.39 (s: 2H); 6.41 (broad d, J=10 Hz: 1H); 6.87 (d, J=10 Hz: 1H); 7.12 (broad t, J=9 Hz: 4H); 7.26 (broad dd, J=9 and 6 Hz: 4H); from 12.90 to 13.60 (broad unresolved complex: 2H).

Example 10-8

The Z and E isomers of cyclopropyl[6,6-bis(4-fluorophenyl)-6,7-dihydro-1H-indazol-3-yl]methanone oxime may be prepared in the following manner:

The procedure is performed as in Example 6-1, but starting with 0.7 g of cyclopropyl[6,6-bis(4-fluorophenyl)-6,7-dihydro-1H-indazol-3-yl]methanone, obtained in Example 10-7, 0.52 g of hydroxylamine hydrochloride and 0.61 g of sodium acetate.

The crude mixture of the Z and E isomers is separated by flash chromatography on a column of silica [eluent: dichloromethane/ethanol (95/05 by volume)], collecting 35 cm$^3$ fractions.

Fractions 3 to 7 are combined and concentrated to dryness under reduced pressure (13 kPa). The residue is taken up in 6 cm$^3$ of isopropyl ether, drained by suction, washed with three times 1 cm$^3$ of isopropyl ether and then dried under reduced pressure (13 kPa), at a temperature in the region of 40° C. 0.19 g of the Z isomer of cyclopropyl[6,6-bis(4-fluorophenyl)-6,7-dihydro-1H-indazol-3-yl]methanone oxime, corresponding to Example 10-8A, is thus obtained in the form of a solid, the characteristics of which are as follows:

melting point=206° C. (Köfler block)

$^1$H NMR spectrum: (300 MHz, $(CD_3)_2SO$ d6, δ in ppm): 0.78 (mt: 4H); 1.79 (mt: 1H); 3.38 (s: 2H); 6.25 (broad d, J=10 Hz: 1H); 6.95 (broad d, J=10 Hz: 1H); 7.10 (broad t, J=9 Hz: 4H); 7.26 (broad dd, J=9 and 6 Hz: 4H); from 11.00 to 11.65 (broad unresolved complex: 1H); from 12.40 to 12.90 (broad unresolved complex: 1H).

Fractions 10 to 14 are combined and concentrated to dryness under reduced pressure (13 kPa). 0.3 g of the E isomer of cyclopropyl[6,6-bis(4-fluorophenyl)-6,7-dihydro-1H-indazol-3-yl]methanone oxime, corresponding to Example 10-8B, is thus obtained in the form of a white foam, the characteristics of which are as follows:

$^1$H NMR spectrum: (400 MHz, $(CD_3)_2SO$ d6 at a temperature of 383 K, δ in ppm): 0.83 (mt: 2H); 0.93 (mt: 2H); 2.23 (mt: 1H); 3.41 (s: 2H); 6.10 (d, J=10 Hz: 1H); 6.76 (d, J=10 Hz: 1H); 7.05 (broad t, J=9 Hz: 4H); 7.28 (broad dd, J=9 and 5.5 Hz: 4H); from 10.25 to 10.60 (unresolved complex: 1H); from 11.6 to 12.20 (broad unresolved complex: 1H).

Example 11

Ethyl 5,5-diphenyl-4,5-dihydro-2H-isoindole-1-carboxylate may be prepared in the following manner:

0.307 g of ethyl glycinate hydrochloride is added to a suspension of 0.589 g of 2-chloro-5,5-diphenylcyclohexa-1,3-dienecarbaldehyde in 20 cm$^3$ of N,N-dimethylformamide. The reaction mixture is refluxed for about 20 hours. After cooling to a temperature in the region of 20° C., the mixture is concentrated to dryness under reduced pressure (13 kPa). The residue is taken up in 100 cm$^3$ of ethyl acetate, washed with three times 50 cm$^3$ of water and then dried over magnesium sulphate, filtered and concentrated to dryness under reduced pressure. After purification by flash chromatography on a column of silica [eluent: dichloromethane], 0.11 g of ethyl 5,5-diphenyl-4,5-dihydro-2H-isoindole-1-carboxylate is obtained in the form of a brown solid, the characteristics of which are as follows:

melting point: 160° C. (Köfler block)

Rf TLC silica (eluent: dichloromethane)=0.23

$^1$H NMR spectrum: (300 MHz, $(CD_3)_2SO$ d6, δ in ppm): 1.27 (t, J=7 Hz: 3H); 3.24 (s: 2H); 4.20 (q, J=7 Hz: 2H); 6.47 (broad d, J=10 Hz: 1H); 6.53 (d, J=10 Hz: 1H); 6.67 (broad s: 1H); from 7.15 to 7.35 (mt: 10H); 11.65 (unresolved complex: 1H).

2-Chloro-5,5-diphenylcyclohexa-1,3-dienecarbaldehyde may be prepared in the following manner:

0.193 cm$^3$ of phosphorus oxychloride is added to a solution of 0.607 g of 6-dimethylaminomethylene-4,4-diphenylcyclohex-2-enone in 15 cm$^3$ of dichloromethane. The mixture is heated to the reflux temperature and refluxing is maintained for about 3 hours. After cooling to a temperature in the region of 20° C., the solution is concentrated to dryness under reduced pressure (13 kPa). The residue is dissolved in 20 cm$^3$ of tetrahydrofuran and 20 cm$^3$ of water are added in a single portion. The mixture is refluxed for about 24 hours. After cooling to a temperature in the region of 20° C., the mixture is concentrated to dryness under reduced pressure (13 kPa). The residue is taken up in 10 cm$^3$ of ethyl acetate. The solution is washed three times with 30 cm$^3$ of water and then dried over magnesium sulphate, filtered and concentrated to dryness under reduced pressure (13 kPa). 0.6 g of 2-chloro-5,5-diphenylcyclohexa-1,3-dienecarbaldehyde is thus obtained in the form of an orange-coloured resin, which is used without further modification in subsequent syntheses and the characteristics of which are as follows:

mass spectrum (IE): M$^+$=294

$^1$H NMR spectrum: (300 MHz, $(CD_3)_2SO$ d6, δ in ppm): 3.09 (s: 2H); 6.38 (d, J=10 Hz: 1H); 7.14 (broad d, J=7.5 Hz: 4H); 7.23 (d, J=10 Hz: 1H); 7.26 (tt, J=7.5 and 2.5 Hz: 2H); 7.33 (broad t, J=7.5 Hz: 4H); 10.09 (s: 1H).

6-Dimethylaminomethylene-4,4-diphenylcyclohex-2-enone may be prepared in the following manner:

4.77 g of N,N-dimethylformamide dimethyl acetal are added to a solution of 2.48 g of 4,4-diphenylcyclohex-2-enone in 20 Cm$^3$ of N,N-dimethylformamide. The mixture is refluxed for about 4 hours. After cooling to a temperature in the region of 20° C., the solution is concentrated to dryness under reduced pressure (13 kPa). The residue is taken up in 50 cm³ of diisopropyl ether and allowed to precipitate for about 20 hours at a temperature in the region of 20° C. The solid is drained by suction, washed with three times 10 cm³ of diisopropyl ether and then dried under reduced pressure (13 kPa) over potassium hydroxide at a temperature in the region of 20° C. 1.7 g of 6-dimethylaminomethylene-4,4-diphenylcyclohex-2-enone are thus obtained in the form of a cream-coloured powder, the characteristics of which are as follows:

melting point: 130° C. (Köfler block)

¹H NMR spectrum: (300 MHz, (CD₃)₂SO d6, δ in ppm): 3.08 (s: 6H); 3.44 (broad s: 2H); 6.03 (d, J=10 Hz: 1H); from 7.15 to 7.40 (mt: 12H).

Example 12

Ethyl 6,6-diphenyl-6,7-dihydro-1H-indole-3-carboxylate may be prepared in the following manner:

0.27 g of 2-oxo-5,5-diphenylcyclohex-3-enylamine hydrochloride is dissolved in 3 cm³ of methanol and the solution is cooled to a temperature in the region of 0° C. 0.14 cm³ of ethyl 3-dimethylaminoacrylate is added to the preceding solution and the mixture is stirred for about 60 hours at a temperature in the region of 20° C. The reaction mixture is then concentrated to dryness under reduced pressure (13 kPa) and the residue is taken up in 12 cm³ of tetrahydrofuran. 0.3 g of ethyl 3-(2-oxo-5,5-diphenylcyclohex-3-enylamino)acrylate is obtained in the form of an orange-coloured oil, which is used without further modification in subsequent syntheses and the characteristics of which are as follows:

LCMS (Thermo Hypersil column 4.6×50 mm; 5 μm C18; flow rate: 1 cm³/min; solvent: A=water, 0.05% trifluoroacetic acid; B=acetonitrile, 0.05% trifluoroacetic acid; gradient: 95% to 10% of A over 4 minutes and return to the initial conditions over 2.5 minutes; amount injected 10 μl of a solution at about 5×10⁻³ M; detection: UV Diode Array Detector 190 to 600 nm; mode of ionization: electrospray): [(MH)⁺]=362; tr=4.64 min 0.3 g of ethyl 3-(2-oxo-5,5-diphenylcyclohex-3-enylamino)acrylate is dissolved in 6 cm³ of ethanol. The solution obtained is cooled to a temperature in the region of 0° C. 2 cm³ of sodium ethoxide solution (obtained from 0.23 g of sodium in 20 cm³ of ethanol) are added to the preceding solution at a temperature of between 0 and 5° C. After warming to a temperature in the region of 20° C., the resulting mixture is stirred for about 18 hours. About ten grams of crushed ice are then added to the reaction mixture and this mixture is then concentrated under reduced pressure (13 kPa) to half its volume. The mixture thus obtained is extracted five times with diethyl ether (three times 100 cm³, twice 50 cm³). The combined organic phases are successively washed with 100 cm³ and then 50 cm³ of saturated aqueous sodium chloride solution and then dried over magnesium sulphate, filtered and concentrated to dryness under reduced pressure (13 kPa). The residue is purified by flash chromatography on a column of silica (eluent: cyclohexane/ethyl acetate (85/15 by volume)]. 0.013 g of ethyl 6,6-diphenyl-6,7-dihydro-1H-indole-3-carboxylate is thus obtained in the form of a yellow solid, the characteristics of which are as follows:

Rf TLC silica [eluent: cyclohexane/ethyl acetate (70/30 by volume)]=0.37

¹H NMR spectrum: (300 MHz, (CD₃)₂SO d6, δ in ppm): 1.24 (t, J=7 Hz: 3H); 3.30 (broad s: 2H); 4.14 (q, J=7 Hz: 2H); 6.16 (d, J=10 Hz: 1H); 6.88 (d, J=10 Hz: 1H); from 7.15 to 7.35 (mt: 11H); 11.45 (unresolved complex: 1H).

2-Oxo-5,5-diphenylcyclohex-3-enylammonium chloride may be prepared in the following manner:

0.7 g of zinc powder is added portionwise to a solution of 0.5 g of 5,5-diphenylcyclohex-3-ene-1,2-dione 1-oxime and 6 cm³ of trifluoroacetic acid, cooled to a temperature of between 0 and 5° C., while maintaining the temperature below 25° C. After stirring for two hours at a temperature in the region of 20° C., the reaction mixture is poured into 100 cm³ of aqueous 2N sodium hydroxide solution cooled to a temperature in the region of 5° C. After adding 50 cm³ of diethyl ether, the mixture is filtered and the insoluble material is washed with 50 cm³ of ether. After separating out the filtrate by settling, the aqueous phase is extracted with twice 50 cm³ of diethyl ether. The combined organic phases are washed with four times 25 cm³ of water and then with four times 25 cm³ of saturated aqueous sodium chloride solution, followed by drying over magnesium sulphate and filtration. The filtrate is acidified with 2 cm³ of a 1N solution of hydrogen chloride in diethyl ether. The mixture is concentrated to dryness under reduced pressure (13 kPa) and the residue is dissolved in 3 cm³ of acetone. After adding 10 cm³ of diethyl ether, the precipitate is drained by suction, washed with twice 3 cm³ of diethyl ether and then dried under reduced pressure (13 kPa) at a temperature in the region of 20° C. 0.2 g of 2-oxo-5,5-diphenylcyclohex-3-enylammonium chloride is thus obtained in the form of a pink solid, the characteristics of which are as follows:

Rf TLC silica of the product dissolved in a dichloromethane/methanol/32% aqueous ammonium hydroxide (12/3/0.5 by volume) mixture [eluent: dichloromethane/methanol (95/5 by volume)]=0.30

¹H NMR spectrum: (300 MHz, (CD₃)₂SO d6, δ in ppm): 2.61 (t, J=13.5 Hz: 1H); 3.14 (d mt, J=13.5 Hz: 1H); 3.92 (d mt, J=13.5 Hz: 1H); 6.35 (d, J=10 Hz: 1H); from 7.05 to 7.45 (mt: 10H); 7.81 (dd, J=10 and 2 Hz: 1H); 8.46 (unresolved complex: 3H).

5,5-Diphenylcyclohex-3-ene-1,2-dione 1-oxime may be prepared in the following manner:

A solution of 10.1 g of 4,4-diphenylcyclohex-2-enone in 60 cm³ of tert-butanol is added to a solution of 6.5 g of potassium tert-butoxide in 50 cm³ of tert-butanol at a temperature in the region of 30° C. After stirring for about 15 minutes at a temperature in the region of 30° C., this solution is added dropwise to 14 cm³ of tert-butyl nitrite. The reaction mixture is stirred at a temperature in the region of 20° C. for 2 hours. 100 cm³ of aqueous 3 M hydrochloric acid solution and 100 cm³ of diethyl ether are then added to the preceding mixture at a temperature in the region of 20° C. After separation of the phases by settling, the aqueous phase is extracted with 100 cm³ of diethyl ether. The combined organic phases are washed with three times 100 cm³ of saturated aqueous sodium bicarbonate solution and then with 100 cm³ of saturated aqueous sodium chloride solution, and then dried over magnesium sulphate, filtered and concentrated. After concentrating to dryness under reduced pressure (13 kPa), the residue is purified by flash chromatography on a column of silica (eluent: cyclohexane/ethyl acetate (80/20 by volume)]. 2.23 g of 5,5-diphenylcyclohex-3-ene-1,2-dione 1-oxime are thus obtained in the form of a yellow foam, which is used without further modification for subsequent syntheses and the characteristics of which are as follows:

Rf TLC silica [eluent: dichloromethane/methanol (95/5 by volume)]=0.36

¹H NMR spectrum: (300 MHz, (CD$_3$)$_2$SO d6, δ in ppm): 3.52 (s: 2H); 6.32 (d, J=10.5 Hz: 1H); 7.20 (broad d, J=7.5 Hz: 4H); 7.27 (tt, J=7.5 and 1.5 Hz: 2H); 7.36 (broad t, J=7.5 Hz: 4H); 7.86 (dd, J=10.5 Hz: 1H); 12.65 (s: 1H).

Example 13

Ethyl 7-methyl-6,6-diphenyl-6,7-dihydro-1H-indazole-3-carboxylate may be prepared in the following manner:

0.41 cm³ of ethyl diazoacetate is added dropwise to a solution, cooled to −78° C., of 0.8 g of 5-methyl-4,4-diphenylcyclohex-2-enone, which may be obtained according to J. Amer. Chem. Soc. 1995, 107, 5245–61, in 30 cm³ of tetrahydrofuran, followed by slow addition of 11.67 cm³ of lithium diisopropylamide solution prepared from 3 cm³ of 1.6M n-butyllithium and 0.67 cm³ of diisopropylamine in solution in 8 cm³ of tetrahydrofuran. After stirring the reaction mixture at a temperature in the region of −70° C. for 2 hours, 0.34 cm³ of glacial acetic acid is added and the temperature is allowed to rise to the region of 20° C. 100 cm³ of ethyl ether are added and the organic phases are then washed with five times 70 cm³ of distilled water, dried over sodium sulphate and concentrated to dryness under reduced pressure. The residue is dissolved in 25 cm³ of toluene, heated at a temperature in the region of 110° C. for 4 hours and then concentrated to dryness under reduced pressure. The residue obtained is purified by flash chromatography on silica gel (35–70 μm), eluting with a cyclohexane/ethyl acetate (80/20) mixture; 0.133 g of ethyl 7-methyl-6,6-diphenyl-6,7-dihydro-1H-indazole-3-carboxylate is obtained in the form of an off-white solid, the characteristics of which are as follows:

melting point=125° C. (Köfler block)

Rf TLC silica (eluent: cyclohexane/ethyl acetate 70/30) =0.17

¹H NMR spectrum: (300 MHz, (CD$_3$)$_2$SO d6, δ in ppm): 0.70 (d, J=7 Hz: 3H); 1.30 (t, J=7.5 Hz: 3H); 3.80 (q, J=7 Hz: 1H); 4.26 (mt: 2H); 6.58 (d, J=10 Hz: 1H); 6.78 (d, J=10 Hz: 1H); from 7.05 to 7.40 (mt: 10H).

Example 14

Ethyl 1-(4-aminophenyl)-6,6-diphenyl-1H-indazole-3-carboxylate may be prepared in the following manner:

A solution of 0.6 g of ethyl 1-(4-nitrophenyl)-6,6-diphenyl-1H-indazole-3-carboxylate in 24 cm³ of acetic acid is cooled to the region of 0° C. 4.8 g of zinc are then added portionwise. After warming to a temperature in the region of 20° C., the suspension obtained is stirred for about 4 hours. The insoluble material is filtered off through Celite and washed with three times 10 cm³ of dichloromethane. The filtrate is concentrated to dryness under reduced pressure (13 kPa) and taken up in 50 cm³ of dichloromethane. The solution is washed with three times 20 cm³ of saturated aqueous sodium hydrogen carbonate solution, dried over magnesium sulphate, filtered and concentrated to dryness under reduced pressure (13 kPa). After flash chromatography on a column of silica [eluent: dichloromethane/ethyl acetate (98/2 by volume)], 0.41 g of ethyl 1-(4-aminophenyl)-6,6-diphenyl-1H-indazole-3-carboxylate is thus obtained in the form of a solid, the characteristics of which are as follows:

Rf TLC silica (eluent: dichloromethane/methanol 98/2) =0.21

¹H NMR spectrum: (300 MHz, (CD$_3$)$_2$SO d6, δ in ppm): 1.30 (t, J=7 Hz: 3H); 3.46 (s, 2H); 4.28 (q, J=7 Hz: 2H); 5.54 (s: 2H); 6.44 (d, J=10 Hz: 1H); 6.70 (d, J=9 Hz: 2H); 6.93 (d, J=10 Hz: 1H); 7.11 (broad d, J=7.5 Hz: 4H); from 7.15 to 7.35 (mt: 8H).

Ethyl 1-(4-nitrophenyl)-6,6-diphenyl-1H-indazole-3-carboxylate may be prepared in the following manner:

A solution of 1 g of ethyl 6,6-diphenyl-6,7-dihydro-2H-indazole-3-carboxylate in 5 cm³ of dimethylformamide is added dropwise to a suspension of 0.151 g of sodium hydride (at 60% in oil) in 4 cm³ of dimethylformamide. After stirring the mixture for one and a half hours in the region of 20° C., 0.46 cm³ of 1-fluoro-4-nitrobenzene is added and the reaction mixture is stirred in the region of 80° C. for about two hours. A further 0.26 cm³ of 1-fluoro-4-nitrobenzene is added to the mixture, cooled to the region of 20° C. After stirring for two hours in the region of 80° C., the mixture is slowly cooled to the region of 20° C. and 10 cm³ of water are added. The mixture is extracted three times with 75 cm³ of ethyl acetate, and the combined organic phases are washed with twice 75 cm³ of water, dried over magnesium sulphate, filtered and concentrated to dryness under reduced pressure (13 kPa). After flash chromatography on a column of silica [eluent: dichloromethane/ethyl acetate (90/10 by volume)], 0.34 g of ethyl 1-(4-nitrophenyl)-6,6-diphenyl-1H-indazole-3-carboxylate is thus obtained in the form of a solid, the characteristics of which are as follows:

melting point: melting at 200° C. (Köfler block)

¹H NMR spectrum: (300 MHz, (CD$_3$)$_2$SO d6, δ in ppm): 1.32 (t, J=7 Hz: 3H); 3.75 (s: 2H); 4.33 (q, J=7 Hz: 2H); 6.54 (d, J=10 Hz: 1H); 6.97 (d, J=10 Hz: 1H); from 7.10 to 7.35 (mt: 10H); 7.98 (d, J=9 Hz: 2H); 8.45 (d, J=9 Hz: 2H).

mass spectrum

EI m/z=465 M⁺ m/z=419 [M-HOC$_2$H$_5$]⁺ base peak m/z=391 [419-CO]⁺ m/z=342 [419-C$_6$H$_5$]⁺ m/z=296 [342-NO$_2$]⁺

DCI m/z=466 MH⁺

| Example | X | Y | Z | R' | R$_1$ | Ar | R$_2$ |
|---|---|---|---|---|---|---|---|
| 1 | N | N | H | H | C$_6$H$_5$ | C$_6$H$_5$ | COOC$_2$H$_5$ |
| 2-1 | N | N | H | H | C$_6$H$_5$ | C$_6$H$_5$ | COO—⟨ |
| 2-2 | N | N | H | H | C$_6$H$_5$ | C$_6$H$_5$ | COOMe |

-continued

| Example | X | Y | Z | R' | R₁ | Ar | R₂ |
|---|---|---|---|---|---|---|---|
| 3-1 | N | N | H | H | C₆H₅ | C₆H₅ |  CO(NH)—cyclopropyl |
| 3-2 | N | N | H | H | C₆H₅ | C₆H₅ |  CON—cyclobutyl |
| 3-3 | N | N | H | H | C₆H₅ | C₆H₅ | CON(CH₃)—OCH₃ |
| 3-4 | N | N | H | H | C₆H₅ | C₆H₅ |  CON—cyclopropyl |
| 4 | N | N | H | H | C₆H₅ | C₆H₅ | CN |
| 5-1 | N | N | H | H | C₆H₅ | C₆H₅ |  CO—cyclopropyl |
| 5-2 | N | N | H | H | C₆H₅ | C₆H₅ |  CO—cyclobutyl |
| 5-3 | N | N | H | H | C₆H₅ | C₆H₅ | COC₆H₅ |
| 5-4 | N | N | N | N | C₆H₅ | C₆H₅ | 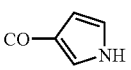 CO—pyrrole |
| 6-1A 6-1B | N | N | H | H | C₆H₅ | C₆H₅ | C(=N—OH)—cyclopropyl |
| 6-2A 6-2B | N | N | H | H | C₆H₅ | C₆H₅ | C(=N—OH)—cyclobutyl |
| 6-3A 6-3B | N | N | H | H | C₆H₅ | C₆H₅ | C(=N—OMe)—cyclopropyl |
| 6-4 | N | N | H | H | C₆H₅ | C₆H₅ | C(H)=N—OMe |
| 6-5 | N | N | H | H | C₆H₅ | C₆H₅ | 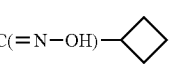 |
| 6-6A 6-6B | N | N | H | H | C₆H₅ | C₆H₅ | 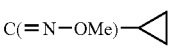 |
| 6-7A 6-7B | N | N | H | H | C₆H₅ | C₆H₅ | 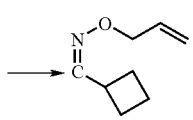 |
| 6-8A 6-8B | N | N | H | H | C₆H₅ | C₆H₅ | 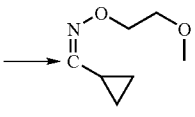 |
| 6-9 | N | N | H | H | C₆H₅ | C₆H₅ | 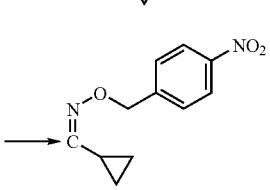 |

-continued

| Example | X | Y | Z | R' | R₁ | Ar | R₂ |
|---|---|---|---|---|---|---|---|
| 6-10A<br>6-10B | N | N | H | H | $C_6H_5$ | $C_6H_5$ | 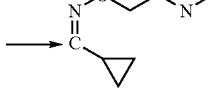 |
| 6-11A<br>6-11B | N | N | H | H | $C_6H_5$ | $C_6H_5$ | 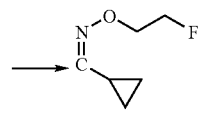 |
| 7-1 | N | N | 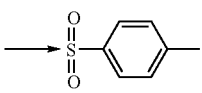 | H | $C_6H_5$ | $C_6H_5$ | $NH_2$ |
| 7-2 | N | N | COCH=CH2 | H | $C_6H_5$ | $C_6H_5$ | $NH_2$ |
| 7-3 | N | N | H | | $C_6H_5$ | $C_6H_5$ | 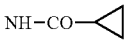 |
| 7-4 | N | N | H | H | $C_6H_5$ | $C_6H_5$ | NH—$COC_6H_5$ |
| 8-1 | N | N | H | H | $C_6H_5$ | $C_6H_5$ | 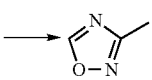 |
| 8-2 | N | N | H | H | $C_6H_5$ | $C_6H_5$ | $C_6H_5$ |
| 8-3 | N | N | H | H | $C_6H_5$ | $C_6H_5$ | 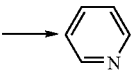 |
| 8-4 | N | N | H | H | $C_6H_5$ | $C_6H_5$ | 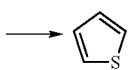 |
| 9-1 | N | N | H | H | $CH_3$ | $C_6H_5$ | $COOC_2H_5$ |
| 9-2 | N | N | H | H | $CH_3$ | $C_6H_5$ | $COOC_2H_5$ |
| 9-3 | N | N | H | H | H | $C_6H_5$ | $COOC_2H_5$ |
| 10-1 | N | N | H | H | 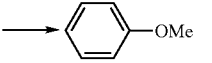 | 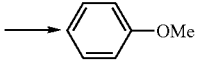 | $COOC_2H_5$ |
| 10-2 | N | N | H | H | 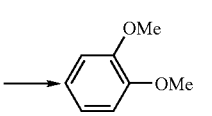 | $C_6H_5$ | $COOC_2H_5$ |
| 10-3A<br>10-3B<br>10-3C | N | N | H | H | $C_6H_5$ | 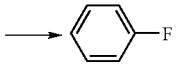 | $COOC_2H_5$ |
| 10-4A<br>10-4B<br>10-4C | N | N | H | H | $C_6H_5$ | 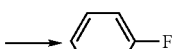 | 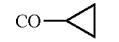 |
| 10-5A<br>10-5B<br>10-5C<br>10-5D<br>10-5E | N | N | H | H | $C_6H_5$ | 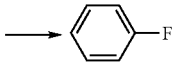 | 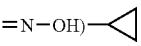 |
| 10-6 | N | N | H | H | 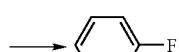 | 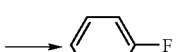 | $COOC_2H_5$ |
| 10-7 | N | N | H | H | 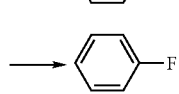 | 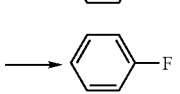 | 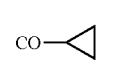 |

-continued

| Example | X | Y | Z | R' | R₁ | Ar | R₂ |
|---|---|---|---|---|---|---|---|
| 10-8A<br>10-8B | N | N | H | H | →⟨C₆H₄⟩—F | →⟨C₆H₄⟩—F | C(=N—OH)—▷ |
| 11 | C | N | H | H | C₆H₅ | C₆H₅ | COOC₂H₅ |
| 12 | N | C | H | H | C₆H₅ | C₆H₅ | COOC₂H₅ |
| 13 | N | N | H | Me | C₆H₅ | C₆H₅ | COOC₂H₅ |
| 14 | N | N | →⟨C₆H₄⟩—NH₂ | H | C₆H₅ | C₆H₅ | COOC₂H₅ |

| | Tubulin | | |
|---|---|---|---|
| Examples | Activity at 25 μM | IC₅₀ (μM) | % detachment 1 μM |
| 1 | + | 1.5 | 20% |
| 2-1 | + | 3.7 | |
| 2-2 | + | 1.25 | |
| 3-1 | + | 2.5 | 20% |
| 3-2 | + | 4.5 | |
| 3-3 | + | 25 | |
| 3-4 | + | 4.5 | |
| 4 | + | 23 | |
| 5-1 | + | 0.8 | 29% |
| 5-2 | + | 1.1 | 19% |
| 5-3 | + | 12.5 | |
| 5-4 | + | 7 | |
| 6-1A | + | 0.6 | 34% |
| 6-1B | + | 3 | |
| 6-2A | + | 1 | 18% |
| 6-2B | + | 25 | |
| 6-3A | + | 0.8 | 26% |
| 6-3B | + | 0.8 | |
| 6-4 | + | 6 | |
| 6-5 | + | 3 | |
| 6-6A | + | 1 | 17% |
| 6-6B | + | 1.2 | |
| 6-7A | + | 1.8 | |
| 6-7B | + | 6 | |
| 6-8A | + | 1.3 | |
| 6-8B | + | 10 | |
| 6-9A | + | 1.5 | |
| 6-9B | + | 2.5 | |
| 6-10A | + | 4.5 | |
| 6-10B | + | 12 | |
| 6-11A | + | 1 | |
| 6-11B | + | 1.3 | |
| 7-1 | + | 6 | |
| 7-2 | + | 5 | 25% |
| 7-4 | + | 6 | 18% |
| 8-1 | + | 9 | 24% |
| 8-2 | + | 1 | |
| 8-3 | + | 6 | |
| 8-4 | + | 1.2 | |
| 9-1 | + | 18 | |
| 9-2 | + | 15 | |
| 9-3 | + | 25 | |
| 10-1 | + | 15–20 | |
| 10-2 | + | 4.5 | |
| 10-3A | + | 1.2 | 16% |
| 10-3B | + | 1 | 19% |
| 10-3C | + | 1.5 | |
| 10-4A | + | 1 | 33% |
| 10-4B | + | 0.8 | |
| 10-4C | + | 1.5 | |
| 10-5A | + | 1 | 25% |
| 10-5B | + | 6 | |
| 10-5C | + | 0.8 | |
| 10-5D | + | 1.5 | |
| 10-5E | + | 6 | |
| 10-6 | + | 1 | |
| 10-7 | + | 1 | 24% |
| 10-8A | + | 1.5 | 17% |
| 10-8B | + | 9 | |
| 11 | + | 6.5 | |
| 12 | + | 2 | 17% |
| 13 | + | 1.5 | |
| 14 | + | 3 | |

The products of the list below are also particularly representative of the invention:

Aziridin-1-yl(6,6-diphenyl-6,7-dihydro-1H-indazol-3-yl)methanone

Cyclobutyl(6,6-diphenyl-6,7-dihydro-1H-indazol-3-yl)methanone O-methyloxime (N-Cyclopropyl)-6,6-diphenyl-1-(4-toluenesulphonyl)-6,7-dihydro-1H-indazol-3-ylamine (N-Cyclobutyl)-6,6-diphenyl-1-(4-toluenesulphonyl)-6,7-dihydro-1H-indazol-3-ylamine (N-Phenyl)-6,6-diphenyl-1-(4-toluenesulphonyl)-6,7-dihydro-1H-indazol-3-ylamine 1-(3-Cyclopropylamino-6,6-diphenyl-6,7-dihydroindazol-1-yl)propenone 1-(3-Cyclobutylamino-6,6-diphenyl-6,7-dihydroindazol-1-yl)propenone 1-(3-Anilino-6,6-diphenyl-6,7-dihydroindazol-1-yl)propenone 1-(3-Carboxy-6,6-diphenyl-6,7-dihydroindazol-1-yl)propenone 3,6,6-Triphenyl-6,7-dihydro-1H-indazole 6,6-Diphenyl-3-(pyrid-2-yl)-6,7-dihydro-1H-indazole
6,6-Diphenyl-3-(pyrid-3-yl)-6,7-dihydro-1H-indazole
6,6-Diphenyl-3-(pyrid-4-yl)-6,7-dihydro-1H-indazole
6,6-Diphenyl-3-(thiophen-2-yl)-6,7-dihydro-1H-indazole
6,6-Diphenyl-3-(thiophen-3-yl)-6,7-dihydro-1H-indazole
6,6-Diphenyl-3-(oxazol-2-yl)-6,7-dihydro-1H-indazole
6,6-Diphenyl-3-(oxazol-4-yl)-6,7-dihydro-1H-indazole
6,6-Diphenyl-3-(oxazol-5-yl)-6,7-dihydro-1H-indazole
6,6-Diphenyl-(thiazol-2-yl)-6,7-dihydro-1H-indazole
6,6-Diphenyl-3-(thiazol-4-yl)-6,7-dihydro-1H-indazole
6,6-Diphenyl-3-(thiazol-5-yl)-6,7-dihydro-1H-indazole
6,6-Diphenyl-3-(imidazol-2-yl)-6,7-dihydro-1H-indazole
6,6-Diphenyl-3-(imidazol-4-yl)-6,7-dihydro-1H-indazole 6,6-Diphenyl-3-(imidazol-5-yl)-6,7-dihydro-1H-indazole
6,6-Diphenyl-3-(3-methoxy[1,2,5]thiadiazol-4-yl)-6,7-dihydro-1H-indazole
6,6-Diphenyl-3-(tetrazol-5-yl)-6,7-dihydro-1H-indazole
6,6-Diphenyl-3-(tetrazol-1-yl)-6,7-dihydro-1H-indazole
Methyl 6-phenyl-6,7-dihydro-1H-indazole-3-carboxylate
(N-Cyclopropyl)-6-phenyl-6,7-dihydro-1H-indazole-3-carboxamide
Aziridin-1-yl(6-phenyl-6,7-dihydro-1H-indazol-3-yl)methanone
Azetidin-1-yl(6-phenyl-6,7-dihydro-1H-indazol-3-yl)methanone
(N-Methoxy-N-methyl)-6-phenyl-6,7-dihydro-1H-indazole-3-carboxamide
6-Phenyl-6,7-dihydro-1H-indazole-3-carbonitrile
Cyclopropyl(6-phenyl-6,7-dihydro-1H-indazol-3-yl)methanone
Cyclobutyl(6-phenyl-6,7-dihydro-1H-indazol-3-yl)methanone
Cyclopropyl(6-phenyl-6,7-dihydro-1H-indazol-3-yl)methanone oxime
Cyclopropyl(6-phenyl-6,7-dihydro-1H-indazol-3-yl)methanone O-methyloxime
Cyclobutyl(6-phenyl-6,7-dihydro-1H-indazol-3-yl)methanone oxime
Cyclobutyl(6-phenyl-6,7-dihydro-1H-indazol-3-yl)methanone O-methyloxime
6-Phenyl-1-(4-toluenesulphonyl)-6,7-dihydro-1H-indazol-3-ylamine
(N-Cyclopropyl)-6-phenyl-1-(4-toluenesulphonyl)-6,7-dihydro-1H-indazol-3-ylamine
(N-Cyclobutyl)-6-phenyl-1-(4-toluenesulphonyl)-6,7-dihydro-1H-indazol-3-ylamine
(N-Phenyl)-6-phenyl-1-(4-toluenesulphonyl)-6,7-dihydro-1H-indazol-3-ylamine
1-(3-Amino-6-phenyl-6,7-dihydroindazol-1-yl)propenone
1-(3-Cyclopropylamino-6-phenyl-6,7-dihydroindazol-1-yl)propenone
1-(3-Cyclobutylamino-6-phenyl-6,7-dihydroindazol-1-yl)propenone
1-(3-Anilino-6-phenyl-6,7-dihydroindazol-1-yl)propenone
6-Phenyl-1-(4-toluenesulphonyl)-6,7-dihydro-1H-indazole-3 carboxylic acid
1-(3-Carboxy-6-phenyl-6,7-dihydroindazol-1-yl)propenone
Cyclopropanecarboxylic acid (6-phenyl-6,7-dihydro-1H-indazol-3-yl)amide
Cyclobutanecarboxylic acid (6-phenyl-6,7-dihydro-1H-indazol-3-yl)amide
3,6-Diphenyl-6,7-dihydro-1H-indazole
6-Phenyl-3-(pyrid-2-yl)-6,7-dihydro-1H-indazole
6-Phenyl-3-(pyrid-3-yl)-6,7-dihydro-1H-indazole
6-Phenyl-3-(pyrid-4-yl)-6,7-dihydro-1H-indazole
6-Phenyl-3-(thiophen-2-yl)-6,7-dihydro-1H-indazole
6-Phenyl-3-(thiophen-3-yl)-6,7-dihydro-1H-indazole
3-(Oxazol-2-yl)-6-phenyl-6,7-dihydro-1H-indazole
3-(Oxazol-4-yl)-6-phenyl-6,7-dihydro-1H-indazole
3-(Oxazol-5-yl)-6-phenyl-6,7-dihydro-1H-indazole
6-Phenyl-3-(thiazol-2-yl)-6,7-dihydro-1H-indazole
6-Phenyl-3-(thiazol-4-yl)-6,7-dihydro-1H-indazole
6-Phenyl-3-(thiazol-5-yl)-6,7-dihydro-1H-indazole
3-(Imidazol-2-yl)-6-phenyl-6,7-dihydro-1H-indazole
3-(Imidazol-4-yl)-6-phenyl-6,7-dihydro-1H-indazole
3-(Imidazol-5-yl)-6-phenyl-6,7-dihydro-1H-indazole
3-(3-Methyl[1,2,4]oxadiazol-5-yl)-6-phenyl-6,7-dihydro-1H-indazole
3-(3-Methoxy[1,2,5]thiadiazol-4-yl)-6-phenyl-6,7-dihydro-1H-indazole
6-Phenyl-3-(tetrazol-5-yl)-6,7-dihydro-1H-indazole
6-Phenyl-3-(tetrazol-1-yl)-6,7-dihydro-1H-indazole
Methyl 6-methyl-6-phenyl-6,7-dihydro-1H-indazole-3-carboxylate
Ethyl 6-methyl-6-phenyl-6,7-dihydro-1H-indazole-3-carboxylate
(N-Cyclopropyl)-6-methyl-6-phenyl-6,7-dihydro-1H-indazole-3-carboxamide
Aziridin-1-yl(6-methyl-6-phenyl-6,7-dihydro-1H-indazol-3-yl)methanone
Azetidin-1-yl(6-methyl-6-phenyl-6,7-dihydro-1H-indazol-3-yl)methanone
(N-Methoxy-N-methyl)-6-methyl-6-phenyl-6,7-dihydro-1H-indazole-3-carboxamide
6-Methyl-6-phenyl-6,7-dihydro-1H-indazole-3-carbonitrile
Cyclopropyl(6-methyl-6-phenyl-6,7-dihydro-1H-indazol-3-yl)methanone
Cyclobutyl(6-methyl-6-phenyl-6,7-dihydro-1H-indazol-3-yl)methanone
Cyclopropyl(6-methyl-6-phenyl-6,7-dihydro-1H-indazol-3-yl)methanone oxime
Cyclopropyl(6-methyl-6-phenyl-6,7-dihydro-1H-indazol-3-yl)methanone O-methyloxime
Cyclobutyl(6-methyl-6-phenyl-6,7-dihydro-1H-indazol-3-yl)methanone oxime
Cyclobutyl(6-methyl-6-phenyl-6,7-dihydro-1H-indazol-3-yl)methanone O-methyloxime
6-Methyl-6-phenyl-1-(4-toluenesulphonyl)-6,7-dihydro-1H-indazol-3-ylamine
(N-Cyclopropyl)-6-methyl-6-phenyl-1-(4-toluenesulphonyl)-6,7-dihydro-1H-indazol-3-ylamine
(N-Cyclobutyl)-6-methyl-6-phenyl-1-(4-toluenesulphonyl)-6,7-dihydro-1H-indazol-3-ylamine
(N-Phenyl)-6-methyl-6-phenyl-1-(4-toluenesulphonyl)-6,7-dihydro-1H-indazol-3-ylamine
1-(3-Amino-6-methyl-6-phenyl-6,7-dihydroindazol-1-yl)propenone
1-(3-Cyclopropylamino-6-methyl-6-phenyl-6,7-dihydroindazol-1-yl)propenone
1-(3-Cyclobutylamino-6-methyl-6-phenyl-6,7-dihydroindazol-1-yl)propenone
1-(3-Anilino-6-methyl-6-phenyl-6,7-dihydroindazol-1-yl)propenone
6-Methyl-6-phenyl-1-(4-toluenesulphonyl)-6,7-dihydro-1H-indazole-3-carboxylic acid
1-(3-Carboxy-6-methyl-6-phenyl-6,7-dihydroindazol-1-yl)propenone
Cyclopropanecarboxylic acid (6-methyl-6-phenyl-6,7-dihydro-1H-indazol-3-yl)amide
Cyclobutanecarboxylic acid (6-methyl-6-phenyl-6,7-dihydro-1H-indazol-3-yl)amide
3,6-Diphenyl-6-methyl-6,7-dihydro-1H-indazole
6-Methyl-6-phenyl-3-(pyrid-2-yl)-6,7-dihydro-1H-indazole
6-Methyl-6-phenyl-3-(pyrid-3-yl)-6,7-dihydro-1H-indazole
6-Methyl-6-phenyl-3-(pyrid-4-yl)-6,7-dihydro-1H-indazole
6-Methyl-6-phenyl-3-(thiophen-2-yl)-6,7-dihydro-1H-indazole
6-Methyl-6-phenyl-3-(thiophen-3-yl)-6,7-dihydro-1H-indazole
6-Methyl-3-(oxazol-2-yl)-6-phenyl-6,7-dihydro-1H-indazole
6-Methyl-3-(oxazol-4-yl)-6-phenyl-6,7-dihydro-1H-indazole
6-Methyl-3-(oxazol-5-yl)-6-phenyl-6,7-dihydro-1H-indazole
6-Methyl-6-phenyl-3-(thiazol-2-yl)-6,7-dihydro-1H-indazole 6-Methyl-6-phenyl-3-(thiazol-4-yl)-6,7-dihydro-1H-indazole
6-Methyl-6-phenyl-3-(thiazol-5-yl)-6,7-dihydro-1H-indazole
3-(Imidazol-2-yl)-6-methyl-6-phenyl-6,7-dihydro-1H-indazole
3-(Imidazol-4-yl)-6-methyl-6-phenyl-6,7-dihydro-1H-indazole
3-(Imidazol-5-yl)-6-methyl-6-phenyl-6,7-dihydro-1H-indazole
6-Methyl-3-(3-methyl[1,2,4]oxadiazol-5-yl)-6-phenyl-6,7-dihydro-1H-indazole
3-(3-Methoxy[1,2,5]thiadiazol-4-yl)-6-methyl-6-phenyl-6,7-dihydro-1H-indazole
6-Methyl-6-phenyl-3-(tetrazol-5-yl)-6,7-dihydro-1H-indazole
6-Methyl-6-phenyl-3-(tetrazol-1-yl)-6,7-dihydro-1H-indazole
Methyl 6-cyclohexyl-6-phenyl-6,7-dihydro-1H-indazole-3-carboxylate
Ethyl 6-cyclohexyl-6-phenyl-6,7-dihydro-1H-indazole-3-carboxylate
(N-Cyclopropyl)-6-cyclohexyl-6-phenyl-6,7-dihydro-1H-indazole-3-carboxamide
Aziridin-1-yl(6-cyclohexyl-6-phenyl-6,7-dihydro-1H-indazol-3-yl)methanone
Azetidin-1-yl(6-cyclohexyl-6-phenyl-6,7-dihydro-1H-indazol-3-yl)methanone
(N-Methoxy-N-methyl)-6-cyclohexyl-6-phenyl-6,7-dihydro-1H-indazole-3-carboxamide
6-Cyclohexyl-6-phenyl-6,7-dihydro-1H-indazole-3-carbonitrile
Cyclopropyl(6-cyclohexyl-6-phenyl-6,7-dihydro-1H-indazol-3-yl)methanone
Cyclobutyl(6-cyclohexyl-6-phenyl-6,7-dihydro-1H-indazol-3-yl)methanone
Cyclopropyl(6-cyclohexyl-6-phenyl-6,7-dihydro-1H-indazol-3-yl)methanone oxime
Cyclopropyl(6-cyclohexyl-6-phenyl-6,7-dihydro-1H-indazol-3-yl)methanone O-methyloxime
Cyclobutyl(6-cyclohexyl-6-phenyl-6,7-dihydro-1H-indazol-3-yl)methanone oxime
Cyclobutyl(6-cyclohexyl-6-phenyl-6,7-dihydro-1H-indazol-3-yl)methanone O-methyloxime
6-Cyclohexyl-6-phenyl-1-(4-toluenesulphonyl)-6,7-dihydro-1H-indazol-3-ylamine
(N-Cyclopropyl)-6-cyclohexyl-6-phenyl-1-(4-toluenesulphonyl)-6,7-dihydro-1H-indazol-3-ylamine
(N-Cyclobutyl)-6-cyclohexyl-6-phenyl-1-(4-toluenesulphonyl)-6,7-dihydro-1H-indazol-3-ylamine
(N-Phenyl)-6-cyclohexyl-6-phenyl-1-(4-toluenesulphonyl)-6,7-dihydro-1H-indazol-3-ylamine
1-(3-Amino-6-cyclohexyl-6-phenyl-6,7-dihydroindazol-1-yl)propenone
1-(3-Cyclopropylamino-6-cyclohexyl-6-phenyl-6,7-dihydroindazol-1-yl)propenone
1-(3-Cyclobutylamino-6-cyclohexyl-6-phenyl-6,7-dihydroindazol-1-yl)propenone
1-(3-Anilino-6-cyclohexyl-6-phenyl-6,7-dihydroindazol-1-yl)propenone
6-Cyclohexyl-6-phenyl-1-(4-toluenesulphonyl)-6,7-dihydro-1H-indazole-3-carboxylic acid
1-(3-Carboxy-6-cyclohexyl-6-phenyl-6,7-dihydroindazol-1-yl)propenone
Cyclopropanecarboxylic acid (6-cyclohexyl-6-phenyl-6,7-dihydro-1H-indazol-3-yl)amide
Cyclobutanecarboxylic acid (6-cyclohexyl-6-phenyl-6,7-dihydro-1H-indazol-3-yl)amide
6-Cyclohexyl-3,6-diphenyl-6,7-dihydro-1H-indazole
6-Cyclohexyl-6-phenyl-3-(pyrid-2-yl)-6,7-dihydro-1H-indazole
6-Cyclohexyl-6-phenyl-3-(pyrid-3-yl)-6,7-dihydro-1H-indazole
6-Cyclohexyl-6-phenyl-3-(pyrid-4-yl)-6,7-dihydro-1H-indazole
6-Cyclohexyl-6-phenyl-3-(thiophen-2-yl)-6,7-dihydro-1H-indazole
6-Cyclohexyl-6-phenyl-3-(thiophen-3-yl)-6,7-dihydro-1H-indazole
6-Cyclohexyl-3-(oxazol-2-yl)-6-phenyl-6,7-dihydro-1H-indazole
6-Cyclohexyl-3-(oxazol-4-yl)-6-phenyl-6,7-dihydro-1H-indazole
6-Cyclohexyl-3-(oxazol-5-yl)-6-phenyl-6,7-dihydro-1H-indazole
6-Cyclohexyl-6-phenyl-3-(thiazol-2-yl)-6,7-dihydro-1H-indazole
6-Cyclohexyl-6-phenyl-3-(thiazol-4-yl)-6,7-dihydro-1H-indazole
6-Cyclohexyl-6-phenyl-3-(thiazol-5-yl)-6,7-dihydro-1H-indazole
6-Cyclohexyl-3-(imidazol-2-yl)-6-phenyl-6,7-dihydro-1H-indazole
6-Cyclohexyl-3-(imidazol-4-yl)-6-phenyl-6,7-dihydro-1H-indazole
6-Cyclohexyl-3-(Imidazol-5-yl)-6-phenyl-6,7-dihydro-1H-indazole
6-Cyclohexyl-3-(3-methyl[1,2,4]oxadiazol-5-yl)-6-phenyl-6,7-dihydro-1H-indazole
6-Cyclohexyl-3-(3-methoxy[1,2,5]thiadiazol-4-yl)-6-phenyl-6,7-dihydro-1H-indazole
6-Cyclohexyl-6-phenyl-3-(tetrazol-5-yl)-6,7-dihydro-1H-indazole
6-Cyclohexyl-6-phenyl-3-(tetrazol-1-yl)-6,7-dihydro-1H-indazole
Methyl 6-(4-methoxyphenyl)-6-phenyl-6,7-dihydro-1H-indazole-3-carboxylate
Ethyl 6-(4-methoxyphenyl)-6-phenyl-6,7-dihydro-1H-indazole-3-carboxylate
(N-Cyclopropyl)-6-(4-methoxyphenyl)-6-phenyl-6,7-dihydro-1H-indazole-3-carboxamide
Aziridin-1-yl[6-(4-methoxyphenyl)-6-phenyl-6,7-dihydro-1H-indazol-3-yl]methanone
Azetidin-1-yl[6-(4-methoxyphenyl)-6-phenyl-6,7-dihydro-1H-indazol-3-yl]methanone
(N-Methoxy-N-methyl)-6-(4-methoxyphenyl)-6-phenyl-6,7-dihydro-1H-indazole-3-carboxamide
6-(4-Methoxyphenyl)-6-phenyl-6,7-dihydro-1H-indazole-3-carbonitrile
Cyclopropyl[6-(4-methoxyphenyl)-6-phenyl-6,7-dihydro-1H-indazol-3-yl]methanone
Cyclobutyl[6-(4-methoxyphenyl)-6-phenyl-6,7-dihydro-1H-indazol-3-yl]methanone
Cyclopropyl[6-(4-methoxyphenyl)-6-phenyl-6,7-dihydro-1H-indazol-3-yl]methanone oxime
Cyclopropyl[6-(4-methoxyphenyl)-6-phenyl-6,7-dihydro-1H-indazol-3-yl]methanone O-methyloxime
Cyclobutyl[6-(4-methoxyphenyl)-6-phenyl-6,7-dihydro-1H-indazol-3-yl]methanone oxime
Cyclobutyl[6-(4-methoxyphenyl)-6-phenyl-6,7-dihydro-1H-indazol-3-yl]methanone O-methyloxime
6-(4-Methoxyphenyl)-6-phenyl-1-(4-toluenesulphonyl)-6,7-dihydro-1H-indazol-3-ylamine (N-Cyclopropyl)-6-(4-methoxyphenyl)-6-phenyl-1-(4-toluenesulphonyl)-6,7-dihydro-1H-indazol-3-ylamine
(N-Cyclobutyl)-6-(4-methoxyphenyl)-6-phenyl-1-(4-toluenesulphonyl)-6,7-dihydro-1H-indazol-3-ylamine
(N-Phenyl)-6-(4-methoxyphenyl)-6-phenyl-1-(4-toluenesulphonyl)-6,7-dihydro-1H-indazol-3-ylamine
1-[3-Amino-6-(4-methoxyphenyl)-6-phenyl-6,7-dihydroindazol-1-yl]propenone
1-[3-Cyclopropylamino-6-(4-methoxyphenyl)-6-phenyl-6,7-dihydroindazol-1-yl]propenone
1-[3-Cyclobutylamino-6-(4-methoxyphenyl)-6-phenyl-6,7-dihydroindazol-1-yl]propenone
1-[3-Anilino-6-(4-methoxyphenyl)-6-phenyl-6,7-dihydroindazol-1-yl]propenone
6-(4-Methoxyphenyl)-6-phenyl-1-(4-toluenesulphonyl)-6,7-dihydro-1H-indazole-3-carboxylic acid
1-[3-Carboxy-6-(4-methoxyphenyl)-6-phenyl-6,7-dihydroindazol-1-yl]propenone
Cyclopropanecarboxylic acid [6-(4-methoxyphenyl)-6-phenyl-6,7-dihydro-1H-indazol-3-yl]amide
Cyclobutanecarboxylic acid [6-(4-methoxyphenyl)-6-phenyl-6,7-dihydro-1H-indazol-3-yl]amide
3,6-Diphenyl-6-(4-methoxyphenyl)-6,7-dihydro-1H-indazole
6-(4-Methoxyphenyl)-6-phenyl-3-(pyrid-2-yl)-6,7-dihydro-1H-indazole
6-(4-Methoxyphenyl)-6-phenyl-3-(pyrid-3-yl)-6,7-dihydro-1H-indazole
6-(4-Methoxyphenyl)-6-phenyl-3-(pyrid-4-yl)-6,7-dihydro-1H-indazole
6-(4-Methoxyphenyl)-6-phenyl-3-(thiophen-2-yl)-6,7-dihydro-1H-indazole
6-(4-Methoxyphenyl)-6-phenyl-3-(thiophen-3-yl)-6,7-dihydro-1H-indazole
6-(4-Methoxyphenyl)-3-(oxazol-2-yl)-6-phenyl-6,7-dihydro-1H-indazole
6-(4-Methoxyphenyl)-3-(oxazol-4-yl)-6-phenyl-6,7-dihydro-1H-indazole
6-(4-Methoxyphenyl)-3-(oxazol-5-yl)-6-phenyl-6,7-dihydro-1H-indazole
6-(4-Methoxyphenyl)-6-phenyl-3-(thiazol-2-yl)-6,7-dihydro-1H-indazole
6-(4-Methoxyphenyl)-6-phenyl-3-(thiazol-4-yl)-6,7-dihydro-1H-indazole
6-(4-Methoxyphenyl)-6-phenyl-3-(thiazol-5-yl)-6,7-dihydro-1H-indazole
3-(Imidazol-2-yl)-6-(4-methoxyphenyl)-6-phenyl-6,7-dihydro-1H-indazole
3-(Imidazol-4-yl)-6-(4-methoxyphenyl)-6-phenyl-6,7-dihydro-1H-indazole
3-(Imidazol-5-yl)-6-(4-methoxyphenyl)-6-phenyl-6,7-dihydro-1H-indazole
6-(4-Methoxyphenyl)-3-(3-methyl[1,2,4]oxadiazol-5-yl)-6-phenyl-6,7-dihydro-1H-indazole
6-(4-Methoxyphenyl)-3-(3-methoxy[1,2,5]thiadiazol-4-yl)-6-phenyl-6,7-dihydro-1H-indazole
6-(4-Methoxyphenyl)-6-phenyl-3-(tetrazol-5-yl)-6,7-dihydro-1H-indazole
6-(4-Methoxyphenyl)-6-phenyl-3-(tetrazol-1-yl)-6,7-dihydro-1H-indazole
Methyl 6-(3-methoxyphenyl)-6-phenyl-6,7-dihydro-1H-indazole-3-carboxylate
Ethyl 6-(3-methoxyphenyl)-6-phenyl-6,7-dihydro-1H-indazole-3-carboxylate
(N-Cyclopropyl)-6-(3-methoxyphenyl)-6-phenyl-6,7-dihydro-1H-indazole-3-carboxamide
Aziridin-1-yl[6-(3-methoxyphenyl)-6-phenyl-6,7-dihydro-1H-indazol-3-yl]methanone
Azetidin-1-yl[6-(3-methoxyphenyl)-6-phenyl-6,7-dihydro-1H-indazol-3-yl]methanone
(N-Methoxy-N-methyl)-6-(3-methoxyphenyl)-6-phenyl-6,7-dihydro-1H-indazole-3-carboxamide
6-(3-Methoxyphenyl)-6-phenyl-6,7-dihydro-1H-indazole-3-carbonitrile
Cyclopropyl[6-(3-methoxyphenyl)-6-phenyl-6,7-dihydro-1H-indazol-3-yl]methanone
Cyclobutyl[6-(3-methoxyphenyl)-6-phenyl-6,7-dihydro-1H-indazol-3-yl]methanone
Cyclopropyl[6-(3-methoxyphenyl)-6-phenyl-6,7-dihydro-1H-indazol-3-yl]methanone oxime
Cyclopropyl[6-(3-methoxyphenyl)-6-phenyl-6,7-dihydro-1H-indazol-3-yl]methanone O-methyloxime
Cyclobutyl[6-(3-methoxyphenyl)-6-phenyl-6,7-dihydro-1H-indazol-3-yl]methanone oxime
Cyclobutyl[6-(3-methoxyphenyl)-6-phenyl-6,7-dihydro-1H-indazol-3-yl]methanone O-methyloxime
6-(3-Methoxyphenyl)-6-phenyl-1-(4-toluenesulphonyl)-6,7-dihydro-1H-indazol-3-ylamine
(N-Cyclopropyl)-6-(3-methoxyphenyl)-6-phenyl-1-(4-toluenesulphonyl)-6,7-dihydro-1H-indazol-3-ylamine
(N-Cyclobutyl)-6-(3-methoxyphenyl)-6-phenyl-1-(4-toluenesulphonyl)-6,7-dihydro-1H-indazol-3-ylamine
(N-Phenyl)-6-(3-methoxyphenyl)-6-phenyl-1-(4-toluenesulphonyl)-6,7-dihydro-1H-indazol-3-ylamine
1-[3-Amino-6-(3-methoxyphenyl)-6-phenyl-6,7-dihydroindazol-1-yl]propenone
1-[3-Cyclopropylamino-6-(3-methoxyphenyl)-6-phenyl-6,7-dihydroindazol-1-yl]propenone
1-[3-Cyclobutylamino-6-(3-methoxyphenyl)-6-phenyl-6,7-dihydroindazol-1-yl]propenone
1-[3-Anilino-6-(3-methoxyphenyl)-6-phenyl-6,7-dihydroindazol-1-yl]propenone
6-(3-Methoxyphenyl)-6-phenyl-1-(4-toluenesulphonyl)-6,7-dihydro-1H-indazole-3-carboxylic acid
1-[3-Carboxy-6-(3-methoxyphenyl)-6-phenyl-6,7-dihydroindazol-1-yl]propenone
Cyclopropanecarboxylic acid [6-(3-methoxyphenyl)-6-phenyl-6,7-dihydro-1H-indazol-3-yl]amide
Cyclobutanecarboxylic acid [6-(3-methoxyphenyl)-6-phenyl-6,7-dihydro-1H-indazol-3-yl]amide
3,6-Diphenyl-6-(3-methoxyphenyl)-6,7-dihydro-1H-indazole
6-(3-Methoxyphenyl)-6-phenyl-3-(pyrid-2-yl)-6,7-dihydro-1H-indazole
6-(3-Methoxyphenyl)-6-phenyl-3-(pyrid-3-yl)-6,7-dihydro-1H-indazole
6-(3-Methoxyphenyl)-6-phenyl-3-(pyrid-4-yl)-6,7-dihydro-1H-indazole
6-(3-Methoxyphenyl)-6-phenyl-3-(thiophen-2-yl)-6,7-dihydro-1H-indazole
6-(3-Methoxyphenyl)-6-phenyl-3-(thiophen-3-yl)-6,7-dihydro-1H-indazole
6-(3-Methoxyphenyl)-3-(oxazol-2-yl)-6-phenyl-6,7-dihydro-1H-indazole
6-(3-Methoxyphenyl)-3-(oxazol-4-yl)-6-phenyl-6,7-dihydro-1H-indazole
6-(3-Methoxyphenyl)-3-(oxazol-5-yl)-6-phenyl-6,7-dihydro-1H-indazole
6-(3-Methoxyphenyl)-6-phenyl-3-(thiazol-2-yl)-6,7-dihydro-1H-indazole
6-(3-Methoxyphenyl)-6-phenyl-3-(thiazol-4-yl)-6,7-dihydro-1H-indazole 6-(3-Methoxyphenyl)-6-phenyl-3-(thiazol-5-yl)-6,7-dihydro-1H-indazole
3-(Imidazol-2-yl)-6-(3-methoxyphenyl)-6-phenyl-6,7-dihydro-1H-indazole
3-(Imidazol-4-yl)-6-(3-methoxyphenyl)-6-phenyl-6,7-dihydro-1H-indazole
3-(Imidazol-5-yl)-6-(3-methoxyphenyl)-6-phenyl-6,7-dihydro-1H-indazole
6-(3-Methoxyphenyl)-3-(3-methyl[1,2,4]oxadiazol-5-yl)-6-phenyl-6,7-dihydro-1H-indazole
6-(3-Methoxyphenyl)-3-(3-methoxy[1,2,5]thiadiazol-4-yl)-6-phenyl-6,7-dihydro-1H-indazole
6-(3-Methoxyphenyl)-6-phenyl-3-(tetrazol-5-yl)-6,7-dihydro-1H-indazole
6-(3-Methoxyphenyl)-6-phenyl-3-(tetrazol-1-yl)-6,7-dihydro-1H-indazole
Methyl 6-(3,4-dimethoxyphenyl)-6-phenyl-6,7-dihydro-1H-indazole-3-carboxylate
(N-Cyclopropyl)-6-(3,4-dimethoxyphenyl)-6-phenyl-6,7-dihydro-1H-indazole-3-carboxamide
Aziridin-1-yl[6-(3,4-dimethoxyphenyl)-6-phenyl-6,7-dihydro-1H-indazol-3-yl]methanone
Azetidin-1-yl[6-(3,4-dimethoxyphenyl)-6-phenyl-6,7-dihydro-1H-indazol-3-yl]methanone
(N-Methoxy-N-methyl)-6-(3,4-dimethoxyphenyl)-6-phenyl-6,7-dihydro-1H-indazole-3-carboxamide
6-(3,4-Dimethoxyphenyl)-6-phenyl-6,7-dihydro-1H-indazole-3-carbonitrile
Cyclopropyl[6-(3,4-dimethoxyphenyl)-6-phenyl-6,7-dihydro-1H-indazol-3-yl]methanone
Cyclobutyl[6-(3,4-dimethoxyphenyl)-6-phenyl-6,7-dihydro-1H-indazol-3-yl]methanone
Cyclopropyl[6-(3,4-dimethoxyphenyl)-6-phenyl-6,7-dihydro-1H-indazol-3-yl]methanone oxime
Cyclopropyl[6-(3,4-dimethoxyphenyl)-6-phenyl-6,7-dihydro-1H-indazol-3-yl]methanone O-methyloxime
Cyclobutyl[6-(3,4-dimethoxyphenyl)-6-phenyl-6,7-dihydro-1H-indazol-3-yl]methanone oxime
Cyclobutyl[6-(3,4-dimethoxyphenyl)-6-phenyl-6,7-dihydro-1H-indazol-3-yl]methanone O-methyloxime
6-(3,4-Dimethoxyphenyl)-6-phenyl-1-(4-toluenesulphonyl)-6,7-dihydro-1H-indazol-3-ylamine
(N-Cyclopropyl)-6-(3,4-dimethoxyphenyl)-6-phenyl-1-(4-toluenesulphonyl)-6,7-dihydro-1H-indazol-3-ylamine
(N-Cyclobutyl)-6-(3,4-dimethoxyphenyl)-6-phenyl-1-(4-toluenesulphonyl)-6,7-dihydro-1H-indazol-3-ylamine
(N-Phenyl)-6-(3,4-dimethoxyphenyl)-6-phenyl-1-(4-toluenesulphonyl)-6,7-dihydro-1H-indazol-3-ylamine
1-[3-Amino-6-(3,4-dimethoxyphenyl)-6-phenyl-6,7-dihydroindazol-1-yl]propenone
1-[3-Cyclopropylamino-6-(3,4-dimethoxyphenyl)-6-phenyl-6,7-dihydroindazol-1-yl]propenone
1-[3-Cyclobutylamino-6-(3,4-dimethoxyphenyl)-6-phenyl-6,7-dihydroindazol-1-yl]propenone
1-[3-Anilino-6-(3,4-dimethoxyphenyl)-6-phenyl-6,7-dihydroindazol-1-yl]propenone
6-(3,4-Dimethoxyphenyl)-6-phenyl-1-(4-toluenesulphonyl)-6,7-dihydro-1H-indazole-3-carboxylic acid
1-[3-Carboxy-6-(3,4-dimethoxyphenyl)-6-phenyl-6,7-dihydroindazol-1-yl]propenone
Cyclopropanecarboxylic acid [6-(3,4-dimethoxyphenyl)-6-phenyl-6,7-dihydro-1H-indazol-3-yl]amide
Cyclobutanecarboxylic acid [6-(3,4-dimethoxyphenyl)-6-phenyl-6,7-dihydro-1H-indazol-3-yl]amide
6-(3,4-Dimethoxyphenyl)-3,6-diphenyl-6,7-dihydro-1H-indazole
6-(3,4-Dimethoxyphenyl)-6-phenyl-3-(pyrid-2-yl)-6,7-dihydro-1H-indazole
6-(3,4-Dimethoxyphenyl)-6-phenyl-3-(pyrid-3-yl)-6,7-dihydro-1H-indazole
6-(3,4-Dimethoxyphenyl)-6-phenyl-3-(pyrid-4-yl)-6,7-dihydro-1H-indazole
6-(3,4-Dimethoxyphenyl)-6-phenyl-3-(thiophen-2-yl)-6,7-dihydro-1H-indazole
6-(3,4-Dimethoxyphenyl)-6-phenyl-3-(thiophen-3-yl)-6,7-dihydro-1H-indazole
6-(3,4-Dimethoxyphenyl)-3-(oxazol-2-yl)-6-phenyl-6,7-dihydro-1H-indazole
6-(3,4-Dimethoxyphenyl)-3-(oxazol-4-yl)-6-phenyl-6,7-dihydro-1H-indazole
6-(3,4-Dimethoxyphenyl)-3-(oxazol-5-yl)-6-phenyl-6,7-dihydro-1H-indazole
6-(3,4-Dimethoxyphenyl)-6-phenyl-3-(thiazol-2-yl)-6,7-dihydro-1H-indazole
6-(3,4-Dimethoxyphenyl)-6-phenyl-3-(thiazol-4-yl)-6,7-dihydro-1H-indazole
6-(3,4-Dimethoxyphenyl)-6-phenyl-3-(thiazol-5-yl)-6,7-dihydro-1H-indazole
6-(3,4-Dimethoxyphenyl)-3-(imidazol-2-yl)-6-phenyl-6,7-dihydro-1H-indazole
6-(3,4-Dimethoxyphenyl)-3-(imidazol-4-yl)-6-phenyl-6,7-dihydro-1H-indazole
6-(3,4-Dimethoxyphenyl)-3-(imidazol-5-yl)-6-phenyl-6,7-dihydro-1H-indazole
6-(3,4-Dimethoxyphenyl)-3-(3-methyl[1,2,4]oxadiazol-5-yl)-6-phenyl-6,7-dihydro-1H-indazole
6-(3,4-Dimethoxyphenyl)-3-(3-methoxy[1,2,5]thiadiazol-4-yl)-6-phenyl-6,7-dihydro-1H-indazole
6-(3,4-Dimethoxyphenyl)-6-phenyl-3-(tetrazol-5-yl)-6,7-dihydro-1H-indazole
6-(3,4-Dimethoxyphenyl)-6-phenyl-3-(tetrazol-1-yl)-6,7-dihydro-1H-indazole
Methyl 6-(3,4-methylenedioxyphenyl)-6-phenyl-6,7-dihydro-1H-indazole-3-carboxylate
Ethyl 6-(3,4-methylenedioxyphenyl)-6-phenyl-6,7-dihydro-1H-indazole-3-carboxylate
(N-cyclopropyl)-6-(3,4-methylenedioxyphenyl)-6-phenyl-6,7-dihydro-1H-indazole-3-carboxamide
Aziridin-1-yl[6-(3,4-methylenedioxyphenyl)-6-phenyl-6,7-dihydro-1H-indazol-3-yl]methanone
Azetidin-1-yl[6-(3,4-methylenedioxyphenyl)-6-phenyl-6,7-dihydro-1H-indazol-3-yl]methanone
(N-Methoxy-N-methyl)-6-(3,4-methylenedioxyphenyl)-6-phenyl-6,7-dihydro-1H-indazole-3-carboxamide
6-(3,4-Methylenedioxyphenyl)-6-phenyl-6,7-dihydro-1H-indazole-3-carbonitrile
Cyclopropyl[6-(3,4-methylenedioxyphenyl)-6-phenyl-6,7-dihydro-1H-indazol-3-yl]methanone
Cyclobutyl[6-(3,4-methylenedioxyphenyl)-6-phenyl-6,7-dihydro-1H-indazol-3-yl]methanone
Cyclopropyl[6-(3,4-methylenedioxyphenyl)-6-phenyl-6,7-dihydro-1H-indazol-3-yl]methanone oxime
Cyclopropyl[6-(3,4-methylenedioxyphenyl)-6-phenyl-6,7-dihydro-1H-indazol-3-yl]methanone O-methyloxime
Cyclobutyl[6-(3,4-methylenedioxyphenyl)-6-phenyl-6,7-dihydro-1H-indazol-3-yl]methanone oxime
Cyclobutyl[6-(3,4-methylenedioxyphenyl)-6-phenyl-6,7-dihydro-1H-indazol-3-yl]methanone O-methyloxime
6-(3,4-Methylenedioxyphenyl)-6-phenyl-1-(4-toluenesulphonyl)-6,7-dihydro-1H-indazol-3-ylamine
(N-Cyclopropyl)-6-(3,4-methylenedioxyphenyl)-6-phenyl-1-(4-toluenesulphonyl)-6,7-dihydro-1H-indazol-3-ylamine (N-Cyclobutyl)-6-(3,4-methylenedioxyphenyl)-6-phenyl-1-(4-toluenesulphonyl)-6,7-dihydro-1H-indazol-3-ylamine
(N-Phenyl)-6-(3,4-methylenedioxyphenyl)-6-phenyl-1-(4-toluenesulphonyl)-6,7-dihydro-1H-indazol-3-ylamine
1-[3-Amino-6-(3,4-methylenedioxyphenyl)-6-phenyl-6,7-dihydroindazol-1-yl]propenone
1-[3-Cyclopropylamino-6-(3,4-methylenedioxyphenyl)-6-phenyl-6,7-dihydroindazol-1 yl]propenone
1-[3-Cyclobutylamino-6-(3,4-methylenedioxyphenyl)-6-phenyl-6,7-dihydroindazol-1-yl]propenone
1-[3-Anilino-6-(3,4-methylenedioxyphenyl)-6-phenyl-6,7-dihydroindazol-1-yl]propenone
6-(3,4-Methylenedioxyphenyl)-6-phenyl-1-(4-toluenesulphonyl)-6,7-dihydro-1H-indazole-3-carboxylic acid
1-[3-Carboxy-6-(3,4-methylenedioxyphenyl)-6-phenyl-6,7-dihydroindazol-1-yl]propenone
Cyclopropanecarboxylic acid [6-(3,4-methylenedioxyphenyl)-6-phenyl-6,7-dihydro-1H-indazol-3-yl]amide
Cyclobutanecarboxylic acid [6-(3,4-methylenedioxyphenyl)-6-phenyl-6,7-dihydro-1H-indazol-3-yl]amide
3,6-Diphenyl-6-(3,4-methylenedioxyphenyl)-6,7-dihydro-1H-indazole
6-(3,4-Methylenedioxyphenyl)-6-phenyl-3-(pyrid-2-yl)-6,7-dihydro-1H-indazole
6-(3,4-Methylenedioxyphenyl)-6-phenyl-3-(pyrid-3-yl)-6,7-dihydro-1H-indazole
6-(3,4-Methylenedioxyphenyl)-6-phenyl-3-(pyrid-4-yl)-6,7-dihydro-1H-indazole
6-(3,4-Methylenedioxyphenyl)-6-phenyl-3-(thiophen-2-yl)-6,7-dihydro-1H-indazole
6-(3,4-Methylenedioxyphenyl)-6-phenyl-3-(thiophen-3-yl)-6,7-dihydro-1H-indazole
6-(3,4-Methylenedioxyphenyl)-3-(oxazol-2-yl)-6-phenyl-6,7-dihydro-1H-indazole
6-(3,4-Methylenedioxyphenyl)-3-(oxazol-4-yl)-6-phenyl-6,7-dihydro-1H-indazole
6-(3,4-Methylenedioxyphenyl)-3-(oxazol-5-yl)-6-phenyl-6,7-dihydro-1H-indazole
6-(3,4-Methylenedioxyphenyl)-6-phenyl-3-(thiazol-2-yl)-6,7-dihydro-1H-indazole
6-(3,4-Methylenedioxyphenyl)-6-phenyl-3-(thiazol-4-yl)-6,7-dihydro-1H-indazole
6-(3,4-Methylenedioxyphenyl)-6-phenyl-3-(thiazol-5-yl)-6,7-dihydro-1H-indazole
3-(Imidazol-2-yl)-6-(3,4-methylenedioxyphenyl)-6-phenyl-6,7-dihydro-1H-indazole
3-(Imidazol-4-yl)-6-(3,4-methylenedioxyphenyl)-6-phenyl-6,7-dihydro-1H-indazole
3-(Imidazol-5-yl)-6-(3,4-methylenedioxyphenyl)-6-phenyl-6,7-dihydro-1H-indazole
6-(3,4-Methylenedioxyphenyl)-3-(3-methyl[1,2,4]oxadiazol-5-yl)-6-phenyl-6,7-dihydro-1H-indazole
3-(3-Methoxy[1,2,5]thiadiazol-4-yl)-6-(3,4-methylenedioxyphenyl)-6-phenyl-6,7-dihydro-1H-indazole
6-(3,4-Methylenedioxyphenyl)-6-phenyl-3-(tetrazol-5-yl)-6,7-dihydro-1H-indazole
6-(3,4-Methylenedioxyphenyl)-6-phenyl-3-(tetrazol-1-yl)-6,7-dihydro-1H-indazole
Methyl 6-phenyl-6-(2,3,4-trimethoxyphenyl)-6,7-dihydro-1H-indazole-3-carboxylate
Ethyl 6-phenyl-6-(2,3,4-trimethoxyphenyl)-6,7-dihydro-1H-indazole-3-carboxylate
(N-Cyclopropyl)-6-phenyl-6-(2,3,4-trimethoxyphenyl)-6,7-dihydro-1H-indazole-3-carboxamide
Aziridin-1-yl[6-phenyl-6-(2,3,4-trimethoxyphenyl)-6,7-dihydro-1H-indazol-3-yl]methanone
Azetidin-1-yl[6-phenyl-6-(2,3,4-trimethoxyphenyl)-6,7-dihydro-1H-indazol-3-yl]methanone
(N-Methoxy-N-methyl)-6-phenyl-6-(2,3,4-trimethoxyphenyl)-6,7-dihydro-1H-indazole-3-carboxamide
6-Phenyl-6-(2,3,4-trimethoxyphenyl)-6,7-dihydro-1H-indazole-3-carbonitrile
Cyclopropyl[6-phenyl-6-(2,3,4-trimethoxyphenyl)-6,7-dihydro-1H-indazol-3-yl]methanone
Cyclobutyl[6-phenyl-6-(2,3,4-trimethoxyphenyl)-6,7-dihydro-1H-indazol-3-yl]methanone
Cyclopropyl[6-phenyl-6-(2,3,4-trimethoxyphenyl)-6,7-dihydro-1H-indazol-3-yl]methanone oxime
Cyclopropyl[6-phenyl-6-(2,3,4-trimethoxyphenyl)-6,7-dihydro-1H-indazol-3-yl]methanone O-methyloxime
Cyclobutyl[6-phenyl-6-(2,3,4-trimethoxyphenyl)-6,7-dihydro-1H-indazol-3-yl]methanone oxime
Cyclobutyl[6-phenyl-6-(2,3,4-trimethoxyphenyl)-6,7-dihydro-1H-indazol-3-yl]methanone O-methyloxime
6-Phenyl-6-(2,3,4-trimethoxyphenyl)-1-(4-toluenesulphonyl)-6,7-dihydro-1H-indazol-3-ylamine
(N-Cyclopropyl)-6-phenyl-6-(2,3,4-trimethoxyphenyl)-1-(4-toluenesulphonyl)-6,7-dihydro-1H-indazol-3-ylamine
(N-Cyclobutyl)-6-phenyl-6-(2,3,4-trimethoxyphenyl)-1-(4-toluenesulphonyl)-6,7-dihydro-1H-indazol-3-ylamine
(N-Phenyl)-6-phenyl-6-(2,3,4-trimethoxyphenyl)-1-(4-toluenesulphonyl)-6,7-dihydro-1H-indazol-3-ylamine
1-[3-Amino-6-phenyl-6-(2,3,4-trimethoxyphenyl)-6,7-dihydroindazol-1-yl]propenone
1-[3-Cyclopropylamino-6-phenyl-6-(2,3,4-trimethoxyphenyl)-6,7-dihydroindazol-1-yl]propenone
1-[3-Cyclobutylamino-6-phenyl-6-(2,3,4-trimethoxyphenyl)-6,7-dihydroindazol-1-yl]propenone
1-[3-Anilino-6-phenyl-6-(2,3,4-trimethoxyphenyl)-6,7-dihydroindazol-1-yl]propenone
6-Phenyl-6-(2,3,4-trimethoxyphenyl)-1-(4-toluenesulphonyl)-6,7-dihydro-1H-indazole-3-carboxylic acid
1-[3-Carboxy-6-phenyl-6-(2,3,4-trimethoxyphenyl)-6,7-dihydroindazol-1-yl]propenone
Cyclopropanecarboxylic acid [6-phenyl-6-(2,3,4-trimethoxyphenyl)-6,7-dihydro-1H-indazol-3-yl]amide
Cyclobutanecarboxylic acid [6-phenyl-6-(2,3,4-trimethoxyphenyl)-6,7-dihydro-1H-indazol-3-yl]amide
3,6-Diphenyl-6-(2,3,4-trimethoxyphenyl)-6,7-dihydro-1H-indazole
6-Phenyl-3-(pyrid-2-yl)-6-(2,3,4-trimethoxyphenyl)-6,7-dihydro-1H-indazole
6-Phenyl-3-(pyrid-3-yl)-6-(2,3,4-trimethoxyphenyl)-6,7-dihydro-1H-indazole
6-Phenyl-3-(pyrid-4-yl)-6-(2,3,4-trimethoxyphenyl)-6,7-dihydro-1H-indazole
6-Phenyl-3-(thiophen-2-yl)-6-(2,3,4-trimethoxyphenyl)-6,7-dihydro-1H-indazole
6-Phenyl-3-(thiophen-3-yl)-6-(2,3,4-trimethoxyphenyl)-6,7-dihydro-1H-indazole
3-(Oxazol-2-yl)-6-phenyl-6-(2,3,4-trimethoxyphenyl)-6,7-dihydro-1H-indazole
3-(Oxazol-4-yl)-6-phenyl-6-(2,3,4-trimethoxyphenyl)-6,7-dihydro-1H-indazole
6-(2,3,4-Trimethoxyphenyl)-3-(oxazol-5-yl)-6-phenyl-6,7-dihydro-1H-indazole
6-Phenyl-6-(2,3,4-trimethoxyphenyl)-3-(thiazol-2-yl)-6,7-dihydro-1H-indazole
6-Phenyl-3-(thiazol-4-yl)-6-(2,3,4-trimethoxyphenyl)-6,7-dihydro-1H-indazole
6-Phenyl-3-(thiazol-5-yl)-6-(2,3,4-trimethoxyphenyl)-6,7-dihydro-1H-indazole 3-(Imidazol-2-yl)-6-phenyl-6-(2,3,4-trimethoxyphenyl)-6,7-dihydro-1H-indazole
3-(Imidazol-4-yl)-6-phenyl-6-(2,3,4-trimethoxyphenyl)-6,7-dihydro-1H-indazole
3-(Imidazol-5-yl)-6-phenyl-6-(2,3,4-trimethoxyphenyl)-6,7-dihydro-1H-indazole
3-(3-Methyl[1,2,4]oxadiazol-5-yl)-6-phenyl-6-(2,3,4-trimethoxyphenyl)-6,7-dihydro-1H-indazole
3-(3-Methoxy[1,2,5]thiadiazol-4-yl)-6-phenyl-6-(2,3,4-trimethoxyphenyl)-6,7-dihydro-1H-indazole
6-Phenyl-3-(tetrazol-5-yl)-6-(2,3,4-trimethoxyphenyl)-6,7-dihydro-1H-indazole
6-Phenyl-3-(tetrazol-1-yl)-6-(2,3,4-trimethoxyphenyl)-6,7-dihydro-1H-indazole
Methyl 6-phenyl-6-(3,4,5-trimethoxyphenyl)-6,7-dihydro-1H-indazole-3-carboxylate
Ethyl 6-phenyl-6-(3,4,5-trimethoxyphenyl)-6,7-dihydro-1H-indazole-3-carboxylate
(N-Cyclopropyl)-6-phenyl-6-(3,4,5-trimethoxyphenyl)-6,7-dihydro-1H-indazole-3-carboxamide
Aziridin-1-yl[6-phenyl-6-(3,4,5-trimethoxyphenyl)-6,7-dihydro-1H-indazol-3-yl]methanone
Azetidin-1-yl[6-phenyl-6-(3,4,5-trimethoxyphenyl)-6,7-dihydro-1H-indazol-3-yl]methanone
(N-Methoxy-N-methyl)-6-phenyl-6-(3,4,5-trimethoxyphenyl)-6,7-dihydro-1H-indazole-3-carboxamide
6-Phenyl-6-(3,4,5-trimethoxyphenyl)-6,7-dihydro-1H-indazole-3-carbonitrile
Cyclopropyl[6-phenyl-6-(3,4,5-trimethoxyphenyl)-6,7-dihydro-1H-indazol-3-yl]methanone
Cyclobutyl[6-phenyl-6-(3,4,5-trimethoxyphenyl)-6,7-dihydro-1H-indazol-3-yl]methanone
Cyclopropyl[6-phenyl-6-(3,4,5-trimethoxyphenyl)-6,7-dihydro-1H-indazol-3-yl]methanone oxime
Cyclopropyl[6-phenyl-6-(3,4,5-trimethoxyphenyl)-6,7-dihydro-1H-indazol-3-yl]methanone O-methyloxime
Cyclobutyl[6-phenyl-6-(3,4,5-trimethoxyphenyl)-6,7-dihydro-1H-indazol-3-yl]methanone oxime
Cyclobutyl[6-phenyl-6-(3,4,5-trimethoxyphenyl)-6,7-dihydro-1H-indazol-3-yl]methanone O-methyloxime
6-Phenyl-6-(3,4,5-trimethoxyphenyl)-1-(4-toluenesulphonyl)-6,7-dihydro-1H-indazol-3-ylamine
(N-Cyclopropyl)-6-phenyl-6-(3,4,5-trimethoxyphenyl)-1-(4-toluenesulphonyl)-6,7-dihydro-1H-indazol-3-ylamine
(N-Cyclobutyl)-6-phenyl-6-(3,4,5-trimethoxyphenyl)-1-(4-toluenesulphonyl)-6,7-dihydro-1H-indazol-3-ylamine
(N-Phenyl)-6-phenyl-6-(3,4,5-trimethoxyphenyl)-1-(4-toluenesulphonyl)-6,7-dihydro-1H-indazol-3-ylamine
1-[3-Amino-6-phenyl-6-(3,4,5-trimethoxyphenyl)-6,7-dihydroindazol-1-yl]propenone
1-[3-Cyclopropylamino-6-phenyl-6-(3,4,5-trimethoxyphenyl)-6,7-dihydroindazol-1-yl]propenone
1-[3-Cyclobutylamino-6-phenyl-6-(3,4,5-trimethoxyphenyl)-6,7-dihydroindazol-1-yl]propenone
1-[3-Anilino-6-phenyl-6-(3,4,5-trimethoxyphenyl)-6,7-dihydroindazol-1-yl]propenone
6-Phenyl-6-(3,4,5-trimethoxyphenyl)-1-(4-toluenesulphonyl)-6,7-dihydro-1H-indazole-3-carboxylic acid
1-[3-Carboxy-6-phenyl-6-(3,4,5-trimethoxyphenyl)-6,7-dihydroindazol-1-yl]propenone
Cyclopropanecarboxylic acid [6-phenyl-6-(3,4,5-trimethoxyphenyl)-6,7-dihydro-1H-indazol-3-yl]amide
Cyclobutanecarboxylic acid [6-phenyl-6-(3,4,5-trimethoxyphenyl)-6,7-dihydro-1H-indazol-3-yl]amide
3,6-Diphenyl-6-(3,4,5-trimethoxyphenyl)-6,7-dihydro-1H-indazole
6-Phenyl-3-(pyrid-2-yl)-6-(3,4,5-trimethoxyphenyl)-6,7-dihydro-1H-indazole
6-Phenyl-3-(pyrid-3-yl)-6-(3,4,5-trimethoxyphenyl)-6,7-dihydro-1H-indazole
6-Phenyl-3-(pyrid-4-yl)-6-(3,4,5-trimethoxyphenyl)-6,7-dihydro-1H-indazole
6-Phenyl-3-(thiophen-2-yl)-6-(3,4,5-trimethoxyphenyl)-6,7-dihydro-1H-indazole
6-Phenyl-3-(thiophen-3-yl)-6-(3,4,5-trimethoxyphenyl)-6,7-dihydro-1H-indazole
3-(Oxazol-2-yl)-6-phenyl-6-(3,4,5-trimethoxyphenyl)-6,7-dihydro-1H-indazole
3-(Oxazol-4-yl)-6-phenyl-6-(3,4,5-trimethoxyphenyl)-6,7-dihydro-1H-indazole
6-(3,4,5-Trimethoxyphenyl)-3-(oxazol-5-yl)-6-phenyl-6,7-dihydro-1H-indazole
6-Phenyl-6-(3,4,5-trimethoxyphenyl)-3-(thiazol-2-yl)-6,7-dihydro-1H-indazole
6-Phenyl-3-(thiazol-4-yl)-6-(3,4,5-trimethoxyphenyl)-6,7-dihydro-1H-indazole
6-Phenyl-3-(thiazol-5-yl)-6-(3,4,5-trimethoxyphenyl)-6,7-dihydro-1H-indazole
3-(Imidazol-2-yl)-6-phenyl-6-(3,4,5-trimethoxyphenyl)-6,7-dihydro-1H-indazole
3-(Imidazol-4-yl)-6-phenyl-6-(3,4,5-trimethoxyphenyl)-6,7-dihydro-1H-indazole
3-(Imidazol-5-yl)-6-phenyl-6-(3,4,5-trimethoxyphenyl)-6,7-dihydro-1H-indazole
3-(3-Methyl[1,2,4]oxadiazol-5-yl)-6-phenyl-6-(3,4,5-trimethoxyphenyl)-6,7-dihydro-1H-indazole
3-(3-Methoxy[1,2,5]thiadiazol-4-yl)-6-phenyl-6-(3,4,5-trimethoxyphenyl)-6,7-dihydro-1H-indazole
6-Phenyl-3-(tetrazol-5-yl)-6-(3,4,5-trimethoxyphenyl)-6,7-dihydro-1H-indazole
6-Phenyl-3-(tetrazol-1-yl)-6-(3,4,5-trimethoxyphenyl)-6,7-dihydro-1H-indazole
Methyl 6-(3-dimethylaminophenyl)-6-phenyl-6,7-dihydro-1H-indazole-3-carboxylate
Ethyl 6-(3-dimethylaminophenyl)-6-phenyl-6,7-dihydro-1H-indazole-3-carboxylate
(N-Cyclopropyl)-6-(3-dimethylaminophenyl)-6-phenyl-6,7-dihydro-1H-indazole-3-carboxamide
Aziridin-1-yl[6-(3-dimethylaminophenyl)-6-phenyl-6,7-dihydro-1H-indazol-3-yl]methanone
Azetidin-1-yl[6-(3-dimethylaminophenyl)-6-phenyl-6,7-dihydro-1H-indazol-3-yl]methanone
(N-Methoxy-N-methyl)-6-(3-dimethylaminophenyl)-6-phenyl-6,7-dihydro-1H-indazole-3-carboxamide
6-(3-Dimethylaminophenyl)-6-phenyl-6,7-dihydro-1H-indazole-3-carbonitrile
Cyclopropyl[6-(3-dimethylaminophenyl)-6-phenyl-6,7-dihydro-1H-indazol-3-yl]methanone
Cyclobutyl[6-(3-dimethylaminophenyl)-6-phenyl-6,7-dihydro-1H-indazol-3-yl]methanone
Cyclopropyl[6-(3-dimethylaminophenyl)-6-phenyl-6,7-dihydro-1H-indazol-3-yl]methanone oxime
Cyclopropyl[6-(3-dimethylaminophenyl)-6-phenyl-6,7-dihydro-1H-indazol-3-yl]methanone O-methyloxime
Cyclobutyl[6-(3-dimethylaminophenyl)-6-phenyl-6,7-dihydro-1H-indazol-3-yl]methanone oxime
Cyclobutyl[6-(3-dimethylaminophenyl)-6-phenyl-6,7-dihydro-1H-indazol-3-yl]methanone O-methyloxime
6-(3-Dimethylaminophenyl)-6-phenyl-1-(4-toluenesulphonyl)-6,7-dihydro-1H-indazol-3-ylamine
(N-Cyclopropyl)-6-(3-dimethylaminophenyl)-6-phenyl-1-(4-toluenesulphonyl)-6,7-dihydro-1H-indazol-3-ylamine (N-Cyclobutyl)-6-(3-dimethylaminophenyl)-6-phenyl-1-(4-toluenesulphonyl)-6,7-dihydro-1H-indazol-3-ylamine
(N-Phenyl)-6-(3-dimethylaminophenyl)-6-phenyl-1-(4-toluenesulphonyl)-6,7-dihydro-1H-indazol-3-ylamine
1-[3-Amino-6-(3-dimethylaminophenyl)-6-phenyl-6,7-dihydroindazol-1-yl]propenone
1-[3-Cyclopropylamino-6-(3-dimethylaminophenyl)-6-phenyl-6,7-dihydroindazol-1-yl]propenone
1-[3-Cyclobutylamino-6-(3-dimethylaminophenyl)-6-phenyl-6,7-dihydroindazol-1-yl]propenone
1-[3-Anilino-6-(3-dimethylaminophenyl)-6-phenyl-6,7-dihydroindazol-1-yl]propenone
6-(3-Dimethylaminophenyl)-6-phenyl-1-(4-toluenesulphonyl)-6,7-dihydro-1H-indazole-3-carboxylic acid
1-[3-Carboxy-6-(3-dimethylaminophenyl)-6-phenyl-6,7-dihydroindazol-1-yl]propenone
Cyclopropanecarboxylic acid [6-(3-dimethylaminophenyl)-6-phenyl-6,7-dihydro-1H-indazol-3-yl]amide
Cyclobutanecarboxylic acid [6-(3-dimethylaminophenyl)-6-phenyl-6,7-dihydro-1H-indazol-3-yl]amide
6-(3-Dimethylaminophenyl)-3,6-diphenyl-6,7-dihydro-1H-indazole
6-(3-Dimethylaminophenyl)-6-phenyl-3-(pyrid-2-yl)-6,7-dihydro-1H-indazole
6-(3-Dimethylaminophenyl)-6-phenyl-3-(pyrid-3-yl)-6,7-dihydro-1H-indazole
6-(3-Dimethylaminophenyl)-6-phenyl-3-(pyrid-4-yl)-6,7-dihydro-1H-indazole
6-(3-Dimethylaminophenyl)-6-phenyl-3-(thiophen-2-yl)-6,7-dihydro-1H-indazole
6-(3-Dimethylaminophenyl)-6-phenyl-3-(thiophen-3-yl)-6,7-dihydro-1H-indazole
6-(3-Dimethylaminophenyl)-3-(oxazol-2-yl)-6-phenyl-6,7-dihydro-1H-indazole
6-(3-Dimethylaminophenyl)-3-(oxazol-4-yl)-6-phenyl-6,7-dihydro-1H-indazole
6-(3-Dimethylaminophenyl)-3-(oxazol-5-yl)-6-phenyl-6,7-dihydro-1H-indazole
6-(3-Dimethylaminophenyl)-6-phenyl-3-(thiazol-2-yl)-6,7-dihydro-1H-indazole
6-(3-Dimethylaminophenyl)-6-phenyl-3-(thiazol-4-yl)-6,7-dihydro-1H-indazole
6-(3-Dimethylaminophenyl)-6-phenyl-3-(thiazol-5-yl)-6,7-dihydro-1H-indazole
6-(3-Dimethylaminophenyl)-3-(imidazol-2-yl)-6-phenyl-6,7-dihydro-1H-indazole
6-(3-Dimethylaminophenyl)-3-(imidazol-4-yl)-6-phenyl-6,7-dihydro-1H-indazole
6-(3-Dimethylaminophenyl)-3-(imidazol-5-yl)-6-phenyl-6,7-dihydro-1H-indazole
6-(3-Dimethylaminophenyl)-3-(3-methyl[1,2,4]oxadiazol-5-yl)-6-phenyl-6,7-dihydro-1H-indazole
6-(3-Dimethylaminophenyl)-3-(3-methoxy[1,2,5]thiadiazol-4-yl)-6-phenyl-6,7-dihydro-1H-indazole
6-(3-Dimethylaminophenyl)-6-phenyl-3-(tetrazol-5-yl)-6,7-dihydro-1H-indazole
6-(3-Dimethylaminophenyl)-6-phenyl-3-(tetrazol-1-yl)-6,7-dihydro-1H-indazole
Methyl 6-(4-dimethylaminophenyl)-6-phenyl-6,7-dihydro-1H-indazole-3-carboxylate
Ethyl 6-(4-dimethylaminophenyl)-6-phenyl-6,7-dihydro-1H-indazole-3-carboxylate
(N-Cyclopropyl)-6-(4-dimethylaminophenyl)-6-phenyl-6,7-dihydro-1H-indazole-3-carboxamide
Aziridin-1-yl[6-(4-dimethylaminophenyl)-6-phenyl-6,7-dihydro-1H-indazol-3-yl]methanone
Azetidin-1-yl[6-(4-dimethylaminophenyl)-6-phenyl-6,7-dihydro-1H-indazol-3-yl]methanone
(N-Methoxy-N-methyl)-6-(4-dimethylaminophenyl)-6-phenyl-6,7-dihydro-1H-indazole-3-carboxamide
6-(4-Dimethylaminophenyl)-6-phenyl-6,7-dihydro-1H-indazole-3-carbonitrile
Cyclopropyl[6-(4-dimethylaminophenyl)-6-phenyl-6,7-dihydro-1H-indazol-3-yl]methanone
Cyclobutyl[6-(4-dimethylaminophenyl)-6-phenyl-6,7-dihydro-1H-indazol-3-yl]methanone
Cyclopropyl[6-(4-dimethylaminophenyl)-6-phenyl-6,7-dihydro-1H-indazol-3-yl]methanone oxime
Cyclopropyl[6-(4-dimethylaminophenyl)-6-phenyl-6,7-dihydro-1H-indazol-3-yl]methanone O-methyloxime
Cyclobutyl[6-(4-dimethylaminophenyl)-6-phenyl-6,7-dihydro-1H-indazol-3-yl]methanone oxime
Cyclobutyl[6-(4-dimethylaminophenyl)-6-phenyl-6,7-dihydro-1H-indazol-3-yl]methanone O-methyloxime
6-(4-Dimethylaminophenyl)-6-phenyl-1-(4-toluenesulphonyl)-6,7-dihydro-1H-indazol-3-ylamine
(N-Cyclopropyl)-6-(4-dimethylaminophenyl)-6-phenyl-1-(4-toluenesulphonyl)-6,7-dihydro-1H-indazol-3-ylamine
(N-Cyclobutyl)-6-(4-dimethylaminophenyl)-6-phenyl-1-(4-toluenesulphonyl)-6,7-dihydro-1H-indazol-3-ylamine
(N-Phenyl)-6-(4-dimethylaminophenyl)-6-phenyl-1-(4-toluenesulphonyl)-6,7-dihydro-1H-indazol-3-ylamine
1-[3-Amino-6-(4-dimethylaminophenyl)-6-phenyl-6,7-dihydroindazol-1-yl]propenone
1-[3-Cyclopropylamino-6-(4-dimethylaminophenyl)-6-phenyl-6,7-dihydroindazol-1-yl]propenone
1-[3-Cyclobutylamino-6-(4-dimethylaminophenyl)-6-phenyl-6,7-dihydroindazol-1-yl]propenone
1-[3-Anilino-6-(4-dimethylaminophenyl)-6-phenyl-6,7-dihydroindazol-1-yl]propenone
6-(4-Dimethylaminophenyl)-6-phenyl-1-(4-toluenesulphonyl)-6,7-dihydro-1H-indazole-3-carboxylic acid
1-[3-Carboxy-6-(4-dimethylaminophenyl)-6-phenyl-6,7-dihydroindazol-1-yl]propenone
Cyclopropanecarboxylic acid [6-(4-dimethylaminophenyl)-6-phenyl-6,7-dihydro-1H-indazol-3-yl]amide
Cyclobutanecarboxylic acid [6-(4-dimethylaminophenyl)-6-phenyl-6,7-dihydro-1H-indazol-3-yl]amide
6-(4-Dimethylaminophenyl)-3,6-diphenyl-6,7-dihydro-1H-indazole
6-(4-Dimethylaminophenyl)-6-phenyl-3-(pyrid-2-yl)-6,7-dihydro-1H-indazole
6-(4-Dimethylaminophenyl)-6-phenyl-3-(pyrid-3-yl)-6,7-dihydro-1H-indazole
6-(4-Dimethylaminophenyl)-6-phenyl-3-(pyrid-4-yl)-6,7-dihydro-1H-indazole
6-(4-Dimethylaminophenyl)-6-phenyl-3-(thiophen-2-yl)-6,7-dihydro-1H-indazole
6-(4-Dimethylaminophenyl)-6-phenyl-3-(thiophen-3-yl)-6,7-dihydro-1H-indazole
6-(4-Dimethylaminophenyl)-3-(oxazol-2-yl)-6-phenyl-6,7-dihydro-1H-indazole
6-(4-Dimethylaminophenyl)-3-(oxazol-4-yl)-6-phenyl-6,7-dihydro-1H-indazole
6-(4-Dimethylaminophenyl)-3-(oxazol-5-yl)-6-phenyl-6,7-dihydro-1H-indazole
6-(4-Dimethylaminophenyl)-6-phenyl-3-(thiazol-2-yl)-6,7-dihydro-1H-indazole
6-(4-Dimethylaminophenyl)-6-phenyl-3-(thiazol-4-yl)-6,7-dihydro-1H-indazole
6-(4-Dimethylaminophenyl)-6-phenyl-3-(thiazol-5-yl)-6,7-dihydro-1H-indazole 6-(4-Dimethylaminophenyl)-3-(imidazol-2-yl)-6-phenyl-6,7-dihydro-1H-indazole
6-(4-Dimethylaminophenyl)-3-(imidazol-4-yl)-6-phenyl-6,7-dihydro-1H-indazole
6-(4-Dimethylaminophenyl)-3-(imidazol-5-yl)-6-phenyl-6,7-dihydro-1H-indazole
6-(4-Dimethylaminophenyl)-3-(3-methyl[1,2,4]oxadiazol-5-yl)-6-phenyl-6,7-dihydro-1H-indazole
6-(4-Dimethylaminophenyl)-3-(3-methoxy[1,2,5]thiadiazol-4-yl)-6-phenyl-6,7-dihydro-1H-indazole
6-(4-Dimethylaminophenyl)-6-phenyl-3-(tetrazol-5-yl)-6,7-dihydro-1H-indazole
6-(4-Dimethylaminophenyl)-6-phenyl-3-(tetrazol-1-yl)-6,7-dihydro-1H-indazole
Methyl 6-(3-fluorophenyl)-6-phenyl-6,7-dihydro-1H-indazole-3-carboxylate
Ethyl 6-(3-fluorophenyl)-6-phenyl-6,7-dihydro-1H-indazole-3-carboxylate
(N-Cyclopropyl)-6-(3-fluorophenyl)-6-phenyl-6,7-dihydro-1H-indazole-3-carboxamide
Aziridin-1-yl[6-(3-fluorophenyl)-6-phenyl-6,7-dihydro-1H-indazol-3-yl]methanone
Azetidin-1-yl[6-(3-fluorophenyl)-6-phenyl-6,7-dihydro-1H-indazol-3-yl]methanone
(N-Methoxy-N-methyl)-6-(3-fluorophenyl)-6-phenyl-6,7-dihydro-1H-indazole-3-carboxamide
6-(3-Fluorophenyl)-6-phenyl-6,7-dihydro-1H-indazole-3-carbonitrile
Cyclopropyl[6-(3-fluorophenyl)-6-phenyl-6,7-dihydro-1H-indazol-3-yl]methanone
Cyclobutyl[6-(3-fluorophenyl)-6-phenyl-6,7-dihydro-1H-indazol-3-yl]methanone
Cyclopropyl[6-(3-fluorophenyl)-6-phenyl-6,7-dihydro-1H-indazol-3-yl]methanone oxime
Cyclopropyl[6-(3-fluorophenyl)-6-phenyl-6,7-dihydro-1H-indazol-3-yl]methanone O-methyloxime
Cyclobutyl[6-(3-fluorophenyl)-6-phenyl-6,7-dihydro-1H-indazol-3-yl]methanone oxime
Cyclobutyl[6-(3-fluorophenyl)-6-phenyl-6,7-dihydro-1H-indazol-3-yl]methanone O-methyloxime
6-(3-Fluorophenyl)-6-phenyl-1-(4-toluenesulphonyl)-6,7-dihydro-1H-indazol-3-ylamine
(N-Cyclopropyl)-6-(3-fluorophenyl)-6-phenyl-1-(4-toluenesulphonyl)-6,7-dihydro-1H-indazol-3-ylamine
(N-Cyclobutyl)-6-(3-fluorophenyl)-6-phenyl-1-(4-toluenesulphonyl)-6,7-dihydro-1H-indazol-3-ylamine
(N-Phenyl)-6-(3-fluorophenyl)-6-phenyl-1-(4-toluenesulphonyl)-6,7-dihydro-1H-indazol-3-ylamine
1-[3-Amino-6-(3-fluorophenyl)-6-phenyl-6,7-dihydroindazol-1-yl]propenone
1-[3-Cyclopropylamino-6-(3-fluorophenyl)-6-phenyl-6,7-dihydroindazol-1-yl]propenone
1-[3-Cyclobutylamino-6-(3-fluorophenyl)-6-phenyl-6,7-dihydroindazol-1-yl]propenone
1-[3-Anilino-6-(3-fluorophenyl)-6-phenyl-6,7-dihydroindazol-1-yl]propenone
6-(3-Fluorophenyl)-6-phenyl-1-(4-toluenesulphonyl)-6,7-dihydro-1H-indazole-3-carboxylic acid
1-[3-Carboxy-6-(3-fluorophenyl)-6-phenyl-6,7-dihydroindazol-1-yl]propenone
Cyclopropanecarboxylic acid [6-(3-fluorophenyl)-6-phenyl-6,7-dihydro-1H-indazol-3-yl]amide
Cyclobutanecarboxylic acid [6-(3-fluorophenyl)-6-phenyl-6,7-dihydro-1H-indazol-3-yl]amide
6-(3-Fluorophenyl)-3,6-diphenyl-6,7-dihydro-1H-indazole
6-(3-Fluorophenyl)-6-phenyl-3-(pyrid-2-yl)-6,7-dihydro-1H-indazole
6-(3-Fluorophenyl)-6-phenyl-3-(pyrid-3-yl)-6,7-dihydro-1H-indazole
6-(3-Fluorophenyl)-6-phenyl-3-(pyrid-4-yl)-6,7-dihydro-1H-indazole
6-(3-Fluorophenyl)-6-phenyl-3-(thiophen-2-yl)-6,7-dihydro-1H-indazole
6-(3-Fluorophenyl)-6-phenyl-3-(thiophen-3-yl)-6,7-dihydro-1H-indazole
6-(3-Fluorophenyl)-3-(oxazol-2-yl)-6-phenyl-6,7-dihydro-1H-indazole
6-(3-Fluorophenyl)-3-(oxazol-4-yl)-6-phenyl-6,7-dihydro-1H-indazole
6-(3-Fluorophenyl)-3-(oxazol-5-yl)-6-phenyl-6,7-dihydro-1H-indazole
6-(3-Fluorophenyl)-6-phenyl-3-(thiazol-2-yl)-6,7-dihydro-1H-indazole
6-(3-Fluorophenyl)-6-phenyl-3-(thiazol-4-yl)-6,7-dihydro-1H-indazole
6-(3-Fluorophenyl)-6-phenyl-3-(thiazol-5-yl)-6,7-dihydro-1H-indazole
6-(3-Fluorophenyl)-3-(imidazol-2-yl)-6-phenyl-6,7-dihydro-1H-indazole
6-(3-Fluorophenyl)-3-(imidazol-4-yl)-6-phenyl-6,7-dihydro-1H-indazole
6-(3-Fluorophenyl)-3-(imidazol-5-yl)-6-phenyl-6,7-dihydro-1H-indazole
6-(3-Fluorophenyl)-3-(3-methyl[1,2,4]oxadiazol-5-yl)-6-phenyl-6,7-dihydro-1H-indazole
6-(3-Fluorophenyl)-3-(3-methoxy[1,2,5]thiadiazol-4-yl)-6-phenyl-6,7-dihydro-1H-indazole
6-(3-Fluorophenyl)-6-phenyl-3-(tetrazol-5-yl)-6,7-dihydro-1H-indazole
6-(3-Fluorophenyl)-6-phenyl-3-(tetrazol-1-yl)-6,7-dihydro-1H-indazole
Methyl 6-(4-fluorophenyl)-6-phenyl-6,7-dihydro-1H-indazole-3-carboxylate
Ethyl 6-(4-fluorophenyl)-6-phenyl-6,7-dihydro-1H-indazole-3-carboxylate
(N-Cyclopropyl)-6-(4-fluorophenyl)-6-phenyl-6,7-dihydro-1H-indazole-3-carboxamide
Aziridin-1-yl[6-(4-fluorophenyl)-6-phenyl-6,7-dihydro-1H-indazol-3-yl]methanone
Azetidin-1-yl[6-(4-fluorophenyl)-6-phenyl-6,7-dihydro-1H-indazol-3-yl]methanone
(N-Methoxy-N-methyl)-6-(4-fluorophenyl)-6-phenyl-6,7-dihydro-1H-indazole-3-carboxamide
6-(4-Fluorophenyl)-6-phenyl-6,7-dihydro-1H-indazole-3-carbonitrile
Cyclopropyl[6-(4-fluorophenyl)-6-phenyl-6,7-dihydro-1H-indazol-3-yl]methanone
Cyclobutyl[6-(4-fluorophenyl)-6-phenyl-6,7-dihydro-1H-indazol-3-yl]methanone
Cyclopropyl[6-(4-fluorophenyl)-6-phenyl-6,7-dihydro-1H-indazol-3-yl]methanone oxime
Cyclopropyl[6-(4-fluorophenyl)-6-phenyl-6,7-dihydro-1H-indazol-3-yl]methanone O-methyloxime
Cyclobutyl[6-(4-fluorophenyl)-6-phenyl-6,7-dihydro-1H-indazol-3-yl]methanone oxime
Cyclobutyl[6-(4-fluorophenyl)-6-phenyl-6,7-dihydro-1H-indazol-3-yl]methanone O-methyloxime
6-(4-Fluorophenyl)-6-phenyl-1-(4-toluenesulphonyl)-6,7-dihydro-1H-indazol-3-ylamine
(N-Cyclopropyl)-6-(4-fluorophenyl)-6-phenyl-1-(4-toluenesulphonyl)-6,7-dihydro-1H-indazol-3-ylamine
(N-Cyclobutyl)-6-(4-fluorophenyl)-6-phenyl-1-(4-toluenesulphonyl)-6,7-dihydro-1H-indazol-3-ylamine (N-Phenyl)-6-(4-fluorophenyl)-6-phenyl-1-(4-toluene-sulphonyl)-6,7-dihydro-1H-indazol-3-ylamine
1-[3-Amino-6-(4-fluorophenyl)-6-phenyl-6,7-dihydroindazol-1-yl]propenone
1-[3-Cyclopropylamino-6-(4-fluorophenyl)-6-phenyl-6,7-dihydroindazol-1-yl]propenone
1-[3-Cyclobutylamino-6-(4-fluorophenyl)-6-phenyl-6,7-dihydroindazol-1-yl]propenone
1-[3-Anilino-6-(4-fluorophenyl)-6-phenyl-6,7-dihydroindazol-1-yl]propenone
6-(4-Fluorophenyl)-6-phenyl-1-(4-toluenesulphonyl)-6,7-dihydro-1H-indazole-3-carboxylic acid
1-[3-Carboxy-6-(4-fluorophenyl)-6-phenyl-6,7-dihydroindazol-1-yl]propenone
Cyclopropanecarboxylic acid [6-(4-fluorophenyl)-6-phenyl-6,7-dihydro-1H-indazol-3-yl]amide
Cyclobutanecarboxylic acid [6-(4-fluorophenyl)-6-phenyl-6,7-dihydro-1H-indazol-3-yl]amide
6-(4-Fluorophenyl)-3,6-diphenyl-6,7-dihydro-1H-indazole
6-(4-Fluorophenyl)-6-phenyl-3-(pyrid-2-yl)-6,7-dihydro-1H-indazole
6-(4-Fluorophenyl)-6-phenyl-3-(pyrid-3-yl)-6,7-dihydro-1H-indazole
6-(4-Fluorophenyl)-6-phenyl-3-(pyrid-4-yl)-6,7-dihydro-1H-indazole
6-(4-Fluorophenyl)-6-phenyl-3-(thiophen-2-yl)-6,7-dihydro-1H-indazole
6-(4-Fluorophenyl)-6-phenyl-3-(thiophen-3-yl)-6,7-dihydro-1H-indazole
6-(4-Fluorophenyl)-3-(oxazol-2-yl)-6-phenyl-6,7-dihydro-1H-indazole
6-(4-Fluorophenyl)-3-(oxazol-4-yl)-6-phenyl-6,7-dihydro-1H-indazole
6-(4-Fluorophenyl)-3-(oxazol-5-yl)-6-phenyl-6,7-dihydro-1H-indazole
6-(4-Fluorophenyl)-6-phenyl-3-(thiazol-2-yl)-6,7-dihydro-1H-indazole
6-(4-Fluorophenyl)-6-phenyl-3-(thiazol-4-yl)-6,7-dihydro-1H-indazole
6-(4-Fluorolpheny)-6-phenyl-3-(thiazol-5-yl)-6,7-dihydro-1H-indazole
6-(4-Fluorophenyl)-3-(imidazol-2-yl)-6-phenyl-6,7-dihydro-1H-indazole
6-(4-Fluorophenyl)-3-(imidazol-4-yl)-6-phenyl-6,7-dihydro-1H-indazole
6-(4-Fluorophenyl)-3-(imidazol-5-yl)-6-phenyl-6,7-dihydro-1H-indazole
6-(4-Fluorophenyl)-3-(3-methyl[1,2,4]oxadiazol-5-yl)-6-phenyl-6,7-dihydro-1H-indazole
6-(4-Fluorophenyl)-3-(3-methoxy[1,2,5]thiadiazol-4-yl)-6-phenyl-6,7-dihydro-1H-indazole
6-(4-Fluorophenyl)-6-phenyl-3-(tetrazol-5-yl)-6,7-dihydro-1H-indazole
6-(4-Fluorophenyl)-6-phenyl-3-(tetrazol-1-yl)-6,7-dihydro-1H-indazole
Methyl 6-(3,4-difluorophenyl)-6-phenyl-6,7-dihydro-1H-indazole-3-carboxylate
Ethyl 6-(3,4-difluorophenyl)-6-phenyl-6,7-dihydro-1H-indazole-3-carboxylate
(N-Cyclopropyl)-6-(3,4-difluorophenyl)-6-phenyl-6,7-dihydro-1H-indazole-3-carboxamide
Aziridin-1-yl[6-(3,4-difluorophenyl)-6-phenyl-6,7-dihydro-1H-indazol-3-yl]methanone
Azetidin-1-yl[6-(3,4-difluorophenyl)-6-phenyl-6,7-dihydro-1H-indazol-3-yl]methanone
(N-Methoxy-N-methyl)-6-(3,4-difluorophenyl)-6-phenyl-6,7-dihydro-1H-indazole-3-carboxamide
6-(3,4-Difluorophenyl)-6-phenyl-6,7-dihydro-1H-indazole-3-carbonitrile
Cyclopropyl[6-(3,4-difluorophenyl)-6-phenyl-6,7-dihydro-1H-indazol-3-yl]methanone
Cyclobutyl[6-(3,4-difluorophenyl)-6-phenyl-6,7-dihydro-1H-indazol-3-yl]methanone
Cyclopropyl[6-(3,4-difluorophenyl)-6-phenyl-6,7-dihydro-1H-indazol-3-yl]methanone oxime
Cyclopropyl[6-(3,4-difluorophenyl)-6-phenyl-6,7-dihydro-1H-indazol-3-yl]methanone O-methyloxime
Cyclobutyl[6-(3,4-difluorophenyl)-6-phenyl-6,7-dihydro-1H-indazol-3-yl]methanone oxime
Cyclobutyl[6-(3,4-difluorophenyl)-6-phenyl-6,7-dihydro-1H-indazol-3-yl]methanone O-methyloxime
6-(3,4-Difluorophenyl)-6-phenyl-1-(4-toluenesulphonyl)-6,7-dihydro-1H-indazol-3-ylamine
(N-Cyclopropyl)-6-(3,4-difluorophenyl)-6-phenyl-1-(4-toluenesulphonyl)-6,7-dihydro-1H-indazol-3-ylamine
(N-Cyclobutyl)-6-(3,4-difluorophenyl)-6-phenyl-1-(4-toluenesulphonyl)-6,7-dihydro-1H-indazol-3-ylamine
(N-Phenyl)-6-(3,4-difluorophenyl)-6-phenyl-1-(4-toluenesulphonyl)-6,7-dihydro-1H-indazol-3-ylamine
1-[3-Amino-6-(3,4-difluorophenyl)-6-phenyl-6,7-dihydroindazol-1-yl]propenone
1-[3-Cyclopropylamino-6-(3,4-difluorophenyl)-6-phenyl-6,7-dihydroindazol-1-yl]propenone
1-[3-Cyclobutylamino-6-(3,4-difluorophenyl)-6-phenyl-6,7-dihydroindazol-1-yl]propenone
1-[3-Anilino-6-(3,4-difluorophenyl)-6-phenyl-6,7-dihydroindazol-1-yl]propenone
6-(3,4-Difluorophenyl)-6-phenyl-1-(4-toluenesulphonyl)-6,7-dihydro-1H-indazole-3-carboxylic acid
1-[3-Carboxy-6-(3,4-difluorophenyl)-6-phenyl-6,7-dihydroindazol-1-yl]propenone
Cyclopropanecarboxylic acid [6-(3,4-difluorophenyl)-6-phenyl-6,7-dihydro-1H-indazol-3-yl]amide
Cyclobutanecarboxylic acid [6-(3,4-difluorophenyl)-6-phenyl-6,7-dihydro-1H-indazol-3-yl]amide
6-(3,4-Difluorophenyl)-3,6-diphenyl-6,7-dihydro-1H-indazole
6-(3,4-Difluorophenyl)-6-phenyl-3-(pyrid-2-yl)-6,7-dihydro-1H-indazole
6-(3,4-Difluorophenyl)-6-phenyl-3-(pyrid-3-yl)-6,7-dihydro-1H-indazole
6-(3,4-Difluorophenyl)-6-phenyl-3-(pyrid-4-yl)-6,7-dihydro-1H-indazole
6-(3,4-Difluorophenyl)-6-phenyl-3-(thiophen-2-yl)-6,7-dihydro-1H-indazole
6-(3,4-Difluorophenyl)-6-phenyl-3-(thiophen-3-yl)-6,7-dihydro-1H-indazole
6-(3,4-Difluorophenyl)-3-(oxazol-2-yl)-6-phenyl-6,7-dihydro-1H-indazole
6-(3,4-Difluorophenyl)-3-(oxazol-4-yl)-6-phenyl-6,7-dihydro-1H-indazole
6-(3,4-Difluorophenyl)-3-(oxazol-5-yl)-6-phenyl-6,7-dihydro-1H-indazole
6-(3,4-Difluorophenyl)-6-phenyl-3-(thiazol-2-yl)-6,7-dihydro-1H-indazole
6-(3,4-Difluorophenyl)-6-phenyl-3-(thiazol-4-yl)-6,7-dihydro-1H-indazole
6-(3,4-Difluorophenyl)-6-phenyl-3-(thiazol-5-yl)-6,7-dihydro-1H-indazole
6-(3,4-Difluorophenyl)-3-(imidazol-2-yl)-6-phenyl-6,7-dihydro-1H-indazole
6-(3,4-Difluorophenyl)-3-(imidazol-4-yl)-6-phenyl-6,7-dihydro-1H-indazole 6-(3,4-Difluorophenyl)-3-(imidazol-5-yl)-6-phenyl-6,7-dihydro-1H-indazole 6-(3,4-Difluorophenyl)-3-(3-methyl[1,2,4]oxadiazol-5-yl)-6-phenyl-6,7-dihydro-1H-indazole 6-(3,4-Difluorophenyl)-3-(3-methoxy[1,2,5]thiadiazol-4-yl)-6-phenyl-6,7-dihydro-1H-indazole 6-(3,4-Difluorophenyl)-6-phenyl-3-(tetrazol-5-yl)-6,7-dihydro-1H-indazole 6-(3,4-Difluorophenyl)-6-phenyl-3-(tetrazol-1-yl)-6,7-dihydro-1H-indazole Methyl 6-phenyl-6-(pyrid-2-yl)-6,7-dihydro-1H-indazole-3-carboxylate Ethyl 6-phenyl-6-(pyrid-2-yl)-6,7-dihydro-1H-indazole-3-carboxylate (N-Cyclopropyl)-6-phenyl-6-(pyrid-2-yl)-6,7-dihydro-1H-indazole-3-carboxamide Aziridin-1-yl[6-phenyl-6-(pyrid-2-yl)-6,7-dihydro-1H-indazol-3-yl]methanone Azetidin-1-yl[6-phenyl-6-(pyrid-2-yl)-6,7-dihydro-1H-indazol-3-yl]methanone (N-Methoxy-N-methyl)-6-phenyl-6-(pyrid-2-yl)-6,7-dihydro-1H-indazole-3-carboxamide 6-Phenyl-6-(pyrid-2-yl)-6,7-dihydro-1H-indazole-3-carbonitrile Cyclopropyl[6-phenyl-6-(pyrid-2-yl)-6,7-dihydro-1H-indazol-3-yl]methanone Cyclobutyl[6-phenyl-6-(pyrid-2-yl)-6,7-dihydro-1H-indazol-3-yl]methanone Cyclopropyl[6-phenyl-6-(pyrid-2-yl)-6,7-dihydro-1H-indazol-3-yl]methanone oxime Cyclopropyl[6-phenyl-6-(pyrid-2-yl)-6,7-dihydro-1H-indazol-3-yl]methanone O-methyloxime Cyclobutyl[6-phenyl-6-(pyrid-2-yl)-6,7-dihydro-1H-indazol-3-yl]methanone oxime Cyclobutyl[6-phenyl-6-(pyrid-2-yl)-6,7-dihydro-1H-indazol-3-yl]methanone O-methyloxime 6-Phenyl-6-(pyrid-2-yl)-1-(4-toluenesulphonyl)-6,7-dihydro-1H-indazol-3-ylamine (N-Cyclopropyl)-6-phenyl-6-(pyrid-2-yl)-1-(4-toluenesulphonyl)-6,7-dihydro-1H-indazol-3-ylamine (N-Cyclobutyl)-6-phenyl-6-(pyrid-2-yl)-1-(4-toluenesulphonyl)-6,7-dihydro-1H-indazol-3-ylamine (N-Phenyl)-6-phenyl-6-(pyrid-2-yl)-1-(4-toluenesulphonyl)-6,7-dihydro-1H-indazol-3-ylamine 1-[3-Amino-6-phenyl-6-(pyrid-2-yl)-6,7-dihydroindazol-1-yl]propenone 1-[3-Cyclopropylamino-6-phenyl-6-(pyrid-2-yl)-6,7-dihydroindazol-1-yl]propenone 1-[3-Cyclobutylamino-6-phenyl-6-(pyrid-2-yl)-6,7-dihydroindazol-1-yl]propenone 1-[3-Anilino-6-phenyl-6-(pyrid-2-yl)-6,7-dihydroindazol-1-yl]propenone 6-phenyl-6-(pyrid-2-yl)-1-(4-toluenesulphonyl)-6,7-dihydro-1H-indazole-3-carboxylic acid 1-[3-Carboxy-6-phenyl-6-(pyrid-2-yl)-6,7-dihydroindazol-1-yl]propenone Cyclopropanecarboxylic acid [6-phenyl-6-(pyrid-2-yl)-6,7-dihydro-1H-indazol-3-yl]amide Cyclobutanecarboxylic acid [6-phenyl-6-(pyrid-2-yl)-6,7-dihydro-1H-indazol-3-yl]amide 3,6-Diphenyl-6-(pyrid-2-yl)-6,7-dihydro-1H-indazole 6-Phenyl-3,6-bis(pyrid-2-yl)-6,7-dihydro-1H-indazole 6-Phenyl-6-(pyrid-2-yl)-3-(pyrid-3-yl)-6,7-dihydro-1H-indazole 6-Phenyl-6-(pyrid-2-yl)-3-(pyrid-4-yl)-6,7-dihydro-1H-indazole 6-Phenyl-6-(pyrid-2-yl)-3-(thiophen-2-yl)-6,7-dihydro-1H-indazole 6-Phenyl-6-(pyrid-2-yl)-3-(thiophen-3-yl)-6,7-dihydro-1H-indazole 3-(Oxazol-2-yl)-6-phenyl-6-(pyrid-2-yl)-6,7-dihydro-1H-indazole 3-(Oxazol-4-yl)-6-phenyl-6-(pyrid-2-yl)-6,7-dihydro-1H-indazole 3-(Oxazol-5-yl)-6-phenyl-6-(pyrid-2-yl)-6,7-dihydro-1H-indazole 6-Phenyl-6-(pyrid-2-yl)-3-(thiazol-2-yl)-6,7-dihydro-1H-indazole 6-Phenyl-6-(pyrid-2-yl)-3-(thiazol-4-yl)-6,7-dihydro-1H-indazole 6-Phenyl-6-(pyrid-2-yl)-3-(thiazol-5-yl)-6,7-dihydro-1H-indazole 3-(Imidazol-2-yl)-6-phenyl-6-(pyrid-2-yl)-6,7-dihydro-1H-indazole 3-(Imidazol-4-yl)-6-phenyl-6-(pyrid-2-yl)-6,7-dihydro-1H-indazole 3-(Imidazol-5-yl)-6-phenyl-6-(pyrid-2-yl)-6,7-dihydro-1H-indazole 3-(3-Methyl[1,2,4]oxadiazol-5-yl)-6-phenyl-6-(pyrid-2-yl)-6,7-dihydro-1H-indazole 3-(3-Methoxy[1,2,5]thiadiazol-4-yl)-6-phenyl-6-(pyrid-2-yl)-6,7-dihydro-1H-indazole 6-Phenyl-6-(pyrid-2-yl)-3-(tetrazol-5-yl)-6,7-dihydro-1H-indazole 6-Phenyl-6-(pyrid-2-yl)-3-(tetrazol-1-yl)-6,7-dihydro-1H-indazole Methyl 6-phenyl-6-(pyrid-3-yl)-6,7-dihydro-1H-indazole-3-carboxylate Ethyl 6-phenyl-6-(pyrid-3-yl)-6,7-dihydro-1H-indazole-3-carboxylate (N-Cyclopropyl)-6-phenyl-6-(pyrid-3-yl)-6,7-dihydro-1H-indazole-3-carboxamide Aziridin-1-yl[6-phenyl-6-(pyrid-3-yl)-6,7-dihydro-1H-indazol-3-yl]methanone Azetidin-1-yl[6-phenyl-6-(pyrid-3-yl)-6,7-dihydro-1H-indazol-3-yl]methanone (N-Methoxy-N-methyl)-6-phenyl-6-(pyrid-3-yl)-6,7-dihydro-1H-indazole-3-carboxamide 6-Phenyl-6-(pyrid-3-yl)-6,7-dihydro-1H-indazole-3-carbonitrile Cyclopropyl[6-phenyl-6-(pyrid-3-yl)-6,7-dihydro-1H-indazol-3-yl]methanone Cyclobutyl[6-phenyl-6-(pyrid-3-yl)-6,7-dihydro-1H-indazol-3-yl]methanone Cyclopropyl[6-phenyl-6-(pyrid-3-yl)-6,7-dihydro-1H-indazol-3-yl]methanone oxime Cyclopropyl[6-phenyl-6-(pyrid-3-yl)-6,7-dihydro-1H-indazol-3-yl]methanone O-methyloxime Cyclobutyl[6-phenyl-6-(pyrid-3-yl)-6,7-dihydro-1H-indazol-3-yl]methanone oxime Cyclobutyl[6-phenyl-6-(pyrid-3-yl)-6,7-dihydro-1H-indazol-3-yl]methanone O-methyloxime 6-Phenyl-6-(pyrid-3-yl)-1-(4-toluenesulphonyl)-6,7-dihydro-1H-indazol-3-ylamine (N-Cyclopropyl)-6-phenyl-6-(pyrid-3-yl)-1-(4-toluenesulphonyl)-6,7-dihydro-1H-indazol-3-ylamine (N-Cyclobutyl)-6-phenyl-6-(pyrid-3-yl)-1-(4-toluenesulphonyl)-6,7-dihydro-1H-indazol-3-ylamine (N-Phenyl)-6-phenyl-6-(pyrid-3-yl)-1-(4-toluenesulphonyl)-6,7-dihydro-1H-indazol-3-ylamine 1-[3-Amino-6-phenyl-6-(pyrid-3-yl)-6,7-dihydroindazol-1-yl]propenone 1-[3-Cyclopropylamino-6-phenyl-6-(pyrid-3-yl)-6,7-dihydroindazol-1-yl]propenone
1-[3-Cyclobutylamino-6-phenyl-6-(pyrid-3-yl)-6,7-dihydroindazol-1-yl]propenone
1-[3-Anilino-6-phenyl-6-(pyrid-3-yl)-6,7-dihydroindazol-1-yl]propenone
6-Phenyl-6-(pyrid-3-yl)-1-(4-toluenesulphonyl)-6,7-dihydro-1H-indazole-3-carboxylic acid
1-[3-Carboxy-6-phenyl-6-(pyrid-3-yl)-6,7-dihydroindazol-1-yl]propenone
Cyclopropanecarboxylic acid [6-phenyl-6-(pyrid-3-yl)-6,7-dihydro-1H-indazol-3-yl]amide
Cyclobutanecarboxylic acid [6-phenyl-6-(pyrid-3-yl)-6,7-dihydro-1H-indazol-3-yl]amide
3,6-Diphenyl-6-(pyrid-3-yl)-6,7-dihydro-1H-indazole
6-Phenyl-6-(pyrid-3-yl)-3-(pyrid-2-yl)-6,7-dihydro-1H-indazole
6-Phenyl-3,6-bis(pyrid-3-yl)-6,7-dihydro-1H-indazole
6-Phenyl-6-(pyrid-3-yl)-3-(pyrid-4-yl)-6,7-dihydro-1H-indazole
6-Phenyl-6-(pyrid-3-yl)-3-(thiophen-2-yl)-6,7-dihydro-1H-indazole
6-Phenyl-6-(pyrid-3-yl)-3-(thiophen-3-yl)-6,7-dihydro-1H-indazole
3-(Oxazol-2-yl)-6-phenyl-6-(pyrid-3-yl)-6,7-dihydro-1H-indazole
3-(Oxazol-4-yl)-6-phenyl-6-(pyrid-3-yl)-6,7-dihydro-1H-indazole
3-(Oxazol-5-yl)-6-phenyl-6-(pyrid-3-yl)-6,7-dihydro-1H-indazole
6-Phenyl-6-(pyrid-3-yl)-3-(thiazol-2-yl)-6,7-dihydro-1H-indazole
6-Phenyl-6-(pyrid-3-yl)-3-(thiazol-4-yl)-6,7-dihydro-1H-indazole
6-Phenyl-6-(pyrid-3-yl)-3-(thiazol-5-yl)-6,7-dihydro-1H-indazole
3-(Imidazol-2-yl)-6-phenyl-6-(pyrid-3-yl)-6,7-dihydro-1H-indazole
3-(Imidazol-4-yl)-6-phenyl-6-(pyrid-3-yl)-6,7-dihydro-1H-indazole
3-(Imidazol-5-yl)-6-phenyl-6-(pyrid-3-yl)-6,7-dihydro-1H-indazole
3-(3-Methyl[1,2,4]oxadiazol-5-yl)-6-phenyl-6-(pyrid-3-yl)-6,7-dihydro-1H-indazole
3-(3-Methoxy[1,2,5]thiadiazol-4-yl)-6-phenyl-6-(pyrid-3-yl)-6,7-dihydro-1H-indazole
6-Phenyl-6-(pyrid-3-yl)-3-(tetrazol-5-yl)-6,7-dihydro-1H-indazole
6-Phenyl-6-(pyrid-3-yl)-3-(tetrazol-1-yl)-6,7-dihydro-1H-indazole
Methyl 6-phenyl-6-(pyrid-4-yl)-6,7-dihydro-1H-indazole-3-carboxylate
Ethyl 6-phenyl-6-(pyrid-4-yl)-6,7-dihydro-1H-indazole-3-carboxylate
(N-Cyclopropyl)-6-phenyl-6-(pyrid-4-yl)-6,7-dihydro-1H-indazole-3-carboxamide
Aziridin-1-yl[6-phenyl-6-(pyrid-4-yl)-6,7-dihydro-1H-indazol-3-yl]methanone
Azetidin-1-yl[6-phenyl-6-(pyrid-4-yl)-6,7-dihydro-1H-indazol-3-yl]methanone
(N-Methoxy-N-methyl)-6-phenyl-6-(pyrid-4-yl)-6,7-dihydro-1H-indazole-3-carboxamide
6-Phenyl-6-(pyrid-4-yl)-6,7-dihydro-1H-indazole-3-carbonitrile
Cyclopropyl[6-phenyl-6-(pyrid-4-yl)-6,7-dihydro-1H-indazol-3-yl]methanone
Cyclobutyl[6-phenyl-6-(pyrid-4-yl)-6,7-dihydro-1H-indazol-3-yl]methanone
Cyclopropyl[6-phenyl-6-(pyrid-4-yl)-6,7-dihydro-1H-indazol-3-yl]methanone oxime
Cyclopropyl[6-phenyl-6-(pyrid-4-yl)-6,7-dihydro-1H-indazol-3-yl]methanone O-methyloxime
Cyclobutyl[6-phenyl-6-(pyrid-4-yl)-6,7-dihydro-1H-indazol-3-yl]methanone oxime
Cyclobutyl[6-phenyl-6-(pyrid-4-yl)-6,7-dihydro-1H-indazol-3-yl]methanone O-methyloxime
6-Phenyl-6-(pyrid-4-yl)-1-(4-toluenesulphonyl)-6,7-dihydro-1H-indazol-3-ylamine
(N-Cyclopropyl)-6-phenyl-6-(pyrid-4-yl)-1-(4-toluenesulphonyl)-6,7-dihydro-1H-indazol-3-ylamine
(N-Cyclobutyl)-6-phenyl-6-(pyrid-4-yl)-1-(4-toluenesulphonyl)-6,7-dihydro-1H-indazol-3-ylamine
(N-Phenyl)-6-phenyl-6-(pyrid-4-yl)-1-(4-toluenesulphonyl)-6,7-dihydro-1H-indazol-3-ylamine
1-[3-Amino-6-phenyl-6-(pyrid-4-yl)-6,7-dihydroindazol-1-yl]propenone
1-[3-Cyclopropylamino-6-phenyl-6-(pyrid-4-yl)-6,7-dihydroindazol-1-yl]propenone
1-[3-Cyclobutylamino-6-phenyl-6-(pyrid-4-yl)-6,7-dihydroindazol-1-yl]propenone
1-[3-Anilino-6-phenyl-6-(pyrid-4-yl)-6,7-dihydroindazol-1-yl]propenone
6-Phenyl-6-(pyrid-4-yl)-1-(4-toluenesulphonyl)-6,7-dihydro-1H-indazole-3-carboxylic acid
1-[3-Carboxy-6-phenyl-6-(pyrid-4-yl)-6,7-dihydroindazol-1-yl]propenone
Cyclopropanecarboxylic acid [6-phenyl-6-(pyrid-4-yl)-6,7-dihydro-1H-indazol-3-yl]amide
Cyclobutanecarboxylic acid [6-phenyl-6-(pyrid-4-yl)-6,7-dihydro-1H-indazol-3-yl]amide
3,6-Diphenyl-6-(pyrid-4-yl)-6,7-dihydro-1H-indazole
6-Phenyl-6-(pyrid-4-yl)-3-(pyrid-2-yl)-6,7-dihydro-1H-indazole
6-Phenyl-6-(pyrid-4-yl)-3-(pyrid-3-yl)-6,7-dihydro-1H-indazole
6-Phenyl-3,6-bis(pyrid-4-yl)-6,7-dihydro-1H-indazole
6-Phenyl-6-(pyrid-4-yl)-3-(thiophen-2-yl)-6,7-dihydro-1H-indazole
6-Phenyl-6-(pyrid-4-yl)-3-(thiophen-3-yl)-6,7-dihydro-1H-indazole
3-(Oxazol-2-yl)-6-phenyl-6-(pyrid-4-yl)-6,7-dihydro-1H-indazole
3-(Oxazol-4-yl)-6-phenyl-6-(pyrid-4-yl)-6,7-dihydro-1H-indazole
3-(Oxazol-5-yl)-6-phenyl-6-(pyrid-4-yl)-6,7-dihydro-1H-indazole
6-Phenyl-6-(pyrid-4-yl)-3-(thiazol-2-yl)-6,7-dihydro-1H-indazole
6-Phenyl-6-(pyrid-4-yl)-3-(thiazol-4-yl)-6,7-dihydro-1H-indazole
6-Phenyl-6-(pyrid-4-yl)-3-(thiazol-5-yl)-6,7-dihydro-1H-indazole
3-(Imidazol-2-yl)-6-phenyl-6-(pyrid-4-yl)-6,7-dihydro-1H-indazole
3-(Imidazol-4-yl)-6-phenyl-6-(pyrid-4-yl)-6,7-dihydro-1H-indazole
3-(Imidazol-5-yl)-6-phenyl-6-(pyrid-4-yl)-6,7-dihydro-1H-indazole
3-(3-Methyl[1,2,4]oxadiazol-5-yl)-6-phenyl-6-(pyrid-4-yl)-6,7-dihydro-1H-indazole
3-(3-Methoxy[1,2,5]thiadiazol-4-yl)-6-phenyl-6-(pyrid-4-yl)-6,7-dihydro-1H-indazole 6-Phenyl-6-(pyrid-4-yl)-3-(tetrazol-5-yl)-6,7-dihydro-1H-indazole
6-Phenyl-6-(pyrid-4-yl)-3-(tetrazol-1-yl)-6,7-dihydro-1H-indazole
Methyl 6-phenyl-6-(pyrimid-4-yl)-6,7-dihydro-1H-indazole-3-carboxylate
Ethyl 6-phenyl-6-(pyrimid-4-yl)-6,7-dihydro-1H-indazole-3-carboxylate
(N-Cyclopropyl)-6-phenyl-6-(pyrimid-4-yl)-6,7-dihydro-1H-indazole-3-carboxamide
Aziridin-1-yl[6-phenyl-6-(pyrimid-4-yl)-6,7-dihydro-1H-indazol-3-yl]methanone
Azetidin-1-yl[6-phenyl-6-(pyrimid-4-yl)-6,7-dihydro-1H-indazol-3-yl]methanone
(N-Methoxy-N-methyl)-6-phenyl-6-(pyrimid-4-yl)-6,7-dihydro-1H-indazole-3-carboxamide
6-Phenyl-6-(pyrimid-4-yl)-6,7-dihydro-1H-indazole-3-carbonitrile
Cyclopropyl[6-phenyl-6-(pyrimid-4-yl)-6,7-dihydro-1H-indazol-3-yl]methanone
Cyclobutyl[6-phenyl-6-(pyrimid-4-yl)-6,7-dihydro-1H-indazol-3-yl]methanone
Cyclopropyl[6-phenyl-6-(pyrimid-4-yl)-6,7-dihydro-1H-indazol-3-yl]methanone oxime
Cyclopropyl[6-phenyl-6-(pyrimid-4-yl)-6,7-dihydro-1H-indazol-3-yl]methanone O-methyloxime
Cyclobutyl[6-phenyl-6-(pyrimid-4-yl)-6,7-dihydro-1H-indazol-3-yl]methanone oxime
Cyclobutyl[6-phenyl-6-(pyrimid-4-yl)-6,7-dihydro-1H-indazol-3-yl]methanone O-methyloxime
6-Phenyl-6-(pyrimid-4-yl)-1-(4-toluenesulphonyl)-6,7-dihydro-1H-indazol-3-ylamine
(N-Cyclopropyl)-6-phenyl-6-(pyrimid-4-yl)-1-(4-toluenesulphonyl)-6,7-dihydro-1H-indazol-3-ylamine
(N-Cyclobutyl)-6-phenyl-6-(pyrimid-4-yl)-1-(4-toluenesulphonyl)-6,7-dihydro-1H-indazol-3-ylamine
(N-Phenyl)-6-phenyl-6-(pyrimid-4-yl)-1-(4-toluenesulphonyl)-6,7-dihydro-1H-indazol-3-ylamine
1-[3-Amino-6-phenyl-6-(pyrimid-4-yl)-6,7-dihydroindazol-1-yl]propenone
1-[3-Cyclopropylamino-6-phenyl-6-(pyrimid-4-yl)-6,7-dihydroindazol-1-yl]propenone
1-[3-Cyclobutylamino-6-phenyl-6-(pyrimid-4-yl)-6,7-dihydroindazol-1-yl]propenone
1-[3-Anilino-6-phenyl-6-(pyrimid-4-yl)-6,7-dihydroindazol-1-yl]propenone
6-Phenyl-6-(pyrimid-4-yl)-1-(4-toluenesulphonyl)-6,7-dihydro-1H-indazole-3-carboxylic acid
1-[3-Carboxy-6-phenyl-6-(pyrimid-4-yl)-6,7-dihydroindazol-1-yl]propenone
Cyclopropanecarboxylic acid [6-phenyl-6-(pyrimid-4-yl)-6,7-dihydro-1H-indazol-3-yl]amide
Cyclobutanecarboxylic acid [6-phenyl-6-(pyrimid-4-yl)-6,7-dihydro-1H-indazol-3-yl]amide
3,6-Diphenyl-6-(pyrimid-4-yl)-6,7-dihydro-1H-indazole
6-Phenyl-6-(pyrimid-4-yl)-3-(pyrid-2-yl)-6,7-dihydro-1H-indazole
6-Phenyl-6-(pyrimid-4-yl)-3-(pyrid-3-yl)-6,7-dihydro-1H-indazole
6-Phenyl-6-(pyrimid-4-yl)-3-(pyrid-4-yl)-6,7-dihydro-1H-indazole
6-Phenyl-6-(pyrimid-4-yl)-3-(thiophen-2-yl)-6,7-dihydro-1H-indazole
6-Phenyl-6-(pyrimid-4-yl)-3-(thiophen-3-yl)-6,7-dihydro-1H-indazole
3-(Oxazol-2-yl)-6-phenyl-6-(pyrimid-4-yl)-6,7-dihydro-1H-indazole
3-(Oxazol-4-yl)-6-phenyl-6-(pyrimid-4-yl)-6,7-dihydro-1H-indazole
3-(Oxazol-5-yl)-6-phenyl-6-(pyrimid-4-yl)-6,7-dihydro-1H-indazole
6-Phenyl-6-(pyrimid-4-yl)-3-(thiazol-2-yl)-6,7-dihydro-1H-indazole
6-Phenyl-6-(pyrimid-4-yl)-3-(thiazol-4-yl)-6,7-dihydro-1H-indazole
6-Phenyl-6-(pyrimid-4-yl)-3-(thiazol-5-yl)-6,7-dihydro-1H-indazole
3-(Imidazol-2-yl)-6-phenyl-6-(pyrimid-4-yl)-6,7-dihydro-1H-indazole
3-(Imidazol-4-yl)-6-phenyl-6-(pyrimid-4-yl)-6,7-dihydro-1H-indazole
3-(Imidazol-5-yl)-6-phenyl-6-(pyrimid-4-yl)-6,7-dihydro-1H-indazole
3-(3-Methyl[1,2,4]oxadiazol-5-yl)-6-phenyl-6-(pyrimid-4-yl)-6,7-dihydro-1H-indazole
3-(3-Methoxy[1,2,5]thiadiazol-4-yl)-6-phenyl-6-(pyrimid-4-yl)-6,7-dihydro-1H-indazole
6-Phenyl-6-(pyrimid-4-yl)-3-(tetrazol-5-yl)-6,7-dihydro-1H-indazole
6-Phenyl-6-(pyrimid-4-yl)-3-(tetrazol-1-yl)-6,7-dihydro-1H-indazole
Methyl 6-phenyl-6-(thiophen-2-yl)-6,7-dihydro-1H-indazole-3-carboxylate
Ethyl 6-phenyl-6-(thiophen-2-yl)-6,7-dihydro-1H-indazole-3-carboxylate
(N-Cyclopropyl)-6-phenyl-6-(thiophen-2-yl)-6,7-dihydro-1H-indazole-3-carboxamide
Aziridin-1-yl[6-phenyl-6-(thiophen-2-yl)-6,7-dihydro-1H-indazol-3-yl]methanone
Azetidin-1-yl[6-phenyl-6-(thiophen-2-yl)-6,7-dihydro-1H-indazol-3-yl]methanone
(N-Methoxy-N-methyl)-6-phenyl-6-(thiophen-2-yl)-6,7-dihydro-1H-indazole-3-carboxamide
6-Phenyl-6-(thiophen-2-yl)-6,7-dihydro-1H-indazole-3-carbonitrile
Cyclopropyl[6-phenyl-6-(thiophen-2-yl)-6,7-dihydro-1H-indazol-3-yl]methanone
Cyclobutyl[6-phenyl-6-(thiophen-2-yl)-6,7-dihydro-1H-indazol-3-yl]methanone
Cyclopropyl[6-phenyl-6-(thiophen-2-yl)-6,7-dihydro-1H-indazol-3-yl]methanone oxime
Cyclopropyl[6-phenyl-6-(thiophen-2-yl)-6,7-dihydro-1H-indazol-3-yl]methanone O-methyloxime
Cyclobutyl[6-phenyl-6-(thiophen-2-yl)-6,7-dihydro-1H-indazol-3-yl]methanone oxime
Cyclobutyl[6-phenyl-6-(thiophen-2-yl)-6,7-dihydro-1H-indazol-3-yl]methanone O-methyloxime
6-Phenyl-6-(thiophen-2-yl)-1-(4-toluenesulphonyl)-6,7-dihydro-1H-indazol-3-ylamine
(N-Cyclopropyl)-6-phenyl-6-(thiophen-2-yl)-1-(4-toluenesulphonyl)-6,7-dihydro-1H-indazol-3-ylamine
(N-Cyclobutyl)-6-phenyl-6-(thiophen-2-yl)-1-(4-toluenesulphonyl)-6,7-dihydro-1H-indazol-3-ylamine
(N-Phenyl)-6-phenyl-6-(thiophen-2-yl)-1-(4-toluenesulphonyl)-6,7-dihydro-1H-indazol-3-ylamine
1-[3-Amino-6-phenyl-6-(thiophen-2-yl)-6,7-dihydroindazol-1-yl]propenone
1-[3-Cyclopropylamino-6-phenyl-6-(thiophen-2-yl)-6,7-dihydroindazol-1-yl]propenone
1-[3-Cyclobutylamino-6-phenyl-6-(thiophen-2-yl)-6,7-dihydroindazol-1-yl]propenone
1-[3-Anilino-6-phenyl-6-(thiophen-2-yl)-6,7-dihydroindazol-1-yl]propenone 6-Phenyl-6-(thiophen-2-yl)-1-(4-toluenesulphonyl)-6,7-dihydro-1H-indazole-3-carboxylic acid
1-[3-Carboxy-6-phenyl-6-(thiophen-2-yl)-6,7-dihydroindazol-1-yl]propenone
Cyclopropanecarboxylic acid [6-phenyl-6-(thiophen-2-yl)-6,7-dihydro-1H-indazol-3-yl]amide
Cyclobutanecarboxylic acid [6-phenyl-6-(thiophen-2-yl)-6,7-dihydro-1H-indazol-3-yl]amide
3,6-Diphenyl-6-(thiophen-2-yl)-6,7-dihydro-1H-indazole
6-Phenyl-3-(pyrid-2-yl)-6-(thiophen-2-yl)-6,7-dihydro-1H-indazole
6-Phenyl-3-(pyrid-3-yl)-6-(thiophen-2-yl)-6,7-dihydro-1H-indazole
6-Phenyl-3-(pyrid-4-yl)-6-(thiophen-2-yl)-6,7-dihydro-1H-indazole
6-Phenyl-3,6-bis(thiophen-2-yl)-6,7-dihydro-1H-indazole
6-Phenyl-3-(thiophen-3-yl)-6-(thiophen-2-yl)-6,7-dihydro-1H-indazole
3-(Oxazol-2-yl)-6-phenyl-6-(thiophen-2-yl)-6,7-dihydro-1H-indazole
3-(Oxazol-4-yl)-6-phenyl-6-(thiophen-2-yl)-6,7-dihydro-1H-indazole
3-(Oxazol-5-yl)-6-phenyl-6-(thiophen-2-yl)-6,7-dihydro-1H-indazole
6-Phenyl-3-(thiazol-2-yl)-6-(thiophen-2-yl)-6,7-dihydro-1H-indazole
6-Phenyl-3-(thiazol-4-yl)-6-(thiophen-2-yl)-6,7-dihydro-1H-indazole
6-Phenyl-3-(thiazol-5-yl)-6-(thiophen-2-yl)-6,7-dihydro-1H-indazole
3-(Imidazol-2-yl)-6-phenyl-6-(thiophen-2-yl)-6,7-dihydro-1H-indazole
3-(Imidazol-4-yl)-6-phenyl-6-(thiophen-2-yl)-6,7-dihydro-1H-indazole
3-(Imidazol-5-yl)-6-phenyl-6-(thiophen-2-yl)-6,7-dihydro-1H-indazole
3-(3-Methyl[1,2,4]oxadiazol-5-yl)-6-phenyl-6-(thiophen-2-yl)-6,7-dihydro-1H-indazole
3-(3-Methoxy[1,2,5]thiadiazol-4-yl)-6-phenyl-6-(thiophen-2-yl)-6,7-dihydro-1H-indazole
6-Phenyl-3-(tetrazol-5-yl)-6-(thiophen-2-yl)-6,7-dihydro-1H-indazole
6-Phenyl-3-(tetrazol-1-yl)-6-(thiophen-2-yl)-6,7-dihydro-1H-indazole
Methyl 6-phenyl-6-(thiophen-3-yl)-6,7-dihydro-1H-indazole-3-carboxylate
Ethyl 6-phenyl-6-(thiophen-3-yl)-6,7-dihydro-1H-indazole-3-carboxylate
(N-Cyclopropyl)-6-phenyl-6-(thiophen-3-yl)-6,7-dihydro-1H-indazole-3-carboxamide
Aziridin-1-yl[6-phenyl-6-(thiophen-3-yl)-6,7-dihydro-1H-indazol-3-yl]methanone
Azetidin-1-yl[6-phenyl-6-(thiophen-3-yl)-6,7-dihydro-1H-indazol-3-yl]methanone
(N-Methoxy-N-methyl)-6-phenyl-6-(thiophen-3-yl)-6,7-dihydro-1H-indazole-3-carboxamide
6-Phenyl-6-(thiophen-3-yl)-6,7-dihydro-1H-indazole-3-carbonitrile
Cyclopropyl[6-phenyl-6-(thiophen-3-yl)-6,7-dihydro-1H-indazol-3-yl]methanone
Cyclobutyl[6-phenyl-6-(thiophen-3-yl)-6,7-dihydro-1H-indazol-3-yl]methanone
Cyclopropyl[6-phenyl-6-(thiophen-3-yl)-6,7-dihydro-1H-indazol-3-yl]methanone oxime
Cyclopropyl[6-phenyl-6-(thiophen-3-yl)-6,7-dihydro-1H-indazol-3-yl]methanone O-methyloxime
Cyclobutyl[6-phenyl-6-(thiophen-3-yl)-6,7-dihydro-1H-indazol-3-yl]methanone oxime
Cyclobutyl[6-phenyl-6-(thiophen-3-yl)-6,7-dihydro-1H-indazol-3-yl]methanone O-methyloxime
6-Phenyl-6-(thiophen-3-yl)-1-(4-toluenesulphonyl)-6,7-dihydro-1H-indazol-3-ylamine
(N-Cyclopropyl)-6-phenyl-6-(thiophen-3-yl)-1-(4-toluenesulphonyl)-6,7-dihydro-1H-indazol-3-ylamine
(N-Cyclobutyl)-6-phenyl-6-(thiophen-3-yl)-1-(4-toluenesulphonyl)-6,7-dihydro-1H-indazol-3-ylamine
(N-Phenyl)-6-phenyl-6-(thiophen-3-yl)-1-(4-toluenesulphonyl)-6,7-dihydro-1H-indazol-3-ylamine
1-[3-Amino-6-phenyl-6-(thiophen-3-yl)-6,7-dihydroindazol-1-yl]propenone
1-[3-Cyclopropylamino-6-phenyl-6-(thiophen-3-yl)-6,7-dihydroindazol-1-yl]propenone
1-[3-Cyclobutylamino-6-phenyl-6-(thiophen-3-yl)-6,7-dihydroindazol-1-yl]propenone
1-[3-Anilino-6-phenyl-6-(thiophen-3-yl)-6,7-dihydroindazol-1-yl]propenone
6-Phenyl-6-(thiophen-3-yl)-1-(4-toluenesulphonyl)-6,7-dihydro-1H-indazole-3-carboxylic acid
1-[3-Carboxy-6-phenyl-6-(thiophen-3-yl)-6,7-dihydroindazol-1-yl]propenone
Cyclopropanecarboxylic acid [6-phenyl-6-(thiophen-3-yl)-6,7-dihydro-1H-indazol-3-yl]amide
Cyclobutanecarboxylic acid [6-phenyl-6-(thiophen-3-yl)-6,7-dihydro-1H-indazol-3-yl]amide
3,6-Diphenyl-6-(thiophen-3-yl)-6,7-dihydro-1H-indazole
6-Phenyl-3-(pyrid-2-yl)-6-(thiophen-3-yl)-6,7-dihydro-1H-indazole
6-Phenyl-3-(pyrid-3-yl)-6-(thiophen-3-yl)-6,7-dihydro-1H-indazole
6-Phenyl-3-(pyrid-4-yl)-6-(thiophen-3-yl)-6,7-dihydro-1H-indazole
6-Phenyl-3,6-bis(thiophen-3-yl)-6,7-dihydro-1H-indazole
6-Phenyl-3-(thiophen-2-yl)-6-(thiophen-3-yl)-6,7-dihydro-1H-indazole
3-(Oxazol-2-yl)-6-phenyl-6-(thiophen-3-yl)-6,7-dihydro-1H-indazole
3-(Oxazol-4-yl)-6-phenyl-6-(thiophen-3-yl)-6,7-dihydro-1H-indazole
3-(Oxazol-5-yl)-6-phenyl-6-(thiophen-3-yl)-6,7-dihydro-1H-indazole
6-Phenyl-3-(thiazol-2-yl)-6-(thiophen-3-yl)-6,7-dihydro-1H-indazole
6-Phenyl-3-(thiazol-4-yl)-6-(thiophen-3-yl)-6,7-dihydro-1H-indazole
6-Phenyl-3-(thiazol-5-yl)-6-(thiophen-3-yl)-6,7-dihydro-1H-indazole
3-(Imidazol-2-yl)-6-phenyl-6-(thiophen-3-yl)-6,7-dihydro-1H-indazole
3-(Imidazol-4-yl)-6-phenyl-6-(thiophen-3-yl)-6,7-dihydro-1H-indazole
3-(Imidazol-5-yl)-6-phenyl-6-(thiophen-3-yl)-6,7-dihydro-1H-indazole
3-(3-Methyl[1,2,4]oxadiazol-5-yl)-6-phenyl-6-(thiophen-3-yl)-6,7-dihydro-1H-indazole
3-(3-Methoxy[1,2,5]thiadiazol-4-yl)-6-phenyl-6-(thiophen-3-yl)-6,7-dihydro-1H-indazole
6-Phenyl-3-(tetrazol-5-yl)-6-(thiophen-3-yl)-6,7-dihydro-1H-indazole
6-Phenyl-3-(tetrazol-1-yl)-6-(thiophen-3-yl)-6,7-dihydro-1H-indazole
Methyl 6-phenyl-6-(thiazol-4-yl)-6,7-dihydro-1H-indazole-3-carboxylate Ethyl 6-phenyl-6-(thiazol-4-yl)-6,7-dihydro-1H-indazole-3-carboxylate
(N-Cyclopropyl)-6-phenyl-6-(thiazol-4-yl)-6,7-dihydro-1H-indazole-3-carboxamide
Aziridin-1-yl[6-phenyl-6-(thiazol-4-yl)-6,7-dihydro-1H-indazol-3-yl]methanone
Azetidin-1-yl[6-phenyl-6-(thiazol-4-yl)-6,7-dihydro-1H-indazol-3-yl]methanone
(N-Methoxy-N-methyl)-6-phenyl-6-(thiazol-4-yl)-6,7-dihydro-1H-indazole-3-carboxamide
6-Phenyl-6-(thiazol-4-yl)-6,7-dihydro-1H-indazole-3-carbonitrile
Cyclopropyl[6-phenyl-6-(thiazol-4-yl)-6,7-dihydro-1H-indazol-3-yl]methanone
Cyclobutyl[6-phenyl-6-(thiazol-4-yl)-6,7-dihydro-1H-indazol-3-yl]methanone
Cyclopropyl[6-phenyl-6-(thiazol-4-yl)-6,7-dihydro-1H-indazol-3-yl]methanone oxime
Cyclopropyl[6-phenyl-6-(thiazol-4-yl)-6,7-dihydro-1H-indazol-3-yl]methanone O-methyloxime
Cyclobutyl[6-phenyl-6-(thiazol-4-yl)-6,7-dihydro-1H-indazol-3-yl]methanone oxime
Cyclobutyl[6-phenyl-6-(thiazol-4-yl)-6,7-dihydro-1H-indazol-3-yl]methanone O-methyloxime
6-Phenyl-6-(thiazol-4-yl)-1-(4-toluenesulphonyl)-6,7-dihydro-1H-indazol-3-ylamine
(N-Cyclopropyl)-6-phenyl-6-(thiazol-4-yl)-1-(4-toluenesulphonyl)-6,7-dihydro-1H-indazol-3-ylamine
(N-Cyclobutyl)-6-phenyl-6-(thiazol-4-yl)-1-(4-toluenesulphonyl)-6,7-dihydro-1H-indazol-3-ylamine
(N-Phenyl)-6-phenyl-6-(thiazol-4-yl)-1-(4-toluenesulphonyl)-6,7-dihydro-1H-indazol-3-ylamine
1-[3-Amino-6-phenyl-6-(thiazol-4-yl)-6,7-dihydroindazol-1-yl]propenone
1-[3-Cyclopropylamino-6-phenyl-6-(thiazol-4-yl)-6,7-dihydroindazol-1-yl]propenone
1-[3-Cyclobutylamino-6-phenyl-6-(thiazol-4-yl)-6,7-dihydroindazol-1-yl]propenone
1-[3-Anilino-6-phenyl-6-(thiazol-4-yl)-6,7-dihydroindazol-1-yl]propenone
6-Phenyl-6-(thiazol-4-yl)-1-(4-toluenesulphonyl)-6,7-dihydro-1H-indazole-3-carboxylic acid
1-[3-Carboxy-6-phenyl-6-(thiazol-4-yl)-6,7-dihydroindazol-1-yl]propenone
Cyclopropanecarboxylic acid [6-phenyl-6-(thiazol-4-yl)-6,7-dihydro-1H-indazol-3-yl]amide
Cyclobutanecarboxylic acid [6-phenyl-6-(thiazol-4-yl)-6,7-dihydro-1H-indazol-3-yl]amide
3,6-Diphenyl-6-(thiazol-4-yl)-6,7-dihydro-1H-indazole
6-Phenyl-3-(pyrid-2-yl)-6-(thiazol-4-yl)-6,7-dihydro-1H-indazole
6-Phenyl-3-(pyrid-3-yl)-6-(thiazol-4-yl)-6,7-dihydro-1H-indazole
6-Phenyl-3-(pyrid-4-yl)-6-(thiazol-4-yl)-6,7-dihydro-1H-indazole
6-Phenyl-6-(thiazol-4-yl)-3-(thiophen-3-yl)-6,7-dihydro-1H-indazole
6-Phenyl-6-(thiazol-4-yl)-3-(thiophen-2-yl)-6,7-dihydro-1H-indazole
3-(Oxazol-2-yl)-6-phenyl-6-(thiazol-4-yl)-6,7-dihydro-1H-indazole
3-(Oxazol-4-yl)-6-phenyl-6-(thiazol-4-yl)-6,7-dihydro-1H-indazole
3-(Oxazol-5-yl)-6-phenyl-6-(thiazol-4-yl)-6,7-dihydro-1H-indazole
6-Phenyl-3-(thiazol-2-yl)-6-(thiazol-4-yl)-6,7-dihydro-1H-indazole
6-Phenyl-3,6-di(thiazol-4-yl)-6,7-dihydro-1H-indazole
6-Phenyl-3-(thiazol-5-yl)-6-(thiazol-4-yl)-6,7-dihydro-1H-indazole
3-(Imidazol-2-yl)-6-phenyl-6-(thiazol-4-yl)-6,7-dihydro-1H-indazole
3-(Imidazol-4-yl)-6-phenyl-6-(thiazol-4-yl)-6,7-dihydro-1H-indazole
3-(Imidazol-5-yl)-6-phenyl-6-(thiazol-4-yl)-6,7-dihydro-1H-indazole
3-(3-Methyl[1,2,4]oxadiazol-5-yl)-6-phenyl-6-(thiazol-4-yl)-6,7-dihydro-1H-indazole
3-(3-Methoxy[1,2,5]thiadiazol-4-yl)-6-phenyl-6-(thiazol-4-yl)-6,7-dihydro-1H-indazole
6-Phenyl-3-(tetrazol-5-yl)-6-(thiazol-4-yl)-6,7-dihydro-1H-indazole
6-Phenyl-3-(tetrazol-1-yl)-6-(thiazol-4-yl)-6,7-dihydro-1H-indazole
Methyl 6-phenyl-6-(thiazol-5-yl)-6,7-dihydro-1H-indazole-3-carboxylate
Ethyl 6-phenyl-6-(thiazol-5-yl)-6,7-dihydro-1H-indazole-3-carboxylate
(N-Cyclopropyl)-6-phenyl-6-(thiazol-5-yl)-6,7-dihydro-1H-indazole-3-carboxamide
Aziridin-1-yl[6-phenyl-6-(thiazol-5-yl)-6,7-dihydro-1H-indazol-3-yl]methanone
Azetidin-1-yl[6-phenyl-6-(thiazol-5-yl)-6,7-dihydro-1H-indazol-3-yl]methanone
(N-Methoxy-N-methyl)-6-phenyl-6-(thiazol-5-yl)-6,7-dihydro-1H-indazole-3-carboxamide
6-Phenyl-6-(thiazol-5-yl)-6,7-dihydro-1H-indazole-3-carbonitrile
Cyclopropyl[6-phenyl-6-(thiazol-5-yl)-6,7-dihydro-1H-indazol-3-yl]methanone
Cyclobutyl[6-phenyl-6-(thiazol-5-yl)-6,7-dihydro-1H-indazol-3-yl]methanone
Cyclopropyl[6-phenyl-6-(thiazol-5-yl)-6,7-dihydro-1H-indazol-3-yl]methanone oxime
Cyclopropyl[6-phenyl-6-(thiazol-5-yl)-6,7-dihydro-1H-indazol-3-yl]methanone O-methyloxime
Cyclobutyl[6-phenyl-6-(thiazol-5-yl)-6,7-dihydro-1H-indazol-3-yl]methanone oxime
Cyclobutyl[6-phenyl-6-(thiazol-5-yl)-6,7-dihydro-1H-indazol-3-yl]methanone O-methyloxime
6-Phenyl-6-(thiazol-5-yl)-1-(4-toluenesulphonyl)-6,7-dihydro-1H-indazol-3-ylamine
(N-Cyclopropyl)-6-phenyl-6-(thiazol-5-yl)-1-(4-toluenesulphonyl)-6,7-dihydro-1H-indazol-3-ylamine
(N-Cyclobutyl)-6-phenyl-6-(thiazol-5-yl)-1-(4-toluenesulphonyl)-6,7-dihydro-1H-indazol-3-ylamine
(N-Phenyl)-6-phenyl-6-(thiazol-5-yl)-1-(4-toluenesulphonyl)-6,7-dihydro-1H-indazol-3-ylamine
1-[3-Amino-6-phenyl-6-(thiazol-5-yl)-6,7-dihydroindazol-1-yl]propenone
1-[3-Cyclopropylamino-6-phenyl-6-(thiazol-5-yl)-6,7-dihydroindazol-1-yl]propenone
1-[3-Cyclobutylamino-6-phenyl-6-(thiazol-5-yl)-6,7-dihydroindazol-1-yl]propenone
1-[3-Anilino-6-phenyl-6-(thiazol-5-yl)-6,7-dihydroindazol-1-yl]propenone
6-Phenyl-6-(thiazol-5-yl)-1-(4-toluenesulphonyl)-6,7-dihydro-1H-indazole-3-carboxylic acid
1-[3-Carboxy-6-phenyl-6-(thiazol-5-yl)-6,7-dihydroindazol-1-yl]propenone
Cyclopropanecarboxylic acid [6-phenyl-6-(thiazol-5-yl)-6,7-dihydro-1H-indazol-3-yl]amide
Cyclobutanecarboxylic acid [6-phenyl-6-(thiazol-5-yl)-6,7-dihydro-1H-indazol-3-yl]amide 3,6-Diphenyl-6-(thiazol-5-yl)-6,7-dihydro-1H-indazole
6-Phenyl-3-(pyrid-2-yl)-6-(thiazol-5-yl)-6,7-dihydro-1H-indazole
6-Phenyl-3-(pyrid-3-yl)-6-(thiazol-5-yl)-6,7-dihydro-1H-indazole
6-Phenyl-3-(pyrid-4-yl)-6-(thiazol-5-yl)-6,7-dihydro-1H-indazole
6-Phenyl-6-(thiazol-5-yl)-3-(thiophen-3-yl)-6,7-dihydro-1H-indazole
6-Phenyl-6-(thiazol-5-yl)-3-(thiophen-2-yl)-6,7-dihydro-1H-indazole
3-(Oxazol-2-yl)-6-phenyl-6-(thiazol-5-yl)-6,7-dihydro-1H-indazole
3-(Oxazol-4-yl)-6-phenyl-6-(thiazol-5-yl)-6,7-dihydro-1H-indazole
3-(Oxazol-5-yl)-6-phenyl-6-(thiazol-5-yl)-6,7-dihydro-1H-indazole
6-Phenyl-3-(thiazol-2-yl)-6-(thiazol-5-yl)-6,7-dihydro-1H-indazole
6-Phenyl-3,6-di(thiazol-5-yl)-6,7-dihydro-1H-indazole
6-Phenyl-3-(thiazol-4-yl)-6-(thiazol-5-yl)-6,7-dihydro-1H-indazole
3-(Imidazol-2-yl)-6-phenyl-6-(thiazol-5-yl)-6,7-dihydro-1H-indazole
3-(Imidazol-4-yl)-6-phenyl-6-(thiazol-5-yl)-6,7-dihydro-1H-indazole
3-(Imidazol-5-yl)-6-phenyl-6-(thiazol-5-yl)-6,7-dihydro-1H-indazole
3-(3-Methyl[1,2,4]oxadiazol-5-yl)-6-phenyl-6-(thiazol-5-yl)-6,7-dihydro-1H-indazole
3-(3-Methoxy[1,2,5]thiadiazol-4-yl)-6-phenyl-6-(thiazol-5-yl)-6,7-dihydro-1H-indazole
6-Phenyl-3-(tetrazol-5-yl)-6-(thiazol-5-yl)-6,7-dihydro-1H-indazole
6-Phenyl-3-(tetrazol-1-yl)-6-(thiazol-5-yl)-6,7-dihydro-1H-indazole
Methyl 6,6-bis(4-methoxyphenyl)-6,7-dihydro-1H-indazole-3-carboxylate
(N-Cyclopropyl)-6,6-bis(4-methoxyphenyl)-6,7-dihydro-1H-indazole-3-carboxamide
Aziridin-1-yl[6,6-bis(4-methoxyphenyl)-6,7-dihydro-1H-indazol-3-yl]methanone
Azetidin-1-yl[6,6-bis(4-methoxyphenyl)-6,7-dihydro-1H-indazol-3-yl]methanone
(N-Methoxy-N-methyl)-6,6-bis(4-methoxyphenyl)-6,7-dihydro-1H-indazole-3-carboxamide
6,6-Bis(4-methoxyphenyl)-6,7-dihydro-1H-indazole-3-carbonitrile
Cyclopropyl[6,6-bis(4-methoxyphenyl)-6,7-dihydro-1H-indazol-3-yl]methanone
Cyclobutyl[6,6-bis(4-methoxyphenyl)-6,7-dihydro-1H-indazol-3-yl]methanone
Cyclopropyl[6,6-bis(4-methoxyphenyl)-6,7-dihydro-1H-indazol-3-yl]methanone oxime
Cyclopropyl[6,6-bis(4-methoxyphenyl)-6,7-dihydro-1H-indazol-3-yl]methanone O-methyloxime
Cyclobutyl[6,6-bis(4-methoxyphenyl)-6,7-dihydro-1H-indazol-3-yl]methanone oxime
Cyclobutyl[6,6-bis(4-methoxyphenyl)-6,7-dihydro-1H-indazol-3-yl]methanone O-methyloxime
6,6-Bis(4-methoxyphenyl)-1-(4-toluenesulphonyl)-6,7-dihydro-1H-indazol-3-ylamine
(N-Cyclopropyl)-6,6-bis(4-methoxyphenyl)-1-(4-toluenesulphonyl)-6,7-dihydro-1H-indazol-3-ylamine
(N-Cyclobutyl)-6,6-bis(4-methoxyphenyl)-1-(4-toluenesulphonyl)-6,7-dihydro-1H-indazol-3-ylamine
(N-Phenyl)-6,6-bis(4-methoxyphenyl)-1-(4-toluenesulphonyl)-6,7-dihydro-1H-indazol-3-ylamine
1-[3-Amino-6,6-bis(4-methoxyphenyl)-6,7-dihydroindazol-1-yl]propenone
1-[3-Cyclopropylamino-6,6-bis(4-methoxyphenyl)-6,7-dihydroindazol-1-yl]propenone
1-[3-Cyclobutylamino-6,6-bis(4-methoxyphenyl)-6,7-dihydroindazol-1-yl]propenone
1-[3-Anilino-6,6-bis(4-methoxyphenyl)-6,7-dihydroindazol-1-yl]propenone
6,6-Bis(4-methoxyphenyl)-1-(4-toluenesulphonyl)-6,7-dihydro-1H-indazole-3 carboxylic acid
1-[3-Carboxy-6,6-bis(4-methoxyphenyl)-6,7-dihydroindazol-1-yl]propenone
Cyclopropanecarboxylic acid [6,6-bis(4-methoxyphenyl)-6,7-dihydro-1H-indazol-3-yl]amide
Cyclobutanecarboxylic acid [6,6-bis(4-methoxyphenyl)-6,7-dihydro-1H-indazol-3-yl]amide
6,6-Bis(4-methoxyphenyl)-3-phenyl-6,7-dihydro-1H-indazole
6,6-Bis(4-methoxyphenyl)-3-(pyrid-2-yl)-6,7-dihydro-1H-indazole
6,6-Bis(4-methoxyphenyl)-3-(pyrid-3-yl)-6,7-dihydro-1H-indazole
6,6-Bis(4-methoxyphenyl)-3-(pyrid-4-yl)-6,7-dihydro-1H-indazole
6,6-Bis(4-methoxyphenyl)-3-(thiophen-2-yl)-6,7-dihydro-1H-indazole
6,6-Bis(4-methoxyphenyl)-3-(thiophen-3-yl)-6,7-dihydro-1H-indazole
6,6-Bis(4-methoxyphenyl)-3-(oxazol-2-yl)-6,7-dihydro-1H-indazole
6,6-Bis(4-methoxyphenyl)-3-(oxazol-4-yl)-6,7-dihydro-1H-indazole
6,6-Bis(4-methoxyphenyl)-3-(oxazol-5-yl)-6,7-dihydro-1H-indazole
6,6-Bis(4-methoxyphenyl)-3-(thiazol-2-yl)-6,7-dihydro-1H-indazole
6,6-Bis(4-methoxyphenyl)-3-(thiazol-4-yl)-6,7-dihydro-1H-indazole
6,6-Bis(4-methoxyphenyl)-3-(thiazol-5-yl)-6,7-dihydro-1H-indazole
6,6-Bis(4-methoxyphenyl)-3-(imidazol-2-yl)-6,7-dihydro-1H-indazole
6,6-Bis(4-methoxyphenyl)-3-(imidazol-4-yl)-6,7-dihydro-1H-indazole
6,6-Bis(4-methoxyphenyl)-3-(imidazol-5-yl)-6,7-dihydro-1H-indazole
6,6-Bis(4-methoxyphenyl)-3-(3-methyl[1,2,4]oxadiazol-5-yl)-6,7-dihydro-1H-indazole
6,6-Bis(4-methoxyphenyl)-3-(3-methoxy[1,2,5]thiadiazol-4-yl)-6,7-dihydro-1H-indazole
6,6-Bis(4-methoxyphenyl)-3-(tetrazol-5-yl)-6,7-dihydro-1H-indazole
6,6-Bis(4-methoxyphenyl)-3-(tetrazol-1-yl)-6,7-dihydro-1H-indazole
Methyl 6,6-bis(3-methoxyphenyl)-6,7-dihydro-1H-indazole-3-carboxylate
Ethyl 6,6-bis(3-methoxyphenyl)-6,7-dihydro-1H-indazole-3-carboxylate
(N-Cyclopropyl)-6,6-bis(3-methoxyphenyl)-6,7-dihydro-1H-indazole-3-carboxamide
Aziridin-1-yl[6,6-bis(3-methoxyphenyl)-6,7-dihydro-1H-indazol-3-yl]methanone
Azetidin-1-yl[6,6-bis(3-methoxyphenyl)-6,7-dihydro-1H-indazol-3-yl]methanone (N-Methoxy-N-methyl)-6,6-bis(3-methoxyphenyl)-6,7-dihydro-1H-indazole-3-carboxamide
6,6-Bis(3-methoxyphenyl)-6,7-dihydro-1H-indazole-3-carbonitrile
Cyclopropyl[6,6-bis(3-methoxyphenyl)-6,7-dihydro-1H-indazol-3-yl]methanone
Cyclobutyl[6,6-bis(3-methoxyphenyl)-6,7-dihydro-1H-indazol-3-yl]methanone
Cyclopropyl[6,6-bis(3-methoxyphenyl)-6,7-dihydro-1H-indazol-3-yl]methanone oxime
Cyclopropyl[6,6-bis(3-methoxyphenyl)-6,7-dihydro-1H-indazol-3-yl]methanone O-methyloxime
Cyclobutyl[6,6-bis(3-methoxyphenyl)-6,7-dihydro-1H-indazol-3-yl]methanone oxime
Cyclobutyl[6,6-bis(3-methoxyphenyl)-6,7-dihydro-1H-indazol-3-yl]methanone O-methyloxime
6,6-Bis(3-methoxyphenyl)-1-(4-toluenesulphonyl)-6,7-dihydro-1H-indazol-3-ylamine
(N-Cyclopropyl)-6,6-bis(3-methoxyphenyl)-1-(4-toluenesulphonyl)-6,7-dihydro-1H-indazol-3-ylamine
(N-Cyclobutyl)-6,6-bis(3-methoxyphenyl)-1-(4-toluenesulphonyl)-6,7-dihydro-1H-indazol-3-ylamine
(N-Phenyl)-6,6-bis(3-methoxyphenyl)-1-(4-toluenesulphonyl)-6,7-dihydro-1H-indazol-3-ylamine
1-[3-Amino-6,6-bis(3-methoxyphenyl)-6,7-dihydroindazol-1-yl]propenone
1-[3-Cyclopropylamino-6,6-bis(3-methoxyphenyl)-6,7-dihydroindazol-1-yl]propenone
1-[3-Cyclobutylamino-6,6-bis(3-methoxyphenyl)-6,7-dihydroindazol-1-yl]propenone
1-[3-Anilino-6,6-bis(3-methoxyphenyl)-6,7-dihydroindazol-1-yl]propenone
6,6-bis(3-methoxyphenyl)-1-(4-toluenesulphonyl)-6,7-dihydro-1H-indazole-3 carboxylic acid
1-[3-Carboxy-6,6-bis(3-methoxyphenyl)-6,7-dihydroindazol-1-yl]propenone
Cyclopropanecarboxylic acid [6,6-bis(3-methoxyphenyl)-6,7-dihydro-1H-indazol-3-yl]amide
Cyclobutanecarboxylic acid [6,6-bis(3-methoxyphenyl)-6,7-dihydro-1H-indazol-3-yl]amide
6,6-Bis(3-methoxyphenyl)-3-phenyl-6,7-dihydro-1H-indazole
6,6-Bis(3-methoxyphenyl)-3-(pyrid-2-yl)-6,7-dihydro-1H-indazole
6,6-Bis(3-methoxyphenyl)-3-(pyrid-3-yl)-6,7-dihydro-1H-indazole
6,6-Bis(3-methoxyphenyl)-3-(pyrid-4-yl)-6,7-dihydro-1H-indazole
6,6-Bis(3-methoxyphenyl)-3-(thiophen-2-yl)-6,7-dihydro-1H-indazole
6,6-Bis(3-methoxyphenyl)-3-(thiophen-3-yl)-6,7-dihydro-1H-indazole
6,6-Bis(3-methoxyphenyl)-3-(oxazol-2-yl)-6,7-dihydro-1H-indazole
6,6-Bis(3-methoxyphenyl)-3-(oxazol-4-yl)-6,7-dihydro-1H-indazole
6,6-Bis(3-methoxyphenyl)-3-(oxazol-5-yl)-6,7-dihydro-1H-indazole
6,6-Bis(3-methoxyphenyl)-3-(thiazol-2-yl)-6,7-dihydro-1H-indazole
6,6-Bis(3-methoxyphenyl)-3-(thiazol-4-yl)-6,7-dihydro-1H-indazole
6,6-Bis(3-methoxyphenyl)-3-(thiazol-5-yl)-6,7-dihydro-1H-indazole
6,6-Bis(3-methoxyphenyl)-3-(imidazol-2-yl)-6,7-dihydro-1H-indazole
6,6-Bis(3-methoxyphenyl)-3-(imidazol-4-yl)-6,7-dihydro-1H-indazole
6,6-Bis(3-methoxyphenyl)-3-(imidazol-5-yl)-6,7-dihydro-1H-indazole
6,6-Bis(3-methoxyphenyl)-3-(3-methyl[1,2,4]oxadiazol-5-yl)-6,7-dihydro-1H-indazole
6,6-Bis(3-methoxyphenyl)-3-(3-methoxy[1,2,5]thiadiazol-4-yl)-6,7-dihydro-1H-indazole
6,6-Bis(3-methoxyphenyl)-3-(tetrazol-5-yl)-6,7-dihydro-1H-indazole
6,6-Bis(3-methoxyphenyl)-3-(tetrazol-1-yl)-6,7-dihydro-1H-indazole
Methyl 6,6-bis(4-dimethylaminophenyl)-6,7-dihydro-1H-indazole-3-carboxylate
Ethyl 6,6-bis(4-dimethylaminophenyl)-6,7-dihydro-1H-indazole-3-carboxylate
(N-Cyclopropyl)-6,6-bis(4-dimethylaminophenyl)-6,7-dihydro-1H-indazole-3-carboxamide
Aziridin-1-yl[6,6-bis(4-dimethylaminophenyl)-6,7-dihydro-1H-indazol-3-yl]methanone
Azetidin-1-yl[6,6-bis(4-dimethylaminophenyl)-6,7-dihydro-1H-indazol-3-yl]methanone
(N-Methoxy-N-methyl)-6,6-bis(4-dimethylaminophenyl)-6,7-dihydro-1H-indazole-3-carboxamide
6,6-Bis(4-dimethylaminophenyl)-6,7-dihydro-1H-indazole-3-carbonitrile
Cyclopropyl[6,6-bis(4-dimethylaminophenyl)-6,7-dihydro-1H-indazol-3-yl]methanone
Cyclobutyl[6,6-bis(4-dimethylaminophenyl)-6,7-dihydro-1H-indazol-3-yl]methanone
Cyclopropyl[6,6-bis(4-dimethylaminophenyl)-6,7-dihydro-1H-indazol-3-yl]methanone oxime
Cyclopropyl[6,6-bis(4-dimethylaminophenyl)-6,7-dihydro-1H-indazol-3-yl]methanone O-methyloxime
Cyclobutyl[6,6-bis(4-dimethylaminophenyl)-6,7-dihydro-1H-indazol-3-yl]methanone oxime
Cyclobutyl[6,6-bis(4-dimethylaminophenyl)-6,7-dihydro-1H-indazol-3-yl]methanone O-methyloxime
6,6-Bis(4-dimethylaminophenyl)-1-(4-toluenesulphonyl)-6,7-dihydro-1H-indazol-3-ylamine
(N-Cyclopropyl)-6,6-bis(4-dimethylaminophenyl)-1-(4-toluenesulphonyl)-6,7-dihydro-1H-indazol-3-ylamine
(N-Cyclobutyl)-6,6-bis(4-dimethylaminophenyl)-1-(4-toluenesulphonyl)-6,7-dihydro-1H-indazol-3-ylamine
(N-Phenyl)-6,6-bis(4-dimethylaminophenyl)-1-(4-toluenesulphonyl)-6,7-dihydro-1H-indazol-3-ylamine
1-[3-Amino-6,6-bis(4-dimethylaminophenyl)-6,7-dihydroindazol-1-yl]propenone
1-[3-Cyclopropylamino-6,6-bis(4-dimethylaminophenyl)-6,7-dihydroindazol-1-yl]propenone
1-[3-Cyclobutylamino-6,6-bis(4-dimethylaminophenyl)-6,7-dihydroindazol-1-yl]propenone
1-[3-Anilino-6,6-bis(4-dimethylaminophenyl)-6,7-dihydroindazol-1-yl]propenone
6,6-Bis(4-dimethylaminophenyl)-1-(4-toluenesulphonyl)-6,7-dihydro-1H-indazole-3 carboxylic acid
1-[3-Carboxy-6,6-bis(4-dimethylaminophenyl)-6,7-dihydroindazol-1-yl]propenone
Cyclopropanecarboxylic acid [6,6-bis(4-dimethylaminophenyl)-6,7-dihydro-1H-indazol-3-yl]amide
Cyclobutanecarboxylic acid [6,6-bis(4-dimethylaminophenyl)-6,7-dihydro-1H-indazol-3-yl]amide
6,6-Bis(4-dimethylaminophenyl)-3-phenyl-6,7-dihydro-1H-indazole
6,6-Bis(4-dimethylaminophenyl)-3-(pyrid-2-yl)-6,7-dihydro-1H-indazole 6,6-Bis(4-dimethylaminophenyl)-3-(pyrid-3-yl)-6,7-dihydro-1H-indazole
6,6-Bis(4-dimethylaminophenyl)-3-(pyrid-4-yl)-6,7-dihydro-1H-indazole
6,6-Bis(4-dimethylaminophenyl)-3-(thiophen-2-yl)-6,7-dihydro-1H-indazole
6,6-Bis(4-dimethylaminophenyl)-3-(thiophen-3-yl)-6,7-dihydro-1H-indazole
6,6-Bis(4-dimethylaminophenyl)-3-(oxazol-2-yl)-6,7-dihydro-1H-indazole
6,6-Bis(4-dimethylaminophenyl)-3-(oxazol-4-yl)-6,7-dihydro-1H-indazole
6,6-Bis(4-dimethylaminophenyl)-3-(oxazol-5-yl)-6,7-dihydro-1H-indazole
6,6-Bis(4-dimethylaminophenyl)-3-(thiazol-2-yl)-6,7-dihydro-1H-indazole
6,6-Bis(4-dimethylaminophenyl)-3-(thiazol-4-yl)-6,7-dihydro-1H-indazole
6,6-Bis(4-dimethylaminophenyl)-3-(thiazol-5-yl)-6,7-dihydro-1H-indazole
6,6-Bis(4-dimethylaminophenyl)-3-(imidazol-2-yl)-6,7-dihydro-1H-indazole
6,6-Bis(4-dimethylaminophenyl)-3-(imidazol-4-yl)-6,7-dihydro-1H-indazole
6,6-Bis(4-dimethylaminophenyl)-3-(imidazol-5-yl)-6,7-dihydro-1H-indazole
6,6-Bis(4-dimethylaminophenyl)-3-(3-methyl[1,2,4]oxadiazol-5-yl)-6,7-dihydro-1H-indazole
6,6-Bis(4-dimethylaminophenyl)-3-(3-methoxy[1,2,5]thiadiazol-4-yl)-6,7-dihydro-1H-indazole
6,6-Bis(4-dimethylaminophenyl)-3-(tetrazol-5-yl)-6,7-dihydro-1H-indazole
6,6-Bis(4-dimethylaminophenyl)-3-(tetrazol-1-yl)-6,7-dihydro-1H-indazole
Methyl 6,6-bis(3-dimethylaminophenyl)-6,7-dihydro-1H-indazole-3-carboxylate
Ethyl 6,6-bis(3-dimethylaminophenyl)-6,7-dihydro-1H-indazole-3-carboxylate
(N-Cyclopropyl)-6,6-bis(3-dimethylaminophenyl)-6,7-dihydro-1H-indazole-3-carboxamide
Aziridin-1-yl[6,6-bis(3-dimethylaminophenyl)-6,7-dihydro-1H-indazol-3-yl]methanone
Azetidin-1-yl[6,6-bis(3-dimethylaminophenyl)-6,7-dihydro-1H-indazol-3-yl]methanone
(N-Methoxy-N-methyl)-6,6-bis(3-dimethylaminophenyl)-6,7-dihydro-1H-indazole-3-carboxamide
6,6-Bis(3-dimethylaminophenyl)-6,7-dihydro-1H-indazole-3-carbonitrile
Cyclopropyl[6,6-bis(3-dimethylaminophenyl)-6,7-dihydro-1H-indazol-3-yl]methanone
Cyclobutyl[6,6-bis(3-dimethylaminophenyl)-6,7-dihydro-1H-indazol-3-yl]methanone
Cyclopropyl[6,6-bis(3-dimethylaminophenyl)-6,7-dihydro-1H-indazol-3-yl]methanone oxime
Cyclopropyl[6,6-bis(3-dimethylaminophenyl)-6,7-dihydro-1H-indazol-3-yl]methanone O-methyloxime
Cyclobutyl[6,6-bis(3-dimethylaminophenyl)-6,7-dihydro-1H-indazol-3-yl]methanone oxime
Cyclobutyl[6,6-bis(3-dimethylaminophenyl)-6,7-dihydro-1H-indazol-3-yl]methanone O-methyloxime
6,6-Bis(3-dimethylaminophenyl)-1-(4-toluenesulphonyl)-6,7-dihydro-1H-indazol-3-ylamine
(N-Cyclopropyl)-6,6-bis(3-dimethylaminophenyl)-1-(4-toluenesulphonyl)-6,7-dihydro-1H-indazol-3-ylamine
(N-Cyclobutyl)-6,6-bis(3-dimethylaminophenyl)-1-(4-toluenesulphonyl)-6,7-dihydro-1H-indazol-3-ylamine
(N-Phenyl)-6,6-bis(3-dimethylaminophenyl)-1-(4-toluenesulphonyl)-6,7-dihydro-1H-indazol-3-ylamine
1-[3-Amino-6,6-bis(3-dimethylaminophenyl)-6,7-dihydroindazol-1-yl]propenone
1-[3-Cyclopropylamino-6,6-bis(3-dimethylaminophenyl)-6,7-dihydroindazol-1-yl]propenone
1-[3-Cyclobutylamino-6,6-bis(3-dimethylaminophenyl)-6,7-dihydroindazol-1-yl]propenone
1-[3-Anilino-6,6-bis(3-dimethylaminophenyl)-6,7-dihydroindazol-1-yl]propenone
6,6-Bis(3-dimethylaminophenyl)-1-(4-toluenesulphonyl)-6,7-dihydro-1H-indazole-3 carboxylic acid
1-[3-Carboxy-6,6-bis(3-dimethylaminophenyl)-6,7-dihydroindazol-1-yl]propenone
Cyclopropanecarboxylic acid [6,6-bis(3-dimethylaminophenyl)-6,7-dihydro-1H-indazol-3-yl]amide
Cyclobutanecarboxylic acid [6,6-bis(3-dimethylaminophenyl)-6,7-dihydro-1H-indazol-3-yl]amide
6,6-Bis(3-dimethylaminophenyl)-3-phenyl-6,7-dihydro-1H-indazole
6,6-Bis(3-dimethylaminophenyl)-3-(pyrid-2-yl)-6,7-dihydro-1H-indazole
6,6-Bis(3-dimethylaminophenyl)-3-(pyrid-3-yl)-6,7-dihydro-1H-indazole
6,6-Bis(3-dimethylaminophenyl)-3-(pyrid-4-yl)-6,7-dihydro-1H-indazole
6,6-Bis(3-dimethylaminophenyl)-3-(thiophen-2-yl)-6,7-dihydro-1H-indazole
6,6-Bis(3-dimethylaminophenyl)-3-(thiophen-3-yl)-6,7-dihydro-1H-indazole
6,6-Bis(3-dimethylaminophenyl)-3-(oxazol-2-yl)-6,7-dihydro-1H-indazole
6,6-Bis(3-dimethylaminophenyl)-3-(oxazol-4-yl)-6,7-dihydro-1H-indazole
6,6-Bis(3-dimethylaminophenyl)-3-(oxazol-5-yl)-6,7-dihydro-1H-indazole
6,6-Bis(3-dimethylaminophenyl)-3-(thiazol-2-yl)-6,7-dihydro-1H-indazole
6,6-Bis(3-dimethylaminophenyl)-3-(thiazol-4-yl)-6,7-dihydro-1H-indazole
6,6-Bis(3-dimethylaminophenyl)-3-(thiazol-5-yl)-6,7-dihydro-1H-indazole
6,6-Bis(3-dimethylaminophenyl)-3-(imidazol-2-yl)-6,7-dihydro-1H-indazole
6,6-Bis(3-dimethylaminophenyl)-3-(imidazol-4-yl)-6,7-dihydro-1H-indazole
6,6-Bis(3-dimethylaminophenyl)-3-(imidazol-5-yl)-6,7-dihydro-1H-indazole
6,6-Bis(3-dimethylaminophenyl)-3-(3-methyl[1,2,4]oxadiazol-5-yl)-6,7-dihydro-1H-indazole
6,6-Bis(3-dimethylaminophenyl)-3-(3-methoxy[1,2,5]thiadiazol-4-yl)-6,7-dihydro-1H-indazole
6,6-Bis(3-dimethylaminophenyl)-3-(tetrazol-5-yl)-6,7-dihydro-1H-indazole
6,6-Bis(3-dimethylaminophenyl)-3-(tetrazol-1-yl)-6,7-dihydro-1H-indazole
Methyl 6,6-bis(4-fluorophenyl)-6,7-dihydro-1H-indazole-3-carboxylate
Ethyl 6,6-bis(4-fluorophenyl)-6,7-dihydro-1H-indazole-3-carboxylate
(N-Cyclopropyl)-6,6-bis(4-fluorophenyl)-6,7-dihydro-1H-indazole-3-carboxamide
Aziridin-1-yl[6,6-bis(4-fluorophenyl)-6,7-dihydro-1H-indazol-3-yl]methanone
Azetidin-1-yl[6,6-bis(4-fluorophenyl)-6,7-dihydro-1H-indazol-3-yl]methanone (N-Methoxy-N-methyl)-6,6-bis(4-fluorophenyl)-6,7-dihydro-1H-indazole-3-carboxamide
6,6-Bis(4-fluorophenyl)-6,7-dihydro-1H-indazole-3-carbonitrile
Cyclopropyl[6,6-bis(4-fluorophenyl)-6,7-dihydro-1H-indazol-3-yl]methanone
Cyclobutyl[6,6-bis(4-fluorophenyl)-6,7-dihydro-1H-indazol-3-yl]methanone
Cyclopropyl[6,6-bis(4-fluorophenyl)-6,7-dihydro-1H-indazol-3-yl]methanone oxime
Cyclopropyl[6,6-bis(4-fluorophenyl)-6,7-dihydro-1H-indazol-3-yl]methanone O-methyloxime
Cyclobutyl[6,6-bis(4-fluorophenyl)-6,7-dihydro-1H-indazol-3-yl]methanone oxime
Cyclobutyl[6,6-bis(4-fluorophenyl)-6,7-dihydro-1H-indazol-3-yl]methanone O-methyloxime
6,6-Bis(4-fluorophenyl)-1-(4-toluenesulphonyl)-6,7-dihydro-1H-indazol-3-ylamine
(N-Cyclopropyl)-6,6-bis(4-fluorophenyl)-1-(4-toluenesulphonyl)-6,7-dihydro-1H-indazol-3-ylamine
(N-Cyclobutyl)-6,6-bis(4-fluorophenyl)-1-(4-toluenesulphonyl)-6,7-dihydro-1H-indazol-3-ylamine
(N-Phenyl)-6,6-bis(4-fluorophenyl)-1-(4-toluenesulphonyl)-6,7-dihydro-1H-indazol-3-ylamine
1-[3-Amino-6,6-bis(4-fluorophenyl)-6,7-dihydroindazol-1-yl]propenone
1-[3-Cyclopropylamino-6,6-bis(4-fluorophenyl)-6,7-dihydroindazol-1-yl]propenone
1-[3-Cyclobutylamino-6,6-bis(4-fluorophenyl)-6,7-dihydroindazol-1-yl]propenone
1-[3-Anilino-6,6-bis(4-fluorophenyl)-6,7-dihydroindazol-1-yl]propenone
6,6-Bis(4-fluorophenyl)-1-(4-toluenesulphonyl)-6,7-dihydro-1H-indazole-3 carboxylic acid
1-[3-Carboxy-6,6-bis(4-fluorophenyl)-6,7-dihydroindazol-1-yl]propenone
Cyclopropanecarboxylic acid [6,6-bis(4-fluorophenyl)-6,7-dihydro-1H-indazol-3-yl]amide
Cyclobutanecarboxylic acid [6,6-bis(4-fluorophenyl)-6,7-dihydro-1H-indazol-3-yl]amide
6,6-Bis(4-fluorophenyl)-3-phenyl-6,7-dihydro-1H-indazole
6,6-Bis(4-fluorophenyl)-3-(pyrid-2-yl)-6,7-dihydro-1H-indazole
6,6-Bis(4-fluorophenyl)-3-(pyrid-3-yl)-6,7-dihydro-1H-indazole
6,6-Bis(4-fluorophenyl)-3-(pyrid-4-yl)-6,7-dihydro-1H-indazole
6,6-Bis(4-fluorophenyl)-3-(thiophen-2-yl)-6,7-dihydro-1H-indazole
6,6-Bis(4-fluorophenyl)-3-(thiophen-3-yl)-6,7-dihydro-1H-indazole
6,6-Bis(4-fluorophenyl)-3-(oxazol-2-yl)-6,7-dihydro-1H-indazole
6,6-Bis(4-fluorophenyl)-3-(oxazol-4-yl)-6,7-dihydro-1H-indazole
6,6-Bis(4-fluorophenyl)-3-(oxazol-5-yl)-6,7-dihydro-1H-indazole
6,6-Bis(4-fluorophenyl)-3-(thiazol-2-yl)-6,7-dihydro-1H-indazole
6,6-Bis(4-fluorophenyl)-3-(thiazol-4-yl)-6,7-dihydro-1H-indazole
6,6-Bis(4-fluorophenyl)-3-(thiazol-5-yl)-6,7-dihydro-1H-indazole
6,6-Bis(4-fluorophenyl)-3-(imidazol-2-yl)-6,7-dihydro-1H-indazole
6,6-Bis(4-fluorophenyl)-3-(imidazol-4-yl)-6,7-dihydro-1H-indazole
6,6-Bis(4-fluorophenyl)-3-(imidazol-5-yl)-6,7-dihydro-1H-indazole
6,6-Bis(4-fluorophenyl)-3-(3-methyl[1,2,4]oxadiazol-5-yl)-6,7-dihydro-1H-indazole
6,6-Bis(4-fluorophenyl)-3-(3-methoxy[1,2,5]thiadiazol-4-yl)-6,7-dihydro-1H-indazole
6,6-Bis(4-fluorophenyl)-3-(tetrazol-5-yl)-6,7-dihydro-1H-indazole
6,6-Bis(4-fluorophenyl)-3-(tetrazol-1-yl)-6,7-dihydro-1H-indazole
Methyl 6,6-bis(3-fluorophenyl)-6,7-dihydro-1H-indazole-3-carboxylate
Ethyl 6,6-bis(3-fluorophenyl)-6,7-dihydro-1H-indazole-3-carboxylate
(N-Cyclopropyl)-6,6-bis(3-fluorophenyl)-6,7-dihydro-1H-indazole-3-carboxamide
Aziridin-1-yl[6,6-bis(3-fluorophenyl)-6,7-dihydro-1H-indazol-3-yl]methanone
Azetidin-1-yl[6,6-bis(3-fluorophenyl)-6,7-dihydro-1H-indazol-3-yl]methanone
(N-Methoxy-N-methyl)-6,6-bis(3-fluorophenyl)-6,7-dihydro-1H-indazole-3-carboxamide
6,6-Bis(3-fluorophenyl)-6,7-dihydro-1H-indazole-3-carbonitrile
Cyclopropyl[6,6-bis(3-fluorophenyl)-6,7-dihydro-1H-indazol-3-yl]methanone
Cyclobutyl[6,6-bis(3-fluorophenyl)-6,7-dihydro-1H-indazol-3-yl]methanone
Cyclopropyl[6,6-bis(3-fluorophenyl)-6,7-dihydro-1H-indazol-3-yl]methanone oxime
Cyclopropyl[6,6-bis(3-fluorophenyl)-6,7-dihydro-1H-indazol-3-yl]methanone O-methyloxime
Cyclobutyl[6,6-bis(3-fluorophenyl)-6,7-dihydro-1H-indazol-3-yl]methanone oxime
Cyclobutyl[6,6-bis(3-fluorophenyl)-6,7-dihydro-1H-indazol-3-yl]methanone O-methyloxime
6,6-Bis(3-fluorophenyl)-1-(4-toluenesulphonyl)-6,7-dihydro-1H-indazol-3-ylamine
(N-Cyclopropyl)-6,6-bis(3-fluorophenyl)-1-(4-toluenesulphonyl)-6,7-dihydro-1H-indazol-3-ylamine
(N-Cyclobutyl)-6,6-bis(3-fluorophenyl)-1-(4-toluenesulphonyl)-6,7-dihydro-1H-indazol-3-ylamine
(N-Phenyl)-6,6-bis(3-fluorophenyl)-1-(4-toluenesulphonyl)-6,7-dihydro-1H-indazol-3-ylamine
1-[3-Amino-6,6-bis(3-fluorophenyl)-6,7-dihydroindazol-1-yl]propenone
1-[3-Cyclopropylamino-6,6-bis(3-fluorophenyl)-6,7-dihydroindazol-1-yl]propenone
1-[3-Cyclobutylamino-6,6-bis(3-fluorophenyl)-6,7-dihydroindazol-1-yl]propenone
1-[3-Anilino-6,6-bis(3-fluorophenyl)-6,7-dihydroindazol-1-yl]propenone
6,6-Bis(3-fluorophenyl)-1-(4-toluenesulphonyl)-6,7-dihydro-1H-indazole-3 carboxylic acid
1-[3-Carboxy-6,6-bis(3-fluorophenyl)-6,7-dihydroindazol-1-yl]propenone
Cyclopropanecarboxylic acid [6,6-bis(3-fluorophenyl)-6,7-dihydro-1H-indazol-3-yl]amide
Cyclobutanecarboxylic acid [6,6-bis(3-fluorophenyl)-6,7-dihydro-1H-indazol-3-yl]amide
6,6-Bis(3-fluorophenyl)-3-phenyl-6,7-dihydro-1H-indazole
6,6-Bis(3-fluorophenyl)-3-(pyrid-2-yl)-6,7-dihydro-1H-indazole
6,6-Bis(3-fluorophenyl)-3-(pyrid-3-yl)-6,7-dihydro-1H-indazole
6,6-Bis(3-fluorophenyl)-3-(pyrid-4-yl)-6,7-dihydro-1H-indazole 6,6-Bis(3-fluorophenyl)-3-(thiophen-2-yl)-6,7-dihydro-1H-indazole
6,6-Bis(3-fluorophenyl)-3-(thiophen-3-yl)-6,7-dihydro-1H-indazole
6,6-Bis(3-fluorophenyl)-3-(oxazol-2-yl)-6,7-dihydro-1H-indazole
6,6-Bis(3-fluorophenyl)-3-(oxazol-4-yl)-6,7-dihydro-1H-indazole
6,6-Bis(3-fluorophenyl)-3-(oxazol-5-yl)-6,7-dihydro-1H-indazole
6,6-Bis(3-fluorophenyl)-3-(thiazol-2-yl)-6,7-dihydro-1H-indazole
6,6-Bis(3-fluorophenyl)-3-(thiazol-4-yl)-6,7-dihydro-1H-indazole
6,6-Bis(3-fluorophenyl)-3-(thiazol-5-yl)-6,7-dihydro-1H-indazole
6,6-Bis(3-fluorophenyl)-3-(imidazol-2-yl)-6,7-dihydro-1H-indazole
6,6-Bis(3-fluorophenyl)-3-(imidazol-4-yl)-6,7-dihydro-1H-indazole
6,6-Bis(3-fluorophenyl)-3-(imidazol-5-yl)-6,7-dihydro-1H-indazole
6,6-Bis(3-fluorophenyl)-3-(3-methyl[1,2,4]oxadiazol-5-yl)-6,7-dihydro-1H-indazole
6,6-Bis(3-fluorophenyl)-3-(3-methoxy[1,2,5]thiadiazol-4-yl)-6,7-dihydro-1H-indazole
6,6-Bis(3-fluorophenyl)-3-(tetrazol-5-yl)-6,7-dihydro-1H-indazole
6,6-Bis(3-fluorophenyl)-3-(tetrazol-1-yl)-6,7-dihydro-1H-indazole
Methyl 6,6-bis(pyrid-2-yl)-6,7-dihydro-1H-indazole-3-carboxylate
Ethyl 6,6-bis(pyrid-2-yl)-6,7-dihydro-1H-indazole-3-carboxylate
(N-cyclopropyl)-6,6-bis(pyrid-2-yl)-6,7-dihydro-1H-indazole-3-carboxamide
Aziridin-1-yl[6,6-bis(pyrid-2-yl)-6,7-dihydro-1H-indazol-3-yl]methanone
Azetidin-1-yl[6,6-bis(pyrid-2-yl)-6,7-dihydro-1H-indazol-3-yl]methanone
(N-methoxy-N-methyl)-6,6-bis(pyrid-2-yl)-6,7-dihydro-1H-indazole-3-carboxamide
6,6-Bis(pyrid-2-yl)-6,7-dihydro-1H-indazole-3-carbonitrile
Cyclopropyl[6,6-bis(pyrid-2-yl)-6,7-dihydro-1H-indazol-3-yl]methanone
Cyclobutyl[6,6-bis(pyrid-2-yl)-6,7-dihydro-1H-indazol-3-yl]methanone
Cyclopropyl[6,6-bis(pyrid-2-yl)-6,7-dihydro-1H-indazol-3-yl]methanone oxime
Cyclopropyl[6,6-bis(pyrid-2-yl)-6,7-dihydro-1H-indazol-3-yl]methanone O-methyloxime
Cyclobutyl[6,6-bis(pyrid-2-yl)-6,7-dihydro-1H-indazol-3-yl]methanone oxime
Cyclobutyl[6,6-bis(pyrid-2-yl)-6,7-dihydro-1H-indazol-3-yl]methanone O-methyloxime
6,6-Bis(pyrid-2-yl)-1-(4-toluenesulphonyl)-6,7-dihydro-1H-indazol-3-ylamine
(N-Cyclopropyl)-6,6-bis(pyrid-2-yl)-1-(4-toluenesulphonyl)-6,7-dihydro-1H-indazol-3-ylamine
(N-Cyclobutyl)-6,6-bis(pyrid-2-yl)-1-(4-toluenesulphonyl)-6,7-dihydro-1H-indazol-3-ylamine
(N-Phenyl)-6,6-bis(pyrid-2-yl)-1-(4-toluenesulphonyl)-6,7-dihydro-1H-indazol-3-ylamine
1-[3-Amino-6,6-bis(pyrid-2-yl)-6,7-dihydroindazol-1-yl]propenone
1-[3-Cyclopropylamino-6,6-bis(pyrid-2-yl)-6,7-dihydroindazol-1-yl]propenone
1-[3-Cyclobutylamino-6,6-bis(pyrid-2-yl)-6,7-dihydroindazol-1-yl]propenone
1-[3-Anilino-6,6-bis(pyrid-2-yl)-6,7-dihydroindazol-1-yl]propenone
6,6-Bis(pyrid-2-yl)-1-(4-toluenesulphonyl)-6,7-dihydro-1H-indazole-3 carboxylic acid
1-[3-Carboxy-6,6-bis(pyrid-2-yl)-6,7-dihydroindazol-1-yl]propenone
Cyclopropanecarboxylic acid [6,6-bis(pyrid-2-yl)-6,7-dihydro-1H-indazol-3-yl]amide
Cyclobutanecarboxylic acid [6,6-bis(pyrid-2-yl)-6,7-dihydro-1H-indazol-3-yl]amide
6,6-Bis(pyrid-2-yl)-3-phenyl-6,7-dihydro-1H-indazole
3,6,6-Tris(pyrid-2-yl)-6,7-dihydro-1H-indazole
6,6-Bis(pyrid-2-yl)-3-(pyrid-3-yl)-6,7-dihydro-1H-indazole
6,6-Bis(pyrid-2-yl)-3-(pyrid-4-yl)-6,7-dihydro-1H-indazole
6,6-Bis(pyrid-2-yl)-3-(thiophen-2-yl)-6,7-dihydro-1H-indazole
6,6-Bis(pyrid-2-yl)-3-(thiophen-3-yl)-6,7-dihydro-1H-indazole
6,6-Bis(pyrid-2-yl)-3-(oxazol-2-yl)-6,7-dihydro-1H-indazole
6,6-Bis(pyrid-2-yl)-3-(oxazol-4-yl)-6,7-dihydro-1H-indazole
6,6-Bis(pyrid-2-yl)-3-(oxazol-5-yl)-6,7-dihydro-1H-indazole
6,6-Bis(pyrid-2-yl)-3-(thiazol-2-yl)-6,7-dihydro-1H-indazole
6,6-Bis(pyrid-2-yl)-3-(thiazol-4-yl)-6,7-dihydro-1H-indazole
6,6-Bis(pyrid-2-yl)-3-(thiazol-5-yl)-6,7-dihydro-1H-indazole
6,6-Bis(pyrid-2-yl)-3-(imidazol-2-yl)-6,7-dihydro-1H-indazole
6,6-Bis(pyrid-2-yl)-3-(imidazol-4-yl)-6,7-dihydro-1H-indazole
6,6-Bis(pyrid-2-yl)-3-(imidazol-5-yl)-6,7-dihydro-1H-indazole
6,6-Bis(pyrid-2-yl)-3-(3-methyl[1,2,4]oxadiazol-5-yl)-6,7-dihydro-1H-indazole
6,6-Bis(pyrid-2-yl)-3-(3-methoxy[1,2,5]thiadiazol-4-yl)-6,7-dihydro-1H-indazole
6,6-Bis(pyrid-2-yl)-3-(tetrazol-5-yl)-6,7-dihydro-1H-indazole
6,6-Bis(pyrid-2-yl)-3-(tetrazol-1-yl)-6,7-dihydro-1H-indazole
Methyl 6,6-bis(pyrid-3-yl)-6,7-dihydro-1H-indazole-3-carboxylate
Ethyl 6,6-bis(pyrid-3-yl)-6,7-dihydro-1H-indazole-3-carboxylate
(N-Cyclopropyl)-6,6-bis(pyrid-3-yl)-6,7-dihydro-1H-indazole-3-carboxamide
Aziridin-1-yl[6,6-bis(pyrid-3-yl)-6,7-dihydro-1H-indazol-3-yl]methanone
Azetidin-1-yl[6,6-bis(pyrid-3-yl)-6,7-dihydro-1H-indazol-3-yl]methanone
(N-Methoxy-N-methyl)-6,6-bis(pyrid-3-yl)-6,7-dihydro-1H-indazole-3-carboxamide
6,6-Bis(pyrid-3-yl)-6,7-dihydro-1H-indazole-3-carbonitrile
Cyclopropyl[6,6-bis(pyrid-3-yl)-6,7-dihydro-1H-indazol-3-yl]methanone
Cyclobutyl[6,6-bis(pyrid-3-yl)-6,7-dihydro-1H-indazol-3-yl]methanone
Cyclopropyl[6,6-bis(pyrid-3-yl)-6,7-dihydro-1H-indazol-3-yl]methanone oxime
Cyclopropyl[6,6-bis(pyrid-3-yl)-6,7-dihydro-1H-indazol-3-yl]methanone O-methyloxime Cyclobutyl[6,6-bis(pyrid-3-yl)-6,7-dihydro-1H-indazol-3-yl]methanone oxime
Cyclobutyl[6,6-bis(pyrid-3-yl)-6,7-dihydro-1H-indazol-3-yl]methanone O-methyloxime
6,6-Bis(pyrid-3-yl)-1-(4-toluenesulphonyl)-6,7-dihydro-1H-indazol-3-ylamine
(N-Cyclopropyl)-6,6-bis(pyrid-3-yl)-1-(4-toluenesulphonyl)-6,7-dihydro-1H-indazol-3-ylamine
(N-Cyclobutyl)-6,6-bis(pyrid-3-yl)-1-(4-toluenesulphonyl)-6,7-dihydro-1H-indazol-3-ylamine
(N-Phenyl)-6,6-bis(pyrid-3-yl)-1-(4-toluenesulphonyl)-6,7-dihydro-1H-indazol-3-ylamine
1-[3-Amino-6,6-bis(pyrid-3-yl)-6,7-dihydroindazol-1-yl]propenone
1-[3-Cyclopropylamino-6,6-bis(pyrid-3-yl)-6,7-dihydroindazol-1-yl]propenone
1-[3-Cyclobutylamino-6,6-bis(pyrid-3-yl)-6,7-dihydroindazol-1-yl]propenone
1-[3-Anilino-6,6-bis(pyrid-3-yl)-6,7-dihydroindazol-1-yl]propenone
6,6-Bis(pyrid-3-yl)-1-(4-toluenesulphonyl)-6,7-dihydro-1H-indazole-3 carboxylic acid
1-[3-Carboxy-6,6-bis(pyrid-3-yl)-6,7-dihydroindazol-1-yl]propenone
Cyclopropanecarboxylic acid [6,6-bis(pyrid-3-yl)-6,7-dihydro-1H-indazol-3-yl]amide
Cyclobutanecarboxylic acid [6,6-bis(pyrid-3-yl)-6,7-dihydro-1H-indazol-3-yl]amide
6,6-Bis(pyrid-3-yl)-3-phenyl-6,7-dihydro-1H-indazole
3,6,6-Tris(pyrid-3-yl)-6,7-dihydro-1H-indazole
6,6-Bis(pyrid-3-yl)-3-(pyrid-2-yl)-6,7-dihydro-1H-indazole
6,6-Bis(pyrid-3-yl)-3-(pyrid-4-yl)-6,7-dihydro-1H-indazole
6,6-Bis(pyrid-3-yl)-3-(thiophen-2-yl)-6,7-dihydro-1H-indazole
6,6-Bis(pyrid-3-yl)-3-(thiophen-3-yl)-6,7-dihydro-1H-indazole
6,6-Bis(pyrid-3-yl)-3-(oxazol-2-yl)-6,7-dihydro-1H-indazole
6,6-Bis(pyrid-3-yl)-3-(oxazol-4-yl)-6,7-dihydro-1H-indazole
6,6-Bis(pyrid-3-yl)-3-(oxazol-5-yl)-6,7-dihydro-1H-indazole
6,6-Bis(pyrid-3-yl)-3-(thiazol-2-yl)-6,7-dihydro-1H-indazole
6,6-Bis(pyrid-3-yl)-3-(thiazol-4-yl)-6,7-dihydro-1H-indazole
6,6-Bis(pyrid-3-yl)-3-(thiazol-5-yl)-6,7-dihydro-1H-indazole
6,6-Bis(pyrid-3-yl)-3-(imidazol-2-yl)-6,7-dihydro-1H-indazole
6,6-Bis(pyrid-3-yl)-3-(imidazol-4-yl)-6,7-dihydro-1H-indazole
6,6-Bis(pyrid-3-yl)-3-(imidazol-5-yl)-6,7-dihydro-1H-indazole
6,6-Bis(pyrid-3-yl)-3-(3-methyl[1,2,4]oxadiazol-5-yl)-6,7-dihydro-1H-indazole
6,6-Bis(pyrid-3-yl)-3-(3-methoxy[1,2,5]thiadiazol-4-yl)-6,7-dihydro-1H-indazole
6,6-Bis(pyrid-3-yl)-3-(tetrazol-5-yl)-6,7-dihydro-1H-indazole
6,6-Bis(pyrid-3-yl)-3-(tetrazol-1-yl)-6,7-dihydro-1H-indazole
Methyl 6,6-bis(pyrid-4-yl)-6,7-dihydro-1H-indazole-3-carboxylate
Ethyl 6,6-bis(pyrid-4-yl)-6,7-dihydro-1H-indazole-3-carboxylate
(N-Cyclopropyl)-6,6-bis(pyrid-4-yl)-6,7-dihydro-1H-indazole-3-carboxamide
Aziridin-1-yl[6,6-bis(pyrid-4-yl)-6,7-dihydro-1H-indazol-3-yl]methanone
Azetidin-1-yl[6,6-bis(pyrid-4-yl)-6,7-dihydro-1H-indazol-3-yl]methanone
(N-Methoxy-N-methyl)-6,6-bis(pyrid-4-yl)-6,7-dihydro-1H-indazole-3-carboxamide
6,6-Bis(pyrid-4-yl)-6,7-dihydro-1H-indazole-3-carbonitrile
Cyclopropyl[6,6-bis(pyrid-4-yl)-6,7-dihydro-1H-indazol-3-yl]methanone
Cyclobutyl[6,6-bis(pyrid-4-yl)-6,7-dihydro-1H-indazol-3-yl]methanone
Cyclopropyl[6,6-bis(pyrid-4-yl)-6,7-dihydro-1H-indazol-3-yl]methanone oxime
Cyclopropyl[6,6-bis(pyrid-4-yl)-6,7-dihydro-1H-indazol-3-yl]methanone O-methyloxime
Cyclobutyl[6,6-bis(pyrid-4-yl)-6,7-dihydro-1H-indazol-3-yl]methanone oxime
Cyclobutyl[6,6-bis(pyrid-4-yl)-6,7-dihydro-1H-indazol-3-yl]methanone O-methyloxime
6,6-Bis(pyrid-4-yl)-1-(4-toluenesulphonyl)-6,7-dihydro-1H-indazol-3-ylamine
(N-Cyclopropyl)-6,6-bis(pyrid-4-yl)-1-(4-toluenesulphonyl)-6,7-dihydro-1H-indazol-3-ylamine
(N-Cyclobutyl)-6,6-bis(pyrid-4-yl)-1-(4-toluenesulphonyl)-6,7-dihydro-1H-indazol-3-ylamine
(N-Phenyl)-6,6-bis(pyrid-4-yl)-1-(4-toluenesulphonyl)-6,7-dihydro-1H-indazol-3-ylamine
1-[3-Amino-6,6-bis(pyrid-4-yl)-6,7-dihydroindazol-1-yl]propenone
1-[3-Cyclopropylamino-6,6-bis(pyrid-4-yl)-6,7-dihydroindazol-1-yl]propenone
1-[3-Cyclobutylamino-6,6-bis(pyrid-4-yl)-6,7-dihydroindazol-1-yl]propenone
1-[3-Anilino-6,6-bis(pyrid-4-yl)-6,7-dihydroindazol-1-yl]propenone
6,6-Bis(pyrid-4-yl)-1-(4-toluenesulphonyl)-6,7-dihydro-1H-indazole-3 carboxylic acid
1-[3-Carboxy-6,6-bis(pyrid-4-yl)-6,7-dihydroindazol-1-yl]propenone
Cyclopropanecarboxylic acid [6,6-bis(pyrid-4-yl)-6,7-dihydro-1H-indazol-3-yl]amide
Cyclobutanecarboxylic acid [6,6-bis(pyrid-4-yl)-6,7-dihydro-1H-indazol-3-yl]amide
6,6-Bis(pyrid-4-yl)-3-phenyl-6,7-dihydro-1H-indazole
3,6,6-Tris(pyrid-4-yl)-6,7-dihydro-1H-indazole
6,6-Bis(pyrid-4-yl)-3-(pyrid-2-yl)-6,7-dihydro-1H-indazole
6,6-Bis(pyrid-4-yl)-3-(pyrid-3-yl)-6,7-dihydro-1H-indazole
6,6-Bis(pyrid-4-yl)-3-(thiophen-2-yl)-6,7-dihydro-1H-indazole
6,6-Bis(pyrid-4-yl)-3-(thiophen-3-yl)-6,7-dihydro-1H-indazole
6,6-Bis(pyrid-4-yl)-3-(oxazol-2-yl)-6,7-dihydro-1H-indazole
6,6-Bis(pyrid-4-yl)-3-(oxazol-4-yl)-6,7-dihydro-1H-indazole
6,6-Bis(pyrid-4-yl)-3-(oxazol-5-yl)-6,7-dihydro-1H-indazole
6,6-Bis(pyrid-4-yl)-3-(thiazol-2-yl)-6,7-dihydro-1H-indazole
6,6-Bis(pyrid-4-yl)-3-(thiazol-4-yl)-6,7-dihydro-1H-indazole
6,6-Bis(pyrid-4-yl)-3-(thiazol-5-yl)-6,7-dihydro-1H-indazole
6,6-Bis(pyrid-4-yl)-3-(imidazol-2-yl)-6,7-dihydro-1H-indazole 6,6-Bis(pyrid-4-yl)-3-(imidazol-4-yl)-6,7-dihydro-1H-indazole
6,6-Bis(pyrid-4-yl)-3-(imidazol-5-yl)-6,7-dihydro-1H-indazole
6,6-Bis(pyrid-4-yl)-3-(3-methyl[1,2,4]oxadiazol-5-yl)-6,7-dihydro-1H-indazole
6,6-Bis(pyrid-4-yl)-3-(3-methoxy[1,2,5]thiadiazol-4-yl)-6,7-dihydro-1H-indazole
6,6-Bis(pyrid-4-yl)-3-(tetrazol-5-yl)-6,7-dihydro-1H-indazole
6,6-Bis(pyrid-4-yl)-3-(tetrazol-1-yl)-6,7-dihydro-1H-indazole
Methyl 6,6-bis(pyrimid-4-yl)-6,7-dihydro-1H-indazole-3-carboxylate
Ethyl 6,6-bis(pyrimid-4-yl)-6,7-dihydro-1H-indazole-3-carboxylate
(N-Cyclopropyl)-6,6-bis(pyrimid-4-yl)-6,7-dihydro-1H-indazole-3-carboxamide
Aziridin-1-yl[6,6-bis(pyrimid-4-yl)-6,7-dihydro-1H-indazol-3-yl]methanone
Azetidin-1-yl[6,6-bis(pyrimid-4-yl)-6,7-dihydro-1H-indazol-3-yl]methanone
(N-Methoxy-N-methyl)-6,6-bis(pyrimid-4-yl)-6,7-dihydro-1H-indazole-3-carboxamide
6,6-Bis(pyrimid-4-yl)-6,7-dihydro-1H-indazole-3-carbonitrile
Cyclopropyl[6,6-bis(pyrimid-4-yl)-6,7-dihydro-1H-indazol-3-yl]methanone
Cyclobutyl[6,6-bis(pyrimid-4-yl)-6,7-dihydro-1H-indazol-3-yl]methanone
Cyclopropyl[6,6-bis(pyrimid-4-yl)-6,7-dihydro-1H-indazol-3-yl]methanone oxime
Cyclopropyl[6,6-bis(pyrimid-4-yl)-6,7-dihydro-1H-indazol-3-yl]methanone O-methyloxime
Cyclobutyl[6,6-bis(pyrimid-4-yl)-6,7-dihydro-1H-indazol-3-yl]methanone oxime
Cyclobutyl[6,6-bis(pyrimid-4-yl)-6,7-dihydro-1H-indazol-3-yl]methanone O-methyloxime
6,6-Bis(pyrimid-4-yl)-1-(4-toluenesulphonyl)-6,7-dihydro-1H-indazol-3-ylamine
(N-Cyclopropyl)-6,6-bis(pyrimid-4-yl)-1-(4-toluenesulphonyl)-6,7-dihydro-1H-indazol-3-ylamine
(N-Cyclobutyl)-6,6-bis(pyrimid-4-yl)-1-(4-toluenesulphonyl)-6,7-dihydro-1H-indazol-3-ylamine
(N-Phenyl)-6,6-bis(pyrimid-4-yl)-1-(4-toluenesulphonyl)-6,7-dihydro-1H-indazol-3-ylamine
1-[3-Amino-6,6-bis(pyrimid-4-yl)-6,7-dihydroindazol-1-yl]propenone
1-[3-Cyclopropylamino-6,6-bis(pyrimid-4-yl)-6,7-dihydroindazol-1-yl]propenone
1-[3-Cyclobutylamino-6,6-bis(pyrimid-4-yl)-6,7-dihydroindazol-1-yl]propenone
1-[3-Anilino-6,6-bis(pyrimid-4-yl)-6,7-dihydroindazol-1-yl]propenone
6,6-Bis(pyrimid-4-yl)-1-(4-toluenesulphonyl)-6,7-dihydro-1H-indazole-3 carboxylic acid
1-[3-Carboxy-6,6-bis(pyrimid-4-yl)-6,7-dihydroindazol-1-yl]propenone
Cyclopropanecarboxylic acid [6,6-bis(pyrimid-4-yl)-6,7-dihydro-1H-indazol-3-yl]amide
Cyclobutanecarboxylic acid [6,6-bis(pyrimid-4-yl)-6,7-dihydro-1H-indazol-3-yl]amide
6,6-Bis(pyrimid-4-yl)-3-phenyl-6,7-dihydro-1H-indazole
6,6-Bis(pyrimid-4-yl)-3-(pyrid-2-yl)-6,7-dihydro-1H-indazole
6,6-Bis(pyrimid-4-yl)-3-(pyrid-3-yl)-6,7-dihydro-1H-indazole
6,6-Bis(pyrimid-4-yl)-3-(pyrid-4-yl)-6,7-dihydro-1H-indazole
6,6-Bis(pyrimid-4-yl)-3-(thiophen-2-yl)-6,7-dihydro-1H-indazole
6,6-Bis(pyrimid-4-yl)-3-(thiophen-3-yl)-6,7-dihydro-1H-indazole
6,6-Bis(pyrimid-4-yl)-3-(oxazol-2-yl)-6,7-dihydro-1H-indazole
6,6-Bis(pyrimid-4-yl)-3-(oxazol-4-yl)-6,7-dihydro-1H-indazole
6,6-Bis(pyrimid-4-yl)-3-(oxazol-5-yl)-6,7-dihydro-1H-indazole
6,6-Bis(pyrimid-4-yl)-3-(thiazol-2-yl)-6,7-dihydro-1H-indazole
6,6-Bis(pyrimid-4-yl)-3-(thiazol-4-yl)-6,7-dihydro-1H-indazole
6,6-Bis(pyrimid-4-yl)-3-(thiazol-5-yl)-6,7-dihydro-1H-indazole
6,6-Bis(pyrimid-4-yl)-3-(imidazol-2-yl)-6,7-dihydro-1H-indazole
6,6-Bis(pyrimid-4-yl)-3-(imidazol-4-yl)-6,7-dihydro-1H-indazole
6,6-Bis(pyrimid-4-yl)-3-(imidazol-5-yl)-6,7-dihydro-1H-indazole
6,6-Bis(pyrimid-4-yl)-3-(3-methyl[1,2,4]oxadiazol-5-yl)-6,7-dihydro-1H-indazole
6,6-Bis(pyrimid-4-yl)-3-(3-methoxy[1,2,5]thiadiazol-4-yl)-6,7-dihydro-1H-indazole
6,6-Bis(pyrimid-4-yl)-3-(tetrazol-5-yl)-6,7-dihydro-1H-indazole
6,6-Bis(pyrimid-4-yl)-3-(tetrazol-1-yl)-6,7-dihydro-1H-indazole
Methyl 6,6-bis(thiophen-2-yl)-6,7-dihydro-1H-indazole-3-carboxylate
Ethyl 6,6-bis(thiophen-2-yl)-6,7-dihydro-1H-indazole-3-carboxylate
(N-Cyclopropyl)-6,6-bis(thiophen-2-yl)-6,7-dihydro-1H-indazole-3-carboxamide
Aziridin-1-yl[6,6-bis(thiophen-2-yl)-6,7-dihydro-1H-indazol-3-yl]methanone
Azetidin-1-yl[6,6-bis(thiophen-2-yl)-6,7-dihydro-1H-indazol-3-yl]methanone
(N-Methoxy-N-methyl)-6,6-bis(thiophen-2-yl)-6,7-dihydro-1H-indazole-3-carboxamide
6,6-Bis(thiophen-2-yl)-6,7-dihydro-1H-indazole-3-carbonitrile
Cyclopropyl[6,6-bis(thiophen-2-yl)-6,7-dihydro-1H-indazol-3-yl]methanone
Cyclobutyl[6,6-bis(thiophen-2-yl)-6,7-dihydro-1H-indazol-3-yl]methanone
Cyclopropyl[6,6-bis(thiophen-2-yl)-6,7-dihydro-1H-indazol-3-yl]methanone oxime
Cyclopropyl[6,6-bis(thiophen-2-yl)-6,7-dihydro-1H-indazol-3-yl]methanone O-methyloxime
Cyclobutyl[6,6-bis(thiophen-2-yl)-6,7-dihydro-1H-indazol-3-yl]methanone oxime
Cyclobutyl[6,6-bis(thiophen-2-yl)-6,7-dihydro-1H-indazol-3-yl]methanone O-methyloxime
6,6-Bis(thiophen-2-yl)-1-(4-toluenesulphonyl)-6,7-dihydro-1H-indazol-3-ylamine
(N-Cyclopropyl)-6,6-bis(thiophen-2-yl)-1-(4-toluenesulphonyl)-6,7-dihydro-1H-indazol-3-ylamine
(N-Cyclobutyl)-6,6-bis(thiophen-2-yl)-1-(4-toluenesulphonyl)-6,7-dihydro-1H-indazol-3-ylamine
(N-Phenyl)-6,6-bis(thiophen-2-yl)-1-(4-toluenesulphonyl)-6,7-dihydro-1H-indazol-3-ylamine 1-[3-Amino-6,6-bis(thiophen-2-yl)-6,7-dihydroindazol-1-yl]propenone
1-[3-Cyclopropylamino-6,6-bis(thiophen-2-yl)-6,7-dihydroindazol-1-yl]propenone
1-[3-Cyclobutylamino-6,6-bis(thiophen-2-yl)-6,7-dihydroindazol-1-yl]propenone
1-[3-Anilino-6,6-bis(thiophen-2-yl)-6,7-dihydroindazol-1-yl]propenone
6,6-Bis(thiophen-2-yl)-1-(4-toluenesulphonyl)-6,7-dihydro-1H-indazole-3 carboxylic acid
1-[3-Carboxy-6,6-bis(thiophen-2-yl)-6,7-dihydroindazol-1-yl]propenone
Cyclopropanecarboxylic acid [6,6-bis(thiophen-2-yl)-6,7-dihydro-1H-indazol-3-yl]amide
Cyclobutanecarboxylic acid [6,6-bis(thiophen-2-yl)-6,7-dihydro-1H-indazol-3-yl]amide
6,6-Bis(thiophen-2-yl)-3-phenyl-6,7-dihydro-1H-indazole
6,6-Bis(thiophen-2-yl)-3-(pyrid-2-yl)-6,7-dihydro-1H-indazole
6,6-Bis(thiophen-2-yl)-3-(pyrid-3-yl)-6,7-dihydro-1H-indazole
6,6-Bis(thiophen-2-yl)-3-(pyrid-4-yl)-6,7-dihydro-1H-indazole
3,6,6-Tris(thiophen-2-yl)-6,7-dihydro-1H-indazole
6,6-Bis(thiophen-2-yl)-3-(thiophen-3-yl)-6,7-dihydro-1H-indazole
6,6-Bis(thiophen-2-yl)-3-(oxazol-2-yl)-6,7-dihydro-1H-indazole
6,6-Bis(thiophen-2-yl)-3-(oxazol-4-yl)-6,7-dihydro-1H-indazole
6,6-Bis(thiophen-2-yl)-3-(oxazol-5-yl)-6,7-dihydro-1H-indazole
6,6-Bis(thiophen-2-yl)-3-(thiazol-2-yl)-6,7-dihydro-1H-indazole
6,6-Bis(thiophen-2-yl)-3-(thiazol-4-yl)-6,7-dihydro-1H-indazole
6,6-Bis(thiophen-2-yl)-3-(thiazol-5-yl)-6,7-dihydro-1H-indazole
6,6-Bis(thiophen-2-yl)-3-(imidazol-2-yl)-6,7-dihydro-1H-indazole
6,6-Bis(thiophen-2-yl)-3-(imidazol-4-yl)-6,7-dihydro-1H-indazole
6,6-Bis(thiophen-2-yl)-3-(imidazol-5-yl)-6,7-dihydro-1H-indazole
6,6-Bis(thiophen-2-yl)-3-(3-methyl[1,2,4]oxadiazol-5-yl)-6,7-dihydro-1H-indazole
6,6-Bis(thiophen-2-yl)-3-(3-methoxy[1,2,5]thiadiazol-4-yl)-6,7-dihydro-1H-indazole
6,6-Bis(thiophen-2-yl)-3-(tetrazol-5-yl)-6,7-dihydro-1H-indazole
6,6-Bis(thiophen-2-yl)-3-(tetrazol-1-yl)-6,7-dihydro-1H-indazole
Methyl 6,6-bis(thiophen-3-yl)-6,7-dihydro-1H-indazole-3-carboxylate
Ethyl 6,6-bis(thiophen-3-yl)-6,7-dihydro-1H-indazole-3-carboxylate
(N-Cyclopropyl)-6,6-bis(thiophen-3-yl)-6,7-dihydro-1H-indazole-3-carboxamide
Aziridin-1-yl[6,6-bis(thiophen-3-yl)-6,7-dihydro-1H-indazol-3-yl]methanone
Azetidin-1-yl[6,6-bis(thiophen-3-yl)-6,7-dihydro-1H-indazol-3-yl]methanone
(N-Methoxy-N-methyl)-6,6-bis(thiophen-3-yl)-6,7-dihydro-1H-indazole-3-carboxamide
6,6-Bis(thiophen-3-yl)-6,7-dihydro-1H-indazole-3-carbonitrile
Cyclopropyl[6,6-bis(thiophen-3-yl)-6,7-dihydro-1H-indazol-3-yl]methanone
Cyclobutyl[6,6-bis(thiophen-3-yl)-6,7-dihydro-1H-indazol-3-yl]methanone
Cyclopropyl[6,6-bis(thiophen-3-yl)-6,7-dihydro-1H-indazol-3-yl]methanone oxime
Cyclopropyl[6,6-bis(thiophen-3-yl)-6,7-dihydro-1H-indazol-3-yl]methanone O-methyloxime
Cyclobutyl[6,6-bis(thiophen-3-yl)-6,7-dihydro-1H-indazol-3-yl]methanone oxime
Cyclobutyl[6,6-bis(thiophen-3-yl)-6,7-dihydro-1H-indazol-3-yl]methanone O-methyloxime
6,6-Bis(thiophen-3-yl)-1-(4-toluenesulphonyl)-6,7-dihydro-1H-indazol-3-ylamine
(N-Cyclopropyl)-6,6-bis(thiophen-3-yl)-1-(4-toluenesulphonyl)-6,7-dihydro-1H-indazol-3-ylamine
(N-Cyclobutyl)-6,6-bis(thiophen-3-yl)-1-(4-toluenesulphonyl)-6,7-dihydro-1H-indazol-3-ylamine
(N-Phenyl)-6,6-bis(thiophen-3-yl)-1-(4-toluenesulphonyl)-6,7-dihydro-1H-indazol-3-ylamine
1-[3-Amino-6,6-bis(thiophen-3-yl)-6,7-dihydroindazol-1-yl]propenone
1-[3-Cyclopropylamino-6,6-bis(thiophen-3-yl)-6,7-dihydroindazol-1-yl]propenone
1-[3-Cyclobutylamino-6,6-bis(thiophen-3-yl)-6,7-dihydroindazol-1-yl]propenone
1-[3-Anilino-6,6-bis(thiophen-3-yl)-6,7-dihydroindazol-1-yl]propenone
6,6-Bis(thiophen-3-yl)-1-(4-toluenesulphonyl)-6,7-dihydro-1H-indazole-3 carboxylic acid
1-[3-Carboxy-6,6-bis(thiophen-3-yl)-6,7-dihydroindazol-1-yl]propenone
Cyclopropanecarboxylic acid [6,6-bis(thiophen-3-yl)-6,7-dihydro-1H-indazol-3-yl]amide
Cyclobutanecarboxylic acid [6,6-bis(thiophen-3-yl)-6,7-dihydro-1H-indazol-3-yl]amide
6,6-Bis(thiophen-3-yl)-3-phenyl-6,7-dihydro-1H-indazole
6,6-Bis(thiophen-3-yl)-3-(pyrid-2-yl)-6,7-dihydro-1H-indazole
6,6-Bis(thiophen-3-yl)-3-(pyrid-3-yl)-6,7-dihydro-1H-indazole
6,6-Bis(thiophen-3-yl)-3-(pyrid-4-yl)-6,7-dihydro-1H-indazole
3,6,6-Tris(thiophen-3-yl)-6,7-dihydro-1H-indazole
6,6-Bis(thiophen-3-yl)-3-(thiophen-2-yl)-6,7-dihydro-1H-indazole
6,6-Bis(thiophen-3-yl)-3-(oxazol-2-yl)-6,7-dihydro-1H-indazole
6,6-Bis(thiophen-3-yl)-3-(oxazol-4-yl)-6,7-dihydro-1H-indazole
6,6-Bis(thiophen-3-yl)-3-(oxazol-5-yl)-6,7-dihydro-1H-indazole
6,6-Bis(thiophen-3-yl)-3-(thiazol-2-yl)-6,7-dihydro-1H-indazole
6,6-Bis(thiophen-3-yl)-3-(thiazol-4-yl)-6,7-dihydro-1H-indazole
6,6-Bis(thiophen-3-yl)-3-(thiazol-5-yl)-6,7-dihydro-1H-indazole
6,6-Bis(thiophen-3-yl)-3-(imidazol-2-yl)-6,7-dihydro-1H-indazole
6,6-Bis(thiophen-3-yl)-3-(imidazol-4-yl)-6,7-dihydro-1H-indazole
6,6-Bis(thiophen-3-yl)-3-(imidazol-5-yl)-6,7-dihydro-1H-indazole
6,6-Bis(thiophen-3-yl)-3-(3-methyl[1,2,4]oxadiazol-5-yl)-6,7-dihydro-1H-indazole 6,6-Bis(thiophen-3-yl)-3-(3-methoxy[1,2,5]thiadiazol-4-yl)-6,7-dihydro-1H-indazole
6,6-Bis(thiophen-3-yl)-3-(tetrazol-5-yl)-6,7-dihydro-1H-indazole
6,6-Bis(thiophen-3-yl)-3-(tetrazol-1-yl)-6,7-dihydro-1H-indazole
Methyl 5,5-diphenyl-4,5-dihydro-2H-isoindole-1-carboxylate
(N-Cyclopropyl)-5,5-diphenyl-4,5-dihydro-2H-isoindole-1-carboxamide
Aziridin-1-yl(5,5-diphenyl-4,5-dihydro-2H-isoindol-1-yl)methanone
Azetidin-1-yl(5,5-diphenyl-4,5-dihydro-2H-isoindol-1-yl)methanone
(N-Methoxy-N-methyl)-5,5-diphenyl-4,5-dihydro-2H-isoindole-1-carboxamide
Cyclopropyl(5,5-diphenyl-4,5-dihydro-2H-isoindol-1-yl)methanone
Cyclobutyl(5,5-diphenyl-4,5-dihydro-2H-isoindol-1-yl)methanone
Cyclopropyl(5,5-diphenyl-4,5-dihydro-2H-isoindol-1-yl)methanone oxime
Cyclopropyl(5,5-diphenyl-4,5-dihydro-2H-isoindol-1-yl)methanone O-methyloxime
Cyclobutyl(5,5-diphenyl-4,5-dihydro-2H-isoindol-1-yl)methanone oxime
Cyclobutyl(5,5-diphenyl-4,5-dihydro-2H-isoindol-1-yl)methanone O-methyloxime
Cyclopropanecarboxylic acid (5,5-diphenyl-4,5-dihydro-2H-isoindol-1-yl)amide
Cyclobutanecarboxylic acid (5,5-diphenyl-4,5-dihydro-2H-isoindol-1-yl)amide
1,5,5-Triphenyl-4,5-dihydro-2H-isoindole
5,5-Diphenyl-1-(pyrid-2-yl)-4,5-dihydro-2H-isoindole
5,5-Diphenyl-1-(pyrid-3-yl)-4,5-dihydro-2H-isoindole
5,5-Diphenyl-1-(pyrid-4-yl)-4,5-dihydro-2H-isoindole
5,5-Diphenyl-1-(thiophen-2-yl)-4,5-dihydro-2H-isoindole
5,5-Diphenyl-1-(thiophen-3-yl)-4,5-dihydro-2H-isoindole
1-(Oxazol-2-yl)-5,5-diphenyl-4,5-dihydro-2H-isoindole
1-(Oxazol-4-yl)-5,5-diphenyl-4,5-dihydro-2H-isoindole
1-(Oxazol-5-yl)-5,5-diphenyl-4,5-dihydro-2H-isoindole
5,5-Diphenyl-1-(thiazol-2-yl)-4,5-dihydro-2H-isoindole
5,5-Diphenyl-1-(thiazol-4-yl)-4,5-dihydro-2H-isoindole
5,5-Diphenyl-1-(thiazol-5-yl)-4,5-dihydro-2H-isoindole
1-(Imidazol-2-yl)-5,5-diphenyl-4,5-dihydro-2H-isoindole
1-(Imidazol-4-yl)-5,5-diphenyl-4,5-dihydro-2H-isoindole
1-(Imidazol-5-yl)-5,5-diphenyl-4,5-dihydro-2H-isoindole
1-(3-Methyl[1,2,4]oxadiazol-5-yl)-5,5-diphenyl-4,5-dihydro-2H-isoindole
1-(3-Methoxy[1,2,5]thiadiazol-4-yl)-5,5-diphenyl-4,5-dihydro-2H-isoindole
5,5-Diphenyl-1-(tetrazol-5-yl)-4,5-dihydro-2H-isoindole
5,5-Diphenyl-1-(tetrazol-1-yl)-4,5-dihydro-2H-isoindole
Methyl 6,6-diphenyl-6,7-dihydro-1H-isoindole-3-carboxylate
(N-Cyclopropyl)-6,6-diphenyl-6,7-dihydro-1H-isoindole-3-carboxamide
Aziridin-1-yl(6,6-diphenyl-6,7-dihydro-1H-isoindol-3-yl)methanone
Azetidin-1-yl(6,6-diphenyl-6,7-dihydro-1H-isoindol-3-yl)methanone
(N-Methoxy-N-methyl)-6,6-diphenyl-6,7-dihydro-1H-isoindole-3-carboxamide
6,6-Diphenyl-6,7-dihydro-1H-isoindole-3-carbonitrile
Cyclopropyl(6,6-diphenyl-6,7-dihydro-1H-isoindol-3-yl)methanone
Cyclobutyl(6,6-diphenyl-6,7-dihydro-1H-isoindol-3-yl)methanone
Cyclopropyl(6,6-diphenyl-6,7-dihydro-1H-isoindol-3-yl)methanone oxime
Cyclopropyl(6,6-diphenyl-6,7-dihydro-1H-isoindol-3-yl)methanone O-methyloxime
Cyclobutyl(6,6-diphenyl-6,7-dihydro-1H-isoindol-3-yl)methanone oxime
Cyclobutyl(6,6-diphenyl-6,7-dihydro-1H-isoindol-3-yl)methanone O-methyloxime
Cyclopropanecarboxylic acid (6,6-diphenyl-6,7-dihydro-1H-isoindol-3-yl)amide
Cyclobutanecarboxylic acid (6,6-diphenyl-6,7-dihydro-1H-isoindol-3-yl)amide
3,6,6-Triphenyl-6,7-dihydro-1H-isoindole
6,6-Diphenyl-3-(pyrid-2-yl)-6,7-dihydro-1H-isoindole
6,6-Diphenyl-3-(pyrid-3-yl)-6,7-dihydro-1H-isoindole
6,6-Diphenyl-3-(pyrid-4-yl)-6,7-dihydro-1H-isoindole
6,6-Diphenyl-3-(thiophen-2-yl)-6,7-dihydro-1H-isoindole
6,6-Diphenyl-3-(thiophen-3-yl)-6,7-dihydro-1H-isoindole
3-(Oxazol-2-yl)-6,6-diphenyl-6,7-dihydro-1H-isoindole
3-(Oxazol-4-yl)-6,6-diphenyl-6,7-dihydro-1H-isoindole
3-(Oxazol-5-yl)-6,6-diphenyl-6,7-dihydro-1H-isoindole
6,6-Diphenyl-3-(thiazol-2-yl)-6,7-dihydro-1H-isoindole
6,6-Diphenyl-3-(thiazol-4-yl)-6,7-dihydro-1H-isoindole
6,6-Diphenyl-3-(thiazol-5-yl)-6,7-dihydro-1H-isoindole
3-(Imidazol-2-yl)-6,6-diphenyl-6,7-dihydro-1H-isoindole
3-(Imidazol-4-yl)-6,6-diphenyl-6,7-dihydro-1H-isoindole
3-(Imidazol-5-yl)-6,6-diphenyl-6,7-dihydro-1H-isoindole
3-(3-Methyl[1,2,4]oxadiazol-5-yl)-6,6-diphenyl-6,7-dihydro-1H-isoindole
3-(3-Methoxy[1,2,5]thiadiazol-4-yl)-6,6-diphenyl-6,7-dihydro-1H-isoindole
6,6-Diphenyl-3-(tetrazol-5-yl)-6,7-dihydro-1H-isoindole
6,6-Diphenyl-3-(tetrazol-1-yl)-6,7-dihydro-1H-isoindole

What is claimed is:

1. A compound of formula (1) or formula (2)

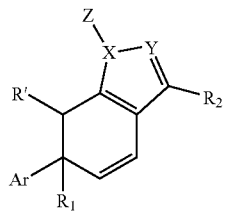

(1)

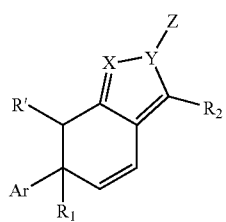

(2)

wherein:
X and Y are N;
Ar is:
phenyl optionally substituted with one or more substituents selected from the group consisting of: halogen, $(C_1-C_4)$alkyl, $(C_1-C_4)$alkoxy, thio$(C_1-C_4)$alkyl, $NO_2$, $NH(C_1-C_4)$alkyl and $N((C_1-C_4)$alkyl$)_2$ wherein said alkyl may optionally form a 4 to 6 membered ring together with the heteroatom to which it is attached and an ortho carbon of the phenyl wherein said 4 to 6 membered ring may contain a second hetero atom selected from the group consisting of O, S and N, Z is H, 4-aminophenyl, $SO_2R_3$ or $COR_3$ wherein $R_3$ is $(C_1–C_4)$alkyl, $(C_3–C_6)$cycloalkyl, Ar as defined above, $(C_2–C_6)$alkenyl or $(C_2–C_6)$alkynyl;

$R_1$ is H, $(C_1–C_4)$alkyl, $(C_3–C_6)$cycloalkyl or Ar as defined above;

R' is H or $(C_1–C_4)$alkyl; and when Z is H, $R_2$ is selected from the group consisting of:
cyano,
C(O)—$ORa_1$ wherein $Ra_1$ is methyl, ethyl or isopropyl,
C(O)—$NHRa_2$ wherein $Ra_2$ is cyclopropyl,
C(O)—$N(Ra_2')$, wherein $N(Ra_2')$ is aziridinyl or azetidinyl, optionally substituted with $(C_1–C_4)$alkyl or Ar as defined above,
C(O)—$N(Ra_3)$—$ORa_3$ wherein each $Ra_3$ may be identical or different and each $Ra_3$ is independently selected from the group consisting of methyl, ethyl or cyclopropyl,
C(O)$Ra_4$ wherein $Ra_4$ is Ar as defined above or $(C_3–C_5)$cycloalkyl optionally substituted with $(C_1–C_4)$alkyl or Ar as defined above,
C($Ra_4$)=N—Rb wherein:
  $Ra_4$ is H, Ar as defined above, or $(C_3–C_5)$cycloalkyl optionally substituted with $(C_1–C_4)$alkyl or Ar as defined above, and Rb is $(C_1–C_2)$alkyl, $(C_3–C_5)$cycloalkyl, hydroxyl, $(C_1–C_4)$alkoxy, $(C_2–C_4)$alkenyloxy, or $(C_1–C_4)$alkylenoxy wherein said $(C_1–C_4)$alkylenoxy optionally may be substituted with halogen or a group selected from the group consisting of carboxyl, $(CH_2)_n$Ar wherein n is 0 or 1 and Ar is as defined above, $(C_1–C_4)$alkoxy, $NH_2$, $NH(C_1–C_4)$alkyl, and $N((C_1–C_4)alkyl)_2$ wherein said alkyls together with the heteroatom to which they are attached may optionally form a 3 to 6 membered ring which may optionally contain a second hetero atom selected from the group consisting of O, S and N,
NH—C(O)$Ra_4$ wherein $Ra_4$ is H, Ar as defined above, or $(C_3–C_5)$cycloalkyl optionally substituted with $(C_1–C_4)$alkyl or Ar as defined above,
$NHRa_4$ wherein $Ra_4$ is H, Ar as defined above, or $(C_3–C_5)$cycloalkyl optionally substituted with $(C_1–C_4)$alkyl or Ar as defined above,
phenyl, and
5 to 6 membered aromatic heterocycle containing 1 to 3 hetero atoms selected from the group consisting of O, N and S; and when Z is $SO_2R_3$ or $COR_3$, $R_2$ is carboxyl, $NH_2$, $NR(C_1–C_4)$alkyl, $N((C_1–C_4)alkyl)_2$ or $(C_3–C_5)$cycloalkylamino; or a stereoisomeric form of the compound of formula (1) or formula (2), or mixtures of the stereoisomeric forms thereof in any ratio; or a pharmaceutically acceptable salt of the compound of formula (1) or formula (2).

2. The compound according to claim 1 wherein Ar is phenyl, 4-fluorophenyl or 4-methoxyphenyl.

3. The compound according to claim 2 wherein $R_1$ is H, $(C_1–C_4)$alkyl, phenyl or substituted phenyl.

4. The compound according to claim 3 wherein $R_2$ is C(O)—$ORa_1$ and wherein $Ra_1$ is methyl, ethyl or isopropyl.

5. The compound according to claim 4 selected from group consisting of:

ethyl 6,6-diphenyl-6,7-dihydro-2H-indazole-3-carboxylate,
isopropyl 6,6-diphenyl-6,7-dihydro-2H-indazole-3-carboxylate,
methyl 6,6-diphenyl-6,7-dihydro-2H-indazole-3-carboxylate,
ethyl 6-(R,S)-6-methyl-6-phenyl-6,7-dihydro-1H-indazole-3-carboxylate,
ethyl 6-(+)-6-methyl-6-phenyl-6,7-dihydro-1H-indazole-3-carboxylate,
ethyl 6-(R,S)-6-phenyl-6,7-dihydro-2H-indazole-3-carboxylate,
ethyl 6-(R)-6-phenyl-6,7-dihydro-2H-indazole-3-carboxylate,
ethyl 6-(S)-6-phenyl-6,7-dihydro-2H-indazole-3-carboxylate,
ethyl 6,6-bis(4-methoxyphenyl)-6,7-dihydro-1H-indazole-3-carboxylate,
ethyl 6-(R,S)-6-(3,4-dimethoxyphenyl)-6-phenyl-6,7-dihydro-1H-indazole-3-carboxylate,
ethyl 6-(R,S)-6-(4-fluorophenyl)-6-phenyl-6,7-dihydro-1H-indazole-3-carboxylate,
ethyl (−)-6-(4-fluorophenyl)-6-phenyl-6,7-dihydro-1H-indazole-3-carboxylate,
ethyl (+)-6-(4-fluorophenyl)-6-phenyl-6,7-dihydro-1H-indazole-3-carboxylate,
ethyl 6,6-bis(4-fluorophenyl)-6,7-dihydro-1H-indazole-3-carboxylate, and
ethyl 7-methyl-6,6-diphenyl-6,7-dihydro-1H-indazole-3-carboxylate.

6. The compound according to claim 3 wherein $R_2$ is $CORa_4$ and $Ra_4$ is Ar or $(C_3–C_5)$cycloalkyl.

7. The compound according to claim 6 selected from the group consisting of:
cyclopropyl(6,6-diphenyl-6,7-dihydro-1H-indazol-3-yl)methanone,
cyclobutyl(6,6-diphenyl-6,7-dihydro-1H-indazol-3-yl)methanone,
(6,6-diphenyl-6,7-dihydro-1H-indazol-3-yl)phenylmethanone,
(6,6-diphenyl-6,7-dihydro-1H-indazol-3-yl)-(1H-pyrrol-3-yl)methanone,
6-(R,S)-cyclopropyl[6-(4-fluorophenyl)-6-phenyl-6,7-dihydro-1H-indazol-3-yl]methanone,
(−)-cyclopropyl[6-(4-fluorophenyl)-6-phenyl-6,7-dihydro-1H-indazol-3-yl]methanone,
(+)-cyclopropyl[6-(4-fluorophenyl)-6-phenyl-6,7-dihydro-1H-indazol-3-yl]methanone, and cyclopropyl[6,6-bis(4-fluorophenyl)-6,7-dihydro-1H-indazol-3-yl]methanone.

8. The compound according to claim 3 wherein $R_2$ is C(O)—$NHRa_2$, C(O)—$N(Ra_3)$—$ORa_3$ or C(O)—$N(Ra_2')$.

9. The compound according to claim 8 selected from the group consisting of:
N-(cyclopropyl)-6,6-diphenyl-6,7-dihydro-1H-indazole-3-carboxamide,
azetidin-1-yl(6,6-diphenyl-6,7-dihydro-1H-indazol-3-yl)methanone,
(N-methoxy-N-methyl)-6,6-diphenyl-6,7-dihydro-1H-indazole-3-carboxamide, and
aziridin-1-yl(6,6-diphenyl-6,7-dihydro-1H-indazol-3-yl)methanone.

10. The compound according to claim 3 wherein $R_2$ is C($Ra_4$)=N—Rb.

11. The compound according to claim 10 selected from the group consisting of:

(E,Z)cyclopropyl(6,6-diphenyl-6,7-dihydro-1H-indazol-3-yl)methanone oxime,
(E)cyclopropyl(6,6-diphenyl-6,7-dihydro-1H-indazol-3-yl)methanone oxime,
(Z)cyclopropyl(6,6-diphenyl-6,7-dihydro-1H-indazol-3-yl)methanone oxime,
(E,Z)cyclobutyl(6,6-diphenyl-6,7-dihydro-1H-indazol-3-yl)methanone oxime,
(E)cyclobutyl(6,6-diphenyl-6,7-dihydro-1H-indazol-3-yl)methanone oxime,
(Z)cyclobutyl(6,6-diphenyl-6,7-dihydro-1H-indazol-3-yl)methanone oxime,
(E,Z)cyclopropyl(6,6-diphenyl-6,7-dihydro-2H-indazol-3-yl)methanone O-methyloxime,
(E)cyclopropyl(6,6-diphenyl-6,7-dihydro-2H-indazol-3-yl)methanone O-methyloxime,
(Z)cyclopropyl(6,6-diphenyl-6,7-dihydro-2H-indazol-3-yl)methanone O-methyloxime,
(E,Z)6,6-diphenyl-6,6-dihydro-1H-indazole-3-carbaldehyde O-methyloxime,
(E,Z)cyclobutyl(6,6-diphenyl-6,7-dihydro-1H-indazol-3-yl)methanone O-allyloxime,
(E)cyclobutyl(6,6-diphenyl-6,7-dihydro-1H-indazol-3-yl)methanone O-allyloxime,
(Z)cyclobutyl(6,6-diphenyl-6,7-dihydro-1H-indazol-3-yl)methanone O-allyloxime,
(E,Z)cyclopropyl(6,6-diphenyl-6,7-dihydro-1H-indazol-3-yl)methanone O-allyloxime,
(Z)cyclopropyl(6,6-diphenyl-6,7-dihydro-1H-indazol-3-yl)methanone O-allyloxime,
(E)cyclopropyl(6,6-diphenyl-6,7-dihydro-1H-indazol-3-yl)methanone O-allyloxime,
(E,Z)cyclopropyl(6,6-diphenyl-6,7-dihydro-1H-indazol-3-yl)methanone O-(2-methoxyethyl)oxime,
(Z)cyclopropyl(6,6-diphenyl-6,7-dihydro-1H-indazol-3-yl)methanone O-(2-methoxyethyl)oxime,
(E)cyclopropyl(6,6-diphenyl-6,7-dihydro-1H-indazol-3-yl)methanone O-(2-methoxyethyl)oxime,
(E,Z)cyclopropyl(6,6-diphenyl-6,7-dihydro-1H-indazol-3-yl)methanone O-benzyloxime,
(Z)cyclopropyl(6,6-diphenyl-6,7-dihydro-1H-indazol-3-yl)methanone O-benzyloxime,
(E)cyclopropyl(6,6-diphenyl-6,7-dihydro-1H-indazol-3-yl)methanone O-benzyloxime,
(E,Z)cyclopropyl(6,6-diphenyl-6,7-dihydro-1H-indazol-3-yl)methanone O-(4-nitrobenzyl)oxime,
(Z)cyclopropyl(6,6-diphenyl-6,7-dihydro-1H-indazol-3-yl)methanone O-(4-nitrobenzyl)oxime,
(E)cyclopropyl(6,6-diphenyl-6,7-dihydro-1H-indazol-3-yl)methanone O-(4-nitrobenzyl)oxime,
(E,Z)cyclopropyl(6,6-diphenyl-6,7-dihydro-1H-indazol-3-yl)methanone O-(2-dimethylaminoethyl)oxime,
(Z)cyclopropyl(6,6-diphenyl-6,7-dihydro-1H-indazol-3-yl)methanone O-(2-dimethylaminoethyl)oxime,
(E)cyclopropyl(6,6-diphenyl-6,7-dihydro-1H-indazol-3-yl)methanone O-(2-dimethylaminoethyl)oxime,
(E,Z)cyclopropyl(6,6-diphenyl-6,7-dihydro-1H-indazol-3-yl)methanone O-(2-fluoroethyl)oxime,
(Z)cyclopropyl(6,6-diphenyl-6,7-dihydro-1H-indazol-3-yl)methanone O-(2-fluoroethyl)oxime,
(E)cyclopropyl(6,6-diphenyl-6,7-dihydro-1H-indazol-3-yl)methanone O-(2-fluoroethyl)oxime,
(E,Z)-6-(R,S)-cyclopropyl[6-(4-fluorophenyl)-6-phenyl-6,7-dihydro-1H-indazol-3-yl]methanone oxime,
(E)-6-(R,S)-cyclopropyl[6-(4-fluorophenyl)-6-phenyl-6,7-dihydro-1H-indazol-3-yl]methanone oxime,
(Z)-6-(R,S)-cyclopropyl[6-(4-fluorophenyl)-6-phenyl-6,7-dihydro-1H-indazol-3-yl]methanone oxime,
(−)-6-(Z)-cyclopropyl[6-(4-fluorophenyl)-6-phenyl-6,7-dihydro-1H-indazol-3-yl]methanone oxime,
(−)-6-(E)-cyclopropyl[6-(4-fluorophenyl)-6-phenyl-6,7-dihydro-1H-indazol-3-yl]methanone oxime,
(+)-6-(Z)-cyclopropyl[6-(4-fluorophenyl)-6-phenyl-6,7-dihydro-1H-indazol-3-yl]methanone oxime,
(E,Z)cyclopropyl[6,6-bis(4-fluorophenyl)-6,7-dihydro-1H-indazol-3-yl]methanone oxime,
(Z)cyclopropyl[6,6-bis(4-fluorophenyl)-6,7-dihydro-1H-indazol-3-yl]methanone oxime, and
(E)cyclopropyl[6,6-bis(4-fluorophenyl)-6,7-dihydro-1H-indazol-3-yl]methanone oxime.

12. The compound according to claim 3 wherein $R_2$ is NH—C(O)Ra$_4$.

13. The compound according to claim 12 selected from the group consisting of:
N-(6,6-diphenyl-6,7-dihydro-1H-indazol-3-yl)cyclopropylamide, and
N-[6,6-diphenyl-6,7-dihydro-1H-indazol-3-yl]benzamide.

14. The compound according to claim 3 wherein $R_2$ is phenyl, pyridyl, oxadiazolyl or thiophenyl.

15. The compound according to claim 14 selected from the group consisting of:
3-(3-methyl[1,2,4]oxadiazol-5-yl)-6,6-diphenyl-6,7-dihydro-1H-indazole,
3,6,6-triphenyl-6,7-dihydro-1H-indazole,
6,6-diphenyl-3-pyrid-3-yl-6,7-dihydro-1H-indazole, and
6,6-diphenyl-3-thiophen-3-yl-6,7-dihydro-1H-indazole.

16. The compound according to claim 3 wherein $R_2$ is CN.

17. The compound according to claim 16 wherein the compound is 6,6-diphenyl-6,7-dihydro-1H-indazole-3-carbonitrile.

18. The compound according to claim 1 wherein Z is $SO_2R_3$ or $COR_3$.

19. The compound according to claim 18 selected from the group consisting of:
6,6-diphenyl-1-(4-toluenesulphonyl)-6,7-dihydro-1H-indazol-3-ylamine and
1-(3-amino-6,6-diphenyl-6,7-dihydroindazol-1-yl)propenone.

20. The compound according to claim 1 wherein Z is 4-aminophenyl.

21. The compound according to claim 20 wherein the compound is ethyl 1-(4-aminophenyl)-6,6-diphenyl-1H-indazole-3-carboxylate.

22. A pharmaceutical composition comprising one or more compounds of formula (1) or formula (2) according to claim 1 and one or more pharmaceutically acceptable carriers, diluents, adjuvants or excipients.

* * * * *